(12) United States Patent
Beaton et al.

(10) Patent No.: US 10,227,333 B2
(45) Date of Patent: Mar. 12, 2019

(54) INHIBITION OF OLIG2 ACTIVITY

(71) Applicant: Curtana Pharmaceuticals, Inc., Austin, TX (US)

(72) Inventors: Graham Beaton, San Diego, CA (US); Fabio Tucci, San Diego, CA (US); Satheesh B. Ravula, San Diego, CA (US); Hua-Yu Wang, San Antonio, TX (US)

(73) Assignee: CURTANA PHARMACEUTICALS, INC., Austin, TX (US)

( * ) Notice: Subject to any disclaimer, the term of this patent is extended or adjusted under 35 U.S.C. 154(b) by 0 days.

(21) Appl. No.: 15/040,948

(22) Filed: Feb. 10, 2016

(65) Prior Publication Data

US 2016/0237069 A1  Aug. 18, 2016

Related U.S. Application Data

(60) Provisional application No. 62/115,065, filed on Feb. 11, 2015.

(51) Int. Cl.
  *C07D 239/48* (2006.01)
  *C07D 405/12* (2006.01)
  *C07D 401/12* (2006.01)
  *C07D 213/74* (2006.01)
  *A61K 31/506* (2006.01)

(52) U.S. Cl.
  CPC .......... *C07D 405/12* (2013.01); *A61K 31/506* (2013.01); *C07D 213/74* (2013.01); *C07D 239/48* (2013.01); *C07D 401/12* (2013.01)

(58) Field of Classification Search
  CPC .......................... C07D 239/48; A61K 31/506
  USPC ................................. 544/321, 323; 514/275
  See application file for complete search history.

(56) References Cited

U.S. PATENT DOCUMENTS

| | | |
|---|---|---|
| 3,598,122 A | 8/1971 | Alejandro |
| 3,598,123 A | 8/1971 | Alejandro |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,151,273 A | 4/1979 | Chiou et al. |
| 4,201,211 A | 5/1980 | Chandrasekaran et al. |
| 4,229,447 A | 10/1980 | Porter |
| 4,230,105 A | 10/1980 | Harwood |
| 4,292,299 A | 9/1981 | Suzuki et al. |
| 4,292,303 A | 9/1981 | Keith et al. |
| 4,327,725 A | 5/1982 | Cortese et al. |
| 4,343,789 A | 8/1982 | Kawata et al. |
| 4,476,116 A | 10/1984 | Anik |
| 4,596,795 A | 6/1986 | Pitha |
| 4,624,848 A | 11/1986 | Lee |
| 4,755,386 A | 7/1988 | Hsiao et al. |
| 4,861,760 A | 8/1989 | Mazuel et al. |
| 4,871,549 A | 10/1989 | Ueda et al. |
| 4,911,920 A | 3/1990 | Jani et al. |
| 4,968,509 A | 11/1990 | Radebaugh et al. |
| 5,010,175 A | 4/1991 | Rutter et al. |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,116,817 A | 5/1992 | Anik |
| 5,212,162 A | 5/1993 | Missel et al. |
| 5,229,135 A | 7/1993 | Philippon et al. |
| 5,260,068 A | 11/1993 | Chen |
| 5,260,069 A | 11/1993 | Chen |
| 5,281,420 A | 1/1994 | Kelm et al. |
| 5,288,514 A | 2/1994 | Ellman |
| 5,323,907 A | 6/1994 | Kalvelage |
| 5,336,168 A | 8/1994 | Sibalis |
| 5,340,591 A | 8/1994 | Nakano et al. |
| 5,403,841 A | 4/1995 | Lang et al. |
| 5,456,923 A | 10/1995 | Nakamichi et al. |
| 5,461,140 A | 10/1995 | Heller et al. |

(Continued)

FOREIGN PATENT DOCUMENTS

| WO | WO-9119735 A1 | 12/1991 |
|---|---|---|
| WO | WO-9320242 A1 | 10/1993 |

(Continued)

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Silverman, The Organic Chemistry of Drug Design and Drug Action, Chapter 8: Prodrugs and Drug Delivery Systems, pp. 352-400, 1992.*
Al-Sha'er et al., Application of docking-based comparative intermolecular contacts analysis to validate Hsp90α docking studies and subsequent in silico screening for inhibitors, J Mol Model, 18(11), pp. 4843-4863 (2012).*

(Continued)

*Primary Examiner* — Deepak R Rao
(74) *Attorney, Agent, or Firm* — Wilson Sonsini Goodrich & Rosati

(57) ABSTRACT

Described herein are compounds and pharmaceutical compositions containing such compounds, which inhibit the activity of Olig2. Also described herein are methods of using such Olig2 inhibitors, alone and in combination with other compounds, for treating cancer and other diseases. In particular the Olig2 inhibitors may be used to treat glioblastoma.

15 Claims, No Drawings

(56) References Cited

U.S. PATENT DOCUMENTS

| | | | |
|---|---|---|---|
| 5,508,040 | A | 4/1996 | Chen |
| 5,516,527 | A | 5/1996 | Curatolo |
| 5,539,083 | A | 7/1996 | Cook et al. |
| 5,567,441 | A | 10/1996 | Chen |
| 5,593,853 | A | 1/1997 | Chen et al. |
| 5,622,721 | A | 4/1997 | Dansereau et al. |
| 5,665,378 | A | 9/1997 | Davis et al. |
| 5,686,105 | A | 11/1997 | Kelm et al. |
| 5,700,410 | A | 12/1997 | Nakamichi et al. |
| 5,700,485 | A | 12/1997 | Berde et al. |
| 5,723,269 | A | 3/1998 | Akagi et al. |
| 5,739,136 | A | 4/1998 | Ellinwood, Jr. et al. |
| 5,837,280 | A | 11/1998 | Kenealy et al. |
| 5,837,284 | A | 11/1998 | Mehta et al. |
| 5,840,329 | A | 11/1998 | Bai |
| 5,858,401 | A | 1/1999 | Bhalani et al. |
| 5,869,090 | A | 2/1999 | Rosenbaum |
| 5,977,175 | A | 11/1999 | Lin |
| 6,083,518 | A | 7/2000 | Lindahl |
| 6,391,452 | B1 | 5/2002 | Antonsen et al. |
| 6,465,014 | B1 | 10/2002 | Moroni et al. |
| 6,667,048 | B1 | 12/2003 | Lambert et al. |
| 6,923,983 | B2 | 8/2005 | Morgan et al. |
| 6,929,801 | B2 | 8/2005 | Klose et al. |
| 6,932,983 | B1 | 8/2005 | Straub et al. |
| 6,946,144 | B1 | 9/2005 | Jordan |
| 6,960,563 | B2 | 11/2005 | Egbaria et al. |
| 2004/0013734 | A1 | 1/2004 | Babcock et al. |
| 2006/0004005 | A1 | 1/2006 | Sattigeri et al. |
| 2006/0293343 | A1 | 12/2006 | Naganuma et al. |
| 2015/0259326 | A1 | 9/2015 | Kesari et al. |
| 2017/0182049 | A1 | 6/2017 | Kesari et al. |

FOREIGN PATENT DOCUMENTS

| | | | |
|---|---|---|---|
| WO | WO-9700271 | A1 | 1/1997 |
| WO | WO-0242276 | A1 | 5/2002 |
| WO | WO-2004005472 | A2 | 1/2004 |
| WO | WO-2005007652 | A2 | 1/2005 |
| WO | WO-2008014291 | A2 | 1/2008 |
| WO | WO-2010001365 | A1 | 1/2010 |
| WO | WO-2011031974 | A1 | 3/2011 |
| WO | WO 2013/053726 | * | 4/2013 |
| WO | WO 2013/188813 | * | 12/2013 |
| WO | WO-2016138479 | A1 | 9/2016 |

OTHER PUBLICATIONS

Tsigelny et al., Development of a pharmacophore model for the catecholamine release-inhibitory peptide catestatin: Virtual screening and functional testing identify novel small molecule therapeutics of hypertension, Bioorganic & Medicinal Chemistry, 21, pp. 5855-5869 (2013).*

Elslager et al., Synthesis and Antimalarial Effects of 1-(3,4-Dichlorophenyl)-3-[4-[(1-ethyl-3-piperidyl)amino]-6-methyl-2-pyrimidinyl]guanidine and Related Substances, Journal of Medicinal Chemistry, vol. 17, No. 1, pp. 75-100, 1974.*

Cho. Recent Advances in Oral Prodrug Discovery. Annual Reports in Medicinal Chemistry 41:395-407 (2006).

Fedorak et al. A novel colon-specific steroid prodrug enhances sodium chloride absorption in rat colitis. Am. J. Physiol. 269:G210-218 (1995).

Hochhaus et al. A selective HPLC/RIA for dexamethasone and its prodrug dexamethasone-21-sulphobenzoate sodium in biological fluids. Biomed. Chrom. 6:283-286 (1992).

Larsen et al. Prodrug forms for the sulfonamide group. II. water-soluble amino acid derivatives of N-methylsulfonylamindes as possible prodrug derivatives. Int'l J of Pharmaceutics 47:103-110 (1988).

Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).

Liberman et al. Pharmaceutical Dosage Forms, 2nd Ed., 1:209-214 (1990).

McLeod et al. A glucocorticoid prodrug facilitates normal mucosal function in rat colitis without adrenal suppression. Gastroenterol 106:405-413 (1994).

Miller et al. Histone deacetylase inhibitors. J. Med. Chem. 46(24):5097-5116 (2003).

Nogrady. Medicinal Chemistry a Biochemical Approach, Oxford University Press, New York, pp. 388-392 (1985).

Rooseboom et al. Enzyme-catalyzed activation of anticancer prodrugs. Pharmacological Reviews 56:53-102 (2004).

Saulnier et al. An Efficient Method for the Synthesis of Guanidino Prodrugs. Bioorganic and Medicinal Chemistry Letters 4(16):1985-1890 (1994).

Silverman. The Organic Chemistry of Drug Design and Drug Action, Academic Press, Inc., San Diego, pp. 352-401 (1992).

Singh et al. Encyclopedia of Pharmaceutical Technology 2nd Ed. pp. 751-753 (2002).

Singh et al. Encyclopedia of Pharmaceutical Technology 2nd Ed. pp. 754-757 (2002).

Sinkula et al. Rationale for design of biologically reversible drug derivatives: prodrugs. J. Pharm. Sci. 64:181-210 (1975).

Al-Nadaf et al. Discovery of new renin inhibitory leads via sequential pharmacophore modeling, QSAR analysis, in silico screening and in vitro evaluation. J Mol Graph Model 29(6):843-864 (2011).

Cheng et al. Potential therapeutic implications of cancer stem cells in glioblastoma. Biochem Pharmacol 80(5):654-665 (2010).

Darnell. Transcription factors as targets for cancer therapy. Nat Rev Cancer 2(10):740-749 (2002).

Dietrich et al. Mechanisms of Disease: the role of stem cells in the biology and treatment of gliomas. Nature Clinical Practice Oncology 5(7):393-404 (2008).

Genther et al. Antifolate studies. Activities of 40 potential antimalarial compounds against sensitive and chlorguanide triazine resistant strains of folate-requiring bacteria and *Escherichia coli*. J Med Chem 20(2):237-243 (1977).

Jubb et al. Structural biology and drug discovery for protein-protein interactions. Trends Pharmacol Sci 33(5):241-248 (2012).

Klekota et al. Identifying biologically active compound classes using phenotypic screening data and sampling statistics. J Chem Inl Model 45(6):1824-1836 (2005).

Lange et al. Rationally designed hydrolytically activated etoposide prodrugs, a novel strategy for the treatment of neuroblastoma. Cancer Lett 197(1-2):225-230 (2003).

Ligon et al. Olig2-regulated lineage-restricted pathway controls replication competence in neural stem cells and malignant glioma. Neuron 53(4):503-517 (2007).

Longo et al. Crystal structure of E47-NeuroDl/beta2 bHLH domain-DNA complex: heterodimer selectivity and DNA recognition. Biochemistry 47(1):218-229 (2008).

Mehta et al. The central nervous system-restricted transcription factor Olig2 opposes p53 responses to genotoxic damage in neural progenitors and malignant glioma. Cancer Cell 119(3):359-371 (2011).

Nebert. Transcription factors and cancer: an overview. Toxicology 181-182:131-141 (2002).

PCT/US2013/045968 International Search Report and Written Opinion dated Nov. 27, 2013.

PCT/US2016/019932 International Preliminary Report on Patentability dated Sep. 8, 2017.

PCT/US2016/019932 International Search Report and Written Opinion dated Jul. 8, 2016.

Pubchem, Substance Record for SID 104352562, Create Date: Feb. 18, 2011. [retrieved on Jun. 6, 2016]. Retrieved from the Internet.< https://pubchem.ncbi.nlm.nih.gov/substance/104352562/version/1#section=Top>.

Pubchem, Substance Record for SID 125468769, Create Date: Nov. 30, 2011. [retrieved on Mar. 26, 2016]. Retrieved from the Internet.< https://pubchem.ncbi.nlm.nih.gov/substance/125468769/version/1#section=Top>.

Registry (STN) CAS 1348398-00-4 (1 pg.) (2011).
Registry (STN) CAS 1368388-10-6 (1 pg.) (2012).

(56) References Cited

OTHER PUBLICATIONS

Rhee et al. Quantitative analysis of mitotic Olig2 cells in adult human brain and gliomas: implications for glioma histogenesis and biology. Glia 57(5):510-523 (2009).
Sinha et al. Synthesis and biological activities of 10-substituted benzo[b][1,5]naphthyridines. J Pharmacol Sci 67(3):407-409 (1978).
U.S. Appl. No. 15/225,700 Office Action dated Jul. 26, 2017.
Wen et al. Malignant gliomas in adults. N Engl J Med 359(5):492-507 (2008).
Yan et al. Novel statistical approach for primary high-throughput screening hit selection. J Chem Inl Model 45(6):1784-1790 (2005).

\* cited by examiner

INHIBITION OF OLIG2 ACTIVITY

CROSS-REFERENCE

This application claims the benefit of U.S. Provisional Application Ser. No. 62/115,065, filed Feb. 11, 2015, which is incorporated by reference in its entirety.

BACKGROUND OF THE INVENTION

Current brain tumor therapeutic agents, which are only able to extend median survival of patients by six months, cause significant systemic toxicity. This toxicity results in serious long term morbidity of the few patients that survive, in terms of cognition, endocrine disorders, and motor effects. Currently brain tumors are essentially incurable with a median survival of fifteen months.

SUMMARY OF THE INVENTION

Described herein are compounds of Formula (I), (IA), (IB), (II), (IIA), (IIB), (III), (IIIA), (IIIB), (IV), (IVA), (IVB), or (V) (hereinafter "compounds of Formula (I), (IA), (IB), (II), (IIA), (IIB), (III), (IIIA), (IIIB), (IV), (IVA), (IVB), or (V)"), compositions that include such compounds, and methods of use thereof, for inhibition of Olig2 activity.

In one aspect, described herein is a compound of Formula (I):

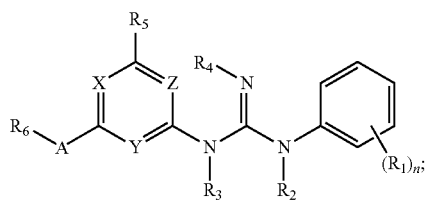

Formula (I)

wherein:
A is a bond, O, $CH_2$, or $N(R_{10})$;
X, Y, and Z are each independently N, or $C(R_7)$;
each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or
two $R_1$ are taken together to form a substituted or unsubstituted heterocyclic ring or a substituted or unsubstituted carbocyclic ring;
$R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;
$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —$(C(R_{14})(R_{15}))_mR_{21}$, —$(C(R_{14})(R_{15}))_mN(R_{11})(R_{12})$, or

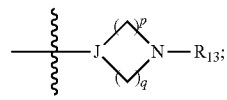

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;
J is C(H), or N;
$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;
each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;
$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)N(R_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{22}$ is independently H, or substituted or unsubstituted $C_1$-$C_6$alkyl;
$R_{23}$ is substituted or unsubstituted $C_1$-$C_6$alkyl;
each $R_8$ is independently H, or substituted or unsubstituted $C_1$-$C_6$alkyl;
$R_9$ is substituted or unsubstituted $C_1$-$C_6$alkyl;
$R_{10}$ is H, or $C_1$-$C_4$alkyl;
m is 2-6;
n is 0-5;
p is 1-3;
q is 1-3; or
a pharmaceutically acceptable salt, solvate, or prodrug thereof.

In one embodiment is a compound of Formula (I) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (I) wherein at least one of $R_2$, $R_3$, and $R_4$ is not H. In another embodiment is a compound of Formula (I) wherein $R_2$ is $C_1$-$C_4$alkyl, $C_3$-$C_6$cycloalkyl, or $C_2$-$C_7$heterocycloalkyl; $R_3$ is H; and $R_4$ is H. In another embodiment is a compound of Formula (I) wherein $R_2$ is $CH_3$ or $C_3$-$C_6$cycloalkyl; $R_3$ is H; and $R_4$ is H. In a further embodiment is a compound of Formula (I) wherein $R_2$ is H; $R_3$ is $C_1$-$C_4$alkyl, $C_3$-$C_6$cycloalkyl, or $C_2$-$C_7$heterocycloalkyl; and $R_4$ is H. In another embodiment is a compound of Formula (I) wherein $R_2$ is H; $R_3$ is $CH_3$; and $R_4$ is H. In another embodiment is a compound of Formula (I) wherein $R_2$ is $C_1$-$C_4$alkyl; $R_3$ is $C_1$-$C_4$alkyl; and $R_4$ is H. In another embodiment is a compound of Formula (I) wherein $R_2$ is $CH_3$; $R_3$ is $CH_3$; and $R_4$ is H. In another embodiment is a compound of Formula (I) wherein $R_2$ is H; $R_3$ is $C_1$-$C_4$alkyl; and $R_4$ is $C_1$-$C_4$alkyl. In another embodiment is a compound of Formula (I) wherein $R_2$ is H; $R_3$ is $CH_3$; and $R_4$ is $CH_3$. In another embodiment is a compound of Formula (I) wherein $R_2$ is H; $R_3$ is $C_1$-$C_4$alkyl; and $R_4$ is —CN. In another embodiment is a compound of Formula (I) wherein $R_2$ is H; $R_3$ is $CH_3$; and $R_4$ is —CN. In another embodiment is a compound of Formula (I) wherein $R_2$ and $R_3$ are taken together to form a 5- or 6-membered heterocyclic ring. In another embodiment is a compound of Formula (I) wherein $R_2$ and $R_3$ are taken together to form a 5-membered heterocyclic ring. In another embodiment is a compound of Formula (I) wherein $R_2$ and $R_3$ are taken together to form a 5-membered heterocyclic ring; and $R_4$ is H. In another embodiment of the aforementioned embodiments, is a compound of Formula (I) wherein $R_6$ is substituted or unsubstituted $C_2$-$C_7$heteroaryl. In another embodiment is a compound of Formula (I) wherein $R_6$ is substituted or unsubstituted pyridyl. In another embodiment is a compound of Formula (I) wherein $R_6$ is unsubstituted pyridyl. In another embodiment of the aforementioned embodiments, is a compound of Formula (I) wherein $R_6$ is

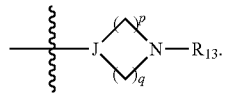

In another embodiment is a compound of Formula (I) wherein $R_{13}$ is substituted or unsubstituted $C_1$-$C_4$alkyl. In another embodiment is a compound of Formula (I) wherein $R_{13}$ is —$CH_3$. In another embodiment is a compound of Formula (I) wherein $R_{13}$ is —$CH_2CH_3$. In another embodiment of the aforementioned embodiments, is a compound of Formula (I) wherein J is C(H). In another embodiment is a compound of Formula (I) wherein p is 2 and q is 1. In another embodiment is a compound of Formula (I) wherein p is 3 and q is 1. In another embodiment is a compound of Formula (I) wherein p is 2 and q is 2. In another embodiment of the aforementioned embodiments, is a compound of Formula (I) wherein J is N. In another embodiment is a compound of Formula (I) wherein p is 2 and q is 2. In another embodiment of the aforementioned embodiments, is a compound of Formula (I) wherein A is $N(R_{10})$. In another embodiment is a compound of Formula (I) wherein $R_{10}$ is H or $CH_3$. In another embodiment of the aforementioned embodiments, is a compound of Formula (I) wherein A is O. In another embodiment of the aforementioned embodiments, is a compound of Formula (I) wherein A is $CH_2$. In another embodiment of the aforementioned embodiments, is a compound of Formula (I) wherein $R_5$ is substituted or unsubstituted $C_1$-$C_6$alkyl. In another embodiment is a compound of Formula (I) wherein $R_5$ is $CH_3$. In another embodiment is a compound of Formula (I) wherein $R_5$ is $CH_2CH_3$. In another embodiment of the aforementioned embodiments, is a compound of Formula (I) wherein n is 2. In another embodiment of the aforementioned embodiments, is a compound of Formula (I) wherein n is 1. In another embodiment of the aforementioned embodiments, is a compound of Formula (I) wherein n is 0. In another embodiment of the aforementioned embodiments, is a compound of Formula (I) wherein each $R_1$ is independently halogen, —CN, —$NO_2$, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (I) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment of the aforementioned embodiments, is a compound of Formula (I) wherein two $R_1$ are taken together to form a substituted or unsubstituted heterocyclic ring or a substituted or unsubstituted carbocyclic ring. In another embodiment of the aforementioned embodiments, is a compound of Formula (I) wherein X is $C(R)_7$; Y is N; and Z is N. In another embodiment of the aforementioned embodiments, is a compound of Formula (I) wherein X is $C(R)_7$; Y is $C(R)_7$; and Z is N. In another embodiment of the aforementioned embodiments, is a compound of Formula (I) wherein X is $C(R)_7$; Y is N; and Z is $C(R)_7$. In another embodiment of the aforementioned embodiments, is a compound of Formula (I) wherein X is $C(R)_7$; Y is $C(R)_7$; and Z is $C(R)_7$. In another embodiment of the aforementioned embodiments, is a compound of Formula (I) wherein $R_7$ is H.

In another aspect is a pharmaceutical composition comprising a compound of Formula (I) or a pharmaceutically acceptable salt, solvate, or prodrug thereof, and at least one pharmaceutically acceptable excipient.

In another aspect is the use of a compound of Formula (I) or a pharmaceutically acceptable salt, pharmaceutically acceptable solvate, or pharmaceutically acceptable prodrug thereof, for the formulation of a medicament for inhibiting the activity of Olig2 in a cell is provided. The method includes contacting the cell with a compound of Formula (I) including embodiments thereof.

In a further aspect is a method of treating a disease, disorder or condition in a subject that would benefit from inhibition of Olig2 activity comprising administering to the subject in need thereof a composition comprising a compound of Formula (I) or a pharmaceutically acceptable salt, solvate, or prodrug thereof. In some embodiments is a method of treating a disease, disorder or condition in a subject that would benefit from inhibition of Olig2 activity comprising administering to the subject in need thereof a composition comprising a compound of Formula (I) or a pharmaceutically acceptable salt, solvate, or prodrug thereof; wherein the disease is cancer or Down's Syndrome.

In another aspect is a method for treating a disease in a subject comprising administering to the subject in need thereof a composition comprising a compound of Formula (I), or a pharmaceutically acceptable salt, solvate, or prodrug thereof; wherein the disease is cancer or Down's Syndrome. In some embodiments is a method for treating cancer in a subject comprising administering to the subject in need thereof a composition comprising a compound of Formula (I) or a pharmaceutically acceptable salt, solvate, or prodrug thereof. In some embodiments is a method for treating Down's Syndrome in a subject comprising administering to the subject in need thereof a composition comprising a compound of Formula (I) or a pharmaceutically acceptable salt, solvate, or prodrug thereof.

In another embodiment is a method for treating cancer in a subject comprising administering to the subject in need thereof a composition comprising a compound of Formula (I) or a pharmaceutically acceptable salt, solvate, or prodrug thereof, wherein the cancer is brain cancer, glioblastoma multiforme, medulloblastoma, astrocytomas, brain stem gliomas, meningiomas, oligodendrogliomas, melanoma, lung cancer, breast cancer, or leukemia.

In another aspect is a method of inhibiting the activity of Olig2 in a cell comprising contacting the cell with a compound of Formula (I) or a pharmaceutically acceptable salt, solvate, or prodrug thereof.

In another aspect is the use of a compound of Formula (I) in the manufacture of a medicament for the treatment of a disease, disorder, or condition that would benefit from inhibition of Olig2 activity.

Other objects, features and advantages of the compounds, compositions, methods, and uses described herein will become apparent from the following detailed description. It should be understood, however, that the detailed description and the specific examples, while indicating specific embodiments, are given by way of illustration only, since various changes and modifications within the spirit and scope of the disclosure will become apparent from this detailed description.

DETAILED DESCRIPTION

The compounds described herein are modulators or inhibitors of the neural and GBM (glioblastoma multiforme) stem cell transcriptional repressor OLIG2 (e.g. NM_005806, NP_005797 for human). OLIG2 (also written herein as Olig2) is the oligodendrocyte trasnsciption factor 2. This protein is a member of the bHLH (basic helix-loop-helix) family. The bHLH family is a family of transcription factors that contain the structure motif characterized by two alpha helices connected by a loop. The transcription factors containing bLHL domains are generally dimeric. Generally one of the helices contains basic amino acid residues that facilitate binding to DNA. OLIG2 is normally restricted to the central nervous system (CNS) in non-disease states, where it is an essential regulator of progenitor cell fate. OLIG2 homodimerizes and hetereodimerizes with the E12 or E47 proteins to then bind and repress the p21 gene promoter among other effects. P21 is a stem cell and tumor suppressor, and is directly repressed by OLIG2. P21 is activated by the tumor suppressor p53. p53 occurs in the intact, wild type form in nearly 70% of primary GBM patient samples. OLIG2 is highly expressed in all diffuse gliomas, and is found in virtually 100% of GBM cells positive for the CD133 stem cell marker. Importantly, OLIG2 is typically not found in normal brain and in tissues outside the CNS unless they are malignant, such as T-cell leukemia, melanoma, lung and breast cancer. No other neural or glial marker gene, and no other transcriptional repressor displays as consistent a link to brain cancers. In contrast, membrane receptors (EGFR, PDGFR, etc) are not uniformly expressed among patients, and various approaches to targeting them has been met with limited success in GBM treatment.

The expression of Olig2 in diffuse gliomas likely results from the transformed stem cell origin of these tumors. It has been found that a small cohort of the cells present in patient GBM expresses neural stem cell markers including CD133 and nestin, among others. The CD133(+) cells isolated from existing GBM are highly tumorigenic when orthotopically implanted into mice. In one study, as few as 100 of the CD133(+) cells extracted from a patient GBM produced an invasive tumor when transplanted into the brain of a recipient mouse, while 100,000 CD133(−) GBM cells were unable to generate a tumor. Consistent with these findings, a strikingly high percentage of GBM occur in close proximity to the neural stem cell germinal zones in the brain, i.e., neural stem cells undergo malignant transformation and migrate some distance from the germinal zones and establish a GBM.

Another significant finding with respect to GBM cancer stem cells (CSCs) is that the CD133(+) cells are significantly more resistant to radiation and cytotoxic agents used to treat GBM than the bulk of the tumor mass which is comprised of CD133(−) cells. This suggests that conventional radio/chemotherapy spares the CSCs within a GBM, and unless these cells are targeted, the tumor invariably is resurgent, with lethal effect. Moreover, the very few patients that survive GBM suffer lifelong morbidity from chemo- and radio-toxicity, in terms of cognition, endocrine balance, and other functions.

Olig2 is highly expressed in GBM CSCs, but is only expressed in low levels by normal brain and is not detected in tissues outside the nervous system. Olig2 inhibitors would offer a therapeutic margin superior to conventional chemotherapy. Low systemic toxicity would be much more compatible with long-term clinical management of GBM than is the case with currently used treatment approaches.

High rates of mortality for patients with brain cancers make this disease a leading cause of cancer related death in men, women and children. Primary brain tumors are actually the most common solid tumor of childhood and the second leading cause of cancer death after leukemia. The toxicity of current treatments causes serious life-long morbidity in the few patients that survive. The development of small molecule, orally available drugs with low toxicity effective in brain cancers would represent a significant advance. Moreover, the compounds may also be effective in other cancers that are stem cell driven and which highly express Olig2. These cancers include T-cell leukemias, skin cancers, small cell lung cancers, and breast cancers. Moreover, these cancers often metastasize to the brain. This would be relevant to millions of patients worldwide.

In some embodiments described herein, are small molecules that inhibit Olig2 which is a transcription factor critical for survival and proliferation of glioblastoma and other brain cancers, i.e., medulloblastoma, astrocytomas, brain stem gliomas, meningiomas, and oligodendrogliomas. Olig2 especially is detected primarily in the brain, generally not outside the nervous system, and it is highly expressed in glioblastoma tumors. This means that Olig2 inhibition should have relatively low toxicity to a patient. Olig2 is also over-expressed in melanomas, lung cancers, breast cancer and T-cell leukemias, so an Olig2 inhibitor may also be applicable to the treatment of these cancers.

No other transcription factor or marker displays as consistent a link to brain cancer as does Olig2, so Olig2 inhibition should compare favorably to other signaling pathway inhibitors in glioblastoma. Olig2 is a robust target in that the hinge region of its dimerization loop is unique compared to other proteins of its class (basic helix-loop-helix proteins).

The Olig2 targeted inhibitors described herein should prove unique in terms of efficacy and toxicity.

The existing agents, therapeutics, and methods used to treat brain cancers include Temozolomide (TMZ-Temodar), radiation, cyclophosphamide, carmustine, carboplatin, and occasional supplementation with Avastin. All these are only somewhat effective standard brain cancer therapeutic agents, and they are very toxic. No brain cancer stem cell inhibitors currently exist for brain tumors.

In another aspect, methods of inhibiting the activity of OLIG2 are provided. The methods include contacting an Olig2 protein with an effective amount of a compound provided herein (e.g., a compound of Formula (I), (IA), (IB), (II), (IIA), (IIB), (III), (IIIA), (IIIB), (IV), (IVA), (IVB), or (V). The compound may have the structure of the Formulae provided herein (or any of the embodiments thereof described above). In some embodiments, the methods of inhibiting a Olig2 protein are conducted within a cell. Thus, in certain embodiments, methods of inhibiting the activity of Olig2 within a cell are provided. The method includes contacting a cell with an effective amount of a compound provided herein. The compound may have the structure of the Formulae provided herein (or any of the embodiments thereof described above). In some embodiments, the cell is a prokaryote or eukaryote. The cell may be a eukaryote (e.g. protozoan cell, fungal cell, plant cell or an animal cell). In some embodiments, the cell is a mammalian cell such as a human cell, cow cell, pig cell, horse cell, dog cell and cat cell, mouse cell, or rat cell. In some embodiments, the cell is a human cell. The cell may form part of an organ or an organism. In certain embodiments, the cell does not form part of an organ or an organism.

In another aspect, a method of inhibiting the activity of Olig2 in a cell is provided. The method includes contacting the cell with a compound as provided herein (e.g. Formula (I), (IA), (IB), (II), (IIA), (IIB), (III), (IIIA), (IIIB), (IV), (IVA), and (IVB)). In some embodiments the compound binds the hinge region of the dimerization loop of Olig2. In some embodiments, the compound inhibits dimerization of Olig2.

Compounds

Compounds described herein inhibit the activity of Olig2 within a cell and may be used in the treatment of diseases or conditions where inhibition of Olig2 activity has a beneficial effect.

In one aspect, described herein is a compound of Formula (I):

Formula (I)

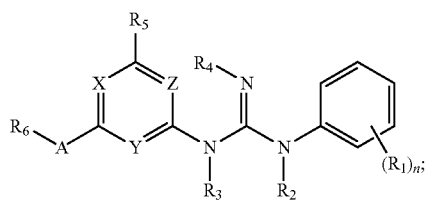

wherein:
A is a bond, O, $CH_2$, or $N(R_{10})$;
X, Y, and Z are each independently N, or $C(R_7)$;
each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;

$R_5$ is halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —(C(R$_{14}$)(R$_{15}$))$_m$R$_{21}$, —(C(R$_{14}$)(R$_{15}$))$_m$N(R$_{11}$)(R$_{12}$), or

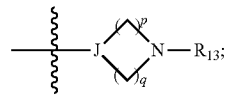

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;

each $R_7$ is independently H, halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —NO$_2$, —OH, —OCF$_3$, —OCH$_2$F, —OCF$_2$H, —CF$_3$, —SR$_{22}$, —N(R$_{22}$)S(=O)$_2$R$_{23}$, —S(=O)$_2$N(R$_{22}$)$_2$, —S(=O)R$_{23}$, —S(=O)$_2$R$_{23}$, —C(=O)R$_{23}$, —CO$_2$R$_{22}$, —C(=O)NR$_{22}$)$_2$, —N(R$_{22}$)C(=O)R$_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In one embodiment is a compound of Formula (I) wherein A is O, $CH_2$, or $N(R_{10})$. In another embodiment is a compound of Formula (I) wherein A is O, $CH_2$, or N(H). In another embodiment is a compound of Formula (I) wherein A is O. In another embodiment is a compound of Formula (I) wherein A is $CH_2$. In another embodiment is a compound of Formula (I) wherein A is $N(R_{10})$. In another embodiment is a compound of Formula (I) wherein A is N(H). In another embodiment is a compound of Formula (I) wherein A is $N(CH_3)$. In another embodiment is a compound of Formula (I) wherein A is a bond.

In another embodiment is a compound of Formula (I) wherein $R_6$ is substituted or unsubstituted $C_3$-$C_8$cycloalkyl. In another embodiment is a compound of Formula (I) wherein $R_6$ is substituted or unsubstituted cyclopropyl. In another embodiment is a compound of Formula (I) wherein $R_6$ is substituted or unsubstituted cyclobutyl. In another embodiment is a compound of Formula (I) wherein $R_6$ is substituted or unsubstituted cyclopentyl. In another embodiment is a compound of Formula (I) wherein $R_6$ is substituted or unsubstituted cyclohexyl.

In another embodiment is a compound of Formula (I) wherein $R_6$ is substituted or unsubstituted $C_2$-$C_7$heteroaryl. In another embodiment is a compound of Formula (I) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (I) wherein $R_6$ is substituted or unsubstituted pyridyl. In another embodiment is a compound of Formula (I) wherein $R_6$ is substituted pyridyl. In another embodiment is a compound of Formula (I) wherein $R_6$ is unsubstituted pyridyl.

In another embodiment is a compound of Formula (I) wherein $R_6$ is —$C(R_{14})(R_{15}))_m R_{21}$. In another embodiment is a compound of Formula (I) wherein $R_6$ is —$C(R_{14})(R_{15}))_m R_{21}$, and each $R_{14}$ and $R_{15}$ are H. In another embodiment is a compound of Formula (I) wherein $R_6$ is —$C(R_{14})(R_{15}))_m R_{21}$, m is 2, and each $R_{14}$ and $R_{15}$ are H. In another embodiment is a compound of Formula (I) wherein $R_6$ is —$(CH_2)_m R_{21}$, m is 2, and $R_{21}$ is substituted or unsubstituted $C_2$-$C_7$heterocycloalkyl. In another embodiment is a compound of Formula (I) wherein $R_6$ is —$(CH_2)_m R_{21}$, m is 2, and $R_{21}$ is substituted or unsubstituted $C_3$-$C_8$cycloalkyl. In another embodiment is a compound of Formula (I) wherein $R_6$ is —$(CH_2)_m R_{21}$, m is 2, and $R_{21}$ is substituted or unsubstituted $C_6$-$C_{10}$aryl. In another embodiment is a compound of Formula (I) wherein $R_6$ is —$(CH_2)_m R_{21}$, m is 2, and $R_{21}$ is substituted or unsubstituted phenyl. In another embodiment is a compound of Formula (I) wherein $R_6$ is —$(CH_2)_m R_{21}$, m is 2, and $R_{21}$ is substituted or unsubstituted $C_2$-$C_7$heteroaryl.

In another embodiment is a compound of Formula (I) wherein $R_6$ is —$(C(R_{14})(R_{15}))_m R_{21}$, m is 3, and each $R_{14}$ and $R_{15}$ are H. In another embodiment is a compound of Formula (I) wherein $R_6$ is —$(CH_2)_m R_{21}$, m is 3, and $R_{21}$ is substituted or unsubstituted $C_2$-$C_7$heterocycloalkyl. In another embodiment is a compound of Formula (I) wherein $R_6$ is —$(CH_2)_m R_{21}$, m is 3, and $R_{21}$ is substituted or unsubstituted $C_3$-$C_8$cycloalkyl. In another embodiment is a compound of Formula (I) wherein $R_6$ is —$(CH_2)_m R_{21}$, m is 3, and $R_{21}$ is substituted or unsubstituted $C_6$-$C_{10}$aryl. In another embodiment is a compound of Formula (I) wherein $R_6$ is —$(CH_2)_m R_{21}$, m is 3, and $R_{21}$ is substituted or unsubstituted phenyl. In another embodiment is a compound of Formula (I) wherein $R_6$ is —$(CH_2)_m R_{21}$, m is 3, and $R_{21}$ is substituted or unsubstituted $C_2$-$C_7$heteroaryl.

In another embodiment is a compound of Formula (I) wherein $R_6$ is —$(C(R_{14})(R_{15}))_m N(R_{11})(R_{12})$—In another embodiment is a compound of Formula (I) wherein $R_6$ is —$(C(R_{14})(R_{15}))_m N(R_{11})(R_{12})$, m is 2, and each $R_{14}$ and $R_{15}$ are H. In another embodiment is a compound of Formula (I) wherein $R_6$ is —$(CH_2)_m N(R_{11})(R_{12})$, m is 2, and $R_{11}$ and $R_{12}$ are each H. In another embodiment is a compound of Formula (I) wherein $R_6$ is —$(CH_2)_m N(R_{11})(R_{12})$, m is 2, $R_{11}$ is substituted or unsubstituted $C_1$-$C_6$alkyl, and $R_{12}$ is H. In another embodiment is a compound of Formula (I) wherein $R_6$ is —$(CH_2)_m N(R_{11})(R_{12})$, m is 2, $R_{11}$ is $CH_3$, and $R_{12}$ is H. In another embodiment is a compound of Formula (I) wherein $R_6$ is —$(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (I) wherein $R_6$ is —$(CH_2)_m N(R_{11})(R_{12})$, m is 2, $R_{11}$ is $CH_3$, and $R_{12}$ is $CH_3$. In another embodiment is a compound of Formula (I) wherein $R_6$ is —$(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (I) wherein $R_6$ is —$(CH_2)_m N(R_{11})(R_{12})$, m is 2, and $R_{11}$ and $R_{12}$ are taken together to form a 5-membered heterocyclic ring. In another embodiment is a compound of Formula (I) wherein $R_6$ is —$(CH_2)_m N(R_{11})(R_{12})$, m is 2, and $R_{11}$ and $R_{12}$ are taken together to form a 6-membered heterocyclic ring.

In another embodiment is a compound of Formula (I) wherein $R_6$ is —$(C(R_{14})(R_{15}))_m N(R_{11})(R_{12})$. In another embodiment is a compound of Formula (I) wherein $R_6$ is —$(C(R_{14})(R_{15}))_m N(R_{11})(R_{12})$, m is 3, and each $R_{14}$ and $R_{15}$ are H. In another embodiment is a compound of Formula (I) wherein $R_6$ is —$(CH_2)_m N(R_{11})(R_{12})$, m is 3, and $R_{11}$ and $R_{12}$ are each H. In another embodiment is a compound of Formula (I) wherein $R_6$ is —$(CH_2)_m N(R_{11})(R_{12})$, m is 3, $R_{11}$ is substituted or unsubstituted $C_1$-$C_6$alkyl, and $R_{12}$ is H. In another embodiment is a compound of Formula (I) wherein $R_6$ is —$(CH_2)_m N(R_{11})(R_{12})$, m is 3, $R_{11}$ is $CH_3$, and $R_{12}$ is H. In another embodiment is a compound of Formula (I) wherein $R_6$ is —$(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (I) wherein $R_6$ is —$(CH_2)_m N(R_{11})(R_{12})$, m is 3, $R_{11}$ is $CH_3$, and $R_{11}$ is $CH_3$. In another embodiment is a compound of Formula (I) wherein $R_6$ is —$(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (I) wherein $R_6$ is —$(CH_2)_m N(R_{11})(R_{12})$, m is 3, and $R_{11}$ and $R_{12}$ are taken together to form a 5-membered heterocyclic ring. In another embodiment is a compound of Formula (I) wherein R$_6$ is —(CH$_2$)$_m$N(R$_{11}$)(R$_{12}$), m is 3, and R$_{11}$ and R$_{12}$ are taken together to form a 6-membered heterocyclic ring.

In another embodiment is a compound of Formula (I) wherein R$_6$ is substituted or unsubstituted C$_2$-C$_7$heterocycloalkyl. In another embodiment is a compound of Formula (I) wherein R$_6$ is

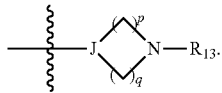

In another embodiment is a compound of Formula (I) wherein R$_6$ is

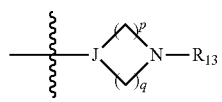

and J is C(H). In another embodiment is a compound of Formula (I) wherein R$_6$ is

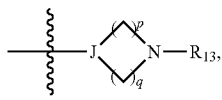

J is C(H), p is 1, and q is 1. In another embodiment is a compound of Formula (I) wherein R$_6$ is

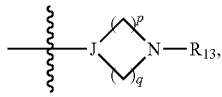

J is C(H), p is 2, and q is 1. In another embodiment is a compound of Formula (I) wherein R$_6$ is

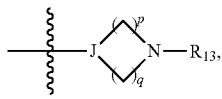

J is C(H), p is 3, and q is 1. In another embodiment is a compound of Formula (I) wherein R$_6$ is

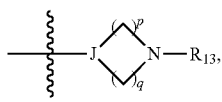

J is C(H), p is 2, and q is 2. In another embodiment is a compound of Formula (I) wherein R$_6$ is

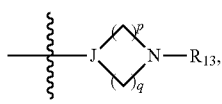

J is C(H), p is 1, q is 1, and R$_{13}$ is substituted or unsubstituted C$_1$-C$_6$alkyl. In another embodiment is a compound of Formula (I) wherein R$_6$ is

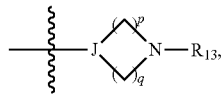

J is C(H), p is 2, q is 1, and R$_{13}$ is substituted or unsubstituted C$_1$-C$_6$alkyl. In another embodiment is a compound of Formula (I) wherein R$_6$ is

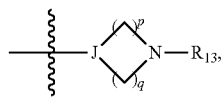

J is C(H), p is 3, q is 1, and R$_{13}$ is substituted or unsubstituted C$_1$-C$_6$alkyl. In another embodiment is a compound of Formula (I) wherein R$_6$ is

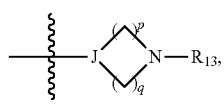

J is C(H), p is 2, q is 2, and R$_{13}$ is substituted or unsubstituted C$_1$-C$_6$alkyl.

In another embodiment is a compound of Formula (I) wherein R$_6$ is

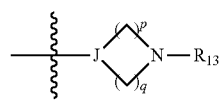

and J is N. In another embodiment is a compound of Formula (I) wherein R$_6$ is

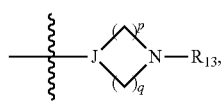

J is N, p is 2, and q is 2. In another embodiment is a compound of Formula (I) wherein R$_6$ is

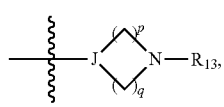

J is N, p is 2, q is 2, and R$_{13}$ is substituted or unsubstituted C$_1$-C$_6$alkyl.

In another embodiment is a compound of Formula (I) wherein R$_5$ is halogen. In another embodiment is a compound of Formula (I) wherein R$_5$ is —CF$_3$. In another embodiment is a compound of Formula (I) wherein R$_5$ is substituted or unsubstituted C$_1$-C$_6$alkyl. In another embodiment is a compound of Formula (I) wherein R$_5$ is —CH$_3$. In another embodiment is a compound of Formula (I) wherein $R_5$ is —$CH_2CH_3$. In another embodiment is a compound of Formula (I) wherein $R_5$ is substituted or unsubstituted $C_1$-$C_6$heteroalkyl. In another embodiment is a compound of Formula (I) wherein $R_5$ is substituted or unsubstituted $C_2$-$C_7$heterocycloalkyl. In another embodiment is a compound of Formula (I) wherein $R_5$ is substituted or unsubstituted $C_3$-$C_8$cycloalkyl. In another embodiment is a compound of Formula (I) wherein $R_5$ is substituted or unsubstituted $C_6$-$C_{10}$aryl. In another embodiment is a compound of Formula (I) wherein $R_5$ is substituted or unsubstituted $C_2$-$C_7$heteroaryl.

In another embodiment is a compound of Formula (I) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (I) wherein $R_2$, $R_3$, and $R_4$ are each H.

In another embodiment is a compound of Formula (I) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (I) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (I) wherein $R_2$ is H; $R_3$ is $C_1$-$C_4$alkyl; and $R_4$ is H. In another embodiment is a compound of Formula (I) wherein $R_2$ is H; $R_3$ is $CH_3$; and $R_4$ is H. In another embodiment is a compound of Formula (I) wherein $R_2$ is H; $R_3$ is $C_1$-$C_4$alkyl; and $R_4$ is $C_1$-$C_4$alkyl. In another embodiment is a compound of Formula (I) wherein $R_2$ is H; $R_3$ is $CH_3$; and $R_4$ is $CH_3$. In another embodiment is a compound of Formula (I) wherein $R_2$ is H; $R_3$ is $C_1$-$C_4$alkyl; and $R_4$ is —CN. In another embodiment is a compound of Formula (I) wherein $R_2$ is H; $R_3$ is $CH_3$; and $R_4$ is —CN. In another embodiment is a compound of Formula (I) wherein $R_2$ is $C_1$-$C_4$alkyl; $R_3$ is $C_1$-$C_4$alkyl; and $R_4$ is H. In another embodiment is a compound of Formula (I) wherein $R_2$ is $CH_3$; $R_3$ is $CH_3$; and $R_4$ is H. In another embodiment is a compound of Formula (I) wherein $R_2$ is $C_1$-$C_4$alkyl; $R_3$ is H; and $R_4$ is H. In another embodiment is a compound of Formula (I) wherein $R_2$ is $CH_3$; $R_3$ is H; and $R_4$ is H. In another embodiment is a compound of Formula (I) wherein $R_2$ is $C_1$-$C_4$alkyl; $R_3$ is H; and $R_4$ is $C_1$-$C_4$alkyl. In another embodiment is a compound of Formula (I) wherein $R_2$ is $CH_3$; $R_3$ is H; and $R_4$ is $CH_3$. In another embodiment is a compound of Formula (I) wherein $R_2$ is $C_1$-$C_4$alkyl; $R_3$ is H; and $R_4$ is —CN. In another embodiment is a compound of Formula (I) wherein $R_2$ is $CH_3$; $R_3$ is H; and $R_4$ is —CN. In another embodiment is a compound of Formula (I) wherein $R_2$ is $C_3$-$C_6$cycloalkyl; $R_3$ is H; and $R_4$ is H. In another embodiment is a compound of Formula (I) wherein $R_2$ is cyclopropyl; $R_3$ is H; and $R_4$ is H. In another embodiment is a compound of Formula (I) wherein $R_2$ is cyclopentyl; $R_3$ is H; and $R_4$ is H. In another embodiment is a compound of Formula (I) wherein $R_2$ is $C_3$-$C_6$cycloalkyl; $R_3$ is H; and $R_4$ is $CH_3$. In another embodiment is a compound of Formula (I) wherein $R_2$ is cyclopropyl; $R_3$ is H; and $R_4$ is $CH_3$. In another embodiment is a compound of Formula (I) wherein $R_2$ is cyclopentyl; $R_3$ is H; and $R_4$ is $CH_3$. In another embodiment is a compound of Formula (I) wherein $R_2$ is $C_3$-$C_6$cycloalkyl; $R_3$ is H; and $R_4$ is —CN. In another embodiment is a compound of Formula (I) wherein $R_2$ is cyclopropyl; $R_3$ is H; and $R_4$ is —CN. In another embodiment is a compound of Formula (I) wherein $R_2$ is cyclopentyl; $R_3$ is H; and $R_4$ is —CN.

In another embodiment is a compound of Formula (I) wherein $R_2$ and $R_3$ are taken together to form a 5- or 6-membered heterocyclic ring. In another embodiment is a compound of Formula (I) wherein $R_2$ and $R_3$ are taken together to form a 5- or 6-membered heterocyclic ring; and $R_4$ is H. In another embodiment is a compound of Formula (I) wherein $R_2$ and $R_3$ are taken together to form a 5-membered heterocyclic ring; and $R_4$ is H. In another embodiment is a compound of Formula (I) wherein $R_2$ and $R_3$ are taken together to form 6-membered heterocyclic ring; and $R_4$ is H.

In another embodiment is a compound of Formula (I) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (I) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment is a compound of Formula (I) wherein each $R_1$ is independently halogen, —CN, —$OCF_3$, —$OCH_2F$, —$OCF_2H$, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (I) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy. In another embodiment is a compound of Formula (I) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 3. In another embodiment is a compound of Formula (I) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 2. In another embodiment is a compound of Formula (I) wherein n is 3, and each $R_1$ is independently halogen. In another embodiment is a compound of Formula (I) wherein n is 2, and each $R_1$ is independently halogen. In another embodiment is a compound of Formula (I) wherein n is 2, and each $R_1$ is independently F or Cl. In another embodiment is a compound of Formula (I) wherein n is 2, and each $R_1$ is F. In another embodiment is a compound of Formula (I) wherein n is 2, and each $R_1$ is independently Cl. In another embodiment is a compound of Formula (I) wherein n is 2, and each $R_1$ is independently halogen or —$CF_3$. In another embodiment is a compound of Formula (I) wherein n is 2, and each $R_1$ is independently F or —$CF_3$. In another embodiment is a compound of Formula (I) wherein n is 2, and each $R_1$ is independently Cl or —$CF_3$. In another embodiment is a compound of Formula (I) wherein n is 1, and $R_1$ is halogen. In another embodiment is a compound of Formula (I) wherein n is 1, and $R_1$ is F. In another embodiment is a compound of Formula (I) wherein n is 1, and $R_1$ is Cl. In another embodiment is a compound of Formula (I) wherein n is 1, and $R_1$ is —$CF_3$. In another embodiment is a compound of Formula (I) wherein n is 1, and $R_1$ is substituted or unsubstituted $C_1$-$C_6$alkyl. In another embodiment is a compound of Formula (I) wherein n is 1, and $R_1$ is $CH_3$. In another embodiment is a compound of Formula (I) wherein n is 1, and $R_1$ is substituted or unsubstituted $C_1$-$C_6$alkoxy. In another embodiment is a compound of Formula (I) wherein n is 1, and $R_1$ is —$OCH_3$. In another embodiment is a compound of Formula (I) wherein n is 1, and $R_1$ is —$OCF_3$. In another embodiment is a compound of Formula (I) wherein n is 1, and $R_1$ is —$OCF_2H$.

In a further embodiment of the aforementioned embodiments of Formula (I), X is $C(R_7)$; Y is N; and Z is N. In a further embodiment of the aforementioned embodiments of Formula (I), X is C(H); Y is N; and Z is N. In a further embodiment of the aforementioned embodiments of Formula (I), X is $C(R_7)$; Y is $C(R_7)$; and Z is N. In a further embodiment of the aforementioned embodiments of Formula (I), X is C(H); Y is C(H); and Z is N. In a further embodiment of the aforementioned embodiments of Formula (I), X is $C(R_7)$; Y is N; and Z is $C(R_7)$. In a further embodiment of the aforementioned embodiments of Formula (I), X is C(H); Y is N; and Z is C(H). In a further embodiment of the aforementioned embodiments of Formula (I), X is $C(R_7)$; Y is $C(R_7)$; and Z is $C(R_7)$. In a further embodiment of the aforementioned embodiments of Formula (I), X is C(H); Y is C(H); and Z is C(H).

In another embodiment is a compound of Formula (IA):

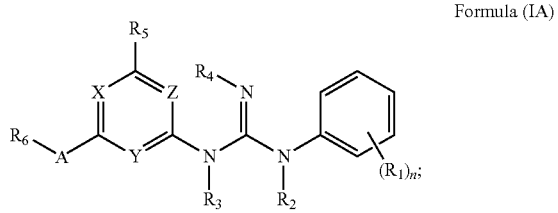

Formula (IA)

wherein:
A is a bond, O, $CH_2$, or $N(R_{10})$;
X, Y, and Z are each independently N, or $C(R_7)$;
each $R_1$ is independently halogen, —CN, —$NO_2$, —OH, —$OCF_3$, —$OCH_2F$, —$OCF_2H$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;
$R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H; or two of $R_2$, $R_3$, and $R_4$ are taken together to form a 5- or 6-membered heterocyclic ring;
$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —$(C(R_{14})(R_{15}))_mR_{21}$, —$(C(R_{14})(R_{15}))_mN(R_{11})(R_{12})$, or

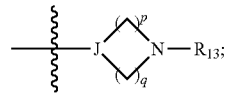

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;
J is C(H), or N;
$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;
each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;
$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)NR_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{22}$ is independently H, or substituted or unsubstituted $C_1$-$C_6$alkyl;
$R_{23}$ is substituted or unsubstituted $C_1$-$C_6$alkyl;
each $R_8$ is independently H, or substituted or unsubstituted $C_1$-$C_6$alkyl;
$R_9$ is substituted or unsubstituted $C_1$-$C_6$alkyl;
$R_{10}$ is H, or $C_1$-$C_4$alkyl;
m is 2-6;
n is 0-5;
p is 1-3;
q is 1-3; or
a pharmaceutically acceptable salt, solvate, or prodrug thereof.

In another embodiment is a compound of Formula (IA) wherein A is O, $CH_2$, or $N(R_{10})$. In another embodiment is a compound of Formula (IA) wherein A is O, $CH_2$, or N(H). In another embodiment is a compound of Formula (IA) wherein A is O. In another embodiment is a compound of Formula (IA) wherein A is $CH_2$. In another embodiment is a compound of Formula (IA) wherein A is $N(R_{10})$. In another embodiment is a compound of Formula (IA) wherein A is N(H). In another embodiment is a compound of Formula (IA) wherein A is N(CH$_3$). In another embodiment is a compound of Formula (IA) wherein A is a bond.

In another embodiment is a compound of Formula (IA) wherein R$_6$ is substituted or unsubstituted C$_3$-C$_8$cycloalkyl. In another embodiment is a compound of Formula (IA) wherein R$_6$ is substituted or unsubstituted cyclopropyl. In another embodiment is a compound of Formula (IA) wherein R$_6$ is substituted or unsubstituted cyclobutyl. In another embodiment is a compound of Formula (IA) wherein R$_6$ is substituted or unsubstituted cyclopentyl. In another embodiment is a compound of Formula (IA) wherein R$_6$ is substituted or unsubstituted cyclohexyl.

In another embodiment is a compound of Formula (IA) wherein R$_6$ is substituted or unsubstituted C$_2$-C$_7$heteroaryl. In another embodiment is a compound of Formula (IA) wherein R$_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IA) wherein R$_6$ is substituted or unsubstituted pyridyl. In another embodiment is a compound of Formula (IA) wherein R$_6$ is substituted pyridyl. In another embodiment is a compound of Formula (IA) wherein R$_6$ is unsubstituted pyridyl.

In another embodiment is a compound of Formula (IA) wherein R$_6$ is —(C(R$_{14}$)(R$_{15}$))$_m$R$_{21}$. In another embodiment is a compound of Formula (IA) wherein R$_6$ is —(C(R$_{14}$)(R$_{15}$))$_m$R$_{21}$, and each R$_{14}$ and R$_{15}$ are H. In another embodiment is a compound of Formula (IA) wherein R$_6$ is —(C(R$_{14}$)(R$_{15}$))$_m$R$_{21}$, m is 2, and each R$_{14}$ and R$_{15}$ are H. In another embodiment is a compound of Formula (IA) wherein R$_6$ is —(CH$_2$)$_m$R$_{21}$, m is 2, and R$_{21}$ is substituted or unsubstituted C$_2$-C$_7$heterocycloalkyl. In another embodiment is a compound of Formula (IA) wherein R$_6$ is —(CH$_2$)$_m$R$_{21}$, m is 2, and R$_{21}$ is substituted or unsubstituted C$_3$-C$_8$cycloalkyl. In another embodiment is a compound of Formula (IA) wherein R$_6$ is —(CH$_2$)$_m$R$_{21}$, m is 2, and R$_{21}$ is substituted or unsubstituted C$_6$-C$_{10}$aryl. In another embodiment is a compound of Formula (IA) wherein R$_6$ is —(CH$_2$)$_m$R$_{21}$, m is 2, and R$_{21}$ is substituted or unsubstituted phenyl. In another embodiment is a compound of Formula (IA) wherein R$_6$ is —(CH$_2$)$_m$R$_{21}$, m is 2, and R$_{21}$ is substituted or unsubstituted C$_2$-C$_7$heteroaryl.

In another embodiment is a compound of Formula (IA) wherein R$_6$ is —(C(R$_{14}$)(R$_{15}$))$_m$R$_{21}$, m is 3, and each R$_{14}$ and R$_{15}$ are H. In another embodiment is a compound of Formula (IA) wherein R$_6$ is —(CH$_2$)$_m$R$_{21}$, m is 3, and R$_{21}$ is substituted or unsubstituted C$_2$-C$_7$heterocycloalkyl. In another embodiment is a compound of Formula (IA) wherein R$_6$ is —(CH$_2$)$_m$R$_{21}$, m is 3, and R$_{21}$ is substituted or unsubstituted C$_3$-C$_8$cycloalkyl. In another embodiment is a compound of Formula (IA) wherein R$_6$ is —(CH$_2$)$_m$R$_{21}$, m is 3, and R$_{21}$ is substituted or unsubstituted C$_6$-C$_{10}$aryl. In another embodiment is a compound of Formula (IA) wherein R$_6$ is —(CH$_2$)$_m$R$_{21}$, m is 3, and R$_{21}$ is substituted or unsubstituted phenyl. In another embodiment is a compound of Formula (IA) wherein R$_6$ is —(CH$_2$)$_m$R$_{21}$, m is 3, and R$_{21}$ is substituted or unsubstituted C$_2$-C$_7$heteroaryl.

In another embodiment is a compound of Formula (IA) wherein R$_6$ is —(C(R$_{14}$)(R$_{15}$))$_m$N(R$_{11}$)(R$_{12}$). In another embodiment is a compound of Formula (IA) wherein R$_6$ is —(C(R$_{14}$)(R$_{15}$))$_m$N(R$_{11}$)(R$_{12}$), m is 2, and each R$_{14}$ and R$_{15}$ are H. In another embodiment is a compound of Formula (IA) wherein R$_6$ is —(CH$_2$)$_m$N(R$_{11}$)(R$_{12}$), m is 2, and R$_{11}$ and R$_{12}$ are each H. In another embodiment is a compound of Formula (IA) wherein R$_6$ is —(CH$_2$)$_m$N(R$_{11}$)(R$_{12}$), m is 2, R$_{11}$ is substituted or unsubstituted C$_1$-C$_6$alkyl, and R$_{11}$ is H. In another embodiment is a compound of Formula (IA) wherein R$_6$ is —(CH$_2$)$_m$N(R$_{11}$)(R$_{12}$), m is 2, R$_{11}$ is CH$_3$, and R$_{12}$ is H. In another embodiment is a compound of Formula (IA) wherein R$_6$ is —(CH$_2$)$_m$N(R$_{11}$)(R$_{12}$), m is 2, R$_{11}$ is substituted or unsubstituted C$_1$-C$_6$alkyl, and R$_{12}$ is substituted or unsubstituted C$_1$-C$_6$alkyl. In another embodiment is a compound of Formula (IA) wherein R$_6$ is —(CH$_2$)$_m$N(R$_{11}$)(R$_{12}$), m is 2, R$_{11}$ is CH$_3$, and R$_{11}$ is CH$_3$. In another embodiment is a compound of Formula (IA) wherein R$_6$ is —(CH$_2$)$_m$N(R$_{11}$)(R$_{12}$), m is 2, and R$_{11}$ and R$_{12}$ are taken together to form a 5-, 6-, 7-, or 8-membered heterocyclic ring. In another embodiment is a compound of Formula (IA) wherein R$_6$ is —(CH$_2$)$_m$N(R$_{11}$)(R$_{12}$), m is 2, and R$_{11}$ and R$_{12}$ are taken together to form a 5-membered heterocyclic ring. In another embodiment is a compound of Formula (IA) wherein R$_6$ is —(CH$_2$)$_m$N(R$_{11}$)(R$_{12}$), m is 2, and R$_{11}$ and R$_{12}$ are taken together to form a 6-membered heterocyclic ring.

In another embodiment is a compound of Formula (IA) wherein R$_6$ is —(C(R$_{14}$)(R$_{15}$))$_m$N(R$_{11}$)(R$_{12}$). In another embodiment is a compound of Formula (IA) wherein R$_6$ is —(C(R$_{14}$)(R$_{15}$))$_m$N(R$_{11}$)(R$_{12}$), m is 3, and each R$_{14}$ and R$_{15}$ are H. In another embodiment is a compound of Formula (IA) wherein R$_6$ is —(CH$_2$)$_m$N(R$_{11}$)(R$_{12}$), m is 3, and R$_{11}$ and R$_{12}$ are each H. In another embodiment is a compound of Formula (IA) wherein R$_6$ is —(CH$_2$)$_m$N(R$_{11}$)(R$_{12}$), m is 3, R$_{11}$ is substituted or unsubstituted C$_1$-C$_6$alkyl, and R$_{12}$ is H. In another embodiment is a compound of Formula (IA) wherein R$_6$ is —(CH$_2$)$_m$N(R$_{11}$)(R$_{12}$), m is 3, R$_{11}$ is CH$_3$, and R$_{12}$ is H. In another embodiment is a compound of Formula (IA) wherein R$_6$ is —(CH$_2$)$_m$N(R$_{11}$)(R$_{12}$), m is 3, R$_{11}$ is substituted or unsubstituted C$_1$-C$_6$alkyl, and R$_{12}$ is substituted or unsubstituted C$_1$-C$_6$alkyl. In another embodiment is a compound of Formula (IA) wherein R$_6$ is —(CH$_2$)$_m$N(R$_{11}$)(R$_{12}$), m is 3, R$_{11}$ is CH$_3$, and R$_{12}$ is CH$_3$. In another embodiment is a compound of Formula (IA) wherein R$_6$ is —(CH$_2$)$_m$N(R$_{11}$)(R$_{12}$), m is 3, and R$_{11}$ and R$_{12}$ are taken together to form a 5-, 6-, 7-, or 8-membered heterocyclic ring. In another embodiment is a compound of Formula (IA) wherein R$_6$ is —(CH$_2$)$_m$N(R$_{11}$)(R$_{12}$), m is 3, and R$_{11}$ and R$_{12}$ are taken together to form a 5-membered heterocyclic ring. In another embodiment is a compound of Formula (IA) wherein R$_6$ is —(CH$_2$)$_m$N(R$_{11}$)(R$_{12}$), m is 3, and R$_{11}$ and R$_{12}$ are taken together to form a 6-membered heterocyclic ring.

In another embodiment is a compound of Formula (IA) wherein R$_6$ is substituted or unsubstituted C$_2$-C$_7$heterocycloalkyl. In another embodiment is a compound of Formula (IA) wherein R$_6$ is

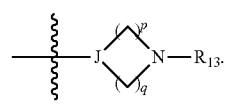

In another embodiment is a compound of Formula (IA) wherein R$_6$ is

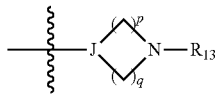

and J is C(H). In another embodiment is a compound of Formula (IA) wherein $R_6$ is

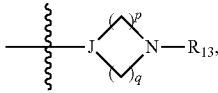

J is C(H), p is 1, and q is 1. In another embodiment is a compound of Formula (IA) wherein $R_6$ is

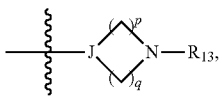

J is C(H), p is 2, and q is 1. In another embodiment is a compound of Formula (IA) wherein $R_6$ is

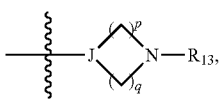

J is C(H), p is 3, and q is 1. In another embodiment is a compound of Formula (IA) wherein $R_6$ is

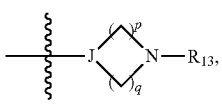

J is C(H), p is 2, and q is 2. In another embodiment is a compound of Formula (IA) wherein $R_6$ is

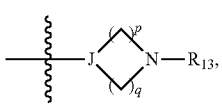

J is C(H), p is 1, q is 1, and $R_{13}$ is substituted or unsubstituted $C_1$-$C_6$alkyl. In another embodiment is a compound of Formula (IA) wherein $R_6$ is

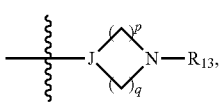

J is C(H), p is 2, q is 1, and $R_{13}$ is substituted or unsubstituted $C_1$-$C_6$alkyl. In another embodiment is a compound of Formula (IA) wherein $R_6$ is

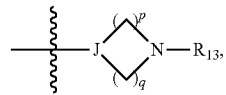

J is C(H), p is 3, q is 1, and $R_{13}$ is substituted or unsubstituted $C_1$-$C_6$alkyl. In another embodiment is a compound of Formula (IA) wherein $R_6$ is

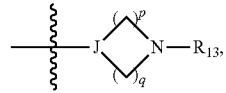

J is C(H), p is 2, q is 2, and $R_{13}$ is substituted or unsubstituted $C_1$-$C_6$alkyl.

In another embodiment is a compound of Formula (IA) wherein $R_6$ is

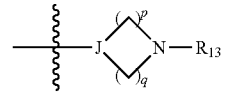

and J is N. In another embodiment is a compound of Formula (IA) wherein $R_6$ is

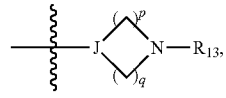

J is N, p is 2, and q is 2. In another embodiment is a compound of Formula (IA) wherein $R_6$ is

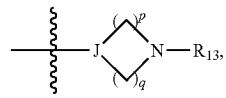

J is N, p is 2, q is 2, and $R_{13}$ is substituted or unsubstituted $C_1$-$C_6$alkyl.

In another embodiment is a compound of Formula (IA) wherein $R_5$ is halogen. In another embodiment is a compound of Formula (IA) wherein $R_5$ is —$CF_3$. In another embodiment is a compound of Formula (IA) wherein $R_5$ is substituted or unsubstituted $C_1$-$C_6$alkyl. In another embodiment is a compound of Formula (IA) wherein $R_5$ is —$CH_3$. In another embodiment is a compound of Formula (IA) wherein $R_5$ is —$CH_2CH_3$. In another embodiment is a compound of Formula (IA) wherein $R_5$ is substituted or unsubstituted $C_1$-$C_6$heteroalkyl. In another embodiment is a compound of Formula (IA) wherein $R_5$ is substituted or unsubstituted $C_2$-$C_7$heterocycloalkyl. In another embodiment is a compound of Formula (IA) wherein $R_5$ is substituted or unsubstituted $C_3$-$C_8$cycloalkyl. In another embodiment is a compound of Formula (IA) wherein $R_5$ is substituted or unsubstituted $C_6$-$C_{10}$aryl. In another embodiment is a compound of Formula (IA) wherein $R_5$ is substituted or unsubstituted $C_2$-$C_7$heteroaryl.

In another embodiment is a compound of Formula (IA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl, wherein at least one of $R_2$, $R_3$, and $R_4$ is not H. In another embodiment is a compound of Formula (IA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl, wherein at least two of $R_2$, $R_3$, and $R_4$ are not H. In another embodiment is a compound of Formula (IA) wherein $R_2$ is H; $R_3$ is $C_1$-$C_4$alkyl; and $R_4$ is H. In another embodiment is a compound of Formula (IA) wherein $R_2$ is H; $R_3$ is $CH_3$; and $R_4$ is H. In another embodiment is a compound of Formula (IA) wherein $R_2$ is H; $R_3$ is $C_1$-$C_4$alkyl; and $R_4$ is $C_1$-$C_4$alkyl. In another embodiment is a compound of Formula (IA) wherein $R_2$ is H; $R_3$ is $CH_3$; and $R_4$ is $CH_3$. In another embodiment is a compound of Formula (IA) wherein $R_2$ is H; $R_3$ is $C_1$-$C_4$alkyl; and $R_4$ is —CN. In another embodiment is a compound of Formula (IA) wherein $R_2$ is H; $R_3$ is $CH_3$; and $R_4$ is —CN. In another embodiment is a compound of Formula (IA) wherein $R_2$ is $C_1$-$C_4$alkyl; $R_3$ is $C_1$-$C_4$alkyl; and $R_4$ is H. In another embodiment is a compound of Formula (IA) wherein $R_2$ is $CH_3$; $R_3$ is $CH_3$; and $R_4$ is H. In another embodiment is a compound of Formula (IA) wherein $R_2$ is $C_1$-$C_4$alkyl; $R_3$ is H; and $R_4$ is H. In another embodiment is a compound of Formula (IA) wherein $R_2$ is $CH_3$; $R_3$ is H; and $R_4$ is H. In another embodiment is a compound of Formula (IA) wherein $R_2$ is $C_1$-$C_4$alkyl; $R_3$ is H; and $R_4$ is $C_1$-$C_4$alkyl. In another embodiment is a compound of Formula (IA) wherein $R_2$ is $CH_3$; $R_3$ is H; and $R_4$ is $CH_3$. In another embodiment is a compound of Formula (IA) wherein $R_2$ is $C_1$-$C_4$alkyl; $R_3$ is H; and $R_4$ is —CN. In another embodiment is a compound of Formula (IA) wherein $R_2$ is $CH_3$; $R_3$ is H; and $R_4$ is —CN. In another embodiment is a compound of Formula (IA) wherein $R_2$ is $C_3$-$C_6$cycloalkyl; $R_3$ is H; and $R_4$ is H. In another embodiment is a compound of Formula (IA) wherein $R_2$ is cyclopropyl; $R_3$ is H; and $R_4$ is H. In another embodiment is a compound of Formula (IA) wherein $R_2$ is cyclopentyl; $R_3$ is H; and $R_4$ is H. In another embodiment is a compound of Formula (IA) wherein $R_2$ is $C_3$-$C_6$cycloalkyl; $R_3$ is H; and $R_4$ is $CH_3$. In another embodiment is a compound of Formula (IA) wherein $R_2$ is cyclopropyl; $R_3$ is H; and $R_4$ is $CH_3$. In another embodiment is a compound of Formula (IA) wherein $R_2$ is cyclopentyl; $R_3$ is H; and $R_4$ is $CH_3$. In another embodiment is a compound of Formula (IA) wherein $R_2$ is $C_3$-$C_6$cycloalkyl; $R_3$ is H; and $R_4$ is —CN. In another embodiment is a compound of Formula (IA) wherein $R_2$ is cyclopropyl; $R_3$ is H; and $R_4$ is —CN. In another embodiment is a compound of Formula (IA) wherein $R_2$ is cyclopentyl; $R_3$ is H; and $R_4$ is —CN.

In another embodiment is a compound of Formula (IA) wherein $R_2$ and $R_3$ are taken together to form a 5- or 6-membered heterocyclic ring. In another embodiment is a compound of Formula (IA) wherein $R_2$ and $R_3$ are taken together to form a 5- or 6-membered heterocyclic ring; and $R_4$ is H. In another embodiment is a compound of Formula (IA) wherein $R_2$ and $R_3$ are taken together to form a 5-membered heterocyclic ring; and $R_4$ is H. In another embodiment is a compound of Formula (IA) wherein $R_2$ and $R_3$ are taken together to form 6-membered heterocyclic ring; and $R_4$ is H.

In another embodiment is a compound of Formula (IA) wherein each $R_1$ is independently halogen, —CN, —$NO_2$, —OH, —$OCF_3$, —$OCH_2F$, —$OCF_2H$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IA) wherein each $R_1$ is independently halogen, —CN, —OH, substituted or unsubstituted $C_1$-$C_6$alkyl, or substituted or unsubstituted $C_1$-$C_6$alkoxy. In another embodiment is a compound of Formula (IA) wherein each $R_1$ is independently halogen, —CN, —$OCF_3$, —$OCH_2F$, —$OCF_2H$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy. In another embodiment is a compound of Formula (IA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy, and n is 3. In another embodiment is a compound of Formula (IA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy, and n is 2. In another embodiment is a compound of Formula (IA) wherein n is 3, and each $R_1$ is independently halogen. In another embodiment is a compound of Formula (IA) wherein n is 2, and each $R_1$ is independently halogen. In another embodiment is a compound of Formula (IA) wherein n is 2, and each $R_1$ is independently F or Cl. In another embodiment is a compound of Formula (IA) wherein n is 2, and each $R_1$ is F. In another embodiment is a compound of Formula (IA) wherein n is 2, and each $R_1$ is independently Cl. In another embodiment is a compound of Formula (IA) wherein n is 1, and $R_1$ is halogen. In another embodiment is a compound of Formula (IA) wherein n is 1, and $R_1$ is F. In another embodiment is a compound of Formula (IA) wherein n is 1, and $R_1$ is Cl. In another embodiment is a compound of Formula (IA) wherein n is 1, and $R_1$ is substituted or unsubstituted $C_1$-$C_6$alkyl. In another embodiment is a compound of Formula (IA) wherein n is 1, and $R_1$ is $CH_3$. In another embodiment is a compound of Formula (IA) wherein n is 1, and $R_1$ is substituted or unsubstituted $C_1$-$C_6$alkoxy. In another embodiment is a compound of Formula (IA) wherein n is 1, and $R_1$ is —$OCH_3$. In another embodiment is a compound of Formula (IA) wherein n is 1, and $R_1$ is —$OCF_3$. In another embodiment is a compound of Formula (IA) wherein n is 1, and $R_1$ is —$OCF_2H$.

In a further embodiment of the aforementioned embodiments of Formula (IA), X is $C(R_7)$; Y is N; and Z is N. In a further embodiment of the aforementioned embodiments of Formula (IA), X is C(H); Y is N; and Z is N. In a further embodiment of the aforementioned embodiments of Formula (IA), X is $C(R_7)$; Y is $C(R_7)$; and Z is N. In a further embodiment of the aforementioned embodiments of Formula (IA), X is C(H); Y is C(H); and Z is N. In a further embodiment of the aforementioned embodiments of Formula (IA), X is $C(R_7)$; Y is N; and Z is $C(R_7)$. In a further embodiment of the aforementioned embodiments of Formula (IA), X is C(H); Y is N; and Z is C(H). In a further embodiment of the aforementioned embodiments of Formula (IA), X is $C(R_7)$; Y is $C(R_7)$; and Z is $C(R_7)$. In a further embodiment of the aforementioned embodiments of Formula (IA), X is C(H); Y is C(H); and Z is C(H).

In another embodiment, described herein is a compound of Formula (IB):

Formula (IB)

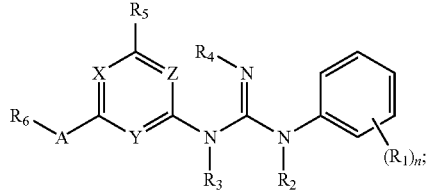

wherein:

A is O;

X, Y, and Z are each independently N, or C($R_7$);

each $R_1$ is independently halogen, —CN, —$NO_2$, —OH, —$OCF_3$, —$OCH_2F$, —$OCF_2H$, —$CF_3$, —$SR_8$, —N($R_8$)S(=O)$_2R_9$, —S(=O)$_2$N($R_8$)$_2$, —S(=O)$R_9$, —S(=O)$_2R_9$, —C(=O)$R_9$, —$CO_2R_8$, —N($R_8$)$_2$, —C(=O)N($R_8$)$_2$, —N($R_8$)C(=O)$R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;

$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —C($R_{14}$)($R_{15}$))$_mR_{21}$, —(C($R_{14}$)($R_{15}$))$_m$N($R_{11}$)($R_{12}$), or

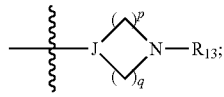

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H);

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;

each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —$NO_2$, —OH, —$OCF_3$, —$OCH_2F$, —$OCF_2H$, —$CF_3$, —$SR_{22}$, —N($R_{22}$)S(=O)$_2R_{23}$, —S(=O)$_2$N($R_{22}$)$_2$, —S(=O)$R_{23}$, —S(=O)$_2R_{23}$, —C(=O)$R_{23}$, —$CO_2R_{22}$, —C(=O)N($R_{22}$)$_2$, —N($R_{22}$)C(=O)$R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

m is 2-6;

n is 0-5;

p is 1-3;

q is 1-3; or a pharmaceutically acceptable salt, solvate, or prodrug thereof.

In another embodiment is a compound of Formula (IB) wherein $R_6$ is substituted or unsubstituted $C_3$-$C_8$cycloalkyl. In another embodiment is a compound of Formula (IB) wherein $R_6$ is substituted or unsubstituted cyclopropyl. In another embodiment is a compound of Formula (IB) wherein $R_6$ is substituted or unsubstituted cyclobutyl. In another embodiment is a compound of Formula (IB) wherein $R_6$ is substituted or unsubstituted cyclopentyl. In another embodiment is a compound of Formula (IB) wherein $R_6$ is substituted or unsubstituted cyclohexyl.

In another embodiment is a compound of Formula (IB) wherein $R_6$ is substituted or unsubstituted $C_2$-$C_7$heteroaryl. In another embodiment is a compound of Formula (IB) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IB) wherein $R_6$ is substituted or unsubstituted pyridyl. In another embodiment is a compound of Formula (IB) wherein $R_6$ is substituted pyridyl. In another embodiment is a compound of Formula (IB) wherein $R_6$ is unsubstituted pyridyl.

In another embodiment is a compound of Formula (IB) wherein $R_6$ is $-C(R_{14})(R_{15}))_mR_{21}$. In another embodiment is a compound of Formula (IB) wherein $R_6$ is $-(C(R_{14})(R_{15}))_mR_{21}$, and each $R_{14}$ and $R_{15}$ are H. In another embodiment is a compound of Formula (IB) wherein $R_6$ is $-(C(R_{14})(R_{15}))_mR_{21}$, m is 2, and each $R_{14}$ and $R_{15}$ are H. In another embodiment is a compound of Formula (IB) wherein $R_6$ is $-(CH_2)_mR_{21}$, m is 2, and $R_{21}$ is substituted or unsubstituted $C_2$-$C_7$heterocycloalkyl. In another embodiment is a compound of Formula (IB) wherein $R_6$ is $-(CH_2)_mR_{21}$, m is 2, and $R_{21}$ is substituted or unsubstituted $C_3$-$C_8$cycloalkyl. In another embodiment is a compound of Formula (IB) wherein $R_6$ is $-(CH_2)_mR_{21}$, m is 2, and $R_{21}$ is substituted or unsubstituted $C_6$-$C_{10}$aryl. In another embodiment is a compound of Formula (IB) wherein $R_6$ is $-(CH_2)_mR_{21}$, m is 2, and $R_{21}$ is substituted or unsubstituted phenyl. In another embodiment is a compound of Formula (IB) wherein $R_6$ is $-(CH_2)_mR_{21}$, m is 2, and $R_{21}$ is substituted or unsubstituted $C_2$-$C_7$heteroaryl.

In another embodiment is a compound of Formula (IB) wherein $R_6$ is $-(C(R_{14})(R_{15}))_mR_{21}$, m is 3, and each $R_{14}$ and $R_{15}$ are H. In another embodiment is a compound of Formula (IB) wherein $R_6$ is $-(CH_2)_mR_{21}$, m is 3, and $R_{21}$ is substituted or unsubstituted $C_2$-$C_7$heterocycloalkyl. In another embodiment is a compound of Formula (IB) wherein $R_6$ is $-(CH_2)_mR_{21}$, m is 3, and $R_{21}$ is substituted or unsubstituted $C_3$-$C_8$cycloalkyl. In another embodiment is a compound of Formula (IB) wherein $R_6$ is $-(CH_2)_mR_{21}$, m is 3, and $R_{21}$ is substituted or unsubstituted $C_6$-$C_{10}$aryl. In another embodiment is a compound of Formula (IB) wherein $R_6$ is $-(CH_2)_mR_{21}$, m is 3, and $R_{21}$ is substituted or unsubstituted phenyl. In another embodiment is a compound of Formula (IB) wherein $R_6$ is $-(CH_2)_mR_{21}$, m is 3, and $R_{21}$ is substituted or unsubstituted $C_2$-$C_7$heteroaryl.

In another embodiment is a compound of Formula (IB) wherein $R_6$ is $-(C(R_{14})(R_{15}))_mN(R_{11})(R_{12})$. In another embodiment is a compound of Formula (IB) wherein $R_6$ is $-(C(R_{14})(R_{15}))_mN(R_{11})(R_{12})$, m is 2, and each $R_{14}$ and $R_{15}$ are H. In another embodiment is a compound of Formula (TB) wherein $R_6$ is $-(CH_2)_mN(R_{11})(R_{12})$, m is 2, and $R_{11}$ and $R_{12}$ are each H. In another embodiment is a compound of Formula (TB) wherein $R_6$ is $-(CH_2)_mN(R_{11})(R_{12})$, m is 2, $R_{11}$ is substituted or unsubstituted $C_1$-$C_6$alkyl, and $R_{12}$ is H. In another embodiment is a compound of Formula (IB) wherein $R_6$ is $-(CH_2)_mN(R_{11})(R_{12})$, m is 2, $R_{11}$ is CH$_3$, and $R_{12}$ is H. In another embodiment is a compound of Formula (TB) wherein $R_6$ is $-(CH_2)_mN(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (TB) wherein $R_6$ is $-(CH_2)_mN(R_{11})(R_{12})$, m is 2, $R_{11}$ is CH$_3$, and $R_{12}$ is CH$_3$. In another embodiment is a compound of Formula (IB) wherein $R_6$ is $-(CH_2)_mN(R_{11})(R_{12})$, m is 2, and $R_{11}$ and $R_{12}$ are taken together to form a 5-, 6-, 7-, or 8-membered heterocyclic ring. In another embodiment is a compound of Formula (IB) wherein $R_6$ is $-(CH_2)_mN(R_{11})(R_{12})$, m is 2, and $R_{11}$ and $R_{12}$ are taken together to form a 5-membered heterocyclic ring. In another embodiment is a compound of Formula (IB) wherein $R_6$ is $-(CH_2)_mN(R_{11})(R_{12})$, m is 2, and $R_{11}$ and $R_{12}$ are taken together to form a 6-membered heterocyclic ring.

In another embodiment is a compound of Formula (IB) wherein $R_6$ is $-(C(R_{14})(R_{15}))_mN(R_{11})(R_{12})$—In another embodiment is a compound of Formula (IB) wherein $R_6$ is $-(C(R_{14})(R_{15}))_mN(R_{11})(R_{12})$, m is 3, and each $R_{14}$ and $R_{15}$ are H. In another embodiment is a compound of Formula (IB) wherein $R_6$ is $-(CH_2)_mN(R_{11})(R_{12})$, m is 3, and $R_{11}$ and $R_{12}$ are each H. In another embodiment is a compound of Formula (IB) wherein $R_6$ is $-(CH_2)_mN(R_{11})(R_{12})$, m is 3, $R_{11}$ is substituted or unsubstituted $C_1$-$C_6$alkyl, and $R_{12}$ is H. In another embodiment is a compound of Formula (IB) wherein $R_6$ is $-(CH_2)_mN(R_{11})(R_{12})$, m is 3, $R_{11}$ is CH$_3$, and $R_{12}$ is H. In another embodiment is a compound of Formula (IB) wherein $R_6$ is $-(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IB) wherein $R_6$ is $-(CH_2)_mN(R_{11})(R_{12})$, m is 3, $R_{11}$ is CH$_3$, and $R_{12}$ is CH$_3$. In another embodiment is a compound of Formula (IB) wherein $R_6$ is $-(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (IB) wherein $R_6$ is $-(CH_2)_mN(R_{11})(R_{12})$, m is 3, and $R_{11}$ and $R_{12}$ are taken together to form a 5-membered heterocyclic ring. In another embodiment is a compound of Formula (IB) wherein $R_6$ is $-(CH_2)_mN(R_{11})(R_{12})$, m is 3, and $R_{11}$ and $R_{12}$ are taken together to form a 6-membered heterocyclic ring.

In another embodiment is a compound of Formula (IB) wherein $R_6$ is substituted or unsubstituted $C_2$-$C_7$heterocycloalkyl. In another embodiment is a compound of Formula (IB) wherein $R_6$ is

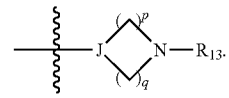

In another embodiment is a compound of Formula (IB) wherein $R_6$ is

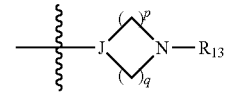

and J is C(H). In another embodiment is a compound of Formula (IB) wherein $R_6$ is

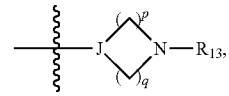

J is C(H), p is 1, and q is 1. In another embodiment is a compound of Formula (IB) wherein $R_6$ is

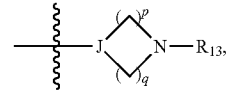

J is C(H), p is 2, and q is 1. In another embodiment is a compound of Formula (IB) wherein $R_6$ is

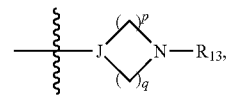

J is C(H), p is 3, and q is 1. In another embodiment is a compound of Formula (IB) wherein $R_6$ is

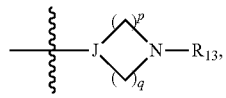

J is C(H), p is 2, and q is 2. In another embodiment is a compound of Formula (IB) wherein $R_6$ is

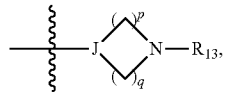

J is C(H), p is 1, q is 1, and $R_{13}$ is substituted or unsubstituted $C_1$-$C_6$alkyl. In another embodiment is a compound of Formula (IB) wherein $R_6$ is

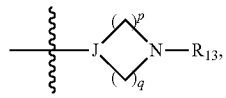

J is C(H), p is 2, q is 1, and $R_{13}$ is substituted or unsubstituted $C_1$-$C_6$alkyl. In another embodiment is a compound of Formula (IB) wherein $R_6$ is

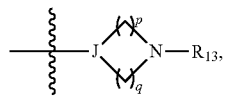

J is C(H), p is 3, q is 1, and $R_{13}$ is substituted or unsubstituted $C_1$-$C_6$alkyl. In another embodiment is a compound of Formula (IB) wherein $R_6$ is

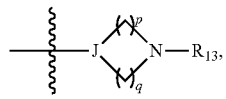

J is C(H), p is 2, q is 2, and $R_{13}$ is substituted or unsubstituted $C_1$-$C_6$alkyl.

In another embodiment is a compound of Formula (IB) wherein $R_5$ is halogen. In another embodiment is a compound of Formula (IB) wherein $R_5$ is —$CF_3$. In another embodiment is a compound of Formula (IB) wherein $R_5$ is substituted or unsubstituted $C_1$-$C_6$alkyl. In another embodiment is a compound of Formula (IB) wherein $R_5$ is —$CH_3$. In another embodiment is a compound of Formula (IB) wherein $R_5$ is —$CH_2CH_3$. In another embodiment is a compound of Formula (IB) wherein $R_5$ is substituted or unsubstituted $C_1$-$C_6$heteroalkyl. In another embodiment is a compound of Formula (IB) wherein $R_5$ is substituted or unsubstituted $C_2$-$C_7$heterocycloalkyl. In another embodiment is a compound of Formula (IB) wherein $R_5$ is substituted or unsubstituted $C_3$-$C_8$cycloalkyl. In another embodiment is a compound of Formula (IB) wherein $R_5$ is substituted or unsubstituted $C_6$-$C_{10}$aryl. In another embodiment is a compound of Formula (IB) wherein $R_5$ is substituted or unsubstituted $C_2$-$C_7$heteroaryl.

In another embodiment is a compound of Formula (IB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (IB) wherein $R_2$, $R_3$, and $R_4$ are each H.

In another embodiment is a compound of Formula (IB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (IB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (IB) wherein $R_2$ is H; $R_3$ is $C_1$-$C_4$alkyl; and $R_4$ is H. In another embodiment is a compound of Formula (IB) wherein $R_2$ is H; $R_3$ is $CH_3$; and $R_4$ is H. In another embodiment is a compound of Formula (IB) wherein $R_2$ is H; $R_3$ is $C_1$-$C_4$alkyl; and $R_4$ is $C_1$-$C_4$alkyl. In another embodiment is a compound of Formula (IB) wherein $R_2$ is H; $R_3$ is $CH_3$; and $R_4$ is $CH_3$. In another embodiment is a compound of Formula (TB) wherein $R_2$ is H; $R_3$ is $C_1$-$C_4$alkyl; and $R_4$ is —CN. In another embodiment is a compound of Formula (TB) wherein $R_2$ is H; $R_3$ is $CH_3$; and $R_4$ is —CN. In another embodiment is a compound of Formula (TB) wherein $R_2$ is $C_1$-$C_4$alkyl; $R_3$ is $C_1$-$C_4$alkyl; and $R_4$ is H. In another embodiment is a compound of Formula (TB) wherein $R_2$ is $CH_3$; $R_3$ is $CH_3$; and $R_4$ is H. In another embodiment is a compound of Formula (TB) wherein $R_2$ is $C_1$-$C_4$alkyl; $R_3$ is H; and $R_4$ is H. In another embodiment is a compound of Formula (TB) wherein $R_2$ is $CH_3$; $R_3$ is H; and $R_4$ is H. In another embodiment is a compound of Formula (TB) wherein $R_2$ is $C_1$-$C_4$alkyl; $R_3$ is H; and $R_4$ is $C_1$-$C_4$alkyl. In another embodiment is a compound of Formula (IB) wherein $R_2$ is $CH_3$; $R_3$ is H; and $R_4$ is $CH_3$. In another embodiment is a compound of Formula (IB) wherein $R_2$ is $C_1$-$C_4$alkyl; $R_3$ is H; and $R_4$ is —CN. In another embodiment is a compound of Formula (IB) wherein $R_2$ is $CH_3$; $R_3$ is H; and $R_4$ is —CN. In another embodiment is a compound of Formula (IB) wherein $R_2$ is $C_3$-$C_6$cycloalkyl; $R_3$ is H; and $R_4$ is H. In another embodiment is a compound of Formula (IB) wherein $R_2$ is cyclopropyl; $R_3$ is H; and $R_4$ is H. In another embodiment is a compound of Formula (IB) wherein $R_2$ is cyclopentyl; $R_3$ is H; and $R_4$ is H. In another embodiment is a compound of Formula (IB) wherein $R_2$ is $C_3$-$C_6$cycloalkyl; $R_3$ is H; and $R_4$ is $CH_3$. In another embodiment is a compound of Formula (IB) wherein $R_2$ is cyclopropyl; $R_3$ is H; and $R_4$ is $CH_3$. In another embodiment is a compound of Formula (IB) wherein $R_2$ is cyclopentyl; $R_3$ is H; and $R_4$ is $CH_3$. In another embodiment is a compound of Formula (IB) wherein $R_2$ is $C_3$-$C_6$cycloalkyl; $R_3$ is H; and $R_4$ is —CN. In another embodiment is a compound of Formula (IB) wherein $R_2$ is cyclopropyl; $R_3$ is H; and $R_4$ is —CN. In another embodiment is a compound of Formula (IB) wherein $R_2$ is cyclopentyl; $R_3$ is H; and $R_4$ is —CN.

In another embodiment is a compound of Formula (IB) wherein $R_2$ and $R_3$ are taken together to form a 5- or 6-membered heterocyclic ring. In another embodiment is a compound of Formula (IB) wherein $R_2$ and $R_3$ are taken together to form a 5- or 6-membered heterocyclic ring; and $R_4$ is H. In another embodiment is a compound of Formula (IB) wherein $R_2$ and $R_3$ are taken together to form a 5-membered heterocyclic ring; and $R_4$ is H. In another embodiment is a compound of Formula (IB) wherein $R_2$ and $R_3$ are taken together to form 6-membered heterocyclic ring; and $R_4$ is H.

In another embodiment is a compound of Formula (IB) wherein each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IB) wherein each $R_1$ is independently halogen, —CN, —OH, —CF$_3$, substituted or unsubstituted $C_1$-$C_6$alkyl, or substituted or unsubstituted $C_1$-$C_6$alkoxy. In another embodiment is a compound of Formula (IB) wherein each $R_1$ is independently halogen, —CN, —OCF$_3$, —OCH$_2$F, —OCF$_2$H, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IB) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy. In another embodiment is a compound of Formula (IB) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 3. In another embodiment is a compound of Formula (IB) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 2. In another embodiment is a compound of Formula (IB) wherein n is 3, and each $R_1$ is independently halogen. In another embodiment is a compound of Formula (IB) wherein n is 2, and each $R_1$ is independently halogen. In another embodiment is a compound of Formula (IB) wherein n is 2, and each $R_1$ is independently F or Cl. In another embodiment is a compound of Formula (IB) wherein n is 2, and each $R_1$ is F. In another embodiment is a compound of Formula (IB) wherein n is 2, and each $R_1$ is independently Cl. In another embodiment is a compound of Formula (IB) wherein n is 2, and each $R_1$ is independently halogen or —CF$_3$. In another embodiment is a compound of Formula (IB) wherein n is 2, and each $R_1$ is independently F or —CF$_3$. In another embodiment is a compound of Formula (IB) wherein n is 2, and each $R_1$ is independently Cl or —CF$_3$. In another embodiment is a compound of Formula (IB) wherein n is 1, and $R_1$ is halogen. In another embodiment is a compound of Formula (IB) wherein n is 1, and $R_1$ is F. In another embodiment is a compound of Formula (IB) wherein n is 1, and $R_1$ is Cl. In another embodiment is a compound of Formula (IB) wherein n is 1, and $R_1$ is —CF$_3$. In another embodiment is a compound of Formula (IB) wherein n is 1, and $R_1$ is substituted or unsubstituted $C_1$-$C_6$alkyl. In another embodiment is a compound of Formula (IB) wherein n is 1, and $R_1$ is CH$_3$. In another embodiment is a compound of Formula (IB) wherein n is 1, and $R_1$ is substituted or unsubstituted $C_1$-$C_6$alkoxy. In another embodiment is a compound of Formula (IB) wherein n is 1, and $R_1$ is —OCH$_3$. In another embodiment is a compound of Formula (IB) wherein n is 1, and $R_1$ is —OCF$_3$. In another embodiment is a compound of Formula (IB) wherein n is 1, and $R_1$ is —OCF$_2$H.

In a further embodiment of the aforementioned embodiments of Formula (IB), X is C(R$_7$); Y is N; and Z is N. In a further embodiment of the aforementioned embodiments of Formula (IB), X is C(H); Y is N; and Z is N. In a further embodiment of the aforementioned embodiments of Formula (IB), X is C(R$_7$); Y is C(R$_7$); and Z is N. In a further embodiment of the aforementioned embodiments of Formula (IB), X is C(H); Y is C(H); and Z is N. In a further embodiment of the aforementioned embodiments of Formula (IB), X is C(R$_7$); Y is N; and Z is C(R$_7$). In a further embodiment of the aforementioned embodiments of Formula (IB), X is C(H); Y is N; and Z is C(H). In a further embodiment of the aforementioned embodiments of Formula (IB), X is C(R$_7$); Y is C(R$_7$); and Z is C(R$_7$). In a further embodiment of the aforementioned embodiments of Formula (IB), X is C(H); Y is C(H); and Z is C(H).

In another aspect, described herein is a compound of Formula (II):

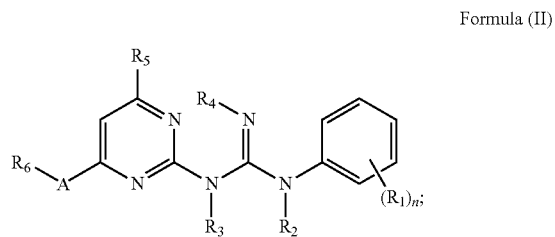

Formula (II)

wherein:

A is a bond, O, CH$_2$, or N(R$_{10}$);

each $R_1$ is independently halogen, —CN, —NO$_2$, —OH, —OCF$_3$, —OCH$_2$F, —OCF$_2$H, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;

$R_5$ is halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —(C(R$_{14}$)(R$_{15}$))$_m$R$_{21}$, —(C(R$_{14}$)(R$_{15}$))$_m$N(R$_{11}$)(R$_{12}$), or

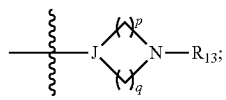

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl; each $R_7$ is independently H, halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —NO$_2$, —OH, —OCF$_3$, —OCH$_2$F, —OCF$_2$H, —CF$_3$, —SR$_{22}$, —N(R$_{22}$)S(═O)$_2$R$_{23}$, —S(═O)$_2$N(R$_{22}$)$_2$, —S(═O)R$_{23}$, —S(═O)$_2$R$_{23}$, —C(═O)R$_{23}$, —CO$_2$R$_{22}$, —C(═O)N(R$_{22}$)$_2$, —N(R$_{22}$)C(═O)R$_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In another embodiment is a compound of Formula (II) wherein A is O, CH$_2$, or N(R$_{10}$). In another embodiment is a compound of Formula (II) wherein A is O, CH$_2$, or N(H). In another embodiment is a compound of Formula (II) wherein A is O. In another embodiment is a compound of Formula (II) wherein A is CH$_2$. In another embodiment is a compound of Formula (II) wherein A is N(R$_{10}$). In another embodiment is a compound of Formula (II) wherein A is N(H). In another embodiment is a compound of Formula (II) wherein A is N(CH$_3$). In another embodiment is a compound of Formula (II) wherein A is a bond.

In another embodiment is a compound of Formula (II) wherein $R_6$ is substituted or unsubstituted $C_3$-$C_8$cycloalkyl. In another embodiment is a compound of Formula (II) wherein $R_6$ is substituted or unsubstituted cyclopropyl. In another embodiment is a compound of Formula (II) wherein $R_6$ is substituted or unsubstituted cyclobutyl. In another embodiment is a compound of Formula (II) wherein $R_6$ is substituted or unsubstituted cyclopentyl. In another embodiment is a compound of Formula (II) wherein $R_6$ is substituted or unsubstituted cyclohexyl.

In another embodiment is a compound of Formula (II) wherein $R_6$ is substituted or unsubstituted $C_2$-$C_7$heteroaryl. In another embodiment is a compound of Formula (II) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (II) wherein $R_6$ is substituted or unsubstituted pyridyl. In another embodiment is a compound of Formula (II) wherein $R_6$ is substituted pyridyl. In another embodiment is a compound of Formula (II) wherein $R_6$ is unsubstituted pyridyl.

In another embodiment is a compound of Formula (II) wherein $R_6$ is —(C(R$_{14}$)(R$_{15}$))$_m$R$_{21}$. In another embodiment is a compound of Formula (II) wherein $R_6$ is —(C(R$_{14}$)(R$_{15}$))$_m$R$_{21}$, and each $R_{14}$ and $R_{15}$ are H. In another embodiment is a compound of Formula (II) wherein $R_6$ is —(C(R$_{14}$)(R$_{15}$))$_m$R$_{21}$, m is 2, and each $R_{14}$ and $R_{15}$ are H. In another embodiment is a compound of Formula (II) wherein $R_6$ is —(CH$_2$)$_m$R$_{21}$, m is 2, and $R_{21}$ is substituted or unsubstituted $C_2$-$C_7$heterocycloalkyl. In another embodiment is a compound of Formula (II) wherein $R_6$ is —(CH$_2$)$_m$R$_{21}$, m is 2, and $R_{21}$ is substituted or unsubstituted $C_3$-$C_8$cycloalkyl. In another embodiment is a compound of Formula (II) wherein $R_6$ is —(CH$_2$)$_m$R$_{21}$, m is 2, and $R_{21}$ is substituted or unsubstituted $C_6$-$C_{10}$aryl. In another embodiment is a compound of Formula (II) wherein $R_6$ is —(CH$_2$)$_m$R$_{21}$, m is 2, and $R_{21}$ is substituted or unsubstituted phenyl. In another embodiment is a compound of Formula (II) wherein $R_6$ is —(CH$_2$)$_m$R$_{21}$, m is 2, and $R_{21}$ is substituted or unsubstituted $C_2$-$C_7$heteroaryl.

In another embodiment is a compound of Formula (II) wherein $R_6$ is —(C(R$_{14}$)(R$_{15}$))$_m$R$_{21}$, m is 3, and each $R_{14}$ and $R_{15}$ are H. In another embodiment is a compound of Formula (II) wherein $R_6$ is —(CH$_2$)$_m$R$_{21}$, m is 3, and $R_{21}$ is substituted or unsubstituted $C_2$-$C_7$heterocycloalkyl. In another embodiment is a compound of Formula (II) wherein $R_6$ is —(CH$_2$)$_m$R$_{21}$, m is 3, and $R_{21}$ is substituted or unsubstituted $C_3$-$C_8$cycloalkyl. In another embodiment is a compound of Formula (II) wherein $R_6$ is —(CH$_2$)$_m$R$_{21}$, m is 3, and $R_{21}$ is substituted or unsubstituted $C_6$-$C_{10}$aryl. In another embodiment is a compound of Formula (II) wherein $R_6$ is —(CH$_2$)$_m$R$_{21}$, m is 3, and $R_{21}$ is substituted or unsubstituted phenyl. In another embodiment is a compound of Formula (II) wherein $R_6$ is —(CH$_2$)$_m$R$_{21}$, m is 3, and $R_{21}$ is substituted or unsubstituted $C_2$-$C_7$heteroaryl.

In another embodiment is a compound of Formula (II) wherein $R_6$ is —(C(R$_{14}$)(R$_{15}$))$_m$N(R$_{11}$)(R$_{12}$). In another embodiment is a compound of Formula (II) wherein $R_6$ is —(C(R$_{14}$)(R$_{15}$))$_m$N(R$_{11}$)(R$_{12}$), m is 2, and each $R_{14}$ and $R_{15}$ are H. In another embodiment is a compound of Formula (II) wherein $R_6$ is —(CH$_2$)$_m$N(R$_{11}$)(R$_{12}$), m is 2, and $R_{11}$ and $R_{12}$ are each H. In another embodiment is a compound of Formula (II) wherein $R_6$ is —$(CH_2)_mN(R_{11})(R_{12})$, m is 2, $R_{11}$ is substituted or unsubstituted $C_1$-$C_6$alkyl, and $R_{12}$ is H. In another embodiment is a compound of Formula (II) wherein $R_6$ is —$(CH_2)_mN(R_{11})(R_{12})$, m is 2, $R_{11}$ is $CH_3$, and $R_{12}$ is H. In another embodiment is a compound of Formula (II) wherein $R_6$ is —$(CH_2)_mN(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (II) wherein $R_6$ is —$(CH_2)_mN(R_{11})(R_{12})$, m is 2, $R_{11}$ is $CH_3$, and $R_{12}$ is $CH_3$. In another embodiment is a compound of Formula (II) wherein $R_6$ is —$(CH_2)_mN(R_{11})(R_{12})$, m is 2, and $R_{11}$ and $R_{12}$ are taken together to form a 5-, 6-, 7-, or 8-membered heterocyclic ring. In another embodiment is a compound of Formula (II) wherein $R_6$ is —$(CH_2)_mN(R_{11})(R_{12})$, m is 2, and $R_{11}$ and $R_{12}$ are taken together to form a 5-membered heterocyclic ring. In another embodiment is a compound of Formula (II) wherein $R_6$ is —$(CH_2)_mN(R_{11})(R_{12})$, m is 2, and $R_{11}$ and $R_{12}$ are taken together to form a 6-membered heterocyclic ring.

In another embodiment is a compound of Formula (II) wherein $R_6$ is —$(C(R_{14})(R_{15}))_mN(R_{11})(R_{12})$. In another embodiment is a compound of Formula (II) wherein $R_6$ is —$(C(R_{14})(R_{15}))_mN(R_{11})(R_{12})$, m is 3, and each $R_{14}$ and $R_{15}$ are H. In another embodiment is a compound of Formula (II) wherein $R_6$ is —$(CH_2)_mN(R_{11})(R_{12})$, m is 3, and $R_{11}$ and $R_{12}$ are each H. In another embodiment is a compound of Formula (II) wherein $R_6$ is —$(CH_2)_mN(R_{11})(R_{12})$, m is 3, $R_{11}$ is substituted or unsubstituted $C_1$-$C_6$alkyl, and $R_{12}$ is H. In another embodiment is a compound of Formula (II) wherein $R_6$ is —$(CH_2)_mN(R_{11})(R_{12})$, m is 3, $R_{11}$ is $CH_3$, and $R_{12}$ is H. In another embodiment is a compound of Formula (II) wherein $R_6$ is —$(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (II) wherein $R_6$ is —$(CH_2)_mN(R_{11})(R_{12})$, m is 3, $R_{11}$ is $CH_3$, and $R_{12}$ is $CH_3$. In another embodiment is a compound of Formula (II) wherein $R_6$ is —$(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (II) wherein $R_6$ is —$(CH_2)_mN(R_{11})(R_{12})$, m is 3, and $R_{11}$ and $R_{12}$ are taken together to form a 5-membered heterocyclic ring. In another embodiment is a compound of Formula (II) wherein $R_6$ is —$(CH_2)_mN(R_{11})(R_{12})$, m is 3, and $R_{11}$ and $R_{12}$ are taken together to form a 6-membered heterocyclic ring.

In another embodiment is a compound of Formula (II) wherein $R_6$ is substituted or unsubstituted $C_2$-$C_7$heterocycloalkyl. In another embodiment is a compound of Formula (II) wherein $R_6$ is

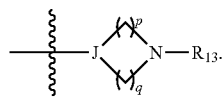

In another embodiment is a compound of Formula (II) wherein $R_6$ is

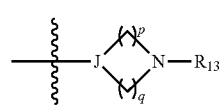

and J is C(H). In another embodiment is a compound of Formula (II) wherein $R_6$ is

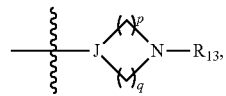

J is C(H), p is 1, and q is 1. In another embodiment is a compound of Formula (II) wherein $R_6$ is

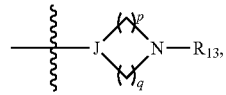

J is C(H), p is 2, and q is 1. In another embodiment is a compound of Formula (II) wherein $R_6$ is

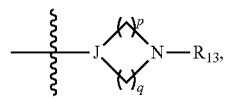

J is C(H), p is 3, and q is 1. In another embodiment is a compound of Formula (II) wherein $R_6$ is

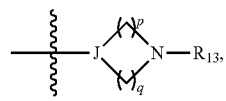

J is C(H), p is 2, and q is 2. In another embodiment is a compound of Formula (II) wherein $R_6$ is

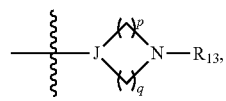

J is C(H), p is 1, q is 1, and $R_{13}$ is substituted or unsubstituted $C_1$-$C_6$alkyl. In another embodiment is a compound of Formula (II) wherein $R_6$ is

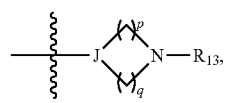

J is C(H), p is 2, q is 1, and $R_{13}$ is substituted or unsubstituted $C_1$-$C_6$alkyl. In another embodiment is a compound of Formula (II) wherein $R_6$ is

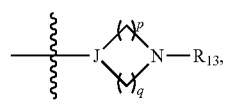

J is C(H), p is 3, q is 1, and $R_{13}$ is substituted or unsubstituted $C_1$-$C_6$alkyl. In another embodiment is a compound of Formula (II) wherein $R_6$ is

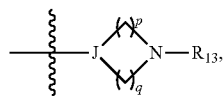

J is C(H), p is 2, q is 2, and $R_{13}$ is substituted or unsubstituted $C_1$-$C_6$alkyl.

In another embodiment is a compound of Formula (II) wherein $R_6$ is

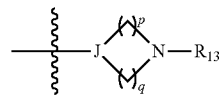

and J is N. In another embodiment is a compound of Formula (II) wherein $R_6$ is

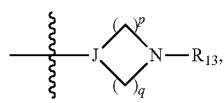

J is N, p is 2, and q is 2. In another embodiment is a compound of Formula (II) wherein $R_6$ is

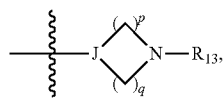

J is N, p is 2, q is 2, and $R_{13}$ is substituted or unsubstituted $C_1$-$C_6$alkyl.

In another embodiment is a compound of Formula (II) wherein $R_5$ is halogen. In another embodiment is a compound of Formula (II) wherein $R_5$ is —$CF_3$. In another embodiment is a compound of Formula (II) wherein $R_5$ is substituted or unsubstituted $C_1$-$C_6$alkyl. In another embodiment is a compound of Formula (II) wherein $R_5$ is —$CH_3$. In another embodiment is a compound of Formula (II) wherein $R_5$ is —$CH_2CH_3$. In another embodiment is a compound of Formula (II) wherein $R_5$ is substituted or unsubstituted $C_1$-$C_6$heteroalkyl. In another embodiment is a compound of Formula (II) wherein $R_5$ is substituted or unsubstituted $C_2$-$C_7$heterocycloalkyl. In another embodiment is a compound of Formula (II) wherein $R_5$ is substituted or unsubstituted $C_3$-$C_8$cycloalkyl. In another embodiment is a compound of Formula (II) wherein $R_5$ is substituted or unsubstituted $C_6$-$C_{10}$aryl. In another embodiment is a compound of Formula (II) wherein $R_5$ is substituted or unsubstituted $C_2$-$C_7$heteroaryl.

In another embodiment is a compound of Formula (II) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (II) wherein $R_2$, $R_3$, and $R_4$ are each H.

In another embodiment is a compound of Formula (II) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (II) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (II) wherein $R_2$ is H; $R_3$ is $C_1$-$C_4$alkyl; and $R_4$ is H. In another embodiment is a compound of Formula (II) wherein $R_2$ is H; $R_3$ is $CH_3$; and $R_4$ is H. In another embodiment is a compound of Formula (II) wherein $R_2$ is H; $R_3$ is $C_1$-$C_4$alkyl; and $R_4$ is $C_1$-$C_4$alkyl. In another embodiment is a compound of Formula (II) wherein $R_2$ is H; $R_3$ is $CH_3$; and $R_4$ is $CH_3$. In another embodiment is a compound of Formula (II) wherein $R_2$ is H; $R_3$ is $C_1$-$C_4$alkyl; and $R_4$ is —CN. In another embodiment is a compound of Formula (II) wherein $R_2$ is H; $R_3$ is $CH_3$; and $R_4$ is —CN. In another embodiment is a compound of Formula (II) wherein $R_2$ is $C_1$-$C_4$alkyl; $R_3$ is $C_1$-$C_4$alkyl; and $R_4$ is H. In another embodiment is a compound of Formula (II) wherein $R_2$ is $CH_3$; $R_3$ is $CH_3$; and $R_4$ is H. In another embodiment is a compound of Formula (II) wherein $R_2$ is $C_1$-$C_4$alkyl; $R_3$ is H; and $R_4$ is H. In another embodiment is a compound of Formula (II) wherein $R_2$ is $CH_3$; $R_3$ is H; and $R_4$ is H. In another embodiment is a compound of Formula (II) wherein $R_2$ is $C_1$-$C_4$alkyl; $R_3$ is H; and $R_4$ is $C_1$-$C_4$alkyl. In another embodiment is a compound of Formula (II) wherein $R_2$ is $CH_3$; $R_3$ is H; and $R_4$ is $CH_3$. In another embodiment is a compound of Formula (II) wherein $R_2$ is $C_1$-$C_4$alkyl; $R_3$ is H; and $R_4$ is —CN. In another embodiment is a compound of Formula (II) wherein $R_2$ is $CH_3$; $R_3$ is H; and $R_4$ is —CN. In another embodiment is a compound of Formula (II) wherein $R_2$ is $C_3$-$C_6$cycloalkyl; $R_3$ is H; and $R_4$ is H. In another embodiment is a compound of Formula (II) wherein $R_2$ is cyclopropyl; $R_3$ is H; and $R_4$ is H. In another embodiment is a compound of Formula (II) wherein $R_2$ is cyclopentyl; $R_3$ is H; and $R_4$ is H. In another embodiment is a compound of Formula (II) wherein $R_2$ is $C_3$-$C_6$cycloalkyl; $R_3$ is H; and $R_4$ is $CH_3$. In another embodiment is a compound of Formula (II) wherein $R_2$ is cyclopropyl; $R_3$ is H; and $R_4$ is $CH_3$. In another embodiment is a compound of Formula (II) wherein $R_2$ is cyclopentyl; $R_3$ is H; and $R_4$ is $CH_3$. In another embodiment is a compound of Formula (II) wherein $R_2$ is $C_3$-$C_6$cycloalkyl; $R_3$ is H; and $R_4$ is —CN. In another embodiment is a compound of Formula (II) wherein $R_2$ is cyclopropyl; $R_3$ is H; and $R_4$ is —CN. In another embodiment is a compound of Formula (II) wherein $R_2$ is cyclopentyl; $R_3$ is H; and $R_4$ is —CN.

In another embodiment is a compound of Formula (II) wherein $R_2$ and $R_3$ are taken together to form a 5- or 6-membered heterocyclic ring. In another embodiment is a compound of Formula (II) wherein $R_2$ and $R_3$ are taken together to form a 5- or 6-membered heterocyclic ring; and $R_4$ is H. In another embodiment is a compound of Formula (II) wherein $R_2$ and $R_3$ are taken together to form a 5-membered heterocyclic ring; and $R_4$ is H. In another embodiment is a compound of Formula (II) wherein $R_2$ and $R_3$ are taken together to form 6-membered heterocyclic ring; and $R_4$ is H.

In another embodiment is a compound of Formula (II) wherein each $R_1$ is independently halogen, —CN, —$NO_2$, —OH, —$OCF_3$, —$OCH_2F$, —$OCF_2H$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (II) wherein each $R_1$ is independently halogen, —CN, —OH, substituted or unsubstituted $C_1$-$C_6$alkyl, or substituted or unsubstituted $C_1$-$C_6$alkoxy. In another embodiment is a compound of Formula (II) wherein each $R_1$ is independently halogen, —CN, —OCF$_3$, —OCH$_2$F, —OCF$_2$H, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (II) wherein each $R_1$ is independently halogen, —CN, —OCF$_3$, —OCH$_2$F, —OCF$_2$H, substituted or unsubstituted $C_1$-$C_6$alkyl, or substituted or unsubstituted $C_1$-$C_6$alkoxy. In another embodiment is a compound of Formula (II) wherein each $R_1$ is independently halogen, —CN, —OCF$_3$, —OCH$_2$F, —OCF$_2$H, substituted or unsubstituted $C_1$-$C_6$alkyl, or substituted or unsubstituted $C_1$-$C_6$alkoxy, and n is 3. In another embodiment is a compound of Formula (II) wherein each $R_1$ is independently halogen, —CN, —OCF$_3$, —OCH$_2$F, —OCF$_2$H, substituted or unsubstituted $C_1$-$C_6$alkyl, or substituted or unsubstituted $C_1$-$C_6$alkoxy, and n is 2. In another embodiment is a compound of Formula (II) wherein n is 3, and each $R_1$ is independently halogen. In another embodiment is a compound of Formula (II) wherein n is 2, and each $R_1$ is independently halogen. In another embodiment is a compound of Formula (II) wherein n is 2, and each $R_1$ is independently F or Cl. In another embodiment is a compound of Formula (II) wherein n is 2, and each $R_1$ is F. In another embodiment is a compound of Formula (II) wherein n is 2, and each $R_1$ is independently Cl. In another embodiment is a compound of Formula (II) wherein n is 1, and $R_1$ is halogen. In another embodiment is a compound of Formula (II) wherein n is 1, and $R_1$ is F. In another embodiment is a compound of Formula (II) wherein n is 1, and $R_1$ is Cl. In another embodiment is a compound of Formula (II) wherein n is 1, and $R_1$ is substituted or unsubstituted $C_1$-$C_6$alkyl. In another embodiment is a compound of Formula (II) wherein n is 1, and $R_1$ is CH$_3$. In another embodiment is a compound of Formula (II) wherein n is 1, and $R_1$ is substituted or unsubstituted $C_1$-$C_6$alkoxy. In another embodiment is a compound of Formula (II) wherein n is 1, and $R_1$ is —OCH$_3$. In another embodiment is a compound of Formula (II) wherein n is 1, and $R_1$ is —OCF$_3$. In another embodiment is a compound of Formula (II) wherein n is 1, and $R_1$ is —OCF$_2$H.

In another embodiment, described herein is a compound of Formula (IIA):

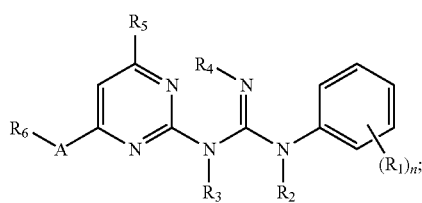

Formula (IIA)

wherein:

A is a bond, O, CH$_2$, or N(R$_{10}$);

each $R_1$ is independently halogen, —CN, —NO$_2$, —OH, —OCF$_3$, —OCH$_2$F, —OCF$_2$H, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H; or two of $R_2$, $R_3$, and $R_4$ are taken together to form a 5- or 6-membered heterocyclic ring;

$R_5$ is halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —(C(R$_{14}$)(R$_{15}$))$_m$R$_{21}$, —(C(R$_{14}$)(R$_{15}$))$_m$N(R$_{11}$)(R$_{12}$), or

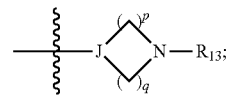

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkylC$_6$-$C_{10}$aryl, or substituted or unsubstituted —$C_1$-$C_4$alkylC$_2$-$C_7$heteroaryl;

each $R_7$ is independently H, halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —NO$_2$, —OH, —OCF$_3$, —OCH$_2$F, —OCF$_2$H, —CF$_3$, —SR$_{22}$, —N(R$_{22}$)S(=O)$_2$R$_{23}$, —S(=O)$_2$N(R$_{22}$)$_2$, —S(=O)R$_{23}$, —S(=O)$_2$R$_{23}$, —C(=O)R$_{23}$, —CO$_2$R$_{22}$, —C(=O)NR$_{22}$)$_2$, —N(R$_{22}$)C(=O)R$_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In another embodiment is a compound of Formula (IIA) wherein A is O, $CH_2$, or $N(R_{10})$. In another embodiment is a compound of Formula (IIA) wherein A is O, $CH_2$, or N(H). In another embodiment is a compound of Formula (IIA) wherein A is O. In another embodiment is a compound of Formula (IIA) wherein A is $CH_2$. In another embodiment is a compound of Formula (IIA) wherein A is $N(R_{10})$. In another embodiment is a compound of Formula (IIA) wherein A is N(H). In another embodiment is a compound of Formula (IIA) wherein A is $N(CH_3)$. In another embodiment is a compound of Formula (IIA) wherein A is a bond.

In another embodiment is a compound of Formula (IIA) wherein $R_6$ is substituted or unsubstituted $C_3$-$C_8$cycloalkyl. In another embodiment is a compound of Formula (IIA) wherein $R_6$ is substituted or unsubstituted cyclopropyl. In another embodiment is a compound of Formula (IIA) wherein $R_6$ is substituted or unsubstituted cyclobutyl. In another embodiment is a compound of Formula (IIA) wherein $R_6$ is substituted or unsubstituted cyclopentyl. In another embodiment is a compound of Formula (IIA) wherein $R_6$ is substituted or unsubstituted cyclohexyl.

In another embodiment is a compound of Formula (IIA) wherein $R_6$ is substituted or unsubstituted $C_2$-$C_7$heteroaryl. In another embodiment is a compound of Formula (IIA) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IIA) wherein $R_6$ is substituted or unsubstituted pyridyl. In another embodiment is a compound of Formula (IIA) wherein $R_6$ is substituted pyridyl. In another embodiment is a compound of Formula (IIA) wherein $R_6$ is unsubstituted pyridyl.

In another embodiment is a compound of Formula (IIA) wherein $R_6$ is —$(C(R_{14})(R_{15}))_mR_{21}$. In another embodiment is a compound of Formula (IIA) wherein $R_6$ is —$(C(R_{14})(R_{15}))_mR_{21}$, and each $R_{14}$ and $R_{15}$ are H. In another embodiment is a compound of Formula (I) wherein $R_6$ is —$(C(R_{14})(R_{15}))_mR_{21}$, m is 2, and each $R_{14}$ and $R_{15}$ are H. In another embodiment is a compound of Formula (IIA) wherein $R_6$ is —$(CH_2)_mR_{21}$, m is 2, and $R_{21}$ is substituted or unsubstituted $C_2$-$C_7$heterocycloalkyl. In another embodiment is a compound of Formula (IIA) wherein $R_6$ is —$(CH_2)_mR_{21}$, m is 2, and $R_{21}$ is substituted or unsubstituted $C_3$-$C_8$cycloalkyl. In another embodiment is a compound of Formula (IIA) wherein $R_6$ is —$(CH_2)_mR_{21}$, m is 2, and $R_{21}$ is substituted or unsubstituted $C_6$-$C_{10}$aryl. In another embodiment is a compound of Formula (IIA) wherein $R_6$ is —$(CH_2)_mR_{21}$, m is 2, and $R_{21}$ is substituted or unsubstituted phenyl. In another embodiment is a compound of Formula (IIA) wherein $R_6$ is —$(CH_2)_mR_{21}$, m is 2, and $R_{21}$ is substituted or unsubstituted $C_2$-$C_7$heteroaryl.

In another embodiment is a compound of Formula (IIA) wherein $R_6$ is —$(C(R_{14})(R_{15}))_mR_{21}$, m is 3, and each $R_{14}$ and $R_{15}$ are H. In another embodiment is a compound of Formula (IIA) wherein $R_6$ is —$(CH_2)_mR_{21}$, m is 3, and $R_{21}$ is substituted or unsubstituted $C_2$-$C_7$heterocycloalkyl. In another embodiment is a compound of Formula (IIA) wherein $R_6$ is —$(CH_2)_mR_{21}$, m is 3, and $R_{21}$ is substituted or unsubstituted $C_3$-$C_8$cycloalkyl. In another embodiment is a compound of Formula (IIA) wherein $R_6$ is —$(CH_2)_mR_{21}$, m is 3, and $R_{21}$ is substituted or unsubstituted $C_6$-$C_{10}$aryl. In another embodiment is a compound of Formula (IIA) wherein $R_6$ is —$(CH_2)_mR_{21}$, m is 3, and $R_{21}$ is substituted or unsubstituted phenyl. In another embodiment is a compound of Formula (IIA) wherein $R_6$ is —$(CH_2)_mR_{21}$, m is 3, and $R_{21}$ is substituted or unsubstituted $C_2$-$C_7$heteroaryl.

In another embodiment is a compound of Formula (IIA) wherein $R_6$ is —$(C(R_{14})(R_{15}))_mN(R_{11})(R_{12})$. In another embodiment is a compound of Formula (IIA) wherein $R_6$ is —$(C(R_{14})(R_{15}))_mN(R_{11})(R_{12})$, m is 2, and each $R_{14}$ and $R_{15}$ are H. In another embodiment is a compound of Formula (IIA) wherein $R_6$ is —$(CH_2)_mN(R_{11})(R_{12})$, m is 2, and $R_{11}$ and $R_{12}$ are each H. In another embodiment is a compound of Formula (IIA) wherein $R_6$ is —$(CH_2)_mN(R_{11})(R_{12})$, m is 2, $R_{11}$ is substituted or unsubstituted $C_1$-$C_6$alkyl, and $R_{12}$ is H. In another embodiment is a compound of Formula (IIA) wherein $R_6$ is —$(CH_2)_mN(R_{11})(R_{12})$, m is 2, $R_{11}$ is $CH_3$, and $R_{12}$ is H. In another embodiment is a compound of Formula (IIA) wherein $R_6$ is —$(CH_2)_mN(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IIA) wherein $R_6$ is —$(CH_2)_mN(R_{11})(R_{12})$, m is 2, $R_{11}$ is $CH_3$, and $R_{12}$ is $CH_3$. In another embodiment is a compound of Formula (IIA) wherein $R_6$ is —$(CH_2)_mN(R_{11})(R_{12})$, m is 2, and $R_{11}$ and $R_{12}$ are taken together to form a 5-, 6-, 7-, or 8-membered heterocyclic ring. In another embodiment is a compound of Formula (IIA) wherein $R_6$ is —$(CH_2)_mN(R_{11})(R_{12})$, m is 2, and $R_{11}$ and $R_{12}$ are taken together to form a 5-membered heterocyclic ring. In another embodiment is a compound of Formula (IIA) wherein $R_6$ is —$(CH_2)_mN(R_{11})(R_{12})$, m is 2, and $R_{11}$ and $R_{12}$ are taken together to form a 6-membered heterocyclic ring.

In another embodiment is a compound of Formula (IIA) wherein $R_6$ is —$(C(R_{14})(R_{15}))_mN(R_{11})(R_{12})$. In another embodiment is a compound of Formula (IIA) wherein $R_6$ is —$(C(R_{14})(R_{15}))_mN(R_{11})(R_{12})$, m is 3, and each $R_{14}$ and $R_{15}$ are H. In another embodiment is a compound of Formula (IIA) wherein $R_6$ is —$(CH_2)_mN(R_{11})(R_{12})$, m is 3, and $R_{11}$ and $R_{12}$ are each H. In another embodiment is a compound of Formula (IIA) wherein $R_6$ is —$(CH_2)_mN(R_{11})(R_{12})$, m is 3, $R_{11}$ is substituted or unsubstituted $C_1$-$C_6$alkyl, and $R_{12}$ is H. In another embodiment is a compound of Formula (IIA) wherein $R_6$ is —$(CH_2)_mN(R_{11})(R_{12})$, m is 3, $R_{11}$ is $CH_3$, and $R_{12}$ is H. In another embodiment is a compound of Formula (IIA) wherein $R_6$ is —$(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IIA) wherein $R_6$ is —$(CH_2)_mN(R_{11})(R_{12})$, m is 3, $R_{11}$ is $CH_3$, and $R_{12}$ is $CH_3$. In another embodiment is a compound of Formula (IIA) wherein $R_6$ is —$(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (IIA) wherein $R_6$ is —$(CH_2)_mN(R_{11})(R_{12})$, m is 3, and $R_{11}$ and $R_{12}$ are taken together to form a 5-membered heterocyclic ring. In another embodiment is a compound of Formula (IIA) wherein $R_6$ is —$(CH_2)_mN(R_{11})(R_{12})$, m is 3, and $R_{11}$ and $R_{12}$ are taken together to form a 6-membered heterocyclic ring.

In another embodiment is a compound of Formula (IIA) wherein $R_6$ is substituted or unsubstituted $C_2$-$C_7$heterocycloalkyl. In another embodiment is a compound of Formula (IIA) wherein $R_6$ is

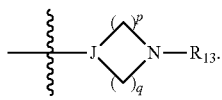

In another embodiment is a compound of Formula (IIA) wherein $R_6$ is

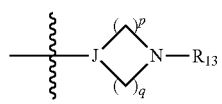

and J is C(H). In another embodiment is a compound of Formula (IIA) wherein $R_6$ is

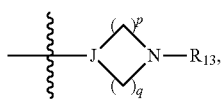

J is C(H), p is 1, and q is 1. In another embodiment is a compound of Formula (IIA) wherein $R_6$ is

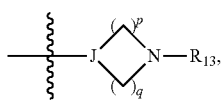

J is C(H), p is 2, and q is 1. In another embodiment is a compound of Formula (IIA) wherein $R_6$ is

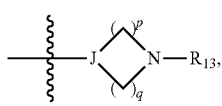

J is C(H), p is 3, and q is 1. In another embodiment is a compound of Formula (IIA) wherein $R_6$ is

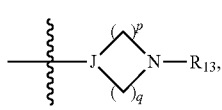

J is C(H), p is 2, and q is 2. In another embodiment is a compound of Formula (IIA) wherein $R_6$ is

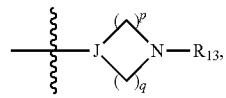

J is C(H), p is 1, q is 1, and $R_{13}$ is substituted or unsubstituted $C_1$-$C_6$alkyl. In another embodiment is a compound of Formula (IIA) wherein $R_6$ is

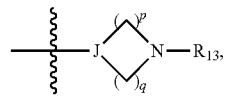

J is C(H), p is 2, q is 1, and $R_{13}$ is substituted or unsubstituted $C_1$-$C_6$alkyl. In another embodiment is a compound of Formula (IIA) wherein $R_6$ is

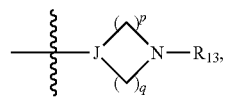

J is C(H), p is 3, q is 1, and $R_{13}$ is substituted or unsubstituted $C_1$-$C_6$alkyl. In another embodiment is a compound of Formula (IIA) wherein $R_6$ is

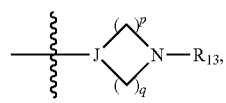

J is C(H), p is 2, q is 2, and $R_{13}$ is substituted or unsubstituted $C_1$-$C_6$alkyl.

In another embodiment is a compound of Formula (IIA) wherein $R_6$ is

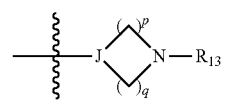

and J is N. In another embodiment is a compound of Formula (IIA) wherein $R_6$ is

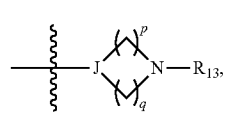

J is N, p is 2, and q is 2. In another embodiment is a compound of Formula (IIA) wherein $R_6$ is

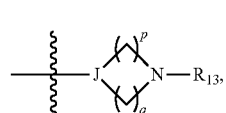

J is N, p is 2, q is 2, and $R_{13}$ is substituted or unsubstituted $C_1$-$C_6$alkyl.

In another embodiment is a compound of Formula (IIA) wherein $R_5$ is halogen. In another embodiment is a compound of Formula (IIA) wherein $R_5$ is —$CF_3$. In another embodiment is a compound of Formula (IIA) wherein $R_5$ is substituted or unsubstituted $C_1$-$C_6$alkyl. In another embodiment is a compound of Formula (IIA) wherein $R_5$ is —$CH_3$. In another embodiment is a compound of Formula (IIA) wherein $R_5$ is —$CH_2CH_3$. In another embodiment is a compound of Formula (IIA) wherein $R_5$ is substituted or unsubstituted $C_1$-$C_6$heteroalkyl. In another embodiment is a compound of Formula (IIA) wherein $R_5$ is substituted or unsubstituted $C_2$-$C_7$heterocycloalkyl. In another embodiment is a compound of Formula (IIA) wherein $R_5$ is substituted or unsubstituted $C_3$-$C_8$cycloalkyl. In another embodiment is a compound of Formula (IIA) wherein $R_5$ is substituted or unsubstituted $C_6$-$C_{10}$aryl. In another embodiment is a compound of Formula (IIA) wherein $R_5$ is substituted or unsubstituted $C_2$-$C_7$heteroaryl.

In another embodiment is a compound of Formula (IIA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H. In another embodiment is a compound of Formula (IIA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least two of $R_2$, $R_3$, and $R_4$ are not H. In another embodiment is a compound of Formula (IIA) wherein $R_2$ is H; $R_3$ is $C_1$-$C_4$alkyl; and $R_4$ is H. In another embodiment is a compound of Formula (IIA) wherein $R_2$ is H; $R_3$ is $CH_3$; and $R_4$ is H. In another embodiment is a compound of Formula (IIA) wherein $R_2$ is H; $R_3$ is $C_1$-$C_4$alkyl; and $R_4$ is $C_1$-$C_4$alkyl. In another embodiment is a compound of Formula (IIA) wherein $R_2$ is H; $R_3$ is $CH_3$; and $R_4$ is $CH_3$. In another embodiment is a compound of Formula (IIA) wherein $R_2$ is H; $R_3$ is $C_1$-$C_4$alkyl; and $R_4$ is —CN. In another embodiment is a compound of Formula (IIA) wherein $R_2$ is H; $R_3$ is $CH_3$; and $R_4$ is —CN. In another embodiment is a compound of Formula (IIA) wherein $R_2$ is $C_1$-$C_4$alkyl; $R_3$ is $C_1$-$C_4$alkyl; and $R_4$ is H. In another embodiment is a compound of Formula (IIA) wherein $R_2$ is $CH_3$; $R_3$ is $CH_3$; and $R_4$ is H. In another embodiment is a compound of Formula (IIA) wherein $R_2$ is $C_1$-$C_4$alkyl; $R_3$ is H; and $R_4$ is H. In another embodiment is a compound of Formula (IIA) wherein $R_2$ is $CH_3$; $R_3$ is H; and $R_4$ is H. In another embodiment is a compound of Formula (IIA) wherein $R_2$ is $C_1$-$C_4$alkyl; $R_3$ is H; and $R_4$ is $C_1$-$C_4$alkyl. In another embodiment is a compound of Formula (IIA) wherein $R_2$ is $CH_3$; $R_3$ is H; and $R_4$ is $CH_3$. In another embodiment is a compound of Formula (IIA) wherein $R_2$ is $C_1$-$C_4$alkyl; $R_3$ is H; and $R_4$ is —CN. In another embodiment is a compound of Formula (IIA) wherein $R_2$ is $CH_3$; $R_3$ is H; and $R_4$ is —CN. In another embodiment is a compound of Formula (IIA) wherein $R_2$ is $C_3$-$C_6$cycloalkyl; $R_3$ is H; and $R_4$ is H. In another embodiment is a compound of Formula (IIA) wherein $R_2$ is cyclopropyl; $R_3$ is H; and $R_4$ is H. In another embodiment is a compound of Formula (IIA) wherein $R_2$ is cyclopentyl; $R_3$ is H; and $R_4$ is H. In another embodiment is a compound of Formula (IIA) wherein $R_2$ is $C_3$-$C_6$cycloalkyl; $R_3$ is H; and $R_4$ is $CH_3$. In another embodiment is a compound of Formula (IIA) wherein $R_2$ is cyclopropyl; $R_3$ is H; and $R_4$ is $CH_3$. In another embodiment is a compound of Formula (IIA) wherein $R_2$ is cyclopentyl; $R_3$ is H; and $R_4$ is $CH_3$. In another embodiment is a compound of Formula (IIA) wherein $R_2$ is $C_3$-$C_6$cycloalkyl; $R_3$ is H; and $R_4$ is —CN. In another embodiment is a compound of Formula (IIA) wherein $R_2$ is cyclopropyl; $R_3$ is H; and $R_4$ is —CN. In another embodiment is a compound of Formula (IIA) wherein $R_2$ is cyclopentyl; $R_3$ is H; and $R_4$ is —CN.

In another embodiment is a compound of Formula (IIA) wherein $R_2$ and $R_3$ are taken together to form a 5- or 6-membered heterocyclic ring. In another embodiment is a compound of Formula (IIA) wherein $R_2$ and $R_3$ are taken together to form a 5- or 6-membered heterocyclic ring; and $R_4$ is H. In another embodiment is a compound of Formula (IIA) wherein $R_2$ and $R_3$ are taken together to form a 5-membered heterocyclic ring; and $R_4$ is H. In another embodiment is a compound of Formula (IIA) wherein $R_2$ and $R_3$ are taken together to form 6-membered heterocyclic ring; and $R_4$ is H.

In another embodiment is a compound of Formula (IIA) wherein each $R_1$ is independently halogen, —CN, —$NO_2$, —OH, —$OCF_3$, —$OCH_2F$, —$OCF_2H$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIA) wherein each $R_1$ is independently halogen, —CN, —OH, substituted or unsubstituted $C_1$-$C_6$alkyl, or substituted or unsubstituted $C_1$-$C_6$alkoxy. In another embodiment is a compound of Formula (IIA) wherein each $R_1$ is independently halogen, —CN, —$OCF_3$, —$OCH_2F$, —$OCF_2H$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy. In another embodiment is a compound of Formula (IIA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy, and n is 3. In another embodiment is a compound of Formula (IIA) wherein each $R_1$ is independently halogen, —CN, —$OCF_3$, —$OCH_2F$, —$OCF_2H$, substituted or unsubstituted $C_1$-$C_6$alkyl, or substituted or unsubstituted $C_1$-$C_6$alkoxy, and n is 2. In another embodiment is a compound of Formula (IIA) wherein n is 3, and each $R_1$ is independently halogen. In another embodiment is a compound of Formula (IIA) wherein n is 2, and each $R_1$ is independently halogen. In another embodiment is a compound of Formula (IIA) wherein n is 2, and each $R_1$ is independently F or Cl. In another embodiment is a compound of Formula (IIA) wherein n is 2, and each $R_1$ is F. In another embodiment is a compound of Formula (IIA) wherein n is 2, and each $R_1$ is independently Cl. In another embodiment is a compound of Formula (IIA) wherein n is 1, and $R_1$ is halogen. In another embodiment is a compound of Formula (IIA) wherein n is 1, and $R_1$ is F. In another embodiment is a compound of Formula (IIA) wherein n is 1, and $R_1$ is Cl. In another embodiment is a compound of Formula (IIA) wherein n is 1, and $R_1$ is substituted or unsubstituted $C_1$-$C_6$alkyl. In another embodiment is a compound of Formula (IIA) wherein n is 1, and $R_1$ is $CH_3$. In another embodiment is a compound of Formula (IIA)

wherein n is 1, and $R_1$ is substituted or unsubstituted $C_1$-$C_6$alkoxy. In another embodiment is a compound of Formula (IIA) wherein n is 1, and $R_1$ is —$OCH_3$. In another embodiment is a compound of Formula (IIA) wherein n is 1, and $R_1$ is —$OCF_3$. In another embodiment is a compound of Formula (IIA) wherein n is 1, and $R_1$ is —$OCF_2H$.

In another embodiment, described herein is a compound of Formula (JIB):

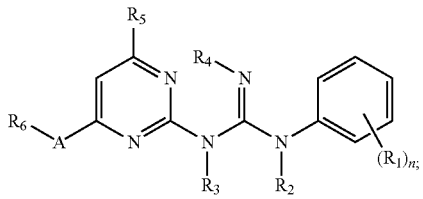

Formula (IIB)

wherein:
A is O;
each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or
two $R_1$ are taken together to form a substituted or unsubstituted heterocyclic ring or a substituted or unsubstituted carbocyclic ring; $R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;
$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —$C(R_{14})(R_{15}))_mR_{21}$, —$C(R_{14})(R_{15}))_mN(R_{11})(R_{12})$, or

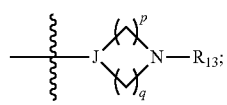

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;
J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;
each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;
$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)NR_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{22}$ is independently H, or substituted or unsubstituted $C_1$-$C_6$alkyl;
$R_{23}$ is substituted or unsubstituted $C_1$-$C_6$alkyl;
each $R_8$ is independently H, or substituted or unsubstituted $C_1$-$C_6$alkyl;
$R_9$ is substituted or unsubstituted $C_1$-$C_6$alkyl;
m is 2-6;
n is 0-5;
p is 1-3;
q is 1-3; or
a pharmaceutically acceptable salt, solvate, or prodrug thereof.

In another embodiment is a compound of Formula (IIB) wherein $R_6$ is substituted or unsubstituted $C_3$-$C_8$cycloalkyl. In another embodiment is a compound of Formula (IIB) wherein $R_6$ is substituted or unsubstituted cyclopropyl. In another embodiment is a compound of Formula (IIB) wherein $R_6$ is substituted or unsubstituted cyclobutyl. In another embodiment is a compound of Formula (IIB) wherein $R_6$ is substituted or unsubstituted cyclopentyl. In another embodiment is a compound of Formula (IIB) wherein $R_6$ is substituted or unsubstituted cyclohexyl.

In another embodiment is a compound of Formula (IIB) wherein $R_6$ is substituted or unsubstituted $C_2$-$C_7$heteroaryl. In another embodiment is a compound of Formula (IIB) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IIB) wherein $R_6$ is substituted or unsubstituted pyridyl. In another embodiment is a compound of Formula (IIB) wherein $R_6$ is substituted pyridyl. In another embodiment is a compound of Formula (IIB) wherein $R_6$ is unsubstituted pyridyl.

In another embodiment is a compound of Formula (IIB) wherein $R_6$ is —$(C(R_{14})(R_{15}))_m R_{21}$. In another embodiment is a compound of Formula (IIB) wherein $R_6$ is —$(C(R_{14})(R_{15}))_m R_{21}$, and each $R_{14}$ and $R_{15}$ are H. In another embodiment is a compound of Formula (IIB) wherein $R_6$ is —$(C(R_{14})(R_{15}))_m R_{21}$, m is 2, and each $R_{14}$ and $R_{15}$ are H. In another embodiment is a compound of Formula (I) wherein $R_6$ is —$(CH_2)_m R_{21}$, m is 2, and $R_{21}$ is substituted or unsubstituted $C_2$-$C_7$heterocycloalkyl. In another embodiment is a compound of Formula (IIB) wherein $R_6$ is —$(CH_2)_m R_{21}$, m is 2, and $R_{21}$ is substituted or unsubstituted $C_3$-$C_8$cycloalkyl. In another embodiment is a compound of Formula (IIB) wherein $R_6$ is —$(CH_2)_m R_{21}$, m is 2, and $R_{21}$ is substituted or unsubstituted $C_6$-$C_{10}$aryl. In another embodiment is a compound of Formula (IIB) wherein $R_6$ is —$(CH_2)_m R_{21}$, m is 2, and $R_{21}$ is substituted or unsubstituted phenyl. In another embodiment is a compound of Formula (IIB) wherein $R_6$ is —$(CH_2)_m R_{21}$, m is 2, and $R_{21}$ is substituted or unsubstituted $C_2$-$C_7$heteroaryl.

In another embodiment is a compound of Formula (IIB) wherein $R_6$ is —$(C(R_{14})(R_{15}))_m R_{21}$, m is 3, and each $R_{14}$ and $R_{15}$ are H. In another embodiment is a compound of Formula (IIB) wherein $R_6$ is —$(CH_2)_m R_{21}$, m is 3, and $R_{21}$ is substituted or unsubstituted $C_2$-$C_7$heterocycloalkyl. In another embodiment is a compound of Formula (IIB) wherein $R_6$ is —$(CH_2)_m R_{21}$, m is 3, and $R_{21}$ is substituted or unsubstituted $C_3$-$C_8$cycloalkyl. In another embodiment is a compound of Formula (IIB) wherein $R_6$ is —$(CH_2)_m R_{21}$, m is 3, and $R_{21}$ is substituted or unsubstituted $C_6$-$C_{10}$aryl. In another embodiment is a compound of Formula (IIB) wherein $R_6$ is —$(CH_2)_m R_{21}$, m is 3, and $R_{21}$ is substituted or unsubstituted phenyl. In another embodiment is a compound of Formula (IIB) wherein $R_6$ is —$(CH_2)_m R_{21}$, m is 3, and $R_{21}$ is substituted or unsubstituted $C_2$-$C_7$heteroaryl.

In another embodiment is a compound of Formula (IIB) wherein $R_6$ is —$(C(R_{14})(R_{15}))_m N(R_{11})(R_{12})$. In another embodiment is a compound of Formula (IIB) wherein $R_6$ is —$(C(R_{14})(R_{15}))_m N(R_{11})(R_{12})$, m is 2, and each $R_{14}$ and $R_{15}$ are H. In another embodiment is a compound of Formula (IIB) wherein $R_6$ is —$(CH_2)_m N(R_{11})(R_{12})$, m is 2, and $R_{11}$ and $R_{12}$ are each H. In another embodiment is a compound of Formula (IIB) wherein $R_6$ is —$(CH_2)_m N(R_{11})(R_{12})$, m is 2, $R_{11}$ is substituted or unsubstituted $C_1$-$C_6$alkyl, and $R_{12}$ is H. In another embodiment is a compound of Formula (IIB) wherein $R_6$ is —$(CH_2)_m N(R_{11})(R_{12})$, m is 2, $R_{11}$ is $CH_3$, and $R_{12}$ is H. In another embodiment is a compound of Formula (IIB) wherein $R_6$ is —$(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IIB) wherein $R_6$ is —$(CH_2)_m N(R_{11})(R_{12})$, m is 2, $R_{11}$ is $CH_3$, and $R_{12}$ is $CH_3$. In another embodiment is a compound of Formula (IIB) wherein $R_6$ is —$(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (IIB) wherein $R_6$ is —$(CH_2)_m N(R_{11})(R_{12})$, m is 2, and $R_{11}$ and $R_{12}$ are taken together to form a 5-membered heterocyclic ring. In another embodiment is a compound of Formula (IIB) wherein $R_6$ is —$(CH_2)_m N(R_{11})(R_{12})$, m is 2, and $R_{11}$ and $R_{12}$ are taken together to form a 6-membered heterocyclic ring.

In another embodiment is a compound of Formula (IIB) wherein $R_6$ is —$(C(R_{14})(R_{15}))_m N(R_{11})(R_{12})$—In another embodiment is a compound of Formula (IIB) wherein $R_6$ is —$(C(R_{14})(R_{15}))_m N(R_{11})(R_{12})$, m is 3, and each $R_{14}$ and $R_{15}$ are H. In another embodiment is a compound of Formula (IIB) wherein $R_6$ is —$(CH_2)_m N(R_{11})(R_{12})$, m is 3, and $R_{11}$ and $R_{12}$ are each H. In another embodiment is a compound of Formula (IIB) wherein $R_6$ is —$(CH_2)_m N(R_{11})(R_{12})$, m is 23, $R_{11}$ is substituted or unsubstituted $C_1$-$C_6$alkyl, and $R_{12}$ is H. In another embodiment is a compound of Formula (IIB) wherein $R_6$ is —$(CH_2)_m N(R_{11})(R_{12})$, m is 3, $R_{11}$ is $CH_3$, and $R_{12}$ is H. In another embodiment is a compound of Formula (IIB) wherein $R_6$ is —$(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IIB) wherein $R_6$ is —$(CH_2)_m N(R_{11})(R_{12})$, m is 3, $R_{11}$ is $CH_3$, and $R_{12}$ is $CH_3$. In another embodiment is a compound of Formula (IIB) wherein $R_6$ is —$(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (IIB) wherein $R_6$ is —$(CH_2)_m N(R_{11})(R_{12})$, m is 3, and $R_{11}$ and $R_{12}$ are taken together to form a 5-membered heterocyclic ring. In another embodiment is a compound of Formula (IIB) wherein $R_6$ is —$(CH_2)_m N(R_{11})(R_{12})$, m is 3, and $R_{11}$ and $R_{12}$ are taken together to form a 6-membered heterocyclic ring.

In another embodiment is a compound of Formula (IIB) wherein $R_6$ is substituted or unsubstituted $C_2$-$C_7$heterocycloalkyl. In another embodiment is a compound of Formula (IIB) wherein $R_6$ is $$\text{—J}\underset{q}{\overset{p}{\diamond}}\text{N—R}_{13}.$$

In another embodiment is a compound of Formula (IIB) wherein $R_6$ is $$\text{—J}\underset{q}{\overset{p}{\diamond}}\text{N—R}_{13}$$

and J is C(H). In another embodiment is a compound of Formula (IIB) wherein $R_6$ is $$\text{—J}\underset{q}{\overset{p}{\diamond}}\text{N—R}_{13},$$

J is C(H), p is 1, and q is 1. In another embodiment is a compound of Formula (IIB) wherein $R_6$ is $$\text{—J}\underset{q}{\overset{p}{\diamond}}\text{N—R}_{13},$$

J is C(H), p is 2, and q is 1. In another embodiment is a compound of Formula (IIB) wherein $R_6$ is

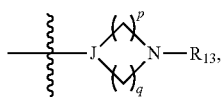

J is C(H), p is 3, and q is 1. In another embodiment is a compound of Formula (IIB) wherein $R_6$ is

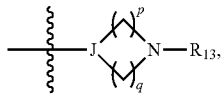

J is C(H), p is 2, and q is 2. In another embodiment is a compound of Formula (IIB) wherein $R_6$ is

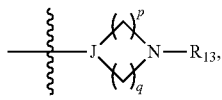

J is C(H), p is 1, q is 1, and $R_{13}$ is substituted or unsubstituted $C_1$-$C_6$alkyl. In another embodiment is a compound of Formula (IIB) wherein $R_6$ is

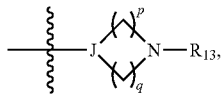

J is C(H), p is 2, q is 1, and $R_{13}$ is substituted or unsubstituted $C_1$-$C_6$alkyl. In another embodiment is a compound of Formula (IIB) wherein $R_6$ is

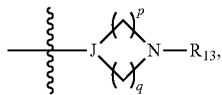

J is C(H), p is 3, q is 1, and $R_{13}$ is substituted or unsubstituted $C_1$-$C_6$alkyl. In another embodiment is a compound of Formula (IIB) wherein $R_6$ is

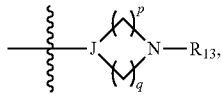

J is C(H), p is 2, q is 2, and $R_{13}$ is substituted or unsubstituted $C_1$-$C_6$alkyl.

In another embodiment is a compound of Formula (IIB) wherein $R_5$ is halogen. In another embodiment is a compound of Formula (IIB) wherein $R_5$ is —$CF_3$. In another embodiment is a compound of Formula (IIB) wherein $R_5$ is substituted or unsubstituted $C_1$-$C_6$alkyl. In another embodiment is a compound of Formula (IIB) wherein $R_5$ is —$CH_3$. In another embodiment is a compound of Formula (IIB) wherein $R_5$ is —$CH_2CH_3$. In another embodiment is a compound of Formula (IIB) wherein $R_5$ is substituted or unsubstituted $C_1$-$C_6$heteroalkyl. In another embodiment is a compound of Formula (IIB) wherein $R_5$ is substituted or unsubstituted $C_2$-$C_7$heterocycloalkyl. In another embodiment is a compound of Formula (IIB) wherein $R_5$ is substituted or unsubstituted $C_3$-$C_8$cycloalkyl. In another embodiment is a compound of Formula (IIB) wherein $R_5$ is substituted or unsubstituted $C_6$-$C_{10}$aryl. In another embodiment is a compound of Formula (IIB) wherein $R_5$ is substituted or unsubstituted $C_2$-$C_7$heteroaryl.

In another embodiment is a compound of Formula (IIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (IIB) wherein $R_2$, $R_3$, and $R_4$ are each H. In another embodiment is a compound of Formula (IIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (IIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (IIB) wherein $R_2$ is H; $R_3$ is $C_1$-$C_4$alkyl; and $R_4$ is H. In another embodiment is a compound of Formula (IIB) wherein $R_2$ is H; $R_3$ is $CH_3$; and $R_4$ is H. In another embodiment is a compound of Formula (IIB) wherein $R_2$ is H; $R_3$ is $C_1$-$C_4$alkyl; and $R_4$ is $C_1$-$C_4$alkyl. In another embodiment is a compound of Formula (IIB) wherein $R_2$ is H; $R_3$ is $CH_3$; and $R_4$ is $CH_3$. In another embodiment is a compound of Formula (IIB) wherein $R_2$ is H; $R_3$ is $C_1$-$C_4$alkyl; and $R_4$ is —CN. In another embodiment is a compound of Formula (IIB) wherein $R_2$ is H; $R_3$ is $CH_3$; and $R_4$ is —CN. In another embodiment is a compound of Formula (IIB) wherein $R_2$ is $C_1$-$C_4$alkyl; $R_3$ is $C_1$-$C_4$alkyl; and $R_4$ is H. In another embodiment is a compound of Formula (IIB) wherein $R_2$ is $CH_3$; $R_3$ is $CH_3$; and $R_4$ is H. In another embodiment is a compound of Formula (IIB) wherein $R_2$ is $C_1$-$C_4$alkyl; $R_3$ is H; and $R_4$ is H. In another embodiment is a compound of Formula (IIB) wherein $R_2$ is $CH_3$; $R_3$ is H; and $R_4$ is H. In another embodiment is a compound of Formula (IIB) wherein $R_2$ is $C_1$-$C_4$alkyl; $R_3$ is H; and $R_4$ is $C_1$-$C_4$alkyl. In another embodiment is a compound of Formula (IIB) wherein $R_2$ is $CH_3$; $R_3$ is H; and $R_4$ is $CH_3$. In another embodiment is a compound of Formula (IIB) wherein $R_2$ is $C_1$-$C_4$alkyl; $R_3$ is H; and $R_4$ is —CN. In another embodiment is a compound of Formula (IIB) wherein $R_2$ is $CH_3$; $R_3$ is H; and $R_4$ is —CN. In another embodiment is a compound of Formula (IIB) wherein $R_2$ is $C_3$-$C_6$cycloalkyl; $R_3$ is H; and $R_4$ is H. In another embodiment is a compound of Formula (IIB) wherein $R_2$ is cyclopropyl; $R_3$ is H; and $R_4$ is H. In another embodiment is a compound of Formula (IIB) wherein $R_2$ is cyclopentyl; $R_3$ is H; and $R_4$ is H. In another embodiment is a compound of Formula (IIB) wherein $R_2$ is $C_3$-$C_6$cycloalkyl; $R_3$ is H; and $R_4$ is $CH_3$. In another embodiment is a compound of Formula (IIB) wherein $R_2$ is cyclopropyl; $R_3$ is H; and $R_4$ is $CH_3$. In another embodiment is a compound of Formula (IIB) wherein $R_2$ is cyclopentyl; $R_3$ is H; and $R_4$ is $CH_3$. In another embodiment is a compound of Formula (IIB) wherein $R_2$ is $C_3$-$C_6$cycloalkyl; $R_3$ is H; and $R_4$ is —CN. In another embodiment is a compound of Formula (IIB) wherein $R_2$ is cyclopropyl; $R_3$ is H; and $R_4$ is —CN. In another embodiment is a compound of Formula (IIB) wherein $R_2$ is cyclopentyl; $R_3$ is H; and $R_4$ is —CN.

In another embodiment is a compound of Formula (IIB) wherein $R_2$ and $R_3$ are taken together to form a 5- or 6-membered heterocyclic ring. In another embodiment is a compound of Formula (IIB) wherein $R_2$ and $R_3$ are taken together to form a 5- or 6-membered heterocyclic ring; and $R_4$ is H. In another embodiment is a compound of Formula (IIB) wherein $R_2$ and $R_3$ are taken together to form a 5-membered heterocyclic ring; and $R_4$ is H. In another embodiment is a compound of Formula (IIB) wherein $R_2$ and $R_3$ are taken together to form 6-membered heterocyclic ring; and $R_4$ is H.

In another embodiment is a compound of Formula (IIB) wherein each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl. In another embodiment is a compound of Formula (IIB) wherein each $R_1$ is independently halogen, —CN, —OH, —CF$_3$, substituted or unsubstituted C$_1$-C$_6$alkyl, or substituted or unsubstituted C$_1$-C$_6$alkoxy. In another embodiment is a compound of Formula (IIB) wherein each $R_1$ is independently halogen, —CN, —OCF$_3$, —OCH$_2$F, —OCF$_2$H, —CF$_3$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl. In another embodiment is a compound of Formula (IIB) wherein each $R_1$ is independently halogen, —CN, —OCF$_3$, —OCH$_2$F, —OCF$_2$H, —CF$_3$, substituted or unsubstituted C$_1$-C$_6$alkyl, or substituted or unsubstituted C$_1$-C$_6$alkoxy. In another embodiment is a compound of Formula (IIB) wherein each $R_1$ is independently halogen, —CN, —OCF$_3$, —OCH$_2$F, —OCF$_2$H, —CF$_3$, substituted or unsubstituted C$_1$-C$_6$alkyl, or substituted or unsubstituted C$_1$-C$_6$alkoxy, and n is 3. In another embodiment is a compound of Formula (IIB) wherein each $R_1$ is independently halogen, —CN, —OCF$_3$, —OCH$_2$F, —OCF$_2$H, —CF$_3$, substituted or unsubstituted C$_1$-C$_6$alkyl, or substituted or unsubstituted C$_1$-C$_6$alkoxy, and n is 2. In another embodiment is a compound of Formula (IIB) wherein n is 3, and each $R_1$ is independently halogen. In another embodiment is a compound of Formula (IIB) wherein n is 2, and each $R_1$ is independently halogen. In another embodiment is a compound of Formula (IIB) wherein n is 2, and each $R_1$ is independently F or Cl. In another embodiment is a compound of Formula (IIB) wherein n is 2, and each $R_1$ is F. In another embodiment is a compound of Formula (IIB) wherein n is 2, and each $R_1$ is independently Cl. In another embodiment is a compound of Formula (IIB) wherein n is 2, and each $R_1$ is independently halogen or —CF$_3$. In another embodiment is a compound of Formula (IIB) wherein n is 2, and each $R_1$ is independently F or —CF$_3$. In another embodiment is a compound of Formula (IIB) wherein n is 2, and each $R_1$ is independently Cl or —CF$_3$. In another embodiment is a compound of Formula (IIB) wherein n is 1, and $R_1$ is halogen. In another embodiment is a compound of Formula (IIB) wherein n is 1, and $R_1$ is F. In another embodiment is a compound of Formula (IIB) wherein n is 1, and $R_1$ is Cl. In another embodiment is a compound of Formula (IIB) wherein n is 1, and $R_1$ is —CF$_3$. In another embodiment is a compound of Formula (IIB) wherein n is 1, and $R_1$ is substituted or unsubstituted C$_1$-C$_6$alkyl. In another embodiment is a compound of Formula (IIB) wherein n is 1, and $R_1$ is CH$_3$. In another embodiment is a compound of Formula (IIB) wherein n is 1, and $R_1$ is substituted or unsubstituted C$_1$-C$_6$alkoxy. In another embodiment is a compound of Formula (IIB) wherein n is 1, and $R_1$ is —OCH$_3$. In another embodiment is a compound of Formula (IIB) wherein n is 1, and $R_1$ is —OCF$_3$. In another embodiment is a compound of Formula (IIB) wherein n is 1, and $R_1$ is —OCF$_2$H.

In another aspect, described herein is a compound of Formula (III):

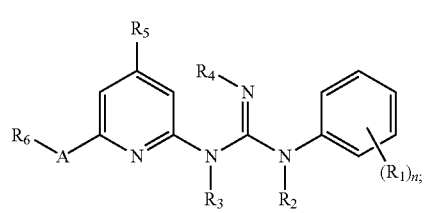

Formula (III)

wherein:

A is a bond, O, CH$_2$, or N(R$_{10}$);

each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, C$_1$-C$_4$alkyl, C$_3$-C$_6$cycloalkyl, or C$_2$-C$_7$heterocycloalkyl; or two of $R_2$, $R_3$, and $R_4$ are taken together to form a 5- or 6-membered heterocyclic ring;

$R_5$ is halogen, —CN, —OH, —CF$_3$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl;

$R_6$ is substituted or unsubstituted C$_2$-C$_7$heterocycloalkyl, substituted or unsubstituted C$_3$-C$_8$cycloalkyl, substituted or unsubstituted C$_2$-C$_7$heteroaryl, —(C(R$_{14}$)(R$_{15}$))$_m$R$_{21}$, —(C(R$_{14}$)(R$_{15}$))$_m$N(R$_{11}$)(R$_{12}$), or

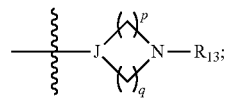

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;

each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —$NO_2$, —OH, —$OCF_3$, —$OCH_2F$, —$OCF_2H$, —$CF_3$, —$SR_{22}$, —N($R_{22}$)S(=O)$_2R_{23}$, —S(=O)$_2$N($R_{22}$)$_2$, —S(=O)$R_{23}$, —S(=O)$_2R_{23}$, —C(=O)$R_{23}$, —$CO_2R_{22}$, —C(=O)N($R_{22}$)$_2$, —N($R_{22}$)C(=O)$R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl; $R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In another embodiment is a compound of Formula (III) wherein A is O, $CH_2$, or N($R_{10}$). In another embodiment is a compound of Formula (III) wherein A is O, $CH_2$, or N(H). In another embodiment is a compound of Formula (III) wherein A is O. In another embodiment is a compound of Formula (III) wherein A is $CH_2$. In another embodiment is a compound of Formula (III) wherein A is N($R_{10}$). In another embodiment is a compound of Formula (III) wherein A is N(H). In another embodiment is a compound of Formula (III) wherein A is N($CH_3$). In another embodiment is a compound of Formula (III) wherein A is a bond.

In another embodiment is a compound of Formula (III) wherein $R_6$ is substituted or unsubstituted $C_3$-$C_8$cycloalkyl. In another embodiment is a compound of Formula (III) wherein $R_6$ is substituted or unsubstituted cyclopropyl. In another embodiment is a compound of Formula (III) wherein $R_6$ is substituted or unsubstituted cyclobutyl. In another embodiment is a compound of Formula (III) wherein $R_6$ is substituted or unsubstituted cyclopentyl. In another embodiment is a compound of Formula (III) wherein $R_6$ is substituted or unsubstituted cyclohexyl.

In another embodiment is a compound of Formula (III) wherein $R_6$ is substituted or unsubstituted $C_2$-$C_7$heteroaryl. In another embodiment is a compound of Formula (III) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (III) wherein $R_6$ is substituted or unsubstituted pyridyl. In another embodiment is a compound of Formula (III) wherein $R_6$ is substituted pyridyl. In another embodiment is a compound of Formula (III) wherein $R_6$ is unsubstituted pyridyl.

In another embodiment is a compound of Formula (III) wherein $R_6$ is —(C($R_{14}$)($R_{15}$))$_m R_{21}$. In another embodiment is a compound of Formula (III) wherein $R_6$ is —(C($R_{14}$)($R_{15}$))$_m R_{21}$, and each $R_{14}$ and $R_{15}$ are H. In another embodiment is a compound of Formula (III) wherein $R_6$ is —(C($R_{14}$)($R_{15}$))$_m R_{21}$, m is 2, and each $R_{14}$ and $R_{15}$ are H. In another embodiment is a compound of Formula (III) wherein $R_6$ is —($CH_2$)$_m R_{21}$, m is 2, and $R_{21}$ is substituted or unsubstituted $C_2$-$C_7$heterocycloalkyl. In another embodiment is a compound of Formula (III) wherein $R_6$ is —($CH_2$)$_m R_{21}$, m is 2, and $R_{21}$ is substituted or unsubstituted $C_3$-$C_8$cycloalkyl. In another embodiment is a compound of Formula (III) wherein $R_6$ is —($CH_2$)$_m R_{21}$, m is 2, and $R_{21}$ is substituted or unsubstituted $C_6$-$C_{10}$aryl. In another embodiment is a compound of Formula (III) wherein $R_6$ is —($CH_2$)$_m R_{21}$, m is 2, and $R_{21}$ is substituted or unsubstituted phenyl. In another embodiment is a compound of Formula (III) wherein $R_6$ is —($CH_2$)$_m R_{21}$, m is 2, and $R_{21}$ is substituted or unsubstituted $C_2$-$C_7$heteroaryl.

In another embodiment is a compound of Formula (III) wherein $R_6$ is —(C($R_{14}$)($R_{15}$))$_m R_{21}$, m is 3, and each $R_{14}$ and $R_{15}$ are H. In another embodiment is a compound of Formula (III) wherein $R_6$ is —($CH_2$)$_m R_{21}$, m is 3, and $R_{21}$ is substituted or unsubstituted $C_2$-$C_7$heterocycloalkyl. In another embodiment is a compound of Formula (III) wherein $R_6$ is —($CH_2$)$_m R_{21}$, m is 3, and $R_{21}$ is substituted or unsubstituted $C_3$-$C_8$cycloalkyl. In another embodiment is a compound of Formula (III) wherein $R_6$ is —($CH_2$)$_m R_{21}$, m is 3, and $R_{21}$ is substituted or unsubstituted $C_6$-$C_{10}$aryl. In another embodiment is a compound of Formula (III) wherein $R_6$ is —($CH_2$)$_m R_{21}$, m is 3, and $R_{21}$ is substituted or unsubstituted phenyl. In another embodiment is a compound of Formula (III) wherein $R_6$ is —($CH_2$)$_m R_{21}$, m is 3, and $R_{21}$ is substituted or unsubstituted $C_2$-$C_7$heteroaryl.

In another embodiment is a compound of Formula (III) wherein $R_6$ is —(C($R_{14}$)($R_{15}$))$_m$N($R_{11}$)($R_{12}$). In another embodiment is a compound of Formula (III) wherein $R_6$ is —(C($R_{14}$)($R_{15}$))$_m$N($R_{11}$)($R_{12}$), m is 2, and each $R_{14}$ and $R_{15}$ are H. In another embodiment is a compound of Formula (III) wherein $R_6$ is —($CH_2$)$_m$N($R_{11}$)($R_{12}$), m is 2, and $R_{11}$ and $R_{12}$ are each H. In another embodiment is a compound of Formula (III) wherein $R_6$ is —($CH_2$)$_m$N($R_{11}$)($R_{12}$), m is 2, $R_{11}$ is substituted or unsubstituted $C_1$-$C_6$alkyl, and $R_{12}$ is H. In another embodiment is a compound of Formula (III) wherein $R_6$ is —($CH_2$)$_m$N($R_{11}$)($R_{12}$), m is 2, $R_{11}$ is $CH_3$, and $R_{12}$ is H. In another embodiment is a compound of Formula (III) wherein $R_6$ is $-(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (III) wherein $R_6$ is $-(CH_2)_m N(R_{11})(R_{12})$, m is 2, $R_{11}$ is $CH_3$, and $R_{12}$ is $CH_3$. In another embodiment is a compound of Formula (III) wherein $R_6$ is $-(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (III) wherein $R_6$ is $-(CH_2)_m N(R_{11})(R_{12})$, m is 2, and $R_{11}$ and $R_{12}$ are taken together to form a 5-membered heterocyclic ring. In another embodiment is a compound of Formula (III) wherein $R_6$ is $-(CH_2)_m N(R_{11})(R_{12})$, m is 2, and $R_{11}$ and $R_{12}$ are taken together to form a 6-membered heterocyclic ring.

In another embodiment is a compound of Formula (III) wherein $R_6$ is $-(C(R_{14})(R_{15}))_m N(R_{11})(R_{12})$. In another embodiment is a compound of Formula (III) wherein $R_6$ is $-(C(R_{14})(R_{15}))_m N(R_{11})(R_{12})$, m is 3, and each $R_{14}$ and $R_{15}$ are H. In another embodiment is a compound of Formula (III) wherein $R_6$ is $-(CH_2)_m N(R_{11})(R_{12})$, m is 3, and $R_{11}$ and $R_{12}$ are each H. In another embodiment is a compound of Formula (III) wherein $R_6$ is $-(CH_2)_m N(R_{11})(R_{12})$, m is 3, $R_{11}$ is substituted or unsubstituted $C_1$-$C_6$alkyl, and $R_{12}$ is H. In another embodiment is a compound of Formula (III) wherein $R_6$ is $-(CH_2)_m N(R_{11})(R_{12})$, m is 3, $R_{11}$ is $CH_3$, and $R_{12}$ is H. In another embodiment is a compound of Formula (III) wherein $R_6$ is $-(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (III) wherein $R_6$ is $-(CH_2)_m N(R_{11})(R_{12})$, m is 3, $R_{11}$ is $CH_3$, and $R_{12}$ is $CH_3$. In another embodiment is a compound of Formula (III) wherein $R_6$ is $-(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (III) wherein $R_6$ is $-(CH_2)_m N(R_{11})(R_{12})$, m is 3, and $R_{11}$ and $R_{12}$ are taken together to form a 5-membered heterocyclic ring. In another embodiment is a compound of Formula (III) wherein $R_6$ is $-(CH_2)_m N(R_{11})(R_{12})$, m is 3, and $R_{11}$ and $R_{12}$ are taken together to form a 6-membered heterocyclic ring.

In another embodiment is a compound of Formula (III) wherein $R_6$ is substituted or unsubstituted $C_2$-$C_7$heterocycloalkyl. In another embodiment is a compound of Formula (III) wherein $R_6$ is

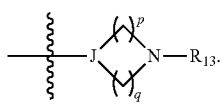

In another embodiment is a compound of Formula (III) wherein $R_6$ is

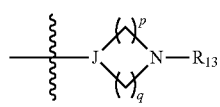

and J is C(H). In another embodiment is a compound of Formula (III) wherein $R_6$ is

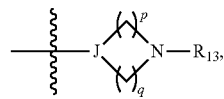

J is C(H), p is 1, and q is 1. In another embodiment is a compound of Formula (III) wherein $R_6$ is

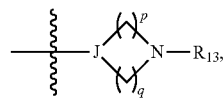

J is C(H), p is 2, and q is 1. In another embodiment is a compound of Formula (III) wherein $R_6$ is

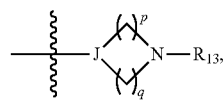

J is C(H), p is 3, and q is 1. In another embodiment is a compound of Formula (III) wherein $R_6$ is

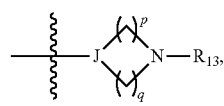

J is C(H), p is 2, and q is 2. In another embodiment is a compound of Formula (III) wherein $R_6$ is

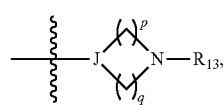

J is C(H), p is 1, q is 1, and $R_{13}$ is substituted or unsubstituted $C_1$-$C_6$alkyl. In another embodiment is a compound of Formula (III) wherein $R_6$ is

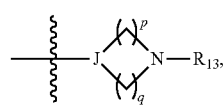

J is C(H), p is 2, q is 1, and $R_{13}$ is substituted or unsubstituted $C_1$-$C_6$alkyl. In another embodiment is a compound of Formula (III) wherein $R_6$ is

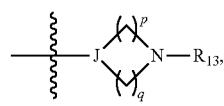

J is C(H), p is 3, q is 1, and $R_{13}$ is substituted or unsubstituted $C_1$-$C_6$alkyl. In another embodiment is a compound of Formula (III) wherein $R_6$ is

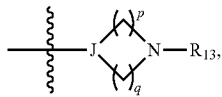

J is C(H), p is 2, q is 2, and $R_{13}$ is substituted or unsubstituted $C_1$-$C_6$alkyl.

In another embodiment is a compound of Formula (III) wherein $R_6$ is

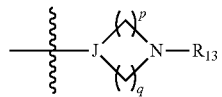

and J is N. In another embodiment is a compound of Formula (III) wherein $R_6$ is

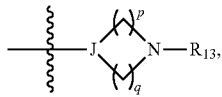

J is N, p is 2, and q is 2. In another embodiment is a compound of Formula (III) wherein $R_6$ is

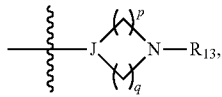

J is N, p is 2, q is 2, and $R_{13}$ is substituted or unsubstituted $C_1$-$C_6$alkyl.

In another embodiment is a compound of Formula (III) wherein $R_5$ is halogen. In another embodiment is a compound of Formula (III) wherein $R_5$ is —$CF_3$. In another embodiment is a compound of Formula (III) wherein $R_5$ is substituted or unsubstituted $C_1$-$C_6$alkyl. In another embodiment is a compound of Formula (III) wherein $R_5$ is —$CH_3$. In another embodiment is a compound of Formula (III) wherein $R_5$ is —$CH_2CH_3$. In another embodiment is a compound of Formula (III) wherein $R_5$ is substituted or unsubstituted $C_1$-$C_6$heteroalkyl. In another embodiment is a compound of Formula (III) wherein $R_5$ is substituted or unsubstituted $C_2$-$C_7$heterocycloalkyl. In another embodiment is a compound of Formula (III) wherein $R_5$ is substituted or unsubstituted $C_3$-$C_8$cycloalkyl. In another embodiment is a compound of Formula (III) wherein $R_5$ is substituted or unsubstituted $C_6$-$C_{10}$aryl. In another embodiment is a compound of Formula (III) wherein $R_5$ is substituted or unsubstituted $C_2$-$C_7$heteroaryl.

In another embodiment is a compound of Formula (III) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (III) wherein $R_2$, $R_3$, and $R_4$ are each H.

In another embodiment is a compound of Formula (III) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (III) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (III) wherein $R_2$ is H; $R_3$ is $C_1$-$C_4$alkyl; and $R_4$ is H. In another embodiment is a compound of Formula (III) wherein $R_2$ is H; $R_3$ is $CH_3$; and $R_4$ is H. In another embodiment is a compound of Formula (III) wherein $R_2$ is H; $R_3$ is $C_1$-$C_4$alkyl; and $R_4$ is $C_1$-$C_4$alkyl. In another embodiment is a compound of Formula (III) wherein $R_2$ is H; $R_3$ is $CH_3$; and $R_4$ is $CH_3$. In another embodiment is a compound of Formula (III) wherein $R_2$ is H; $R_3$ is $C_1$-$C_4$alkyl; and $R_4$ is —CN. In another embodiment is a compound of Formula (III) wherein $R_2$ is H; $R_3$ is $CH_3$; and $R_4$ is —CN. In another embodiment is a compound of Formula (III) wherein $R_2$ is $C_1$-$C_4$alkyl; $R_3$ is $C_1$-$C_4$alkyl; and $R_4$ is H. In another embodiment is a compound of Formula (III) wherein $R_2$ is $CH_3$; $R_3$ is $CH_3$; and $R_4$ is H. In another embodiment is a compound of Formula (III) wherein $R_2$ is $C_1$-$C_4$alkyl; $R_3$ is H; and $R_4$ is H. In another embodiment is a compound of Formula (III) wherein $R_2$ is $CH_3$; $R_3$ is H; and $R_4$ is H. In another embodiment is a compound of Formula (III) wherein $R_2$ is $C_1$-$C_4$alkyl; $R_3$ is H; and $R_4$ is $C_1$-$C_4$alkyl. In another embodiment is a compound of Formula (III) wherein $R_2$ is $CH_3$; $R_3$ is H; and $R_4$ is $CH_3$. In another embodiment is a compound of Formula (III) wherein $R_2$ is $C_1$-$C_4$alkyl; $R_3$ is H; and $R_4$ is —CN. In another embodiment is a compound of Formula (III) wherein $R_2$ is $CH_3$; $R_3$ is H; and $R_4$ is —CN. In another embodiment is a compound of Formula (III) wherein $R_2$ is $C_3$-$C_6$cycloalkyl; $R_3$ is H; and $R_4$ is H. In another embodiment is a compound of Formula (III) wherein $R_2$ is cyclopropyl; $R_3$ is H; and $R_4$ is H. In another embodiment is a compound of Formula (III) wherein $R_2$ is cyclopentyl; $R_3$ is H; and $R_4$ is H. In another embodiment is a compound of Formula (III) wherein $R_2$ is $C_3$-$C_6$cycloalkyl; $R_3$ is H; and $R_4$ is $CH_3$. In another embodiment is a compound of Formula (III) wherein $R_2$ is cyclopropyl; $R_3$ is H; and $R_4$ is $CH_3$. In another embodiment is a compound of Formula (III) wherein $R_2$ is cyclopentyl; $R_3$ is H; and $R_4$ is $CH_3$. In another embodiment is a compound of Formula (III) wherein $R_2$ is $C_3$-$C_6$cycloalkyl; $R_3$ is H; and $R_4$ is —CN. In another embodiment is a compound of Formula (III) wherein $R_2$ is cyclopropyl; $R_3$ is H; and $R_4$ is —CN. In another embodiment is a compound of Formula (III) wherein $R_2$ is cyclopentyl; $R_3$ is H; and $R_4$ is —CN.

In another embodiment is a compound of Formula (III) wherein $R_2$ and $R_3$ are taken together to form a 5- or 6-membered heterocyclic ring. In another embodiment is a compound of Formula (III) wherein $R_2$ and $R_3$ are taken together to form a 5- or 6-membered heterocyclic ring; and $R_4$ is H. In another embodiment is a compound of Formula (III) wherein $R_2$ and $R_3$ are taken together to form a 5-membered heterocyclic ring; and $R_4$ is H. In another embodiment is a compound of Formula (III) wherein $R_2$ and $R_3$ are taken together to form 6-membered heterocyclic ring; and $R_4$ is H.

In another embodiment is a compound of Formula (III) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (III) wherein each $R_1$ is independently halogen, —CN, —OH, —CF$_3$, substituted or unsubstituted $C_1$-$C_6$alkyl, or substituted or unsubstituted $C_1$-$C_6$alkoxy. In another embodiment is a compound of Formula (III) wherein each $R_1$ is independently halogen, —CN, —OCF$_3$, —OCH$_2$F, —OCF$_2$H, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (III) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy. In another embodiment is a compound of Formula (III) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 3. In another embodiment is a compound of Formula (III) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 2. In another embodiment is a compound of Formula (III) wherein n is 3, and each $R_1$ is independently halogen. In another embodiment is a compound of Formula (III) wherein n is 2, and each $R_1$ is independently halogen. In another embodiment is a compound of Formula (III) wherein n is 2, and each $R_1$ is independently F or Cl. In another embodiment is a compound of Formula (III) wherein n is 2, and each $R_1$ is F. In another embodiment is a compound of Formula (III) wherein n is 2, and each $R_1$ is independently Cl. In another embodiment is a compound of Formula (III) wherein n is 2, and each $R_1$ is independently halogen or —CF$_3$. In another embodiment is a compound of Formula (III) wherein n is 2, and each $R_1$ is independently F or —CF$_3$. In another embodiment is a compound of Formula (III) wherein n is 2, and each $R_1$ is independently Cl or —CF$_3$. In another embodiment is a compound of Formula (III) wherein n is 1, and $R_1$ is halogen. In another embodiment is a compound of Formula (III) wherein n is 1, and $R_1$ is F. In another embodiment is a compound of Formula (III) wherein n is 1, and $R_1$ is Cl. In another embodiment is a compound of Formula (III) wherein n is 1, and $R_1$ is —CF$_3$. In another embodiment is a compound of Formula (III) wherein n is 1, and $R_1$ is substituted or unsubstituted $C_1$-$C_6$alkyl. In another embodiment is a compound of Formula (III) wherein n is 1, and $R_1$ is CH$_3$. In another embodiment is a compound of Formula (III) wherein n is 1, and $R_1$ is substituted or unsubstituted $C_1$-$C_6$alkoxy. In another embodiment is a compound of Formula (III) wherein n is 1, and $R_1$ is —OCH$_3$. In another embodiment is a compound of Formula (III) wherein n is 1, and $R_1$ is —OCF$_3$. In another embodiment is a compound of Formula (III) wherein n is 1, and $R_1$ is —OCF$_2$H.

In another aspect, described herein is a compound of Formula (IIIA):

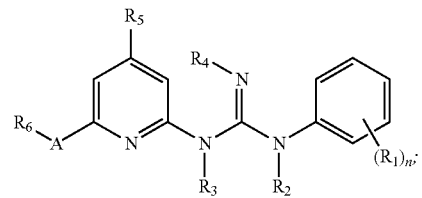

Formula (IIIA)

wherein:

A is a bond, O, CH$_2$, or N($R_{10}$);

each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H; or two of $R_2$, $R_3$, and $R_4$ are taken together to form a 5- or 6-membered heterocyclic ring;

$R_5$ is halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —(C(R$_{14}$)(R$_{15}$))$_m$R$_{21}$, —(C(R$_{14}$)(R$_{15}$))$_m$N(R$_{11}$)(R$_{12}$), or

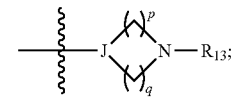

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkylC$_6$-$C_{10}$aryl, or substituted or unsubstituted —$C_1$-$C_4$alkylC$_2$-$C_7$heteroaryl;

each $R_7$ is independently H, halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —NO$_2$, —OH, —OCF$_3$, —OCH$_2$F, —OCF$_2$H, —CF$_3$, —SR$_{22}$, —N(R$_{22}$)S(=O)$_2$R$_{23}$, —S(=O)$_2$N(R$_{22}$)$_2$, —S(=O)R$_{23}$, —S(=O)$_2$R$_{23}$, —C(=O)R$_{23}$, —CO$_2$R$_{22}$, —C(=O)N(R$_{22}$)$_2$, —N(R$_{22}$)C(=O)R$_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In another embodiment is a compound of Formula (IIIA) wherein A is O, CH$_2$, or N(R$_{10}$)—In another embodiment is a compound of Formula (IIIA) wherein A is O, CH$_2$, or N(H). In another embodiment is a compound of Formula (IIIA) wherein A is O. In another embodiment is a compound of Formula (IIIA) wherein A is CH$_2$. In another embodiment is a compound of Formula (IIIA) wherein A is N(R$_{10}$). In another embodiment is a compound of Formula (IIIA) wherein A is N(H). In another embodiment is a compound of Formula (IIIA) wherein A is N(CH$_3$). In another embodiment is a compound of Formula (IIIA) wherein A is a bond.

In another embodiment is a compound of Formula (IIIA) wherein $R_6$ is substituted or unsubstituted $C_3$-$C_8$cycloalkyl. In another embodiment is a compound of Formula (IIIA) wherein $R_6$ is substituted or unsubstituted cyclopropyl. In another embodiment is a compound of Formula (IIIA) wherein $R_6$ is substituted or unsubstituted cyclobutyl. In another embodiment is a compound of Formula (IIIA) wherein $R_6$ is substituted or unsubstituted cyclopentyl. In another embodiment is a compound of Formula (IIIA) wherein $R_6$ is substituted or unsubstituted cyclohexyl.

In another embodiment is a compound of Formula (IIIA) wherein $R_6$ is substituted or unsubstituted $C_2$-$C_7$heteroaryl. In another embodiment is a compound of Formula (IIIA) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IIIA) wherein $R_6$ is substituted or unsubstituted pyridyl. In another embodiment is a compound of Formula (IIIA) wherein $R_6$ is substituted pyridyl. In another embodiment is a compound of Formula (IIIA) wherein $R_6$ is unsubstituted pyridyl.

In another embodiment is a compound of Formula (IIIA) wherein $R_6$ is —(C(R$_{14}$)(R$_{15}$))$_m$R$_{21}$. In another embodiment is a compound of Formula (IIIA) wherein $R_6$ is —(C(R$_{14}$)(R$_{15}$))$_m$R$_{21}$, and each $R_{14}$ and $R_{15}$ are H. In another embodiment is a compound of Formula (IIIA) wherein $R_6$ is —(C(R$_{14}$)(R$_{15}$))$_m$R$_{21}$, m is 2, and each $R_{14}$ and $R_{15}$ are H. In another embodiment is a compound of Formula (IIIA) wherein $R_6$ is —(CH$_2$)$_m$R$_{21}$, m is 2, and $R_{21}$ is substituted or unsubstituted $C_2$-$C_7$heterocycloalkyl. In another embodiment is a compound of Formula (IIIA) wherein $R_6$ is —(CH$_2$)$_m$R$_{21}$, m is 2, and $R_{21}$ is substituted or unsubstituted $C_3$-$C_8$cycloalkyl. In another embodiment is a compound of Formula (IIIA) wherein $R_6$ is —(CH$_2$)$_m$R$_{21}$, m is 2, and $R_{21}$ is substituted or unsubstituted $C_6$-$C_{10}$aryl. In another embodiment is a compound of Formula (IIIA) wherein $R_6$ is —(CH$_2$)$_m$R$_{21}$, m is 2, and $R_{21}$ is substituted or unsubstituted phenyl. In another embodiment is a compound of Formula (IIIA) wherein $R_6$ is —(CH$_2$)$_m$R$_{21}$, m is 2, and $R_{21}$ is substituted or unsubstituted $C_2$-$C_7$heteroaryl.

In another embodiment is a compound of Formula (IIIA) wherein $R_6$ is —(C(R$_{14}$)(R$_{15}$))$_m$R$_{21}$, m is 3, and each $R_{14}$ and $R_{15}$ are H. In another embodiment is a compound of Formula (IIIA) wherein $R_6$ is —(CH$_2$)$_m$R$_{21}$, m is 3, and $R_{21}$ is substituted or unsubstituted $C_2$-$C_7$heterocycloalkyl. In another embodiment is a compound of Formula (IIIA) wherein $R_6$ is —(CH$_2$)$_m$R$_{21}$, m is 3, and $R_{21}$ is substituted or unsubstituted $C_3$-$C_8$cycloalkyl. In another embodiment is a compound of Formula (IIIA) wherein $R_6$ is —(CH$_2$)$_m$R$_{21}$, m is 3, and $R_{21}$ is substituted or unsubstituted $C_6$-$C_{10}$aryl. In another embodiment is a compound of Formula (IIIA) wherein $R_6$ is —(CH$_2$)$_m$R$_{21}$, m is 3, and $R_{21}$ is substituted or unsubstituted phenyl. In another embodiment is a compound of Formula (IIIA) wherein $R_6$ is —(CH$_2$)$_m$R$_{21}$, m is 3, and $R_{21}$ is substituted or unsubstituted $C_2$-$C_7$heteroaryl.

In another embodiment is a compound of Formula (IIIA) wherein $R_6$ is —(C(R$_{14}$)(R$_{15}$))$_m$N(R$_{11}$)(R$_{12}$). In another embodiment is a compound of Formula (IIIA) wherein $R_6$ is —(C(R$_{14}$)(R$_{15}$))$_m$N(R$_{11}$)(R$_{12}$), m is 2, and each $R_{14}$ and $R_{15}$ are H. In another embodiment is a compound of Formula (IIIA) wherein $R_6$ is —(CH$_2$)$_m$N(R$_{11}$)(R$_{12}$), m is 2, and $R_{11}$ and $R_{12}$ are each H. In another embodiment is a compound of Formula (IIIA) wherein $R_6$ is —(CH$_2$)$_m$N(R$_{11}$)(R$_{12}$), m is 2, $R_{11}$ is substituted or unsubstituted $C_1$-$C_6$alkyl, and $R_{12}$ is H. In another embodiment is a compound of Formula (IIIA) wherein $R_6$ is —(CH$_2$)$_m$N(R$_{11}$)(R$_{12}$), m is 2, $R_{11}$ is CH$_3$, and $R_{12}$ is H. In another embodiment is a compound of Formula (IIIA) wherein $R_6$ is —(CH$_2$)$_m$N(R$_{11}$)(R$_{12}$), m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IIIA) wherein $R_6$ is —(CH$_2$)$_m$N(R$_{11}$)(R$_{12}$), m is 2, $R_{11}$ is CH$_3$, and $R_{12}$ is CH$_3$. In another embodiment is a compound of Formula (IIIA) wherein $R_6$ is —(CH$_2$)$_m$N(R$_{11}$)(R$_{12}$), m is 2, and $R_{11}$ and $R_{12}$ are taken together to form a 5-, 6-, 7-, or 8-membered heterocyclic ring. In another embodiment is a compound of Formula (IIIA) wherein $R_6$ is —(CH$_2$)$_m$N(R$_{11}$)(R$_{12}$), m is 2, and $R_{11}$ and $R_{12}$ are taken together to form a 5-membered heterocyclic ring. In another embodiment is a compound of Formula (IIIA) wherein $R_6$ is —$(CH_2)_mN(R_{11})(R_{12})$, m is 2, and $R_{11}$ and $R_{12}$ are taken together to form a 6-membered heterocyclic ring.

In another embodiment is a compound of Formula (IIIA) wherein $R_6$ is —$(C(R_{14})(R_{15}))_mN(R_{11})(R_{12})$. In another embodiment is a compound of Formula (IIIA) wherein $R_6$ is —$(C(R_{14})(R_{15}))_mN(R_{11})(R_{12})$, m is 3, and each $R_{14}$ and $R_{15}$ are H. In another embodiment is a compound of Formula (IIIA) wherein $R_6$ is —$(CH_2)_mN(R_{11})(R_{12})$, m is 3, and $R_{11}$ and $R_{12}$ are each H. In another embodiment is a compound of Formula (IIIA) wherein $R_6$ is —$(CH_2)_mN(R_{11})(R_{12})$, m is 3, $R_{11}$ is substituted or unsubstituted $C_1$-$C_6$alkyl, and $R_{12}$ is H. In another embodiment is a compound of Formula (IIIA) wherein $R_6$ is —$(CH_2)_mN(R_{11})(R_{12})$, m is 3, $R_{11}$ is $CH_3$, and $R_{12}$ is H. In another embodiment is a compound of Formula (IIIA) wherein $R_6$ is —$(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IIIA) wherein $R_6$ is —$(CH_2)_mN(R_{11})(R_{12})$, m is 3, $R_{11}$ is $CH_3$, and $R_{12}$ is $CH_3$. In another embodiment is a compound of Formula (IIIA) wherein $R_6$ is —$(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (IIIA) wherein $R_6$ is —$(CH_2)_mN(R_{11})(R_{12})$, m is 3, and $R_{11}$ and $R_{12}$ are taken together to form a 5-membered heterocyclic ring. In another embodiment is a compound of Formula (IIIA) wherein $R_6$ is —$(CH_2)_mN(R_{11})(R_{12})$, m is 3, and $R_{11}$ and $R_{12}$ are taken together to form a 6-membered heterocyclic ring.

In another embodiment is a compound of Formula (IIIA) wherein $R_6$ is substituted or unsubstituted $C_2$-$C_7$heterocycloalkyl. In another embodiment is a compound of Formula (IIIA) wherein $R_6$ is

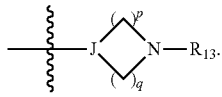

In another embodiment is a compound of Formula (IIIA) wherein $R_6$ is

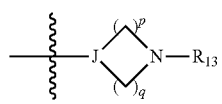

and J is C(H). In another embodiment is a compound of Formula (IIIA) wherein $R_6$ is

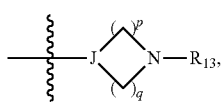

J is C(H), p is 1, and q is 1. In another embodiment is a compound of Formula (IIIA) wherein $R_6$ is

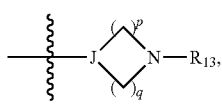

J is C(H), p is 2, and q is 1. In another embodiment is a compound of Formula (IIIA) wherein $R_6$ is

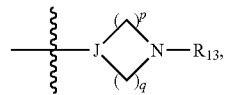

J is C(H), p is 3, and q is 1. In another embodiment is a compound of Formula (IIIA) wherein $R_6$ is

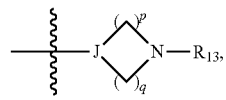

J is C(H), p is 2, and q is 2. In another embodiment is a compound of Formula (IIIA) wherein $R_6$ is

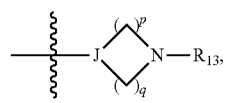

J is C(H), p is 1, q is 1, and $R_{13}$ is substituted or unsubstituted $C_1$-$C_6$alkyl. In another embodiment is a compound of Formula (IIIA) wherein $R_6$ is

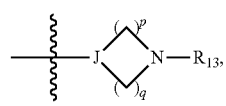

J is C(H), p is 2, q is 1, and $R_{13}$ is substituted or unsubstituted $C_1$-$C_6$alkyl. In another embodiment is a compound of Formula (IIIA) wherein $R_6$ is

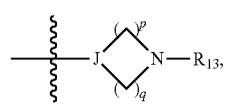

J is C(H), p is 3, q is 1, and $R_{13}$ is substituted or unsubstituted $C_1$-$C_6$alkyl. In another embodiment is a compound of Formula (IIIA) wherein $R_6$ is

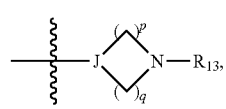

J is C(H), p is 2, q is 2, and $R_{13}$ is substituted or unsubstituted $C_1$-$C_6$alkyl.

In another embodiment is a compound of Formula (IIIA) wherein $R_6$ is

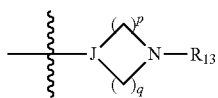

and J is N. In another embodiment is a compound of Formula (IIIA) wherein $R_6$ is

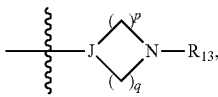

J is N, p is 2, and q is 2. In another embodiment is a compound of Formula (IIIA) wherein $R_6$ is

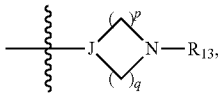

J is N, p is 2, q is 2, and $R_{13}$ is substituted or unsubstituted $C_1$-$C_6$alkyl.

In another embodiment is a compound of Formula (IIIA) wherein $R_5$ is halogen. In another embodiment is a compound of Formula (IIIA) wherein $R_5$ is —$CF_3$. In another embodiment is a compound of Formula (IIIA) wherein $R_5$ is substituted or unsubstituted $C_1$-$C_6$alkyl. In another embodiment is a compound of Formula (IIIA) wherein $R_5$ is —$CH_3$. In another embodiment is a compound of Formula (IIIA) wherein $R_5$ is —$CH_2CH_3$. In another embodiment is a compound of Formula (IIIA) wherein $R_5$ is substituted or unsubstituted $C_1$-$C_6$heteroalkyl. In another embodiment is a compound of Formula (IIIA) wherein $R_5$ is substituted or unsubstituted $C_2$-$C_7$heterocycloalkyl. In another embodiment is a compound of Formula (IIIA) wherein $R_5$ is substituted or unsubstituted $C_3$-$C_8$cycloalkyl. In another embodiment is a compound of Formula (IIIA) wherein $R_5$ is substituted or unsubstituted $C_6$-$C_{10}$aryl. In another embodiment is a compound of Formula (IIIA) wherein $R_5$ is substituted or unsubstituted $C_2$-$C_7$heteroaryl.

In another embodiment is a compound of Formula (IIIA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H. In another embodiment is a compound of Formula (IIIA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least two of $R_2$, $R_3$, and $R_4$ are not H. In another embodiment is a compound of Formula (IIIA) wherein $R_2$ is H; $R_3$ is $C_1$-$C_4$alkyl; and $R_4$ is H. In another embodiment is a compound of Formula (IIIA) wherein $R_2$ is H; $R_3$ is $CH_3$; and $R_4$ is H. In another embodiment is a compound of Formula (IIIA) wherein $R_2$ is H; $R_3$ is $C_1$-$C_4$alkyl; and $R_4$ is $C_1$-$C_4$alkyl. In another embodiment is a compound of Formula (IIIA) wherein $R_2$ is H; $R_3$ is $CH_3$; and $R_4$ is $CH_3$. In another embodiment is a compound of Formula (IIIA) wherein $R_2$ is H; $R_3$ is $C_1$-$C_4$alkyl; and $R_4$ is —CN. In another embodiment is a compound of Formula (IIIA) wherein $R_2$ is H; $R_3$ is $CH_3$; and $R_4$ is —CN. In another embodiment is a compound of Formula (IIIA) wherein $R_2$ is $C_1$-$C_4$alkyl; $R_3$ is $C_1$-$C_4$alkyl; and $R_4$ is H. In another embodiment is a compound of Formula (IIIA) wherein $R_2$ is $CH_3$; $R_3$ is $CH_3$; and $R_4$ is H. In another embodiment is a compound of Formula (IIIA) wherein $R_2$ is $C_1$-$C_4$alkyl; $R_3$ is H; and $R_4$ is H. In another embodiment is a compound of Formula (IIIA) wherein $R_2$ is $CH_3$; $R_3$ is H; and $R_4$ is H. In another embodiment is a compound of Formula (IIIA) wherein $R_2$ is $C_1$-$C_4$alkyl; $R_3$ is H; and $R_4$ is $C_1$-$C_4$alkyl. In another embodiment is a compound of Formula (IIIA) wherein $R_2$ is $CH_3$; $R_3$ is H; and $R_4$ is $CH_3$. In another embodiment is a compound of Formula (IIIA) wherein $R_2$ is $C_1$-$C_4$alkyl; $R_3$ is H; and $R_4$ is —CN. In another embodiment is a compound of Formula (IIIA) wherein $R_2$ is $CH_3$; $R_3$ is H; and $R_4$ is —CN. In another embodiment is a compound of Formula (IIIA) wherein $R_2$ is $C_3$-$C_6$cycloalkyl; $R_3$ is H; and $R_4$ is H. In another embodiment is a compound of Formula (IIIA) wherein $R_2$ is cyclopropyl; $R_3$ is H; and $R_4$ is H. In another embodiment is a compound of Formula (IIIA) wherein $R_2$ is cyclopentyl; $R_3$ is H; and $R_4$ is H. In another embodiment is a compound of Formula (IIIA) wherein $R_2$ is $C_3$-$C_6$cycloalkyl; $R_3$ is H; and $R_4$ is $CH_3$. In another embodiment is a compound of Formula (IIIA) wherein $R_2$ is cyclopropyl; $R_3$ is H; and $R_4$ is $CH_3$. In another embodiment is a compound of Formula (IIIA) wherein $R_2$ is cyclopentyl; $R_3$ is H; and $R_4$ is $CH_3$. In another embodiment is a compound of Formula (IIIA) wherein $R_2$ is $C_3$-$C_6$cycloalkyl; $R_3$ is H; and $R_4$ is —CN. In another embodiment is a compound of Formula (IIIA) wherein $R_2$ is cyclopropyl; $R_3$ is H; and $R_4$ is —CN. In another embodiment is a compound of Formula (IIIA) wherein $R_2$ is cyclopentyl; $R_3$ is H; and $R_4$ is —CN.

In another embodiment is a compound of Formula (IIIA) wherein $R_2$ and $R_3$ are taken together to form a 5- or 6-membered heterocyclic ring. In another embodiment is a compound of Formula (IIIA) wherein $R_2$ and $R_3$ are taken together to form a 5- or 6-membered heterocyclic ring; and $R_4$ is H. In another embodiment is a compound of Formula (IIIA) wherein $R_2$ and $R_3$ are taken together to form a 5-membered heterocyclic ring; and $R_4$ is H. In another embodiment is a compound of Formula (IIIA) wherein $R_2$ and $R_3$ are taken together to form 6-membered heterocyclic ring; and $R_4$ is H.

In another embodiment is a compound of Formula (IIIA) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIIA) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment is a compound of Formula (IIIA) wherein each $R_1$ is independently halogen, —CN, —$OCF_3$, —$OCH_2F$, —$OCF_2H$, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIIA) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy. In another embodiment is a compound of Formula (IIIA) wherein each $R_1$ is independently halogen, —CN, —OCF$_3$, —OCH$_2$F, —OCF$_2$H, —CF$_3$, substituted or unsubstituted C$_1$-C$_6$alkyl, or substituted or unsubstituted C$_1$-C$_6$alkoxy, and n is 3. In another embodiment is a compound of Formula (IIIA) wherein each $R_1$ is independently halogen, —CN, —OCF$_3$, —OCH$_2$F, —OCF$_2$H, —CF$_3$, substituted or unsubstituted C$_1$-C$_6$alkyl, or substituted or unsubstituted C$_1$-C$_6$alkoxy, and n is 2. In another embodiment is a compound of Formula (IIIA) wherein n is 3, and each $R_1$ is independently halogen. In another embodiment is a compound of Formula (IIIA) wherein n is 2, and each $R_1$ is independently halogen. In another embodiment is a compound of Formula (IIIA) wherein n is 2, and each $R_1$ is independently F or Cl. In another embodiment is a compound of Formula (IIIA) wherein n is 2, and each $R_1$ is F. In another embodiment is a compound of Formula (IIIA) wherein n is 2, and each $R_1$ is independently Cl. In another embodiment is a compound of Formula (IIIA) wherein n is 2, and each $R_1$ is independently halogen or —CF$_3$. In another embodiment is a compound of Formula (IIIA) wherein n is 2, and each $R_1$ is independently F or —CF$_3$. In another embodiment is a compound of Formula (IIIA) wherein n is 2, and each $R_1$ is independently Cl or —CF$_3$. In another embodiment is a compound of Formula (IIIA) wherein n is 1, and $R_1$ is halogen. In another embodiment is a compound of Formula (IIIA) wherein n is 1, and $R_1$ is F. In another embodiment is a compound of Formula (IIIA) wherein n is 1, and $R_1$ is Cl. In another embodiment is a compound of Formula (IIIA) wherein n is 1, and $R_1$ is —CF$_3$. In another embodiment is a compound of Formula (IIIA) wherein n is 1, and $R_1$ is substituted or unsubstituted C$_1$-C$_6$alkyl. In another embodiment is a compound of Formula (IIIA) wherein n is 1, and $R_1$ is CH$_3$. In another embodiment is a compound of Formula (IIIA) wherein n is 1, and $R_1$ is substituted or unsubstituted C$_1$-C$_6$alkoxy. In another embodiment is a compound of Formula (IIIA) wherein n is 1, and $R_1$ is —OCH$_3$. In another embodiment is a compound of Formula (IIIA) wherein n is 1, and $R_1$ is —OCF$_3$. In another embodiment is a compound of Formula (IIIA) wherein n is 1, and $R_1$ is —OCF$_2$H.

In another embodiment, described herein is a compound of Formula (IIIB):

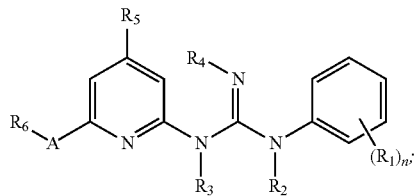

Formula (IIIB)

wherein:

A is O;

each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl; or two $R_1$ are taken together to form a substituted or unsubstituted heterocyclic ring or a substituted or unsubstituted carbocyclic ring;

$R_2$, $R_3$, and $R_4$ are each independently H, —CN, C$_1$-C$_4$alkyl, C$_3$-C$_6$cycloalkyl, or C$_2$-C$_7$heterocycloalkyl; or two of $R_2$, $R_3$, and $R_4$ are taken together to form a 5- or 6-membered heterocyclic ring;

$R_5$ is halogen, —CN, —OH, —CF$_3$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl;

$R_6$ is substituted or unsubstituted C$_2$-C$_7$heterocycloalkyl, substituted or unsubstituted C$_3$-C$_8$cycloalkyl, substituted or unsubstituted C$_2$-C$_7$heteroaryl, —(C(R$_{14}$)(R$_{15}$))$_m$R$_{21}$, —(C(R$_{14}$)(R$_{15}$))$_m$N(R$_{11}$)(R$_{12}$), or

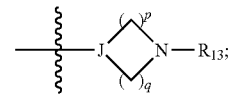

$R_{11}$ and $R_{12}$ are each independently H, or substituted or unsubstituted C$_1$-C$_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted C$_1$-C$_6$alkyl, substituted or unsubstituted C$_2$-C$_7$heterocycloalkyl, substituted or unsubstituted C$_3$-C$_8$cycloalkyl, substituted or unsubstituted —C$_1$-C$_4$alkylC$_6$-C$_{10}$aryl, or substituted or unsubstituted —C$_1$-C$_4$alkylC$_2$-C$_7$heteroaryl; each $R_7$ is independently H, halogen, —CN, —OH, —CF$_3$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl;

each $R_{14}$ and $R_{15}$ are each independently H, or substituted or unsubstituted C$_1$-C$_6$alkyl; or $R_{14}$ and $R_{15}$ are taken together to form a 4-, 5-, 6-membered cycloalkyl ring; $R_{21}$ is halogen, —CN, —NO$_2$, —OH, —OCF$_3$, —OCH$_2$F, —OCF$_2$H, —CF$_3$, —SR$_{22}$, —N(R$_{22}$)S(=O)$_2$R$_{23}$, —S(=O)$_2$N(R$_{22}$)$_2$, —S(=O)R$_{23}$, —S(=O)$_2$R$_{23}$, —C(=O)R$_{23}$, —CO$_2$R$_{22}$, —C(=O)N(R$_{22}$)$_2$, —N(R$_{22}$)C(=O)R$_{23}$, substituted or unsubstituted C$_1$-C$_6$alkyl, substituted or unsubstituted C$_1$-C$_6$alkoxy, substituted or unsubstituted C$_1$-C$_6$heteroalkyl, substituted or unsubstituted C$_2$-C$_7$heterocycloalkyl, substituted or unsubstituted C$_3$-C$_8$cycloalkyl, substituted or unsubstituted C$_6$-C$_{10}$aryl, or substituted or unsubstituted C$_2$-C$_7$heteroaryl;

each $R_{22}$ is independently H, or substituted or unsubstituted C$_1$-C$_6$alkyl; $R_{23}$ is substituted or unsubstituted C$_1$-C$_6$alkyl;

each $R_8$ is independently H, or substituted or unsubstituted $C_1$-$C_6$alkyl;

$R_9$ is substituted or unsubstituted $C_1$-$C_6$alkyl;

m is 2-6;

n is 0-5;

p is 1-3;

q is 1-3; or a pharmaceutically acceptable salt, solvate, or prodrug thereof.

In another embodiment is a compound of Formula (IIIB) wherein $R_6$ is substituted or unsubstituted $C_3$-$C_8$cycloalkyl. In another embodiment is a compound of Formula (IIIB) wherein $R_6$ is substituted or unsubstituted cyclopropyl. In another embodiment is a compound of Formula (IIIB) wherein $R_6$ is substituted or unsubstituted cyclobutyl. In another embodiment is a compound of Formula (IIIB) wherein $R_6$ is substituted or unsubstituted cyclopentyl. In another embodiment is a compound of Formula (IIIB) wherein $R_6$ is substituted or unsubstituted cyclohexyl.

In another embodiment is a compound of Formula (IIIB) wherein $R_6$ is substituted or unsubstituted $C_2$-$C_7$heteroaryl. In another embodiment is a compound of Formula (IIIB) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IIIB) wherein $R_6$ is substituted or unsubstituted pyridyl. In another embodiment is a compound of Formula (IIIB) wherein $R_6$ is substituted pyridyl. In another embodiment is a compound of Formula (IIIB) wherein $R_6$ is unsubstituted pyridyl.

In another embodiment is a compound of Formula (IIIB) wherein $R_6$ is —$(C(R_{14})(R_{15}))_m R_{21}$. In another embodiment is a compound of Formula (IIIB) wherein $R_6$ is —$(C(R_{14})(R_{15}))_m R_{21}$, and each $R_{14}$ and $R_{15}$ are H. In another embodiment is a compound of Formula (IIIB) wherein $R_6$ is —$(C(R_{14})(R_{15}))_m R_{21}$, m is 2, and each $R_{14}$ and $R_{15}$ are H. In another embodiment is a compound of Formula (IIIB) wherein $R_6$ is —$(CH_2)_m R_{21}$, m is 2, and $R_{21}$ is substituted or unsubstituted $C_2$-$C_7$heterocycloalkyl. In another embodiment is a compound of Formula (IIIB) wherein $R_6$ is —$(CH_2)_m R_{21}$, m is 2, and $R_{21}$ is substituted or unsubstituted $C_3$-$C_8$cycloalkyl. In another embodiment is a compound of Formula (IIIB) wherein $R_6$ is —$(CH_2)_m R_{21}$, m is 2, and $R_{21}$ is substituted or unsubstituted $C_6$-$C_{10}$aryl. In another embodiment is a compound of Formula (IIIB) wherein $R_6$ is —$(CH_2)_m R_{21}$, m is 2, and $R_{21}$ is substituted or unsubstituted phenyl. In another embodiment is a compound of Formula (IIIB) wherein $R_6$ is —$(CH_2)_m R_{21}$, m is 2, and $R_{21}$ is substituted or unsubstituted $C_2$-$C_7$heteroaryl.

In another embodiment is a compound of Formula (IIIB) wherein $R_6$ is —$(C(R_{14})(R_{15}))_m R_{21}$, m is 3, and each $R_{14}$ and $R_{15}$ are H. In another embodiment is a compound of Formula (IIIB) wherein $R_6$ is —$(CH_2)_m R_{21}$, m is 3, and $R_{21}$ is substituted or unsubstituted $C_2$-$C_7$heterocycloalkyl. In another embodiment is a compound of Formula (IIIB) wherein $R_6$ is —$(CH_2)_m R_{21}$, m is 3, and $R_{21}$ is substituted or unsubstituted $C_3$-$C_8$cycloalkyl. In another embodiment is a compound of Formula (IIIB) wherein $R_6$ is —$(CH_2)_m R_{21}$, m is 3, and $R_{21}$ is substituted or unsubstituted $C_6$-$C_{10}$aryl. In another embodiment is a compound of Formula (IIIB) wherein $R_6$ is —$(CH_2)_m R_{21}$, m is 3, and $R_{21}$ is substituted or unsubstituted phenyl. In another embodiment is a compound of Formula (IIIB) wherein $R_6$ is —$(CH_2)_m R_{21}$, m is 3, and $R_{21}$ is substituted or unsubstituted $C_2$-$C_7$heteroaryl.

In another embodiment is a compound of Formula (IIIB) wherein $R_6$ is —$(C(R_{14})(R_{15}))_m N(R_{11})(R_{12})$—In another embodiment is a compound of Formula (IIIB) wherein $R_6$ is —$(C(R_{14})(R_{15}))_m N(R_{11})(R_{12})$, m is 2, and each $R_{14}$ and $R_{15}$ are H. In another embodiment is a compound of Formula (IIIB) wherein $R_6$ is —$(CH_2)_m N(R_{11})(R_{12})$, m is 2, and $R_{11}$ and $R_{12}$ are each H. In another embodiment is a compound of Formula (IIIB) wherein $R_6$ is —$(CH_2)_m N(R_{11})(R_{12})$, m is 2, $R_{11}$ is substituted or unsubstituted $C_1$-$C_6$alkyl, and $R_{12}$ is H. In another embodiment is a compound of Formula (IIIB) wherein $R_6$ is —$(CH_2)_m N(R_{11})(R_{12})$, m is 2, $R_{11}$ is $CH_3$, and $R_{12}$ is H. In another embodiment is a compound of Formula (IIIB) wherein $R_6$ is —$(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IIIB) wherein $R_6$ is —$(CH_2)_m N(R_{11})(R_{12})$, m is 2, $R_{11}$ is $CH_3$, and $R_{12}$ is $CH_3$. In another embodiment is a compound of Formula (IIIB) wherein $R_6$ is —$(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (IIIB) wherein $R_6$ is —$(CH_2)_m N(R_{11})(R_{12})$, m is 2, and $R_{11}$ and $R_{12}$ are taken together to form a 5-membered heterocyclic ring. In another embodiment is a compound of Formula (IIIB) wherein $R_6$ is —$(CH_2)_m N(R_{11})(R_{12})$, m is 2, and $R_{11}$ and $R_{12}$ are taken together to form a 6-membered heterocyclic ring.

In another embodiment is a compound of Formula (IIIB) wherein $R_6$ is —$(C(R_{14})(R_{15}))_m N(R_{11})(R_{12})$. In another embodiment is a compound of Formula (IIIB) wherein $R_6$ is —$(C(R_{14})(R_{15}))_m N(R_{11})(R_{12})$, m is 3, and each $R_{14}$ and $R_{15}$ are H. In another embodiment is a compound of Formula (IIIB) wherein $R_6$ is —$(CH_2)_m N(R_{11})(R_{12})$, m is 3, and $R_{11}$ and $R_{12}$ are each H. In another embodiment is a compound of Formula (IIIB) wherein $R_6$ is —$(CH_2)_m N(R_{11})(R_{12})$, m is 3, $R_{11}$ is substituted or unsubstituted $C_1$-$C_6$alkyl, and $R_{12}$ is H. In another embodiment is a compound of Formula (IIIB) wherein $R_6$ is —$(CH_2)_m N(R_{11})(R_{12})$, m is 3, $R_{11}$ is $CH_3$, and $R_{12}$ is H. In another embodiment is a compound of Formula (IIIB) wherein $R_6$ is —$(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IIIB) wherein $R_6$ is —$(CH_2)_m N(R_{11})(R_{12})$, m is 3, $R_{11}$ is $CH_3$, and $R_{12}$ is $CH_3$. In another embodiment is a compound of Formula (IIIB) wherein $R_6$ is —$(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (IIIB) wherein $R_6$ is —$(CH_2)_m N(R_{11})(R_{12})$, m is 3, and $R_{11}$ and $R_{12}$ are taken together to form a 5-membered heterocyclic ring. In another embodiment is a compound of Formula (IIIB) wherein $R_6$ is —$(CH_2)_m N(R_{11})(R_{12})$, m is 3, and $R_{11}$ and $R_{12}$ are taken together to form a 6-membered heterocyclic ring.

In another embodiment is a compound of Formula (IIIB) wherein $R_6$ is substituted or unsubstituted $C_2$-$C_7$heterocycloalkyl. In another embodiment is a compound of Formula (IIIB) wherein $R_6$ is

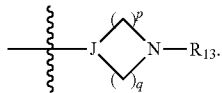

In another embodiment is a compound of Formula (IIIB) wherein $R_6$ is

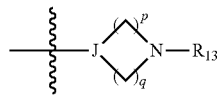

and J is C(H). In another embodiment is a compound of Formula (IIIB) wherein $R_6$ is

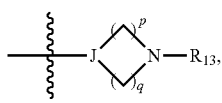

J is C(H), p is 1, and q is 1. In another embodiment is a compound of Formula (IIIB) wherein $R_6$ is

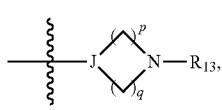

J is C(H), p is 2, and q is 1. In another embodiment is a compound of Formula (IIIB) wherein $R_6$ is

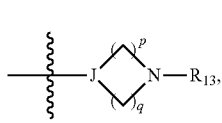

J is C(H), p is 3, and q is 1. In another embodiment is a compound of Formula (IIIB) wherein $R_6$ is

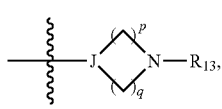

J is C(H), p is 2, and q is 2. In another embodiment is a compound of Formula (IIIB) wherein $R_6$ is

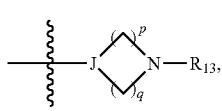

J is C(H), p is 1, q is 1, and $R_{13}$ is substituted or unsubstituted $C_1$-$C_6$alkyl. In another embodiment is a compound of Formula (IIIB) wherein $R_6$ is J is C(H), p is 2, q is 1, and $R_{13}$ is substituted or unsubstituted $C_1$-$C_6$alkyl. In another embodiment is a compound of Formula (IIIB) wherein $R_6$ is J is C(H), p is 3, q is 1, and $R_{13}$ is substituted or unsubstituted $C_1$-$C_6$alkyl. In another embodiment is a compound of Formula (IIIB) wherein $R_6$ is J is C(H), p is 2, q is 2, and $R_{13}$ is substituted or unsubstituted $C_1$-$C_6$alkyl.

In another embodiment is a compound of Formula (IIIB) wherein $R_5$ is halogen. In another embodiment is a compound of Formula (IIIB) wherein $R_5$ is —$CF_3$. In another embodiment is a compound of Formula (IIIB) wherein $R_5$ is substituted or unsubstituted $C_1$-$C_6$alkyl. In another embodiment is a compound of Formula (IIIB) wherein $R_5$ is —$CH_3$. In another embodiment is a compound of Formula (IIIB) wherein $R_5$ is —$CH_2CH_3$. In another embodiment is a compound of Formula (IIIB) wherein $R_5$ is substituted or unsubstituted $C_1$-$C_6$heteroalkyl. In another embodiment is a compound of Formula (IIIB) wherein $R_5$ is substituted or unsubstituted $C_2$-$C_7$heterocycloalkyl. In another embodiment is a compound of Formula (IIIB) wherein $R_5$ is substituted or unsubstituted $C_3$-$C_8$cycloalkyl. In another embodiment is a compound of Formula (IIIB) wherein $R_5$ is substituted or unsubstituted $C_6$-$C_{10}$aryl. In another embodiment is a compound of Formula (IIIB) wherein $R_5$ is substituted or unsubstituted $C_2$-$C_7$heteroaryl.

In another embodiment is a compound of Formula (IIIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (IIIB) wherein $R_2$, $R_3$, and $R_4$ are each H.

In another embodiment is a compound of Formula (IIIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (IIIB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (IIIB) wherein $R_2$ is H; $R_3$ is $C_1$-$C_4$alkyl; and $R_4$ is H. In another embodiment is a compound of Formula (IIIB) wherein $R_2$ is H; $R_3$ is $CH_3$; and $R_4$ is H. In another embodiment is a compound of Formula (IIIB) wherein $R_2$ is H; $R_3$ is $C_1$-$C_4$alkyl; and $R_4$ is $C_1$-$C_4$alkyl. In another embodiment is a compound of Formula (IIIB) wherein $R_2$ is H; $R_3$ is $CH_3$; and $R_4$ is $CH_3$. In another embodiment is a compound of Formula (IIIB) wherein $R_2$ is H; $R_3$ is $C_1$-$C_4$alkyl; and $R_4$ is —CN. In another embodiment is a compound of Formula (IIIB) wherein $R_2$ is H; $R_3$ is $CH_3$; and $R_4$ is —CN. In another embodiment is a compound of Formula (IIIB) wherein $R_2$ is $C_1$-$C_4$alkyl; $R_3$ is $C_1$-$C_4$alkyl; and $R_4$ is H. In another embodiment is a compound of Formula (IIIB) wherein $R_2$ is $CH_3$; $R_3$ is $CH_3$; and $R_4$ is H. In another embodiment is a compound of Formula (IIIB) wherein $R_2$ is $C_1$-$C_4$alkyl; $R_3$ is H; and $R_4$ is H. In another embodiment is a compound of Formula (IIIB) wherein $R_2$ is $CH_3$; $R_3$ is H; and $R_4$ is H. In another embodiment is a compound of Formula (IIIB) wherein $R_2$ is $C_1$-$C_4$alkyl; $R_3$ is H; and $R_4$ is $C_1$-$C_4$alkyl. In another embodiment is a compound of Formula (IIIB) wherein $R_2$ is $CH_3$; $R_3$ is H; and $R_4$ is $CH_3$. In another embodiment is a compound of Formula (IIIB) wherein $R_2$ is $C_1$-$C_4$alkyl; $R_3$ is H; and $R_4$ is —CN. In another embodiment is a compound of Formula (IIIB) wherein $R_2$ is $CH_3$; $R_3$ is H; and $R_4$ is —CN. In another embodiment is a compound of Formula (IIIB) wherein $R_2$ is $C_3$-$C_6$cycloalkyl; $R_3$ is H; and $R_4$ is H. In another embodiment is a compound of Formula (IIIB) wherein $R_2$ is cyclopropyl; $R_3$ is H; and $R_4$ is H. In another embodiment is a compound of Formula (IIIB) wherein $R_2$ is cyclopentyl; $R_3$ is H; and $R_4$ is H. In another embodiment is a compound of Formula (IIIB) wherein $R_2$ is $C_3$-$C_6$cycloalkyl; $R_3$ is H; and $R_4$ is $CH_3$. In another embodiment is a compound of Formula (IIIB) wherein $R_2$ is cyclopropyl; $R_3$ is H; and $R_4$ is $CH_3$. In another embodiment is a compound of Formula (IIIB) wherein $R_2$ is cyclopentyl; $R_3$ is H; and $R_4$ is $CH_3$. In another embodiment is a compound of Formula (IIIB) wherein $R_2$ is $C_3$-$C_6$cycloalkyl; $R_3$ is H; and $R_4$ is —CN. In another embodiment is a compound of Formula (IIIB) wherein $R_2$ is cyclopropyl; $R_3$ is H; and $R_4$ is —CN. In another embodiment is a compound of Formula (IIIB) wherein $R_2$ is cyclopentyl; $R_3$ is H; and $R_4$ is —CN.

In another embodiment is a compound of Formula (IIIB) wherein $R_2$ and $R_3$ are taken together to form a 5- or 6-membered heterocyclic ring. In another embodiment is a compound of Formula (IIIB) wherein $R_2$ and $R_3$ are taken together to form a 5- or 6-membered heterocyclic ring; and $R_4$ is H. In another embodiment is a compound of Formula (IIIB) wherein $R_2$ and $R_3$ are taken together to form a 5-membered heterocyclic ring; and $R_4$ is H. In another embodiment is a compound of Formula (IIIB) wherein $R_2$ and $R_3$ are taken together to form 6-membered heterocyclic ring; and $R_4$ is H.

In another embodiment is a compound of Formula (IIIB) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIIB) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment is a compound of Formula (IIIB) wherein each $R_1$ is independently halogen, —CN, —$OCF_3$, —$OCH_2F$, —$OCF_2H$, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IIIB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy. In another embodiment is a compound of Formula (IIIB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 3. In another embodiment is a compound of Formula (IIIB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 2. In another embodiment is a compound of Formula (IIIB) wherein n is 3, and each $R_1$ is independently halogen. In another embodiment is a compound of Formula (IIIB) wherein n is 2, and each $R_1$ is independently halogen. In another embodiment is a compound of Formula (IIIB) wherein n is 2, and each $R_1$ is independently F or Cl. In another embodiment is a compound of Formula (IIIB) wherein n is 2, and each $R_1$ is F. In another embodiment is a compound of Formula (IIIB) wherein n is 2, and each $R_1$ is independently Cl. In another embodiment is a compound of Formula (IIIB) wherein n is 2, and each $R_1$ is independently halogen or —$CF_3$. In another embodiment is a compound of Formula (IIIB) wherein n is 2, and each $R_1$ is independently F or —$CF_3$. In another embodiment is a compound of Formula (IIIB) wherein n is 2, and each $R_1$ is independently Cl or —$CF_3$. In another embodiment is a compound of Formula (IIIB) wherein n is 1, and $R_1$ is halogen. In another embodiment is a compound of Formula (IIIB) wherein n is 1, and $R_1$ is F. In another embodiment is a compound of Formula (IIIB) wherein n is 1, and $R_1$ is Cl. In another embodiment is a compound of Formula (IIIB) wherein n is 1, and $R_1$ is —$CF_3$. In another embodiment is a compound of Formula (IIIB) wherein n is 1, and $R_1$ is substituted or unsubstituted $C_1$-$C_6$alkyl. In another embodiment is a compound of Formula (IIIB) wherein n is 1, and $R_1$ is $CH_3$. In another embodiment is a compound of Formula (IIIB) wherein n is 1, and $R_1$ is substituted or unsubstituted $C_1$-$C_6$alkoxy. In another embodiment is a compound of Formula (IIIB) wherein n is 1, and $R_1$ is —$OCH_3$. In another embodiment is a compound of Formula (IIIB) wherein n is 1, and $R_1$ is —$OCF_3$. In another embodiment is a compound of Formula (IIIB) wherein n is 1, and $R_1$ is —$OCF_2H$.

In another aspect, described herein is a compound of Formula (IV):

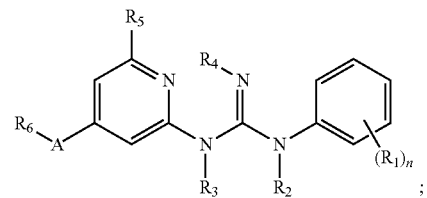

Formula (IV)

wherein:

A is a bond, O, $CH_2$, or $N(R_{10})$;

each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —S(=O)₂R₉, —C(=O)R₉, —CO₂R₈, —N(R₈)₂, —C(=O)N(R₈)₂, —N(R₈)C(=O)R₉, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl; or two R₁ are taken together to form a substituted or unsubstituted heterocyclic ring or a substituted or unsubstituted carbocyclic ring;

R₂, R₃, and R₄ are each independently H, —CN, C₁-C₄alkyl, C₃-C₆cycloalkyl, or C₂-C₇heterocycloalkyl; or two of R₂, R₃, and R₄ are taken together to form a 5- or 6-membered heterocyclic ring;

R₅ is halogen, —CN, —OH, —CF₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl;

R₆ is substituted or unsubstituted C₂-C₇heterocycloalkyl, substituted or unsubstituted C₃-C₈cycloalkyl, substituted or unsubstituted C₂-C₇heteroaryl, —C(R₁₄)(R₁₅))ₘR₂₁, —C(R₁₄)(R₁₅))ₘN(R₁₁)(R₁₂), or

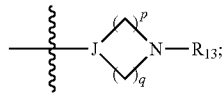

R₁₁ and R₁₂ are each independently H, or substituted or unsubstituted C₁-C₆alkyl; or R₁₁ and R₁₂ are taken together to form a 5-, 6-, 7-, or 8-membered heterocyclic ring; J is C(H), or N;

R₁₃ is H, substituted or unsubstituted C₁-C₆alkyl, substituted or unsubstituted C₂-C₇heterocycloalkyl, substituted or unsubstituted C₃-C₈cycloalkyl, substituted or unsubstituted —C₁-C₄alkylC₆-C₁₀aryl, or substituted or unsubstituted —C₁-C₄alkylC₂-C₇heteroaryl;

each R₇ is independently H, halogen, —CN, —OH, —CF₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl;

each R₁₄ and R₁₅ are each independently H, or substituted or unsubstituted C₁-C₆alkyl; or R₁₄ and R₁₅ are taken together to form a 4-, 5-, 6-membered cycloalkyl ring;

R₂₁ is halogen, —CN, —NO₂, —OH, —OCF₃, —OCH₂F, —OCF₂H, —CF₃, —SR₂₂, —N(R₂₂)S(=O)₂R₂₃, —S(=O)₂N(R₂₂)₂, —S(=O)R₂₃, —S(=O)₂R₂₃, —C(=O)R₂₃, —CO₂R₂₂, —C(=O)N(R₂₂)₂, —N(R₂₂)C(=O)R₂₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl;

each R₂₂ is independently H, or substituted or unsubstituted C₁-C₆alkyl;

R₂₃ is substituted or unsubstituted C₁-C₆alkyl;

each R₈ is independently H, or substituted or unsubstituted C₁-C₆alkyl;

R₉ is substituted or unsubstituted C₁-C₆alkyl;

R₁₀ is H, or C₁-C₄alkyl;

m is 2-6;

n is 0-5;

p is 1-3;

q is 1-3; or a pharmaceutically acceptable salt, solvate, or prodrug thereof.

In another embodiment is a compound of Formula (IV) wherein A is O, CH₂, or N(R₁₀). In another embodiment is a compound of Formula (IV) wherein A is O, CH₂, or N(H). In another embodiment is a compound of Formula (IV) wherein A is O. In another embodiment is a compound of Formula (IV) wherein A is CH₂. In another embodiment is a compound of Formula (IV) wherein A is N(R₁₀). In another embodiment is a compound of Formula (IV) wherein A is N(H). In another embodiment is a compound of Formula (IV) wherein A is N(CH₃). In another embodiment is a compound of Formula (IV) wherein A is a bond.

In another embodiment is a compound of Formula (IV) wherein R₆ is substituted or unsubstituted C₃-C₈cycloalkyl. In another embodiment is a compound of Formula (IV) wherein R₆ is substituted or unsubstituted cyclopropyl. In another embodiment is a compound of Formula (IV) wherein R₆ is substituted or unsubstituted cyclobutyl. In another embodiment is a compound of Formula (IV) wherein R₆ is substituted or unsubstituted cyclopentyl. In another embodiment is a compound of Formula (IV) wherein R₆ is substituted or unsubstituted cyclohexyl.

In another embodiment is a compound of Formula (IV) wherein R₆ is substituted or unsubstituted C₂-C₇heteroaryl. In another embodiment is a compound of Formula (IV) wherein R₆ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IV) wherein R₆ is substituted or unsubstituted pyridyl. In another embodiment is a compound of Formula (IV) wherein R₆ is substituted pyridyl. In another embodiment is a compound of Formula (IV) wherein R₆ is unsubstituted pyridyl.

In another embodiment is a compound of Formula (IV) wherein R₆ is —C(R₁₄)(R₁₅))ₘR₂₁. In another embodiment is a compound of Formula (IV) wherein R₆ is —C(R₁₄)(R₁₅))ₘR₂₁, and each R₁₄ and R₁₅ are H. In another embodiment is a compound of Formula (IV) wherein R₆ is —C(R₁₄)(R₁₅))ₘR₂₁, m is 2, and each R₁₄ and R₁₅ are H. In another embodiment is a compound of Formula (IV) wherein R₆ is —(CH₂)ₘR₂₁, m is 2, and R₂₁ is substituted or unsubstituted C₂-C₇heterocycloalkyl. In another embodiment is a compound of Formula (IV) wherein $R_6$ is —$(CH_2)_mR_{21}$, m is 2, and $R_{21}$ is substituted or unsubstituted $C_3$-$C_8$cycloalkyl. In another embodiment is a compound of Formula (IV) wherein $R_6$ is —$(CH_2)_mR_{21}$, m is 2, and $R_{21}$ is substituted or unsubstituted $C_6$-$C_{10}$aryl. In another embodiment is a compound of Formula (IV) wherein $R_6$ is —$(CH_2)_mR_{21}$, m is 2, and $R_{21}$ is substituted or unsubstituted phenyl. In another embodiment is a compound of Formula (IV) wherein $R_6$ is —$(CH_2)_mR_{21}$, m is 2, and $R_{21}$ is substituted or unsubstituted $C_2$-$C_7$heteroaryl.

In another embodiment is a compound of Formula (IV) wherein $R_6$ is —$(C(R_{14})(R_{15}))_mR_{21}$, m is 3, and each $R_{14}$ and $R_{15}$ are H. In another embodiment is a compound of Formula (IV) wherein $R_6$ is —$(CH_2)_mR_{21}$, m is 3, and $R_{21}$ is substituted or unsubstituted $C_2$-$C_7$heterocycloalkyl. In another embodiment is a compound of Formula (IV) wherein $R_6$ is —$(CH_2)_mR_{21}$, m is 3, and $R_{21}$ is substituted or unsubstituted $C_3$-$C_8$cycloalkyl. In another embodiment is a compound of Formula (IV) wherein $R_6$ is —$(CH_2)_mR_{21}$, m is 3, and $R_{21}$ is substituted or unsubstituted $C_6$-$C_{10}$aryl. In another embodiment is a compound of Formula (IV) wherein $R_6$ is —$(CH_2)_mR_{21}$, m is 3, and $R_{21}$ is substituted or unsubstituted phenyl. In another embodiment is a compound of Formula (IV) wherein $R_6$ is —$(CH_2)_mR_{21}$, m is 3, and $R_{21}$ is substituted or unsubstituted $C_2$-$C_7$heteroaryl.

In another embodiment is a compound of Formula (IV) wherein $R_6$ is —$(C(R_{14})(R_{15}))_mN(R_{11})(R_{12})$. In another embodiment is a compound of Formula (IV) wherein $R_6$ is —$(C(R_{14})(R_{15}))_mN(R_{11})(R_{12})$, m is 2, and each $R_{14}$ and $R_{15}$ are H. In another embodiment is a compound of Formula (IV) wherein $R_6$ is —$(CH_2)_mN(R_{11})(R_{12})$, m is 2, and $R_{11}$ and $R_{12}$ are each H. In another embodiment is a compound of Formula (IV) wherein $R_6$ is —$(CH_2)_mN(R_{11})(R_{12})$, m is 2, $R_{11}$ is substituted or unsubstituted $C_1$-$C_6$alkyl, and $R_{12}$ is H. In another embodiment is a compound of Formula (IV) wherein $R_6$ is —$(CH_2)_mN(R_{11})(R_{12})$, m is 2, $R_{11}$ is $CH_3$, and $R_{12}$ is H. In another embodiment is a compound of Formula (IV) wherein $R_6$ is —$(CH_2)_mN(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IV) wherein $R_6$ is —$(CH_2)_mN(R_{11})(R_{12})$, m is 2, $R_{11}$ is $CH_3$, and $R_{12}$ is $CH_3$. In another embodiment is a compound of Formula (IV) wherein $R_6$ is —$(CH_2)_mN(R_{11})(R_{12})$, m is 2, and $R_{11}$ and $R_{12}$ are taken together to form a 5-, 6-, 7-, or 8-membered heterocyclic ring. In another embodiment is a compound of Formula (IV) wherein $R_6$ is —$(CH_2)_mN(R_{11})(R_{12})$, m is 2, and $R_{11}$ and $R_{12}$ are taken together to form a 5-membered heterocyclic ring. In another embodiment is a compound of Formula (IV) wherein $R_6$ is —$(CH_2)_mN(R_{11})(R_{12})$, m is 2, and $R_{11}$ and $R_{12}$ are taken together to form a 6-membered heterocyclic ring.

In another embodiment is a compound of Formula (IV) wherein $R_6$ is —$(C(R_{14})(R_{15}))_mN(R_{11})(R_{12})$—In another embodiment is a compound of Formula (IV) wherein $R_6$ is —$(C(R_{14})(R_{15}))_mN(R_{11})(R_{12})$, m is 3, and each $R_{14}$ and $R_{15}$ are H. In another embodiment is a compound of Formula (IV) wherein $R_6$ is —$(CH_2)_mN(R_{11})(R_{12})$, m is 3, and $R_{11}$ and $R_{12}$ are each H. In another embodiment is a compound of Formula (IV) wherein $R_6$ is —$(CH_2)_mN(R_{11})(R_{12})$, m is 3, $R_{11}$ is substituted or unsubstituted $C_1$-$C_6$alkyl, and $R_{12}$ is H. In another embodiment is a compound of Formula (IV) wherein $R_6$ is —$(CH_2)_mN(R_{11})(R_{12})$, m is 3, $R_{11}$ is $CH_3$, and $R_{12}$ is H. In another embodiment is a compound of Formula (IV) wherein $R_6$ is —$(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IV) wherein $R_6$ is —$(CH_2)_mN(R_{11})(R_{12})$, m is 3, $R_{11}$ is $CH_3$, and $R_{12}$ is $CH_3$. In another embodiment is a compound of Formula (IV) wherein $R_6$ is —$(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (IV) wherein $R_6$ is —$(CH_2)_mN(R_{11})(R_{12})$, m is 3, and $R_{11}$ and $R_{12}$ are taken together to form a 5-membered heterocyclic ring. In another embodiment is a compound of Formula (IV) wherein $R_6$ is —$(CH_2)_mN(R_{11})(R_{12})$, m is 3, and $R_{11}$ and $R_{12}$ are taken together to form a 6-membered heterocyclic ring.

In another embodiment is a compound of Formula (IV) wherein $R_6$ is substituted or unsubstituted $C_2$-$C_7$heterocycloalkyl. In another embodiment is a compound of Formula (IV) wherein $R_6$ is

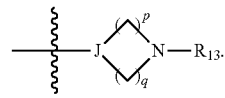

In another embodiment is a compound of Formula (IV) wherein $R_6$ is

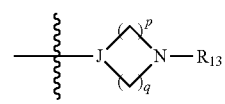

and J is C(H). In another embodiment is a compound of Formula (IV) wherein $R_6$ is

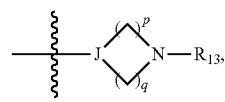

J is C(H), p is 1, and q is 1. In another embodiment is a compound of Formula (IV) wherein $R_6$ is

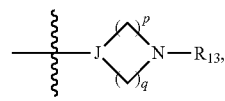

J is C(H), p is 2, and q is 1. In another embodiment is a compound of Formula (IV) wherein $R_6$ is

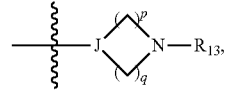

J is C(H), p is 3, and q is 1. In another embodiment is a compound of Formula (IV) wherein $R_6$ is

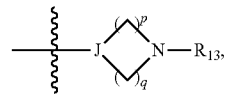

J is C(H), p is 2, and q is 2. In another embodiment is a compound of Formula (IV) wherein $R_6$ is

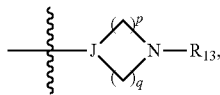

J is C(H), p is 1, q is 1, and $R_{13}$ is substituted or unsubstituted $C_1$-$C_6$alkyl. In another embodiment is a compound of Formula (IV) wherein $R_6$ is

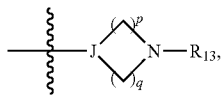

J is C(H), p is 2, q is 1, and $R_{13}$ is substituted or unsubstituted $C_1$-$C_6$alkyl. In another embodiment is a compound of Formula (IV) wherein $R_6$ is

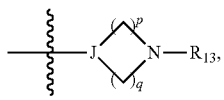

J is C(H), p is 3, q is 1, and $R_{13}$ is substituted or unsubstituted $C_1$-$C_6$alkyl. In another embodiment is a compound of Formula (IV) wherein $R_6$ is

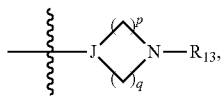

J is C(H), p is 2, q is 2, and $R_{13}$ is substituted or unsubstituted $C_1$-$C_6$alkyl.

In another embodiment is a compound of Formula (IV) wherein $R_6$ is

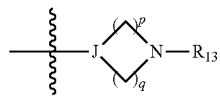

and J is N. In another embodiment is a compound of Formula (IV) wherein $R_6$ is

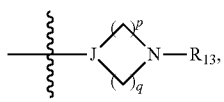

J is N, p is 2, and q is 2. In another embodiment is a compound of Formula (IV) wherein $R_6$ is

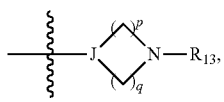

J is N, p is 2, q is 2, and $R_{13}$ is substituted or unsubstituted $C_1$-$C_6$alkyl.

In another embodiment is a compound of Formula (IV) wherein $R_5$ is halogen. In another embodiment is a compound of Formula (IV) wherein $R_5$ is —$CF_3$. In another embodiment is a compound of Formula (IV) wherein $R_5$ is substituted or unsubstituted $C_1$-$C_6$alkyl. In another embodiment is a compound of Formula (IV) wherein $R_5$ is —$CH_3$. In another embodiment is a compound of Formula (IV) wherein $R_5$ is —$CH_2CH_3$. In another embodiment is a compound of Formula (IV) wherein $R_5$ is substituted or unsubstituted $C_1$-$C_6$heteroalkyl. In another embodiment is a compound of Formula (IV) wherein $R_5$ is substituted or unsubstituted $C_2$-$C_7$heterocycloalkyl. In another embodiment is a compound of Formula (IV) wherein $R_5$ is substituted or unsubstituted $C_3$-$C_8$cycloalkyl. In another embodiment is a compound of Formula (IV) wherein $R_5$ is substituted or unsubstituted $C_6$-$C_{10}$aryl. In another embodiment is a compound of Formula (IV) wherein $R_5$ is substituted or unsubstituted $C_2$-$C_7$heteroaryl.

In another embodiment is a compound of Formula (IV) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (IV) wherein $R_2$, $R_3$, and $R_4$ are each H.

In another embodiment is a compound of Formula (IV) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (IV) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (IV) wherein $R_2$ is H; $R_3$ is $C_1$-$C_4$alkyl; and $R_4$ is H. In another embodiment is a compound of Formula (IV) wherein $R_2$ is H; $R_3$ is $CH_3$; and $R_4$ is H. In another embodiment is a compound of Formula (IV) wherein $R_2$ is H; $R_3$ is $C_1$-$C_4$alkyl; and $R_4$ is $C_1$-$C_4$alkyl. In another embodiment is a compound of Formula (IV) wherein $R_2$ is H; $R_3$ is $CH_3$; and $R_4$ is $CH_3$. In another embodiment is a compound of Formula (IV) wherein $R_2$ is H; $R_3$ is $C_1$-$C_4$alkyl; and $R_4$ is —CN. In another embodiment is a compound of Formula (IV) wherein $R_2$ is H; $R_3$ is $CH_3$; and $R_4$ is —CN. In another embodiment is a compound of Formula (IV) wherein $R_2$ is $C_1$-$C_4$alkyl; $R_3$ is $C_1$-$C_4$alkyl; and $R_4$ is H. In another embodiment is a compound of Formula (IV) wherein $R_2$ is $CH_3$; $R_3$ is $CH_3$; and $R_4$ is H. In another embodiment is a compound of Formula (IV) wherein $R_2$ is $C_1$-$C_4$alkyl; $R_3$ is H; and $R_4$ is H. In another embodiment is a compound of Formula (IV) wherein $R_2$ is $CH_3$; $R_3$ is H; and $R_4$ is H. In another embodiment is a compound of Formula (IV) wherein $R_2$ is $C_1$-$C_4$alkyl; $R_3$ is H; and $R_4$ is $C_1$-$C_4$alkyl. In another embodiment is a compound of Formula (IV) wherein $R_2$ is $CH_3$; $R_3$ is H; and $R_4$ is $CH_3$. In another embodiment is a compound of Formula (IV) wherein $R_2$ is $C_1$-$C_4$alkyl; $R_3$ is H; and $R_4$ is —CN. In another embodiment is a compound of Formula (IV) wherein $R_2$ is $CH_3$; $R_3$ is H; and $R_4$ is —CN. In another embodiment is a compound of Formula (IV) wherein $R_2$ is $C_3$-$C_6$cycloalkyl; $R_3$ is H; and $R_4$ is H. In another embodiment is a compound of Formula (IV) wherein $R_2$ is cyclopropyl; $R_3$ is H; and $R_4$ is H. In another embodiment is a compound of Formula (IV) wherein $R_2$ is cyclopentyl; $R_3$ is H; and $R_4$ is H. In another embodiment is a compound of Formula (IV) wherein $R_2$ is $C_3$-$C_6$cycloalkyl; $R_3$ is H; and $R_4$ is $CH_3$. In another embodiment is a compound of Formula (IV) wherein $R_2$ is cyclopropyl; $R_3$ is H; and $R_4$ is $CH_3$. In another embodiment is a compound of Formula (IV) wherein $R_2$ is cyclopentyl; $R_3$ is H; and $R_4$ is $CH_3$. In another embodiment is a compound of Formula (IV) wherein $R_2$ is $C_3$-$C_6$cycloalkyl; $R_3$ is H; and $R_4$ is —CN. In another embodiment is a compound of Formula (IV) wherein $R_2$ is cyclopropyl; $R_3$ is H; and $R_4$ is —CN. In another embodiment is a compound of Formula (IV) wherein $R_2$ is cyclopentyl; $R_3$ is H; and $R_4$ is —CN.

In another embodiment is a compound of Formula (IV) wherein $R_2$ and $R_3$ are taken together to form a 5- or 6-membered heterocyclic ring. In another embodiment is a compound of Formula (IV) wherein $R_2$ and $R_3$ are taken together to form a 5- or 6-membered heterocyclic ring; and $R_4$ is H. In another embodiment is a compound of Formula (IV) wherein $R_2$ and $R_3$ are taken together to form a 5-membered heterocyclic ring; and $R_4$ is H. In another embodiment is a compound of Formula (IV) wherein $R_2$ and $R_3$ are taken together to form 6-membered heterocyclic ring; and $R_4$ is H.

In another embodiment is a compound of Formula (IV) wherein each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IV) wherein each $R_1$ is independently halogen, —CN, —OH, —CF$_3$, substituted or unsubstituted $C_1$-$C_6$alkyl, or substituted or unsubstituted $C_1$-$C_6$alkoxy. In another embodiment is a compound of Formula (IV) wherein each $R_1$ is independently halogen, —CN, —OCF$_3$, —OCH$_2$F, —OCF$_2$H, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IV) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy. In another embodiment is a compound of Formula (IV) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 3. In another embodiment is a compound of Formula (IV) wherein each $R_1$ is independently halogen, —CN, —OCF$_3$, —OCH$_2$F, —OCF$_2$H, —CF$_3$, substituted or unsubstituted $C_1$-$C_6$alkyl, or substituted or unsubstituted $C_1$-$C_6$alkoxy, and n is 2. In another embodiment is a compound of Formula (IV) wherein n is 3, and each $R_1$ is independently halogen. In another embodiment is a compound of Formula (IV) wherein n is 2, and each $R_1$ is independently halogen. In another embodiment is a compound of Formula (IV) wherein n is 2, and each $R_1$ is independently F or Cl. In another embodiment is a compound of Formula (IV) wherein n is 2, and each $R_1$ is F. In another embodiment is a compound of Formula (IV) wherein n is 2, and each $R_1$ is independently Cl. In another embodiment is a compound of Formula (IV) wherein n is 2, and each $R_1$ is independently halogen or —CF$_3$. In another embodiment is a compound of Formula (IV) wherein n is 2, and each $R_1$ is independently F or —CF$_3$. In another embodiment is a compound of Formula (IV) wherein n is 2, and each $R_1$ is independently Cl or —CF$_3$. In another embodiment is a compound of Formula (IV) wherein n is 1, and $R_1$ is halogen. In another embodiment is a compound of Formula (IV) wherein n is 1, and $R_1$ is F. In another embodiment is a compound of Formula (IV) wherein n is 1, and $R_1$ is Cl. In another embodiment is a compound of Formula (IV) wherein n is 1, and $R_1$ is —CF$_3$. In another embodiment is a compound of Formula (IV) wherein n is 1, and $R_1$ is substituted or unsubstituted $C_1$-$C_6$alkyl. In another embodiment is a compound of Formula (IV) wherein n is 1, and $R_1$ is CH$_3$. In another embodiment is a compound of Formula (IV) wherein n is 1, and $R_1$ is substituted or unsubstituted $C_1$-$C_6$alkoxy. In another embodiment is a compound of Formula (IV) wherein n is 1, and $R_1$ is —OCH$_3$. In another embodiment is a compound of Formula (IV) wherein n is 1, and $R_1$ is —OCF$_3$. In another embodiment is a compound of Formula (IV) wherein n is 1, and $R_1$ is —OCF$_2$H.

In another aspect, described herein is a compound of Formula (IVA):

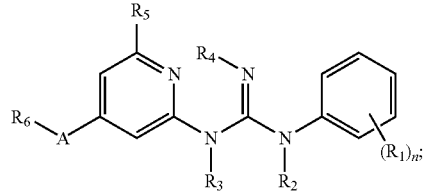

Formula (IVA)

wherein:
A is a bond, O, CH$_2$, or N(R$_{10}$);
each $R_1$ is independently halogen, —CN, —NO$_2$, —OH, —OCF$_3$, —OCH$_2$F, —OCF$_2$H, —CF$_3$, —SR$_8$, —N(R$_8$)S(=O)$_2$R$_9$, —S(=O)$_2$N(R$_8$)$_2$, —S(=O)R$_9$, —S(=O)$_2$R$_9$, —C(=O)R$_9$, —CO$_2$R$_8$, —N(R$_8$)$_2$, —C(=O)N(R$_8$)$_2$, —N(R$_8$)C(=O)R$_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or
two $R_1$ are taken together to form a substituted or unsubstituted heterocyclic ring or a substituted or unsubstituted carbocyclic ring;
$R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H; or two of $R_2$, $R_3$, and $R_4$ are taken together to form a 5- or 6-membered heterocyclic ring;
$R_5$ is halogen, —CN, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; $R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —$(C(R_{14})(R_{15}))_m R_{21}$, —$(C(R_{14})(R_{15}))_m N(R_{11})(R_{12})$, or

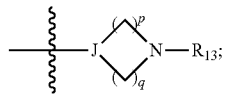

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;

each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2 R_{23}$, —$S(=O)_2 N(R_{22})_2$, —$S(=O)R_{23}$, —$S(=O)_2 R_{23}$, —$C(=O)R_{23}$, —$CO_2 R_{22}$, —$C(=O)NR_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In another embodiment is a compound of Formula (IVA) wherein A is O, $CH_2$, or $N(R_{10})$—In another embodiment is a compound of Formula (IVA) wherein A is O, $CH_2$, or N(H). In another embodiment is a compound of Formula (IVA) wherein A is O. In another embodiment is a compound of Formula (IVA) wherein A is $CH_2$. In another embodiment is a compound of Formula (IVA) wherein A is $N(R_{10})$. In another embodiment is a compound of Formula (IVA) wherein A is N(H). In another embodiment is a compound of Formula (IVA) wherein A is $N(CH_3)$. In another embodiment is a compound of Formula (IVA) wherein A is a bond.

In another embodiment is a compound of Formula (IVA) wherein $R_6$ is substituted or unsubstituted $C_3$-$C_8$cycloalkyl. In another embodiment is a compound of Formula (IVA) wherein $R_6$ is substituted or unsubstituted cyclopropyl. In another embodiment is a compound of Formula (IVA) wherein $R_6$ is substituted or unsubstituted cyclobutyl. In another embodiment is a compound of Formula (IVA) wherein $R_6$ is substituted or unsubstituted cyclopentyl. In another embodiment is a compound of Formula (IVA) wherein $R_6$ is substituted or unsubstituted cyclohexyl.

In another embodiment is a compound of Formula (IVA) wherein $R_6$ is substituted or unsubstituted $C_2$-$C_7$heteroaryl. In another embodiment is a compound of Formula (IVA) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IVA) wherein $R_6$ is substituted or unsubstituted pyridyl. In another embodiment is a compound of Formula (IVA) wherein $R_6$ is substituted pyridyl. In another embodiment is a compound of Formula (IVA) wherein $R_6$ is unsubstituted pyridyl.

In another embodiment is a compound of Formula (IVA) wherein $R_6$ is —$(C(R_{14})(R_{15}))_m R_{21}$. In another embodiment is a compound of Formula (IVA) wherein $R_6$ is —$(C(R_{14})(R_{15}))_m R_{21}$, and each $R_{14}$ and $R_{15}$ are H. In another embodiment is a compound of Formula (IVA) wherein $R_6$ is —$(C(R_{14})(R_{15}))_m R_{21}$, m is 2, and each $R_{14}$ and $R_{15}$ are H. In another embodiment is a compound of Formula (IVA) wherein $R_6$ is —$(CH_2)_m R_{21}$, m is 2, and $R_{21}$ is substituted or unsubstituted $C_2$-$C_7$heterocycloalkyl. In another embodiment is a compound of Formula (IVA) wherein $R_6$ is —$(CH_2)_m R_{21}$, m is 2, and $R_{21}$ is substituted or unsubstituted $C_3$-$C_8$cycloalkyl. In another embodiment is a compound of Formula (IVA) wherein $R_6$ is —$(CH_2)_m R_{21}$, m is 2, and $R_{21}$ is substituted or unsubstituted $C_6$-$C_{10}$aryl. In another embodiment is a compound of Formula (IVA) wherein $R_6$ is —$(CH_2)_m R_{21}$, m is 2, and $R_{21}$ is substituted or unsubstituted phenyl. In another embodiment is a compound of Formula (IVA) wherein $R_6$ is —$(CH_2)_m R_{21}$, m is 2, and $R_{21}$ is substituted or unsubstituted $C_2$-$C_7$heteroaryl.

In another embodiment is a compound of Formula (IVA) wherein $R_6$ is —$(C(R_{14})(R_{15}))_m R_{21}$, m is 3, and each $R_{14}$ and $R_{15}$ are H. In another embodiment is a compound of Formula (IVA) wherein $R_6$ is —$(CH_2)_m R_{21}$, m is 3, and $R_{21}$ is substituted or unsubstituted $C_2$-$C_7$heterocycloalkyl. In another embodiment is a compound of Formula (IVA) wherein $R_6$ is —$(CH_2)_m R_{21}$, m is 3, and $R_{21}$ is substituted or unsubstituted $C_3$-$C_8$cycloalkyl. In another embodiment is a compound of Formula (IVA) wherein $R_6$ is —$(CH_2)_m R_{21}$, m is 3, and $R_{21}$ is substituted or unsubstituted $C_6$-$C_{10}$aryl. In another embodiment is a compound of Formula (IVA) wherein $R_6$ is —$(CH_2)_m R_{21}$, m is 3, and $R_{21}$ is substituted or unsubstituted phenyl. In another embodiment is a compound of Formula (IVA) wherein $R_6$ is —$(CH_2)_m R_{21}$, m is 3, and $R_{21}$ is substituted or unsubstituted $C_2$-$C_7$heteroaryl.

In another embodiment is a compound of Formula (IVA) wherein $R_6$ is —$(C(R_{14})(R_{15}))_m N(R_{11})(R_{12})$. In another embodiment is a compound of Formula (IVA) wherein $R_6$ is —$C(R_{14})(R_{15})_m N(R_{11})(R_{12})$, m is 2, and each $R_{14}$ and $R_{15}$ are H. In another embodiment is a compound of Formula (IVA) wherein $R_6$ is —$(CH_2)_m N(R_{11})(R_{12})$, m is 2, and $R_{11}$ and $R_{12}$ are each H. In another embodiment is a compound of Formula (IVA) wherein $R_6$ is —$(CH_2)_m N(R_{11})(R_{12})$, m is 2, $R_{11}$ is substituted or unsubstituted $C_1$-$C_6$alkyl, and $R_{12}$ is H. In another embodiment is a compound of Formula (IVA) wherein $R_6$ is —$(CH_2)_m N(R_{11})(R_{12})$, m is 2, $R_{11}$ is $CH_3$, and $R_{12}$ is H. In another embodiment is a compound of Formula (IVA) wherein $R_6$ is —$(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IVA) wherein $R_6$ is —$(CH_2)_m N(R_{11})(R_{12})$, m is 2, $R_{11}$ is $CH_3$, and $R_{12}$ is $CH_3$. In another embodiment is a compound of Formula (IVA) wherein $R_6$ is —$(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (IVA) wherein $R_6$ is —$(CH_2)_m N(R_{11})(R_{12})$, m is 2, and $R_{11}$ and $R_{12}$ are taken together to form a 5-membered heterocyclic ring. In another embodiment is a compound of Formula (IVA) wherein $R_6$ is —$(CH_2)_m N(R_{11})(R_{12})$, m is 2, and $R_{11}$ and $R_{12}$ are taken together to form a 6-membered heterocyclic ring.

In another embodiment is a compound of Formula (IVA) wherein $R_6$ is —$(C(R_{14})(R_{15}))_m N(R_{11})(R_{12})$. In another embodiment is a compound of Formula (IVA) wherein $R_6$ is —$C(R_{14})(R_{15}))_m N(R_{11})(R_{12})$, m is 3, and each $R_{14}$ and $R_{15}$ are H. In another embodiment is a compound of Formula (IVA) wherein $R_6$ is —$(CH_2)_m N(R_{11})(R_{12})$, m is 3, and $R_{11}$ and $R_{12}$ are each H. In another embodiment is a compound of Formula (IVA) wherein $R_6$ is —$(CH_2)_m N(R_{11})(R_{12})$, m is 3, $R_{11}$ is substituted or unsubstituted $C_1$-$C_6$alkyl, and $R_{12}$ is H. In another embodiment is a compound of Formula (IVA) wherein $R_6$ is —$(CH_2)_m N(R_{11})(R_{12})$, m is 3, $R_{11}$ is $CH_3$, and $R_{12}$ is H. In another embodiment is a compound of Formula (IVA) wherein $R_6$ is —$(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IVA) wherein $R_6$ is —$(CH_2)_m N(R_{11})(R_{12})$, m is 3, $R_{11}$ is $CH_3$, and $R_{12}$ is $CH_3$. In another embodiment is a compound of Formula (IVA) wherein $R_6$ is —$(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (IVA) wherein $R_6$ is —$(CH_2)_m N(R_{11})(R_{12})$, m is 3, and $R_{11}$ and $R_{12}$ are taken together to form a 5-membered heterocyclic ring. In another embodiment is a compound of Formula (IVA) wherein $R_6$ is —$(CH_2)_m N(R_{11})(R_{12})$, m is 3, and $R_{11}$ and $R_{12}$ are taken together to form a 6-membered heterocyclic ring.

In another embodiment is a compound of Formula (IVA) wherein $R_6$ is substituted or unsubstituted $C_2$-$C_7$heterocycloalkyl. In another embodiment is a compound of Formula (IVA) wherein $R_6$ is

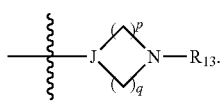

In another embodiment is a compound of Formula (IVA) wherein $R_6$ is

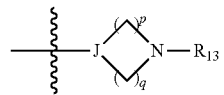

and J is C(H). In another embodiment is a compound of Formula (IVA) wherein $R_6$ is

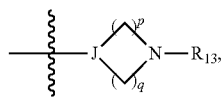

J is C(H), p is 1, and q is 1. In another embodiment is a compound of Formula (IVA) wherein $R_6$ is

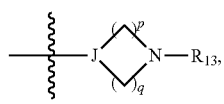

J is C(H), p is 2, and q is 1. In another embodiment is a compound of Formula (IVA) wherein $R_6$ is

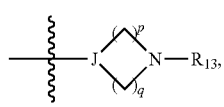

J is C(H), p is 3, and q is 1. In another embodiment is a compound of Formula (IVA) wherein $R_6$ is

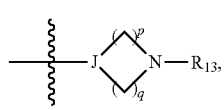

J is C(H), p is 2, and q is 2. In another embodiment is a compound of Formula (IVA) wherein $R_6$ is

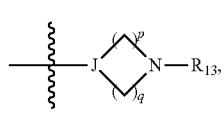

J is C(H), p is 1, q is 1, and $R_{13}$ is substituted or unsubstituted $C_1$-$C_6$alkyl. In another embodiment is a compound of Formula (IVA) wherein $R_6$ is

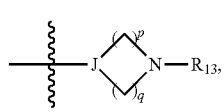

J is C(H), p is 2, q is 1, and $R_{13}$ is substituted or unsubstituted $C_1$-$C_6$alkyl. In another embodiment is a compound of Formula (IVA) wherein $R_6$ is

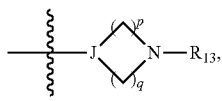

J is C(H), p is 3, q is 1, and $R_{13}$ is substituted or unsubstituted $C_1$-$C_6$alkyl. In another embodiment is a compound of Formula (IVA) wherein $R_6$ is

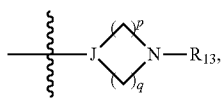

J is C(H), p is 2, q is 2, and $R_{13}$ is substituted or unsubstituted $C_1$-$C_6$alkyl.

In another embodiment is a compound of Formula (IVA) wherein $R_6$ is

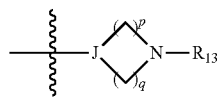

and J is N. In another embodiment is a compound of Formula (IVA) wherein $R_6$ is

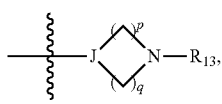

J is N, p is 2, and q is 2. In another embodiment is a compound of Formula (IVA) wherein $R_6$ is

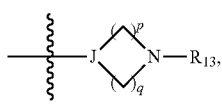

J is N, p is 2, q is 2, and $R_{13}$ is substituted or unsubstituted $C_1$-$C_6$alkyl.

In another embodiment is a compound of Formula (IVA) wherein $R_5$ is halogen. In another embodiment is a compound of Formula (IVA) wherein $R_5$ is —$CF_3$. In another embodiment is a compound of Formula (IVA) wherein $R_5$ is substituted or unsubstituted $C_1$-$C_6$alkyl. In another embodiment is a compound of Formula (IVA) wherein $R_5$ is —$CH_3$. In another embodiment is a compound of Formula (IVA) wherein $R_5$ is —$CH_2CH_3$. In another embodiment is a compound of Formula (IVA) wherein $R_5$ is substituted or unsubstituted $C_1$-$C_6$heteroalkyl. In another embodiment is a compound of Formula (IVA) wherein $R_5$ is substituted or unsubstituted $C_2$-$C_7$heterocycloalkyl. In another embodiment is a compound of Formula (IVA) wherein $R_5$ is substituted or unsubstituted $C_3$-$C_8$cycloalkyl. In another embodiment is a compound of Formula (IVA) wherein $R_5$ is substituted or unsubstituted $C_6$-$C_{10}$aryl. In another embodiment is a compound of Formula (IVA) wherein $R_5$ is substituted or unsubstituted $C_2$-$C_7$heteroaryl.

In another embodiment is a compound of Formula (IVA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least one of $R_2$, $R_3$, and $R_4$ is not H. In another embodiment is a compound of Formula (IVA) wherein $R_2$, $R_3$, and $R_4$ are each independently H, —CN, $C_1$-$C_4$alkyl, $C_3$-$C_6$cycloalkyl, or $C_2$-$C_7$heterocycloalkyl wherein at least two of $R_2$, $R_3$, and $R_4$ are not H. In another embodiment is a compound of Formula (IVA) wherein $R_2$ is H; $R_3$ is $C_1$-$C_4$alkyl; and $R_4$ is H. In another embodiment is a compound of Formula (IVA) wherein $R_2$ is H; $R_3$ is $CH_3$; and $R_4$ is H. In another embodiment is a compound of Formula (IVA) wherein $R_2$ is H; $R_3$ is $C_1$-$C_4$alkyl; and $R_4$ is $C_1$-$C_4$alkyl. In another embodiment is a compound of Formula (IVA) wherein $R_2$ is H; $R_3$ is $CH_3$; and $R_4$ is $CH_3$. In another embodiment is a compound of Formula (IVA) wherein $R_2$ is H; $R_3$ is $C_1$-$C_4$alkyl; and $R_4$ is —CN. In another embodiment is a compound of Formula (IVA) wherein $R_2$ is H; $R_3$ is $CH_3$; and $R_4$ is —CN. In another embodiment is a compound of Formula (IVA) wherein $R_2$ is $C_1$-$C_4$alkyl; $R_3$ is $C_1$-$C_4$alkyl; and $R_4$ is H. In another embodiment is a compound of Formula (IVA) wherein $R_2$ is $CH_3$; $R_3$ is $CH_3$; and $R_4$ is H. In another embodiment is a compound of Formula (IVA) wherein $R_2$ is $C_1$-$C_4$alkyl; $R_3$ is H; and $R_4$ is H. In another embodiment is a compound of Formula (IVA) wherein $R_2$ is $CH_3$; $R_3$ is H; and $R_4$ is H. In another embodiment is a compound of Formula (IVA) wherein $R_2$ is $C_1$-$C_4$alkyl; $R_3$ is H; and $R_4$ is $C_1$-$C_4$alkyl. In another embodiment is a compound of Formula (IVA) wherein $R_2$ is $CH_3$; $R_3$ is H; and $R_4$ is $CH_3$. In another embodiment is a compound of Formula (IVA) wherein $R_2$ is $C_1$-$C_4$alkyl; $R_3$ is H; and $R_4$ is —CN. In another embodiment is a compound of Formula (IVA) wherein $R_2$ is $CH_3$; $R_3$ is H; and $R_4$ is —CN. In another embodiment is a compound of Formula (IVA) wherein $R_2$ is $C_3$-$C_6$cycloalkyl; $R_3$ is H; and $R_4$ is H. In another embodiment is a compound of Formula (IVA) wherein $R_2$ is cyclopropyl; $R_3$ is H; and $R_4$ is H. In another embodiment is a compound of Formula (IVA) wherein $R_2$ is cyclopentyl; $R_3$ is H; and $R_4$ is H. In another embodiment is a compound of Formula (IVA) wherein $R_2$ is $C_3$-$C_6$cycloalkyl; $R_3$ is H; and $R_4$ is $CH_3$. In another embodiment is a compound of Formula (IVA) wherein $R_2$ is cyclopropyl; $R_3$ is H; and $R_4$ is $CH_3$. In another embodiment is a compound of Formula (IVA) wherein $R_2$ is cyclopentyl; $R_3$ is H; and $R_4$ is $CH_3$. In another embodiment is a compound of Formula (IVA) wherein $R_2$ is $C_3$-$C_6$cycloalkyl; $R_3$ is H; and $R_4$ is —CN. In another embodiment is a compound of Formula (IVA) wherein $R_2$ is cyclopropyl; $R_3$ is H; and $R_4$ is —CN. In another embodiment is a compound of Formula (IVA) wherein $R_2$ is cyclopentyl; $R_3$ is H; and $R_4$ is —CN.

In another embodiment is a compound of Formula (IVA) wherein $R_2$ and $R_3$ are taken together to form a 5- or 6-membered heterocyclic ring. In another embodiment is a compound of Formula (IVA) wherein $R_2$ and $R_3$ are taken together to form a 5- or 6-membered heterocyclic ring; and $R_4$ is H. In another embodiment is a compound of Formula (IVA) wherein $R_2$ and $R_3$ are taken together to form a 5-membered heterocyclic ring; and $R_4$ is H. In another embodiment is a compound of Formula (IVA) wherein $R_2$ and $R_3$ are taken together to form 6-membered heterocyclic ring; and $R_4$ is H.

In another embodiment is a compound of Formula (IVA) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl. In another embodiment is a compound of Formula (IVA) wherein each R₁ is independently halogen, —CN, —OH, —CF₃, substituted or unsubstituted C₁-C₆alkyl, or substituted or unsubstituted C₁-C₆alkoxy. In another embodiment is a compound of Formula (IVA) wherein each R₁ is independently halogen, —CN, —OCF₃, —OCH₂F, —OCF₂H, —CF₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl. In another embodiment is a compound of Formula (IVA) wherein each R₁ is independently halogen, —CN, —OCF₃, —OCH₂F, —OCF₂H, —CF₃, substituted or unsubstituted C₁-C₆alkyl, or substituted or unsubstituted C₁-C₆alkoxy. In another embodiment is a compound of Formula (IVA) wherein each R₁ is independently halogen, —CN, —OCF₃, —OCH₂F, —OCF₂H, —CF₃, substituted or unsubstituted C₁-C₆alkyl, or substituted or unsubstituted C₁-C₆alkoxy, and n is 3. In another embodiment is a compound of Formula (IVA) wherein each R₁ is independently halogen, —CN, —OCF₃, —OCH₂F, —OCF₂H, —CF₃, substituted or unsubstituted C₁-C₆alkyl, or substituted or unsubstituted C₁-C₆alkoxy, and n is 2. In another embodiment is a compound of Formula (IVA) wherein n is 3, and each R₁ is independently halogen. In another embodiment is a compound of Formula (IVA) wherein n is 2, and each R₁ is independently halogen. In another embodiment is a compound of Formula (IVA) wherein n is 2, and each R₁ is independently F or Cl. In another embodiment is a compound of Formula (IVA) wherein n is 2, and each R₁ is F. In another embodiment is a compound of Formula (IVA) wherein n is 2, and each R₁ is independently Cl. In another embodiment is a compound of Formula (IVA) wherein n is 2, and each R₁ is independently halogen or —CF₃. In another embodiment is a compound of Formula (IVA) wherein n is 2, and each R₁ is independently F or —CF₃. In another embodiment is a compound of Formula (IVA) wherein n is 2, and each R₁ is independently Cl or —CF₃. In another embodiment is a compound of Formula (IVA) wherein n is 1, and R₁ is halogen. In another embodiment is a compound of Formula (IVA) wherein n is 1, and R₁ is F. In another embodiment is a compound of Formula (IVA) wherein n is 1, and R₁ is Cl. In another embodiment is a compound of Formula (IVA) wherein n is 1, and R₁ is —CF₃. In another embodiment is a compound of Formula (IVA) wherein n is 1, and R₁ is substituted or unsubstituted C₁-C₆alkyl. In another embodiment is a compound of Formula (IVA) wherein n is 1, and R₁ is CH₃. In another embodiment is a compound of Formula (IVA) wherein n is 1, and R₁ is substituted or unsubstituted C₁-C₆alkoxy. In another embodiment is a compound of Formula (IVA) wherein n is 1, and R₁ is —OCH₃. In another embodiment is a compound of Formula (IVA) wherein n is 1, and R₁ is —OCF₃. In another embodiment is a compound of Formula (IVA) wherein n is 1, and R₁ is —OCF₂H.

In another embodiment, described herein is a compound of Formula (IVB):

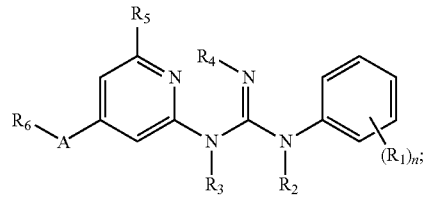

Formula (IVB)

wherein:

A is O;

each R₁ is independently halogen, —CN, —NO₂, —OH, —OCF₃, —OCH₂F, —OCF₂H, —CF₃, —SR₈, —N(R₈)S(=O)₂R₉, —S(=O)₂N(R₈)₂, —S(=O)R₉, —S(=O)₂R₉, —C(=O)R₉, —CO₂R₈, —N(R₈)₂, —C(=O)N(R₈)₂, —N(R₈)C(=O)R₉, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl; or two R₁ are taken together to form a substituted or unsubstituted heterocyclic ring or a substituted or unsubstituted carbocyclic ring;

R₂, R₃, and R₄ are each independently H, —CN, C₁-C₄alkyl, C₃-C₆cycloalkyl, or C₂-C₇heterocycloalkyl; or two of R₂, R₃, and R₄ are taken together to form a 5- or 6-membered heterocyclic ring;

R₅ is halogen, —CN, —OH, —CF₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted C₃-C₈cycloalkyl, substituted or unsubstituted C₆-C₁₀aryl, or substituted or unsubstituted C₂-C₇heteroaryl;

R₆ is substituted or unsubstituted C₂-C₇heterocycloalkyl, substituted or unsubstituted C₃-C₈cycloalkyl, substituted or unsubstituted C₂-C₇heteroaryl, —(C(R₁₄)(R₁₅))ₘR₂₁, —(C(R₁₄)(R₁₅))ₘN(R₁₁)(R₁₂), or

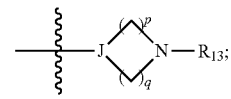

R₁₁ and R₁₂ are each independently H, or substituted or unsubstituted C₁-C₆alkyl; or R₁₁ and R₁₂ are taken together to form a 5-, 6-, 7-, or 8-membered heterocyclic ring;

J is C(H), or N;

R₁₃ is H, substituted or unsubstituted C₁-C₆alkyl, substituted or unsubstituted C₂-C₇heterocycloalkyl, substituted or unsubstituted C₃-C₈cycloalkyl, substituted or unsubstituted —C₁-C₄alkylC₆-C₁₀aryl, or substituted or unsubstituted —C₁-C₄alkylC₂-C₇heteroaryl; each R₇ is independently H, halogen, —CN, —OH, —CF₃, substituted or unsubstituted C₁-C₆alkyl, substituted or unsubstituted C₁-C₆alkoxy, substituted or unsubstituted C₁-C₆heteroalkyl, substituted or unsubstituted C₂-C₇heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)NR_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl;

$R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

m is 2-6;

n is 0-5;

p is 1-3;

q is 1-3; or a pharmaceutically acceptable salt, solvate, or prodrug thereof.

In another embodiment is a compound of Formula (IVB) wherein $R_6$ is substituted or unsubstituted $C_3$-$C_8$cycloalkyl. In another embodiment is a compound of Formula (IVB) wherein $R_6$ is substituted or unsubstituted cyclopropyl. In another embodiment is a compound of Formula (IVB) wherein $R_6$ is substituted or unsubstituted cyclobutyl. In another embodiment is a compound of Formula (IVB) wherein $R_6$ is substituted or unsubstituted cyclopentyl. In another embodiment is a compound of Formula (IVB) wherein $R_6$ is substituted or unsubstituted cyclohexyl.

In another embodiment is a compound of Formula (IVB) wherein $R_6$ is substituted or unsubstituted $C_2$-$C_7$heteroaryl. In another embodiment is a compound of Formula (IVB) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (IVB) wherein $R_6$ is substituted or unsubstituted pyridyl. In another embodiment is a compound of Formula (IVB) wherein $R_6$ is substituted pyridyl. In another embodiment is a compound of Formula (IVB) wherein $R_6$ is unsubstituted pyridyl.

In another embodiment is a compound of Formula (IVB) wherein $R_6$ is —$(C(R_{14})(R_{15}))_mR_{21}$. In another embodiment is a compound of Formula (IVB) wherein $R_6$ is —$(C(R_{14})(R_{15}))_mR_{21}$, and each $R_{14}$ and $R_{15}$ are H. In another embodiment is a compound of Formula (IVB) wherein $R_6$ is —$(C(R_{14})(R_{15}))_mR_{21}$, m is 2, and each $R_{14}$ and $R_{15}$ are H. In another embodiment is a compound of Formula (IVB) wherein $R_6$ is —$(CH_2)_mR_{21}$, m is 2, and $R_{21}$ is substituted or unsubstituted $C_2$-$C_7$heterocycloalkyl. In another embodiment is a compound of Formula (IVB) wherein $R_6$ is —$(CH_2)_mR_{21}$, m is 2, and $R_{21}$ is substituted or unsubstituted $C_3$-$C_8$cycloalkyl. In another embodiment is a compound of Formula (IVB) wherein $R_6$ is —$(CH_2)_mR_{21}$, m is 2, and $R_{21}$ is substituted or unsubstituted $C_6$-$C_{10}$aryl. In another embodiment is a compound of Formula (IVB) wherein $R_6$ is —$(CH_2)_mR_{21}$, m is 2, and $R_{21}$ is substituted or unsubstituted phenyl. In another embodiment is a compound of Formula (IVB) wherein $R_6$ is —$(CH_2)_mR_{21}$, m is 2, and $R_{21}$ is substituted or unsubstituted $C_2$-$C_7$heteroaryl.

In another embodiment is a compound of Formula (IVB) wherein $R_6$ is —$(C(R_{14})(R_{15}))_mR_{21}$, m is 3, and each $R_{14}$ and $R_{15}$ are H. In another embodiment is a compound of Formula (IVB) wherein $R_6$ is —$(CH_2)_mR_{21}$, m is 3, and $R_{21}$ is substituted or unsubstituted $C_2$-$C_7$heterocycloalkyl. In another embodiment is a compound of Formula (IVB) wherein $R_6$ is —$(CH_2)_mR_{21}$, m is 3, and $R_{21}$ is substituted or unsubstituted $C_3$-$C_8$cycloalkyl. In another embodiment is a compound of Formula (IVB) wherein $R_6$ is —$(CH_2)_mR_{21}$, m is 3, and $R_{21}$ is substituted or unsubstituted $C_6$-$C_{10}$aryl. In another embodiment is a compound of Formula (IVB) wherein $R_6$ is —$(CH_2)_mR_{21}$, m is 3, and $R_{21}$ is substituted or unsubstituted phenyl. In another embodiment is a compound of Formula (IVB) wherein $R_6$ is —$(CH_2)_mR_{21}$, m is 3, and $R_{21}$ is substituted or unsubstituted $C_2$-$C_7$heteroaryl.

In another embodiment is a compound of Formula (IVB) wherein $R_6$ is —$(C(R_{14})(R_{15}))_mN(R_{11})(R_{12})$—In another embodiment is a compound of Formula (IVB) wherein $R_6$ is —$(C(R_{14})(R_{15}))_mN(R_{11})(R_{12})$, m is 2, and each $R_{14}$ and $R_{15}$ are H. In another embodiment is a compound of Formula (IVB) wherein $R_6$ is —$(CH_2)_mN(R_{11})(R_{12})$, m is 2, and $R_{11}$ and $R_{12}$ are each H. In another embodiment is a compound of Formula (IVB) wherein $R_6$ is —$(CH_2)_mN(R_{11})(R_{12})$, m is 2, $R_{11}$ is substituted or unsubstituted $C_1$-$C_6$alkyl, and $R_{12}$ is H. In another embodiment is a compound of Formula (IVB) wherein $R_6$ is —$(CH_2)_mN(R_{11})(R_{12})$, m is 2, $R_{11}$ is $CH_3$, and $R_{12}$ is H. In another embodiment is a compound of Formula (IVB) wherein $R_6$ is —$(CH_2)_mN(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (IVB) wherein $R_6$ is —$(CH_2)_mN(R_{11})(R_{12})$, m is 2, $R_{11}$ is $CH_3$, and $R_{12}$ is $CH_3$. In another embodiment is a compound of Formula (IVB) wherein $R_6$ is —$(CH_2)_mN(R_{11})(R_{12})$, m is 2, and $R_{11}$ and $R_{12}$ are taken together to form a 5-, 6-, 7-, or 8-membered heterocyclic ring. In another embodiment is a compound of Formula (IVB) wherein $R_6$ is —$(CH_2)_mN(R_{11})(R_{12})$, m is 2, and $R_{11}$ and $R_{12}$ are taken together to form a 5-membered heterocyclic ring. In another embodiment is a compound of Formula (IVB) wherein $R_6$ is —$(CH_2)_mN(R_{11})(R_{12})$, m is 2, and $R_{11}$ and $R_{12}$ are taken together to form a 6-membered heterocyclic ring.

In another embodiment is a compound of Formula (IVB) wherein $R_6$ is —$(C(R_{14})(R_{15}))_mN(R_{11})(R_{12})$—In another embodiment is a compound of Formula (IVB) wherein $R_6$ is —$(C(R_{14})(R_{15}))_mN(R_{11})(R_{12})$, m is 3, and each $R_{14}$ and $R_{15}$ are H. In another embodiment is a compound of Formula (IVB) wherein $R_6$ is —$(CH_2)_mN(R_{11})(R_{12})$, m is 3, and $R_{11}$ and $R_{12}$ are each H. In another embodiment is a compound of Formula (IVB) wherein $R_6$ is —$(CH_2)_mN(R_{11})(R_{12})$, m is 3, $R_{11}$ is substituted or unsubstituted $C_1$-$C_6$alkyl, and $R_u$ is H. In another embodiment is a compound of Formula (IVB) wherein $R_6$ is —$(CH_2)_mN(R_{11})(R_{12})$, m is 3, $R_{11}$ is $CH_3$, and $R_{12}$ is H. In another embodiment is a compound of Formula (IVB) wherein $R_6$ is —$(CH_2)_mN(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (IVB) wherein $R_6$ is —$(CH_2)_mN(R_{11})(R_{12})$, m is 3, $R_{11}$ is $CH_3$, and $R_{12}$ is $CH_3$. In another embodiment is a compound of Formula (IVB) wherein $R_6$ is —$(CH_2)_mN(R_{11})(R_{12})$, m is 3, and $R_{11}$ and $R_{12}$ are taken together to form a 5-, 6-, 7-, or 8-membered heterocyclic ring. In another embodiment is a compound of Formula (IVB) wherein $R_6$ is —$(CH_2)_mN(R_{11})(R_{12})$, m is 3, and $R_{11}$ and $R_{12}$ are taken together to form a 5-membered heterocyclic ring. In another embodiment is a compound of Formula (IVB) wherein $R_6$ is —$(CH_2)_mN(R_{11})(R_{12})$, m is 3, and $R_{11}$ and $R_{12}$ are taken together to form a 6-membered heterocyclic ring.

In another embodiment is a compound of Formula (IVB) wherein $R_6$ is substituted or unsubstituted $C_2$-$C_7$heterocycloalkyl. In another embodiment is a compound of Formula (IVB) wherein $R_6$ is

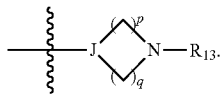

In another embodiment is a compound of Formula (IVB) wherein $R_6$ is

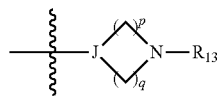

and J is C(H). In another embodiment is a compound of Formula (IVB) wherein $R_6$ is

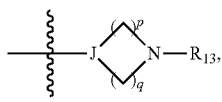

J is C(H), p is 1, and q is 1. In another embodiment is a compound of Formula (IVB) wherein $R_6$ is

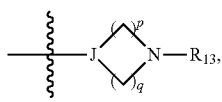

J is C(H), p is 2, and q is 1. In another embodiment is a compound of Formula (IVB) wherein $R_6$ is

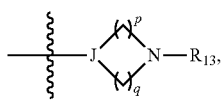

J is C(H), p is 3, and q is 1. In another embodiment is a compound of Formula (IVB) wherein $R_6$ is

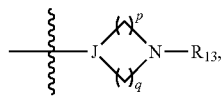

J is C(H), p is 2, and q is 2. In another embodiment is a compound of Formula (IVB) wherein $R_6$ is

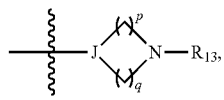

J is C(H), p is 1, q is 1, and $R_{13}$ is substituted or unsubstituted $C_1$-$C_6$alkyl. In another embodiment is a compound of Formula (IVB) wherein $R_6$ is

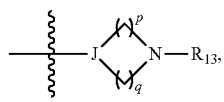

J is C(H), p is 2, q is 1, and $R_{13}$ is substituted or unsubstituted $C_1$-$C_6$alkyl. In another embodiment is a compound of Formula (IVB) wherein $R_6$ is

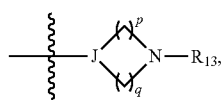

J is C(H), p is 3, q is 1, and $R_{13}$ is substituted or unsubstituted $C_1$-$C_6$alkyl. In another embodiment is a compound of Formula (IVB) wherein $R_6$ is

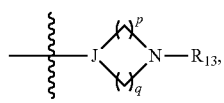

J is C(H), p is 2, q is 2, and $R_{13}$ is substituted or unsubstituted $C_1$-$C_6$alkyl.

In another embodiment is a compound of Formula (IVB) wherein $R_5$ is halogen. In another embodiment is a compound of Formula (IVB) wherein $R_5$ is —$CF_3$. In another embodiment is a compound of Formula (IVB) wherein $R_5$ is substituted or unsubstituted $C_1$-$C_6$alkyl. In another embodiment is a compound of Formula (IVB) wherein $R_5$ is —$CH_3$. In another embodiment is a compound of Formula (IVB) wherein $R_5$ is —$CH_2CH_3$. In another embodiment is a compound of Formula (IVB) wherein $R_5$ is substituted or unsubstituted $C_1$-$C_6$heteroalkyl. In another embodiment is a compound of Formula (IVB) wherein $R_5$ is substituted or unsubstituted $C_2$-$C_7$heterocycloalkyl. In another embodiment is a compound of Formula (IVB) wherein $R_5$ is substituted or unsubstituted $C_3$-$C_8$cycloalkyl. In another embodiment is a compound of Formula (IVB) wherein $R_5$ is substituted or unsubstituted $C_6$-$C_{10}$aryl. In another embodiment is a compound of Formula (IVB) wherein $R_5$ is substituted or unsubstituted $C_2$-$C_7$heteroaryl.

In another embodiment is a compound of Formula (IVB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl. In another embodiment is a compound of Formula (IVB) wherein $R_2$, $R_3$, and $R_4$ are each H.

In another embodiment is a compound of Formula (IVB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least one of $R_2$, $R_3$, and $R_4$ is not H. In another embodiment is a compound of Formula (IVB) wherein $R_2$, $R_3$, and $R_4$ are each independently H, —CN, $C_1$-$C_4$alkyl, $C_3$-$C_6$cycloalkyl, or $C_2$-$C_7$heterocycloalkyl; and at least two of $R_2$, $R_3$, and $R_4$ are not H. In another embodiment is a compound of Formula (IVB) wherein $R_2$ is H; $R_3$ is $C_1$-$C_4$alkyl; and $R_4$ is H. In another embodiment is a compound of Formula (IVB) wherein $R_2$ is H; $R_3$ is $CH_3$; and $R_4$ is H. In another embodiment is a compound of Formula (IVB) wherein $R_2$ is H; $R_3$ is $C_1$-$C_4$alkyl; and $R_4$ is $C_1$-$C_4$alkyl. In another embodiment is a compound of Formula (IVB) wherein $R_2$ is H; $R_3$ is $CH_3$; and $R_4$ is $CH_3$. In another embodiment is a compound of Formula (IVB) wherein $R_2$ is H; $R_3$ is $C_1$-$C_4$alkyl; and $R_4$ is —CN. In another embodiment is a compound of Formula (IVB) wherein $R_2$ is H; $R_3$ is $CH_3$; and $R_4$ is —CN. In another embodiment is a compound of Formula (IVB) wherein $R_2$ is $C_1$-$C_4$alkyl; $R_3$ is $C_1$-$C_4$alkyl; and $R_4$ is H. In another embodiment is a compound of Formula (IVB) wherein $R_2$ is $CH_3$; $R_3$ is $CH_3$; and $R_4$ is H. In another embodiment is a compound of Formula (IVB) wherein $R_2$ is $C_1$-$C_4$alkyl; $R_3$ is H; and $R_4$ is H. In another embodiment is a compound of Formula (IVB) wherein $R_2$ is $CH_3$; $R_3$ is H; and $R_4$ is H. In another embodiment is a compound of Formula (IVB) wherein $R_2$ is $C_1$-$C_4$alkyl; $R_3$ is H; and $R_4$ is $C_1$-$C_4$alkyl. In another embodiment is a compound of Formula (IVB) wherein $R_2$ is $CH_3$; $R_3$ is H; and $R_4$ is $CH_3$. In another embodiment is a compound of Formula (IVB) wherein $R_2$ is $C_1$-$C_4$alkyl; $R_3$ is H; and $R_4$ is —CN. In another embodiment is a compound of Formula (IVB) wherein $R_2$ is $CH_3$; $R_3$ is H; and $R_4$ is —CN. In another embodiment is a compound of Formula (IVB) wherein $R_2$ is $C_3$-$C_6$cycloalkyl; $R_3$ is H; and $R_4$ is H. In another embodiment is a compound of Formula (IVB) wherein $R_2$ is cyclopropyl; $R_3$ is H; and $R_4$ is H. In another embodiment is a compound of Formula (IVB) wherein $R_2$ is cyclopentyl; $R_3$ is H; and $R_4$ is H. In another embodiment is a compound of Formula (IVB) wherein $R_2$ is $C_3$-$C_6$cycloalkyl; $R_3$ is H; and $R_4$ is $CH_3$. In another embodiment is a compound of Formula (IVB) wherein $R_2$ is cyclopropyl; $R_3$ is H; and $R_4$ is $CH_3$. In another embodiment is a compound of Formula (IVB) wherein $R_2$ is cyclopentyl; $R_3$ is H; and $R_4$ is $CH_3$. In another embodiment is a compound of Formula (IVB) wherein $R_2$ is $C_3$-$C_6$cycloalkyl; $R_3$ is H; and $R_4$ is —CN. In another embodiment is a compound of Formula (IVB) wherein $R_2$ is cyclopropyl; $R_3$ is H; and $R_4$ is —CN. In another embodiment is a compound of Formula (IVB) wherein $R_2$ is cyclopentyl; $R_3$ is H; and $R_4$ is —CN.

In another embodiment is a compound of Formula (IVB) wherein $R_2$ and $R_3$ are taken together to form a 5- or 6-membered heterocyclic ring. In another embodiment is a compound of Formula (IVB) wherein $R_2$ and $R_3$ are taken together to form a 5- or 6-membered heterocyclic ring; and $R_4$ is H. In another embodiment is a compound of Formula (IVB) wherein $R_2$ and $R_3$ are taken together to form a 5-membered heterocyclic ring; and $R_4$ is H. In another embodiment is a compound of Formula (IVB) wherein $R_2$ and $R_3$ are taken together to form 6-membered heterocyclic ring; and $R_4$ is H.

In another embodiment is a compound of Formula (IVB) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IVB) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment is a compound of Formula (IVB) wherein each $R_1$ is independently halogen, —CN, —$OCF_3$, —$OCH_2F$, —$OCF_2H$, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (IVB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy. In another embodiment is a compound of Formula (IVB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 3. In another embodiment is a compound of Formula (IVB) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 2. In another embodiment is a compound of Formula (IVB) wherein n is 3, and each $R_1$ is independently halogen. In another embodiment is a compound of Formula (IVB) wherein n is 2, and each $R_1$ is independently halogen. In another embodiment is a compound of Formula (IVB) wherein n is 2, and each $R_1$ is independently F or Cl. In another embodiment is a compound of Formula (IVB) wherein n is 2, and each $R_1$ is F. In another embodiment is a compound of Formula (IVB) wherein n is 2, and each $R_1$ is independently Cl. In another embodiment is a compound of Formula (IVB) wherein n is 2, and each $R_1$ is independently halogen or —$CF_3$. In another embodiment is a compound of Formula (IVB) wherein n is 2, and each $R_1$ is independently F or —$CF_3$. In another embodiment is a compound of Formula (IVB) wherein n is 2, and each $R_1$ is independently Cl or —$CF_3$. In another embodiment is a compound of Formula (IVB) wherein n is 1, and $R_1$ is halogen. In another embodiment is a compound of Formula (IVB) wherein n is 1, and $R_1$ is F. In another embodiment is a compound of Formula (IVB) wherein n is 1, and $R_1$ is Cl. In another embodiment is a compound of Formula (IVB) wherein n is 1, and $R_1$ is —$CF_3$. In another embodiment is a compound of Formula (IVB) wherein n is 1, and $R_1$ is substituted or unsubstituted $C_1$-$C_6$alkyl. In another embodiment is a compound of Formula (IVB) wherein n is 1, and $R_1$ is $CH_3$. In another embodiment is a compound of Formula (IVB) wherein n is 1, and $R_1$ is substituted or unsubstituted $C_1$-$C_6$alkoxy. In another embodiment is a compound of Formula (IVB) wherein n is 1, and $R_1$ is —$OCH_3$. In another embodiment is a compound of Formula (IVB) wherein n is 1, and $R_1$ is —$OCF_3$. In another embodiment is a compound of Formula (IVB) wherein n is 1, and $R_1$ is —$OCF_2H$.

In one aspect, described herein is a compound of Formula (V):

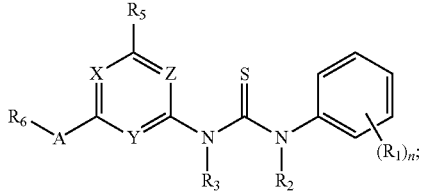

Formula (V)

wherein:

A is a bond, O, $CH_2$, or $N(R_{10})$;

X, Y, and Z are each independently N, or $C(R_7)$;

each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;

$R_2$ and $R_3$, are each independently H, —CN, $C_1$-$C_4$alkyl, $C_3$-$C_6$cycloalkyl, or $C_2$-$C_7$heterocycloalkyl; or $R_2$ and $R_3$ taken together to form a 5- or 6-membered heterocyclic ring;

$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

$R_6$ is substituted or unsubstituted $C_2$-$C_7$heterocycloalkyl, substituted or unsubstituted $C_3$-$C_8$cycloalkyl, substituted or unsubstituted $C_2$-$C_7$heteroaryl, —$C(R_{14})(R_{15}))_mR_{21}$, —$C(R_{14})(R_{15}))_mN(R_{11})(R_{12})$, or

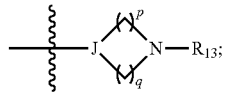

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;

J is C(H), or N;

$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;

each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;

$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)N(R_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;

each $R_{22}$ is independently H, or substituted or unsubstituted $C_1$-$C_6$alkyl; $R_{23}$ is substituted or unsubstituted $C_1$-$C_6$alkyl;

each $R_8$ is independently H, or substituted or unsubstituted $C_1$-$C_6$alkyl;

$R_9$ is substituted or unsubstituted $C_1$-$C_6$alkyl;

$R_{10}$ is H, or $C_1$-$C_4$alkyl;

m is 2-6;

n is 0-5;

p is 1-3;

q is 1-3; or a pharmaceutically acceptable salt, solvate, or prodrug thereof.

In one embodiment is a compound of Formula (V) wherein A is O, $CH_2$, or $N(R_{10})$. In another embodiment is a compound of Formula (V) wherein A is O, $CH_2$, or N(H). In another embodiment is a compound of Formula (V) wherein A is O. In another embodiment is a compound of Formula (V) wherein A is $CH_2$. In another embodiment is a compound of Formula (V) wherein A is $N(R_{10})$. In another embodiment is a compound of Formula (V) wherein A is N(H). In another embodiment is a compound of Formula (V) wherein A is $N(CH_3)$. In another embodiment is a compound of Formula (V) wherein A is a bond.

In another embodiment is a compound of Formula (V) wherein $R_6$ is substituted or unsubstituted $C_3$-$C_8$cycloalkyl. In another embodiment is a compound of Formula (V) wherein $R_6$ is substituted or unsubstituted cyclopropyl. In another embodiment is a compound of Formula (V) wherein $R_6$ is substituted or unsubstituted cyclobutyl. In another embodiment is a compound of Formula (V) wherein $R_6$ is substituted or unsubstituted cyclopentyl. In another embodiment is a compound of Formula (V) wherein $R_6$ is substituted or unsubstituted cyclohexyl.

In another embodiment is a compound of Formula (V) wherein $R_6$ is substituted or unsubstituted $C_2$-$C_7$heteroaryl. In another embodiment is a compound of Formula (V) wherein $R_6$ is substituted or unsubstituted furanyl, thiophenyl, pyrrolyl, pyridyl, oxazolyl, thiazolyl, imidazolyl, isoxazolyl, isothiazolyl, pyrazolyl, pyridazinyl, pyrimidinyl, pyrazinyl, oxadiazolyl, thiadiazolyl, triazolyl, indolyl, benzothiophenyl, benzoxazolyl, benzothiazolyl, benzimidazolyl, benzoxadiazolyl, benzothiadiazolyl, benzotriazolyl, pyrazolopyridinyl, imidazopyridinyl, pyrrolopyridinyl, pyrrolopyrimidinyl, indolizinyl, purinyl, furopyridinyl, thienopyridinyl, furopyrrolyl, furofuranyl, thienofuranyl, 1,4-dihydropyrrolopyrrolyl, thienopyrrolyl, thienothiophenyl, quinolinyl, isoquinolinyl, quinoxalinyl, furopyrazolyl, thienopyrazolyl, selenophenyl, selenazolyl, and benzoisoxazolyl. In another embodiment is a compound of Formula (V) wherein $R_6$ is substituted or unsubstituted pyridyl. In another embodiment is a compound of Formula (V) wherein $R_6$ is substituted pyridyl. In another embodiment is a compound of Formula (V) wherein $R_6$ is unsubstituted pyridyl.

In another embodiment is a compound of Formula (V) wherein $R_6$ is —$(C(R_{14})(R_{15}))_m R_{21}$. In another embodiment is a compound of Formula (V) wherein $R_6$ is —$(C(R_{14})(R_{15}))_m R_{21}$, and each $R_{14}$ and $R_{15}$ are H. In another embodiment is a compound of Formula (V) wherein $R_6$ is —$(C(R_{14})(R_{15}))_m R_{21}$, m is 2, and each $R_{14}$ and $R_{15}$ are H. In another embodiment is a compound of Formula (V) wherein $R_6$ is —$(CH_2)_m R_{21}$, m is 2, and $R_{21}$ is substituted or unsubstituted $C_2$-$C_7$heterocycloalkyl. In another embodiment is a compound of Formula (V) wherein $R_6$ is —$(CH_2)_m R_{21}$, m is 2, and $R_{21}$ is substituted or unsubstituted $C_3$-$C_8$cycloalkyl. In another embodiment is a compound of Formula (V) wherein $R_6$ is —$(CH_2)_m R_{21}$, m is 2, and $R_{21}$ is substituted or unsubstituted $C_6$-$C_{10}$aryl. In another embodiment is a compound of Formula (V) wherein $R_6$ is —$(CH_2)_m R_{21}$, m is 2, and $R_{21}$ is substituted or unsubstituted phenyl. In another embodiment is a compound of Formula (V) wherein $R_6$ is —$(CH_2)_m R_{21}$, m is 2, and $R_{21}$ is substituted or unsubstituted $C_2$-$C_7$heteroaryl.

In another embodiment is a compound of Formula (V) wherein $R_6$ is —$(C(R_{14})(R_{15}))_m R_{21}$, m is 3, and each $R_{14}$ and $R_{15}$ are H. In another embodiment is a compound of Formula (V) wherein $R_6$ is —$(CH_2)_m R_{21}$, m is 3, and $R_{21}$ is substituted or unsubstituted $C_2$-$C_7$heterocycloalkyl. In another embodiment is a compound of Formula (V) wherein $R_6$ is —$(CH_2)_m R_{21}$, m is 3, and $R_{21}$ is substituted or unsubstituted $C_3$-$C_8$cycloalkyl. In another embodiment is a compound of Formula (V) wherein $R_6$ is —$(CH_2)_m R_{21}$, m is 3, and $R_{21}$ is substituted or unsubstituted $C_6$-$C_{10}$aryl. In another embodiment is a compound of Formula (V) wherein $R_6$ is —$(CH_2)_m R_{21}$, m is 3, and $R_{21}$ is substituted or unsubstituted phenyl. In another embodiment is a compound of Formula (V) wherein $R_6$ is —$(CH_2)_m R_{21}$, m is 3, and $R_{21}$ is substituted or unsubstituted $C_2$-$C_7$heteroaryl.

In another embodiment is a compound of Formula (V) wherein $R_6$ is —$(C(R_{14})(R_{15}))_m N(R_{11})(R_{12})$. In another embodiment is a compound of Formula (V) wherein $R_6$ is —$(C(R_{14})(R_{15}))_m N(R_{11})(R_{12})$, m is 2, and each $R_{14}$ and $R_{15}$ are H. In another embodiment is a compound of Formula (V) wherein $R_6$ is —$(CH_2)_m N(R_{11})(R_{12})$, m is 2, and $R_{11}$ and $R_{12}$ are each H. In another embodiment is a compound of Formula (V) wherein $R_6$ is —$(CH_2)_m N(R_{11})(R_{12})$, m is 2, $R_{11}$ is substituted or unsubstituted $C_1$-$C_6$alkyl, and $R_{12}$ is H. In another embodiment is a compound of Formula (V) wherein $R_6$ is —$(CH_2)_m N(R_{11})(R_{12})$, m is 2, $R_{11}$ is $CH_3$, and $R_{12}$ is H. In another embodiment is a compound of Formula (V) wherein $R_6$ is —$(CH_2)_m N(R_{11})(R_{12})$, m is 2, $R_{11}$ is substituted or unsubstituted $C_1$-$C_6$alkyl, and $R_{12}$ is substituted or unsubstituted $C_1$-$C_6$alkyl. In another embodiment is a compound of Formula (V) wherein $R_6$ is —$(CH_2)_m N(R_{11})(R_{12})$, m is 2, $R_{11}$ is $CH_3$, and $R_{12}$ is $CH_3$. In another embodiment is a compound of Formula (V) wherein $R_6$ is —$(CH_2)_m N(R_{11})(R_{12})$, m is 2, and $R_{11}$ and $R_{12}$ are taken together to form a 5-, 6-, 7-, or 8-membered heterocyclic ring. In another embodiment is a compound of Formula (V) wherein $R_6$ is —$(CH_2)_m N(R_{11})(R_{12})$, m is 2, and $R_{11}$ and $R_{12}$ are taken together to form a 5-membered heterocyclic ring. In another embodiment is a compound of Formula (V) wherein $R_6$ is —$(CH_2)_m N(R_{11})(R_{12})$, m is 2, and $R_{11}$ and $R_{12}$ are taken together to form a 6-membered heterocyclic ring.

In another embodiment is a compound of Formula (V) wherein $R_6$ is —$(C(R_{14})(R_{15}))_m N(R_{11})(R_{12})$. In another embodiment is a compound of Formula (V) wherein $R_6$ is —$(C(R_{14})(R_{15}))_m N(R_{11})(R_{12})$, m is 3, and each $R_{14}$ and $R_{15}$ are H. In another embodiment is a compound of Formula (V) wherein $R_6$ is —$(CH_2)_m N(R_{11})(R_{12})$, m is 3, and $R_{11}$ and $R_{12}$ are each H. In another embodiment is a compound of Formula (V) wherein $R_6$ is —$(CH_2)_m N(R_{11})(R_{12})$, m is 3, $R_{11}$ is substituted or unsubstituted $C_1$-$C_6$alkyl, and $R_{12}$ is H. In another embodiment is a compound of Formula (V) wherein $R_6$ is —$(CH_2)_m N(R_{11})(R_{12})$, m is 3, $R_{11}$ is $CH_3$, and $R_{12}$ is H. In another embodiment is a compound of Formula (V) wherein $R_6$ is —$(CH_2)_m N(R_{11})(R_{12})$, m is 3, $R_{11}$ is substituted or unsubstituted $C_1$-$C_6$alkyl, and $R_{12}$ is substituted or unsubstituted $C_1$-$C_6$alkyl. In another embodiment is a compound of Formula (V) wherein $R_6$ is —$(CH_2)_m N(R_{11})(R_{12})$, m is 3, $R_{11}$ is $CH_3$, and $R_{12}$ is $CH_3$. In another embodiment is a compound of Formula (V) wherein $R_6$ is —$(CH_2)_m N(R_{11})(R_{12})$, m is 3, and $R_{11}$ and $R_{12}$ are taken together to form a 5-, 6-, 7-, or 8-membered heterocyclic ring. In another embodiment is a compound of Formula (V) wherein $R_6$ is —$(CH_2)_m N(R_{11})(R_{12})$, m is 3, and $R_{11}$ and $R_{12}$ are taken together to form a 5-membered heterocyclic ring. In another embodiment is a compound of Formula (V) wherein $R_6$ is —$(CH_2)_m N(R_{11})(R_{12})$, m is 3, and $R_{11}$ and $R_{12}$ are taken together to form a 6-membered heterocyclic ring.

In another embodiment is a compound of Formula (V) wherein $R_6$ is substituted or unsubstituted $C_2$-$C_7$heterocycloalkyl. In another embodiment is a compound of Formula (V) wherein $R_6$ is

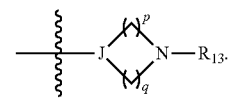

In another embodiment is a compound of Formula (V) wherein $R_6$ is

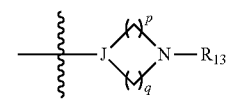

and J is C(H). In another embodiment is a compound of Formula (V) wherein $R_6$ is

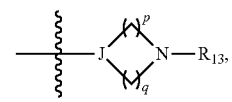

J is C(H), p is 1, and q is 1. In another embodiment is a compound of Formula (V) wherein $R_6$ is

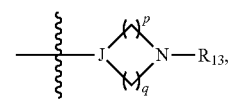

J is C(H), p is 2, and q is 1. In another embodiment is a compound of Formula (V) wherein $R_6$ is

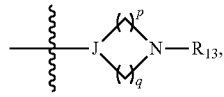

J is C(H), p is 3, and q is 1. In another embodiment is a compound of Formula (V) wherein $R_6$ is

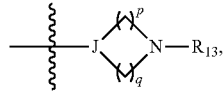

J is C(H), p is 2, and q is 2. In another embodiment is a compound of Formula (V) wherein $R_6$ is

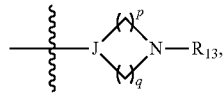

J is C(H), p is 1, q is 1, and $R_{13}$ is substituted or unsubstituted $C_1$-$C_6$alkyl. In another embodiment is a compound of Formula (V) wherein $R_6$ is

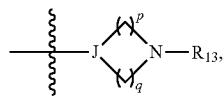

J is C(H), p is 2, q is 1, and $R_{13}$ is substituted or unsubstituted $C_1$-$C_6$alkyl. In another embodiment is a compound of Formula (V) wherein $R_6$ is

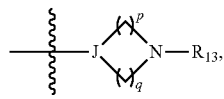

J is C(H), p is 3, q is 1, and $R_{13}$ is substituted or unsubstituted $C_1$-$C_6$alkyl. In another embodiment is a compound of Formula (V) wherein $R_6$ is

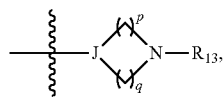

J is C(H), p is 2, q is 2, and $R_{13}$ is substituted or unsubstituted $C_1$-$C_6$alkyl.

In another embodiment is a compound of Formula (V) wherein $R_6$ is

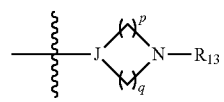

and J is N. In another embodiment is a compound of Formula (V) wherein $R_6$ is

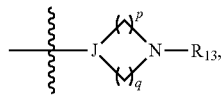

J is N, p is 2, and q is 2. In another embodiment is a compound of Formula (V) wherein $R_6$ is

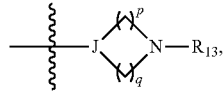

J is N, p is 2, q is 2, and $R_{13}$ is substituted or unsubstituted $C_1$-$C_6$alkyl.

In another embodiment is a compound of Formula (V) wherein $R_5$ is halogen. In another embodiment is a compound of Formula (V) wherein $R_5$ is —$CF_3$. In another embodiment is a compound of Formula (V) wherein $R_5$ is substituted or unsubstituted $C_1$-$C_6$alkyl. In another embodiment is a compound of Formula (V) wherein $R_5$ is —$CH_3$. In another embodiment is a compound of Formula (V) wherein $R_5$ is —$CH_2CH_3$. In another embodiment is a compound of Formula (V) wherein $R_5$ is substituted or unsubstituted $C_1$-$C_6$heteroalkyl. In another embodiment is a compound of Formula (V) wherein $R_5$ is substituted or unsubstituted $C_2$-$C_7$heterocycloalkyl. In another embodiment is a compound of Formula (V) wherein $R_5$ is substituted or unsubstituted $C_3$-$C_8$cycloalkyl. In another embodiment is a compound of Formula (V) wherein $R_5$ is substituted or unsubstituted $C_6$-$C_{10}$aryl. In another embodiment is a compound of Formula (V) wherein $R_5$ is substituted or unsubstituted $C_2$-$C_7$heteroaryl.

In another embodiment is a compound of Formula (V) wherein $R_2$ and $R_3$ are each independently H, —CN, $C_1$-$C_4$alkyl, $C_3$-$C_6$cycloalkyl, or $C_2$-$C_7$heterocycloalkyl. In another embodiment is a compound of Formula (V) wherein $R_2$ and $R_3$, are each H.

In another embodiment is a compound of Formula (V) wherein $R_2$ and $R_3$ are each independently H, —CN, $C_1$-$C_4$alkyl, $C_3$-$C_6$cycloalkyl, or $C_2$-$C_7$heterocycloalkyl; and at least one of $R_2$ and $R_3$ is not H. In another embodiment is a compound of Formula (V) wherein $R_2$ is H; $R_3$ is $C_1$-$C_4$alkyl. In another embodiment is a compound of Formula (V) wherein $R_2$ is H; $R_3$ is $CH_3$. In another embodiment is a compound of Formula (V) wherein $R_2$ is $C_1$-$C_4$alkyl; $R_3$ is $C_1$-$C_4$alkyl. In another embodiment is a compound of Formula (V) wherein $R_2$ is $CH_3$; $R_3$ is $CH_3$. In another embodiment is a compound of Formula (V) wherein $R_2$ is $C_1$-$C_4$alkyl; $R_3$ is H. In another embodiment is a compound of Formula (V) wherein $R_2$ is $CH_3$; $R_3$ is H. In another embodiment is a compound of Formula (V) wherein $R_2$ is $C_3$-$C_6$cycloalkyl; $R_3$ is H. In another embodiment is a compound of Formula (V) wherein $R_2$ is cyclopropyl; $R_3$ is H. In another embodiment is a compound of Formula (V) wherein $R_2$ is cyclopentyl; $R_3$ is H.

In another embodiment is a compound of Formula (V) wherein $R_2$ and $R_3$ are taken together to form a 5- or 6-membered heterocyclic ring. In another embodiment is a compound of Formula (V) wherein $R_2$ and $R_3$ are taken together to form a 5- or 6-membered heterocyclic ring. In another embodiment is a compound of Formula (V) wherein $R_2$ and $R_3$ are taken together to form a 5-membered heterocyclic ring.

In another embodiment is a compound of Formula (V) wherein each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (V) wherein each $R_1$ is independently halogen, —CN, —OH, —$CF_3$, substituted or unsubstituted $C_1$-$C_6$alkyl, or substituted or unsubstituted $C_1$-$C_6$alkoxy. In another embodiment is a compound of Formula (V) wherein each $R_1$ is independently halogen, —CN, —$OCF_3$, —$OCH_2F$, —$OCF_2H$, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl. In another embodiment is a compound of Formula (V) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy. In another embodiment is a compound of Formula (V) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 3. In another embodiment is a compound of Formula (V) wherein each $R_1$ is independently halogen, —CN, —$OCF_3$, —$OCH_2F$, —$OCF_2H$, —$CF_3$, substituted or unsubstituted $C_1$-$C_6$alkyl, or substituted or unsubstituted $C_1$-$C_6$alkoxy, and n is 2. In another embodiment is a compound of Formula (V) wherein n is 3, and each $R_1$ is independently halogen. In another embodiment is a compound of Formula (V) wherein n is 2, and each $R_1$ is independently halogen. In another embodiment is a compound of Formula (V) wherein n is 2, and each $R_1$ is independently F or Cl. In another embodiment is a compound of Formula (V) wherein n is 2, and each $R_1$ is F. In another embodiment is a compound of Formula (V) wherein n is 2, and each $R_1$ is independently Cl. In another embodiment is a compound of Formula (V) wherein n is 2, and each $R_1$ is independently halogen or —$CF_3$. In another embodiment is a compound of Formula (V) wherein n is 2, and each $R_1$ is independently F or —$CF_3$. In another embodiment is a compound of Formula (V) wherein n is 2, and each $R_1$ is independently Cl or —$CF_3$. In another embodiment is a compound of Formula (V) wherein n is 1, and $R_1$ is halogen. In another embodiment is a compound of Formula (V) wherein n is 1, and $R_1$ is F. In another embodiment is a compound of Formula (V) wherein n is 1, and $R_1$ is Cl. In another embodiment is a compound of Formula (V) wherein n is 1, and $R_1$ is —$CF_3$. In another embodiment is a compound of Formula (V) wherein n is 1, and $R_1$ is substituted or unsubstituted $C_1$-$C_6$alkyl. In another embodiment is a compound of Formula (V) wherein n is 1, and $R_1$ is $CH_3$. In another embodiment is a compound of Formula (V) wherein n is 1, and $R_1$ is substituted or unsubstituted $C_1$-$C_6$alkoxy. In another embodiment is a compound of Formula (V) wherein n is 1, and $R_1$ is —$OCH_3$. In another embodiment is a compound of Formula (V) wherein n is 1, and $R_1$ is —$OCF_3$. In another embodiment is a compound of Formula (V) wherein n is 1, and $R_1$ is —$OCF_2H$.

In a further embodiment of the aforementioned embodiments of Formula (V), X is $C(R_7)$; Y is N; and Z is N. In a further embodiment of the aforementioned embodiments of Formula (V), X is C(H); Y is N; and Z is N. In a further embodiment of the aforementioned embodiments of Formula (V), X is $C(R_7)$; Y is $C(R_7)$; and Z is N. In a further embodiment of the aforementioned embodiments of Formula (V), X is C(H); Y is C(H); and Z is N. In a further embodiment of the aforementioned embodiments of Formula (V), X is $C(R_7)$; Y is N; and Z is $C(R_7)$. In a further embodiment of the aforementioned embodiments of Formula (V), X is C(H); Y is N; and Z is C(H). In a further embodiment of the aforementioned embodiments of Formula (V), X is $C(R_7)$; Y is $C(R_7)$; and Z is $C(R_7)$. In a further embodiment of the aforementioned embodiments of Formula (V), X is C(H); Y is C(H); and Z is C(H).

In another embodiment is a compound selected from: 3-(3,4-dichlorophenyl)-1-(4-(1-ethylpiperidin-3-ylamino)-6-methylpyrimidin-2-yl)-1-methylguanidine; 1-(3,4-dichlorophenyl)-3-(4-(1-ethylpiperidin-3-ylamino)-6-methylpyrimidin-2-yl)-1-methylguanidine; 1-(3,4-dichlorophenyl)-3-(4-(1-ethylpiperidin-3-ylamino)-6-methylpyrimidin-2-yl)-1,3-dimethylguanidine; 2-(3-(3,4-dichlorophenyl)-2-iminoimidazolidin-1-yl)-N-(1-ethylpiperidin-3-yl)-6-methylpyrimidin-4-amine; 3-(3,4-dichlorophenyl)-1-(4-(1-ethylpiperidin-3-ylamino)-6-methylpyrimidin-2-yl)-1,2-dimethylguanidine; 2-cyano-3-(3,4-dichlorophenyl)-1-(4-(1-ethylpiperidin-3-ylamino)-6-methylpyrimidin-2-yl)-1-methylguanidine; 3-(3,4-dichlorophenyl)-1-(4-(1-ethylpiperidin-3-yloxy)-6-methylpyrimidin-2-yl)-1-methylguanidine; 1-(3,4-dichlorophenyl)-3-(4-(1-ethylpiperidin-3-yloxy)-6-methylpyrimidin-2-yl)-1,3-dimethylguanidine; 3-(3,4-dichlorophenyl)-1-(4-(1-ethylpiperidin-3-yloxy)-6-methylpyrimidin-2-yl)-1,2-dimethylguanidine; 2-cyano-3-(3,4-dichlorophenyl)-1-(4-(1-ethylpiperidin-3-yloxy)-6-methylpyrimidin-2-yl)-1-methylguanidine; 1-(3,4-dichlorophenyl)-3-(4-(1-ethylpiperidin-3-yloxy)-6-methylpyrimidin-2-yl)imidazolidin-2-imine; 3-(3,4-dichlorophenyl)-1-(6-(1-ethylpiperidin-3-yloxy)-4-methylpyridin-2-yl)-1-methylguanidine; 1-(3,4-dichlorophenyl)-3-(6-(1-ethylpiperidin-3-yloxy)-4-methylpyridin-2-yl)-1,3-dimethylguanidine; 3-(3,4-dichlorophenyl)-1-(6-(1-ethylpiperidin-3-yloxy)-4-methylpyridin-2-yl)-1,2-dimethylguanidine; 2-cyano-3-(3,4-dichlorophenyl)-1-(6-(1-ethylpiperidin-3-yloxy)-4-methylpyridin-2-yl)-1-methylguanidine; 1-(3,4-dichlorophenyl)-3-(6-(1-ethylpiperidin-3-yloxy)-4-methylpyridin-2-yl)imidazolidin-2-imine; 3-(3,4-dichlorophenyl)-1-(6-(1-ethylpiperidin-3-ylamino)-4-methylpyridin-2-yl)-1-methylguanidine; 1-(3,4-dichlorophenyl)-3-(6-(1-ethylpiperidin-3-ylamino)-4-methylpyridin-2-yl)-1,3-dimethylguanidine; 3-(3,4-dichlorophenyl)-1-(6-(1-ethylpiperidin-3-ylamino)-4-methylpyridin-2-yl)-1,2-dimethylguanidine; 2-cyano-3-(3,4-dichlorophenyl)-1-(6-(1-ethylpiperidin-3-ylamino)-4-methylpyridin-2-yl)-1-methylguanidine; 6-(3-(3,4-dichlorophenyl)-2-iminoimidazolidin-1-yl)-N-(1-ethylpiperidin-3-yl)-4-methylpyridin-2-amine; 3-(3,4-dichlorophenyl)-1-(4-(1-ethylpiperidin-3-ylamino)-6-methylpyridin-2-yl)-1-methylguanidine; 1-(3,4-dichlorophenyl)-3-(4-(1-ethylpiperidin-3-ylamino)-6-methylpyridin-2-yl)-1,3-dimethylguanidine; 3-(3,4-dichlorophenyl)-1-(4-(1-ethylpiperidin-3-ylamino)-6-methylpyridin-2-yl)-1,2-dimethylguanidine; 2-cyano-3-(3, 4-dichlorophenyl)-1-(4-(1-ethylpiperidin-3-ylamino)-6-methylpyridin-2-yl)-1-methylguanidine; 2-(3-(3,4-dichlorophenyl)-2-iminoimidazolidin-1-yl)-N-(1-ethylpiperidin-3-yl)-6-methylpyridin-4-amine; 3-(3,4-dichlorophenyl)-1-(4-(1-ethylpiperidin-3-yloxy)-6-methylpyridin-2-yl)-1-methylguanidine; 1-(3,4-dichlorophenyl)-3-(4-(1-ethylpiperidin-3-yloxy)-6-methylpyridin-2-yl)-1,3-dimethylguanidine; 3-(3,4-dichlorophenyl)-1-(4-(1-ethylpiperidin-3-yloxy)-6-methylpyridin-2-yl)-1,2-dimethylguanidine; 2-cyano-3-(3,4-dichlorophenyl)-1-(4-(1-ethylpiperidin-3-yloxy)-6-methylpyridin-2-yl)-1-methylguanidine; 1-(3,4-dichlorophenyl)-3-(4-(1-ethylpiperidin-3-yloxy)-6-methylpyridin-2-yl)imidazolidin-2-imine; 3-(3,4-dichlorophenyl)-1-methyl-1-(4-methyl-6-(pyridin-3-ylamino)pyrimidin-2-yl)guanidine; 1-(3,4-dichlorophenyl)-1,3-dimethyl-3-(4-methyl-6-(pyridin-3-ylamino)pyrimidin-2-yl)guanidine; 3-(3,4-dichlorophenyl)-1,2-dimethyl-1-(4-methyl-6-(pyridin-3-ylamino)pyrimidin-2-yl)guanidine; 2-cyano-3-(3,4-dichlorophenyl)-1-methyl-1-(4-methyl-6-(pyridin-3-ylamino)pyrimidin-2-yl)guanidine; 2-(3-(3,4-dichlorophenyl)-2-iminoimidazolidin-1-yl)-6-methyl-N-(pyridin-3-yl)pyrimidin-4-amine; 3-(3,4-dichlorophenyl)-1-methyl-1-(4-methyl-6-(pyridin-3-yloxy)pyrimidin-2-yl)guanidine; 1-(3,4-dichlorophenyl)-1,3-dimethyl-3-(4-methyl-6-(pyridin-3-yloxy)pyrimidin-2-yl)guanidine; 3-(3,4-dichlorophenyl)-1,2-dimethyl-1-(4-methyl-6-(pyridin-3-yloxy)pyrimidin-2-yl)guanidine; 2-cyano-3-(3,4-dichlorophenyl)-1-methyl-1-(4-methyl-6-(pyridin-3-yloxy)pyrimidin-2-yl)guanidine; 1-(3,4-dichlorophenyl)-3-(4-methyl-6-(pyridin-3-yloxy)pyrimidin-2-yl)imidazolidin-2-imine; 3-(3,4-dichlorophenyl)-1-methyl-1-(4-methyl-6-(pyridin-3-yloxy)pyridin-2-yl)guanidine; 1-(3,4-dichlorophenyl)-1,3-dimethyl-3-(4-methyl-6-(pyridin-3-yloxy)pyridin-2-yl)guanidine; 3-(3,4-dichlorophenyl)-1,2-dimethyl-1-(4-methyl-6-(pyridin-3-yloxy)pyridin-2-yl)guanidine; 2-cyano-3-(3,4-dichlorophenyl)-1-methyl-1-(4-methyl-6-(pyridin-3-yloxy)pyridin-2-yl)guanidine; 1-(3,4-dichlorophenyl)-3-(4-methyl-6-(pyridin-3-yloxy)pyridin-2-yl)imidazolidin-2-imine; 3-(3,4-dichlorophenyl)-1-methyl-1-(4-methyl-6-(pyridin-3-ylmethyl)pyridin-2-yl)guanidine; 1-(3,4-dichlorophenyl)-1,3-dimethyl-3-(4-methyl-6-(pyridin-3-ylmethyl)pyridin-2-yl)guanidine; 3-(3,4-dichlorophenyl)-1,2-dimethyl-1-(4-methyl-6-(pyridin-3-ylmethyl)pyridin-2-yl)guanidine; 2-cyano-3-(3,4-dichlorophenyl)-1-methyl-1-(4-methyl-6-(pyridin-3-ylmethyl)pyridin-2-yl)guanidine; 1-(3,4-dichlorophenyl)-3-(4-methyl-6-(pyridin-3-ylmethyl)pyridin-2-yl)imidazolidin-2-imine; 3-(3,4-dichlorophenyl)-1-methyl-1-(4-methyl-6-(pyridin-3-ylmethyl)pyrimidin-2-yl)guanidine; 1-(3,4-dichlorophenyl)-1,3-dimethyl-3-(4-methyl-6-(pyridin-3-ylmethyl)pyrimidin-2-yl)guanidine; 3-(3,4-dichlorophenyl)-1,2-dimethyl-1-(4-methyl-6-(pyridin-3-ylmethyl)pyrimidin-2-yl)guanidine; 2-cyano-3-(3,4-dichlorophenyl)-1-methyl-1-(4-methyl-6-(pyridin-3-ylmethyl)pyrimidin-2-yl)guanidine; 1-(3,4-dichlorophenyl)-3-(4-methyl-6-(pyridin-3-ylmethyl)pyrimidin-2-yl)imidazolidin-2-imine; 3-(3,4-dichlorophenyl)-1-(4-(1-ethylpiperidin-4-ylamino)-6-methylpyrimidin-2-yl)-1-methylguanidine; 1-(3,4-dichlorophenyl)-3-(4-(1-ethylpiperidin-4-ylamino)-6-methylpyrimidin-2-yl)-1,3-dimethylguanidine; 3-(3,4-dichlorophenyl)-1-(4-(1-ethylpiperidin-4-ylamino)-6-methylpyrimidin-2-yl)-1,2-dimethylguanidine; 2-cyano-3-(3,4-dichlorophenyl)-1-(4-(1-ethylpiperidin-4-ylamino)-6-methylpyrimidin-2-yl)-1-methylguanidine; 2-(3-(3,4-dichlorophenyl)-2-iminoimidazolidin-1-yl)-N-(1-ethylpiperidin-4-yl)-6-methylpyrimidin-4-amine; 3-(3,4-dichlorophenyl)-1-(4-(1-ethylpiperidin-4-yloxy)-6-methylpyrimidin-2-yl)-1-methylguanidine; 1-(3,4-dichlorophenyl)-3-(4-(1-ethylpiperidin-4-yloxy)-6-methylpyrimidin-2-yl)-1,3-dimethylguanidine; 3-(3,4-dichlorophenyl)-1-(4-(1-ethylpiperidin-4-yloxy)-6-methylpyrimidin-2-yl)-1,2-dimethylguanidine; 2-cyano-3-(3,4-dichlorophenyl)-1-(4-(1-ethylpiperidin-4-yloxy)-6-methylpyrimidin-2-yl)-1-methylguanidine; 1-(3,4-dichlorophenyl)-3-(4-(1-ethylpiperidin-4-yloxy)-6-methylpyrimidin-2-yl)imidazolidin-2-imine; 3-(3,4-dichlorophenyl)-1-(4-((4-ethylpiperazin-1-yl)methyl)-6-methylpyrimidin-2-yl)-1-methylguanidine; 1-(3,4-dichlorophenyl)-3-(4-((4-ethylpiperazin-1-yl)methyl)-6-methylpyrimidin-2-yl)-1,3-dimethylguanidine; 3-(3,4-dichlorophenyl)-1-(4-((4-ethylpiperazin-1-yl)methyl)-6-methylpyrimidin-2-yl)-1,2-dimethylguanidine; 2-cyano-3-(3,4-dichlorophenyl)-1-(4-((4-ethylpiperazin-1-yl)methyl)-6-methylpyrimidin-2-yl)-1-methylguanidine; and 1-(3,4-dichlorophenyl)-3-(4-((4-ethylpiperazin-1-yl)methyl)-6-methylpyrimidin-2-yl)imidazolidin-2-imine.

In another embodiment is a compound selected from: 3-(3,4-difluorophenyl)-1-(4-(1-ethylpiperidin-3-ylamino)-6-methylpyrimidin-2-yl)-1-methylguanidine; 3-(3-chloro-4-fluorophenyl)-1-(4-(1-ethylpiperidin-3-ylamino)-6-methylpyrimidin-2-yl)-1-methylguanidine; 1-(4-(1-ethylpiperidin-3-ylamino)-6-methylpyrimidin-2-yl)-3-(3-fluoro-4-(trifluoromethyl)phenyl)-1-methylguanidine; 1-(4-(1-ethylpiperidin-3-ylamino)-6-methylpyrimidin-2-yl)-3-(3-fluorophenyl)-1-methylguanidine; 3-(4-chlorophenyl)-1-(4-(1-ethylpiperidin-3-ylamino)-6-methylpyrimidin-2-yl)-1-methylguanidine; 3-(4-cyanophenyl)-1-(4-(1-ethylpiperidin-3-ylamino)-6-methylpyrimidin-2-yl)-1-methylguanidine; 1-(4-(1-ethylpiperidin-3-ylamino)-6-methylpyrimidin-2-yl)-3-(4-methoxyphenyl)-1-methylguanidine; 1-(4-(1-ethylpiperidin-3-ylamino)-6-methylpyrimidin-2-yl)-1-methyl-3-(4-(trifluoromethoxy)phenyl)guanidine; 1-(4-(1-ethylpiperidin-3-ylamino)-6-methylpyrimidin-2-yl)-3-(4-(fluoromethoxy)phenyl)-1-methylguanidine; 3-(2-chlorophenyl)-1-(4-(1-ethylpiperidin-3-ylamino)-6-methylpyrimidin-2-yl)-1-methylguanidine; 1-(4-chloro-3-fluorophenyl)-3-(4-(1-ethylpiperidin-3-ylamino)-6-methylpyrimidin-2-yl)-1,3-dimethylguanidine; 1-(3-chlorophenyl)-3-(4-(1-ethylpiperidin-3-ylamino)-6-methylpyrimidin-2-yl)-1,3-dimethylguanidine; 1-(3-cyanophenyl)-3-(4-(1-ethylpiperidin-3-ylamino)-6-methylpyrimidin-2-yl)-1,3-dimethylguanidine; 1-(4-(1-ethylpiperidin-3-ylamino)-6-methylpyrimidin-2-yl)-1,3-dimethyl-3-(2-(trifluoromethyl)phenyl)guanidine; 1-(3,4-difluorophenyl)-3-(4-(1-ethylpiperidin-3-ylamino)-6-methylpyrimidin-2-yl)-1-methylguanidine; 3-(4-(1-ethylpiperidin-3-ylamino)-6-methylpyrimidin-2-yl)-1-(4-fluorophenyl)-1-methylguanidine; 3-(4-(1-ethylpiperidin-3-ylamino)-6-methylpyrimidin-2-yl)-1-(4-fluoro-3-(trifluoromethyl)phenyl)-1-methylguanidine; 3-(4-(1-ethylpiperidin-3-ylamino)-6-methylpyrimidin-2-yl)-1-methyl-1-(3-(trifluoromethoxy)phenyl)guanidine; 3-(4-(1-ethylpiperidin-3-ylamino)-6-methylpyrimidin-2-yl)-1,2-dimethyl-1-(4-(trifluoromethoxy)phenyl)guanidine; 1-(3-chlorophenyl)-3-(4-(1-ethylpiperidin-3-ylamino)-6-methylpyrimidin-2-yl)-1,2-dimethylguanidine; 1-(4-cyanophenyl)-3-(4-(1-ethylpiperidin-3-ylamino)-6-methylpyrimidin-2-yl)-1,2-dimethylguanidine; 1-(4-chlorophenyl)-2-cyano-3-(4-(1-ethylpiperidin-3-ylamino)-6-methylpyrimidin-2-yl)-1-methylguanidine; 2-cyano-1-(3,4-difluorophenyl)-3-(4-(1-ethylpiperidin-3-ylamino)-6-methylpyrimidin-2-yl)-1-methylguanidine; 2-cyano-3-(4-

(1-ethylpiperidin-3-ylamino)-6-methylpyrimidin-2-yl)-1-(4-methoxyphenyl)-1-methylguanidine; 1-cyclopropyl-3-(4-(1-ethylpiperidin-3-ylamino)-6-methylpyrimidin-2-yl)-1-(4-(trifluoromethoxy)phenyl)guanidine; 1-cyclopropyl-1-(3,4-dichlorophenyl)-3-(4-(1-ethylpiperidin-3-ylamino)-6-methylpyrimidin-2-yl)guanidine; 1-cyclopropyl-3-(4-(1-ethylpiperidin-3-ylamino)-6-methylpyrimidin-2-yl)-1-(4-fluorophenyl)guanidine; 1-(4-chlorophenyl)-1-cyclopropyl-3-(4-(1-ethylpiperidin-3-ylamino)-6-methylpyrimidin-2-yl)-2-methylguanidine; 1-cyclopentyl-3-(4-(1-ethylpiperidin-3-ylamino)-6-methylpyrimidin-2-yl)-1-(3-(fluoromethoxy)phenyl)guanidine; 1-(3-cyanophenyl)-1-cyclopentyl-3-(4-(1-ethylpiperidin-3-ylamino)-6-methylpyrimidin-2-yl)guanidine; 1-cyclopentyl-3-(4-(1-ethylpiperidin-3-ylamino)-6-methylpyrimidin-2-yl)-1-(3-fluoro-4-(trifluoromethyl)phenyl)guanidine; 1-(4-chlorophenyl)-1-cyclopentyl-3-(4-(1-ethylpiperidin-3-ylamino)-6-methylpyrimidin-2-yl)guanidine; 3-(4-chloro-3-fluorophenyl)-1-(4-(1-ethylpiperidin-3-yloxy)-6-methylpyrimidin-2-yl)-1-methylguanidine; 1-(4-(1-ethylpiperidin-3-yloxy)-6-methylpyrimidin-2-yl)-3-(4-methoxyphenyl)-1-methylguanidine; 1-(4-(1-ethylpiperidin-3-yloxy)-6-methylpyrimidin-2-yl)-3-(2-fluorophenyl)-1-methylguanidine; 3-(4-(1-ethylpiperidin-3-yloxy)-6-methylpyrimidin-2-yl)-1-(3-fluoro-4-(trifluoromethyl)phenyl)-1-methylguanidine; 3-(4-(1-ethylpiperidin-3-yloxy)-6-methylpyrimidin-2-yl)-1-(4-fluorophenyl)-1-methylguanidine; 1-(3-chloro-4-fluorophenyl)-3-(4-(1-ethylpiperidin-3-yloxy)-6-methylpyrimidin-2-yl)-1,2-dimethylguanidine; 1-(3-cyanophenyl)-3-(4-(1-ethylpiperidin-3-yloxy)-6-methylpyrimidin-2-yl)-1,2-dimethylguanidine; 1-cyclopropyl-3-(4-(1-ethylpiperidin-3-yloxy)-6-methylpyrimidin-2-yl)-1-(3-fluorophenyl)guanidine; 1-cyclopropyl-1-(4-(difluoromethoxy)phenyl)-3-(4-(1-ethylpiperidin-3-yloxy)-6-methylpyrimidin-2-yl)guanidine; 1-(4-cyanophenyl)-3-(4-(1-ethylpiperidin-4-ylamino)-6-methylpyrimidin-2-yl)-1-methylguanidine; 3-(4-(1-ethylpiperidin-4-yloxy)-6-methylpyrimidin-2-yl)-1-(4-fluoro-3-(trifluoromethyl)phenyl)-1-methylguanidine; 1-(2-chlorophenyl)-3-(4-(1-ethylpiperidin-4-yloxy)-6-methylpyrimidin-2-yl)-1-methylguanidine; 1-cyclopentyl-1-(3,4-difluorophenyl)-3-(4-(1-ethylpiperidin-4-ylamino)-6-methylpyrimidin-2-yl)guanidine; 1-cyclopentyl-1-(3,4-dichlorophenyl)-3-(4-((1-ethylpiperidin-4-yl)(methyl)amino)-6-methylpyrimidin-2-yl)guanidine; 1-cyclopentyl-3-(4-((1-ethylpiperidin-4-yl)(methyl)amino)-6-methylpyrimidin-2-yl)-1-(4-(trifluoromethyl)phenyl)guanidine; 3-(4-((1-ethylpiperidin-4-yl)(methyl)amino)-6-methylpyrimidin-2-yl)-1-(2-fluorophenyl)-1-methylguanidine; 3-(4-((1-ethylpiperidin-4-yl)(methyl)amino)-6-methylpyrimidin-2-yl)-1-(3-methoxyphenyl)-1,2-dimethylguanidine; 1-(4-chlorophenyl)-3-(4-((1-ethylpiperidin-4-yl)(methyl)amino)-6-methylpyrimidin-2-yl)-1,2-dimethylguanidine; 2-cyano-3-(4-((1-ethylpiperidin-4-yl)(methyl)amino)-6-methylpyrimidin-2-yl)-1-(4-fluorophenyl)-1-methylguanidine; 1-(3,4-difluorophenyl)-3-(4-((4-ethylpiperazin-1-yl)methyl)-6-methylpyrimidin-2-yl)-1-methylguanidine; 1-cyclopropyl-3-(4-((4-ethylpiperazin-1-yl)methyl)-6-methylpyrimidin-2-yl)-1-(3-fluoro-4-(trifluoromethyl)phenyl)guanidine; 1-(4-chloro-3-fluorophenyl)-1-cyclopentyl-3-(4-((4-ethylpiperazin-1-yl)methyl)-6-methylpyrimidin-2-yl)guanidine; 1-(3,4-dichlorophenyl)-3-(4-(1-ethylazetidin-3-ylamino)-6-methylpyrimidin-2-yl)-1-methylguanidine; 3-(3,4-dichlorophenyl)-1-(4-(1-ethylazetidin-3-ylamino)-6-methylpyrimidin-2-yl)-1-methylguanidine; 3-(3-chloro-4-fluorophenyl)-1-(4-(1-ethylazetidin-3-ylamino)-6-methylpyrimidin-2-yl)-1,2-dimethylguanidine; 2-cyano-1-(4-(1-ethylazetidin-3-ylamino)-6-methylpyrimidin-2-yl)-3-(3-fluorophenyl)-1-methylguanidine; 1-(4-cyanophenyl)-3-(4-(1-ethylazetidin-3-ylamino)-6-methylpyrimidin-2-yl)-1-methylguanidine; 3-(4-(1-ethylazetidin-3-yloxy)-6-methylpyrimidin-2-yl)-1-(4-fluoro-3-(trifluoromethyl)phenyl)-1-methylguanidine; 1-(3-chlorophenyl)-3-(4-(1-ethylazetidin-3-yloxy)-6-methylpyrimidin-2-yl)-1-methylguanidine; 1-cyclopropyl-1-(3,4-dichlorophenyl)-3-(4-(1-ethylazetidin-3-yloxy)-6-methylpyrimidin-2-yl)guanidine; 1-(4-chloro-3-fluorophenyl)-1-methyl-3-(4-methyl-6-(pyridin-3-ylamino)pyrimidin-2-yl)guanidine; 1-methyl-3-(4-methyl-6-(pyridin-3-ylamino)pyrimidin-2-yl)-1-(4-(trifluoromethoxy)phenyl)guanidine; 1-(3,4-difluorophenyl)-1,2-dimethyl-3-(4-methyl-6-(pyridin-3-ylamino)pyrimidin-2-yl)guanidine; 1-cyclopentyl-2-methyl-3-(4-methyl-6-(pyridin-3-ylamino)pyrimidin-2-yl)-1-(3-(trifluoromethyl)phenyl)guanidine; 1-(4-chlorophenyl)-1-cyclopentyl-3-(4-methyl-6-(pyridin-3-ylamino)pyrimidin-2-yl)guanidine; 1-(4-(difluoromethoxy)phenyl)-1-methyl-3-(4-methyl-6-(methyl(pyridin-3-yl)amino)pyrimidin-2-yl)guanidine; 1-methyl-3-(4-methyl-6-(methyl(pyridin-3-yl)amino)pyrimidin-2-yl)-1-(4-(trifluoromethyl)phenyl)guanidine; 1-(3-methoxyphenyl)-1-methyl-3-(4-methyl-6-(pyridin-3-yloxy)pyrimidin-2-yl)guanidine; 1-(3-chloro-4-fluorophenyl)-1-cyclopropyl-3-(4-methyl-6-(pyridin-3-yloxy)pyrimidin-2-yl)guanidine; 1-(3,4-dichlorophenyl)-1,2-dimethyl-3-(4-methyl-6-(pyridin-3-yloxy)pyrimidin-2-yl)guanidine; 1-(3,4-dichlorophenyl)-3-(4-(2-(dimethylamino)ethylamino)-6-methylpyrimidin-2-yl)-1,2-dimethylguanidine; 1-(3,4-dichlorophenyl)-3-(4-(2-(dimethylamino)ethylamino)-6-methylpyrimidin-2-yl)-1-methylguanidine; 3-(3,4-dichlorophenyl)-1-(4-(2-(dimethylamino)ethylamino)-6-methylpyrimidin-2-yl)-1-methylguanidine; 1-(3-chloro-4-fluorophenyl)-1-cyclopentyl-3-(4-(2-(dimethylamino)ethylamino)-6-methylpyrimidin-2-yl)guanidine; 3-(3,4-dichlorophenyl)-1-(4-((2-(dimethylamino)ethyl)(methyl)amino)-6-methylpyrimidin-2-yl)-1-methylguanidine; 3-(3,4-dichlorophenyl)-1-(4-((2-(dimethylamino)ethyl)(methyl)amino)-6-methylpyrimidin-2-yl)-1,2-dimethylguanidine; 3-(4-chlorophenyl)-2-cyano-1-(4-((2-(dimethylamino)ethyl)(methyl)amino)-6-methylpyrimidin-2-yl)-1-methylguanidine; 3-(4-((2-(dimethylamino)ethyl)(methyl)amino)-6-methylpyrimidin-2-yl)-1-methyl-1-(3-(trifluoromethoxy)phenyl)guanidine; 3-(4-(2-(dimethylamino)ethoxy)-6-methylpyrimidin-2-yl)-1-(4-fluoro-3-(trifluoromethyl)phenyl)-1-methylguanidine; and 1-(3,4-difluorophenyl)-3-(4-(2-(dimethylamino)ethoxy)-6-methylpyrimidin-2-yl)-1-methylguanidine.

In another embodiment is a compound selected from: 3-(3-chlorophenyl)-1-cyclopropyl-1-(4-(1-ethylpiperidin-3-ylamino)-6-methylpyrimidin-2-yl)-2-methylguanidine; 1-cyclopentyl-1-(4-(1-ethylpiperidin-3-ylamino)-6-methylpyrimidin-2-yl)-3-(4-fluoro-3-(trifluoromethyl)phenyl)guanidine; 2-cyano-1-cyclopropyl-1-(4-(1-ethylpiperidin-3-ylamino)-6-methylpyrimidin-2-yl)-3-(4-methoxyphenyl)guanidine; 1-cyclopentyl-1-(4-(1-ethylpiperidin-3-yloxy)-6-methylpyrimidin-2-yl)-3-(4-fluorophenyl)guanidine; 1-cyclopropyl-3-(4-(difluoromethoxy)phenyl)-1-(4-(1-ethylpiperidin-3-yloxy)-6-methylpyrimidin-2-yl)guanidine; 1-(4-(1-ethylpiperidin-4-yloxy)-6-methylpyrimidin-2-yl)-3-(2-fluorophenyl)-1-methylguanidine; 3-(4-cyanophenyl)-1-(4-(1-ethylpiperidin-4-ylamino)-6-methylpyrimidin-2-yl)-1-methylguanidine; 1-cyclopropyl-3-(3,4-dichlorophenyl)-1-(4-(1-ethylpiperidin-4-ylamino)-6-methylpyrimidin-2-yl)

guanidine; 1-(4-((1-ethylpiperidin-4-yl)(methyl)amino)-6-methylpyrimidin-2-yl)-3-(3-methoxyphenyl)-1,2-dimethylguanidine; 3-(4-chloro-3-fluorophenyl)-2-cyano-1-(4-((4-ethylpiperazin-1-yl)methyl)-6-methylpyrimidin-2-yl)-1-methylguanidine; 1-cyclopropyl-1-(4-(1-ethylazetidin-3-ylamino)-6-methylpyrimidin-2-yl)-3-(4-(trifluoromethyl)phenyl)guanidine; 3-(3-chlorophenyl)-1-(4-(1-ethylazetidin-3-yloxy)-6-methylpyrimidin-2-yl)-1,2-dimethylguanidine; 1-(4-(1-ethylpyrrolidin-3-ylamino)-6-methylpyrimidin-2-yl)-3-(3-fluoro-4-(trifluoromethyl)phenyl)-1,2-dimethylguanidine; 1-(3-chloro-4-fluorophenyl)-3-(4-(1-ethylpyrrolidin-3-ylamino)-6-methylpyrimidin-2-yl)-1-methylguanidine; 1-(4-chlorophenyl)-3-(4-((1-ethylpyrrolidin-3-yl)(methyl)amino)-6-methylpyrimidin-2-yl)-1-methylguanidine; 1-cyclopropyl-1-(4-(1-ethylpyrrolidin-3-yloxy)-6-methyl-pyrimidin-2-yl)-3-(3-(trifluoromethoxy)phenyl)guanidine; 1-cyclopropyl-1-(4-methyl-6-(methyl(pyridin-3-yl)amino)pyrimidin-2-yl)-3-(4-(trifluoromethyl)phenyl)guanidine; 1-cyclopentyl-1-(4-(2-(dimethylamino)ethoxy)-6-methyl-pyrimidin-2-yl)-3-(4-fluoro-3-(trifluoromethyl)phenyl)guanidine; 1-(3,4-dichlorophenyl)-3-(4-(1-((dimethylamino)methyl)cyclopentyl)-6-methylpyrimidin-2-yl)-1,2-dimethylguanidine; 3-(2-chlorophenyl)-1-(4-(1-((dimethylamino)methyl)cyclobutyl)-6-methylpyrimidin-2-yl)-1-methylguanidine; and 3-(4-cyanophenyl)-1-(4-(1-((dimethylamino)methyl)cyclohexyl)-6-methylpyrimidin-2-yl)-1-methylguanidine.

In another embodiment is a compound selected from:

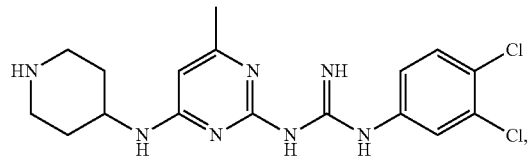

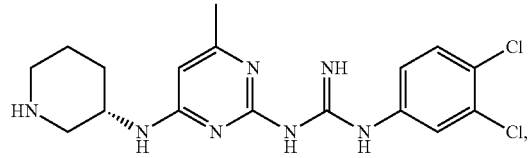

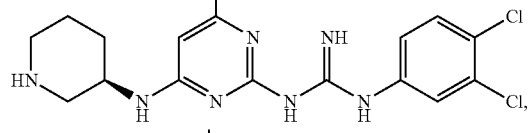

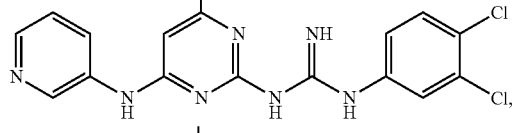

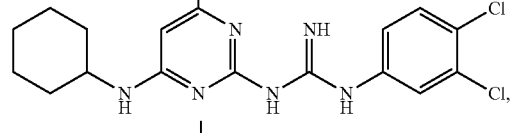

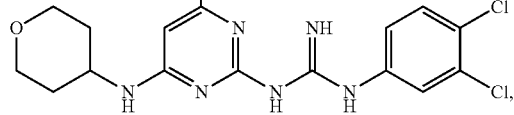

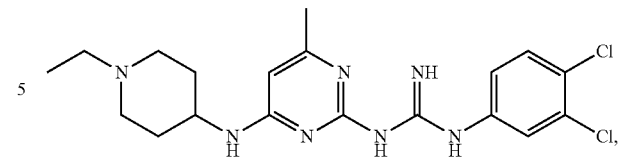

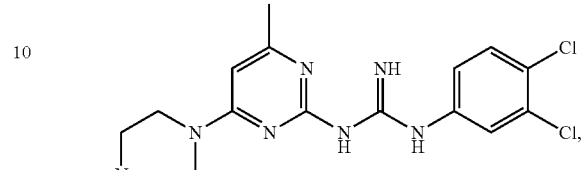

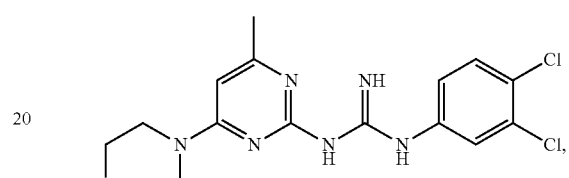

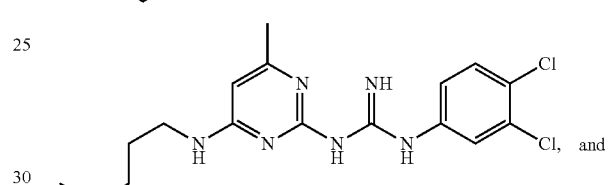, and

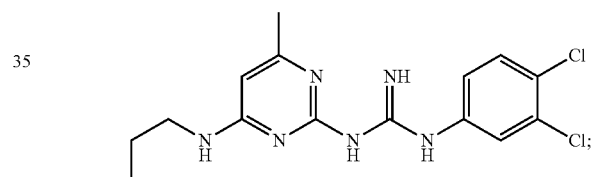;

or a pharmaceutically acceptable salt, solvate, or prodrug thereof.

In another embodiment is a compound selected from:

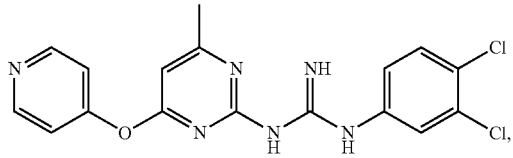

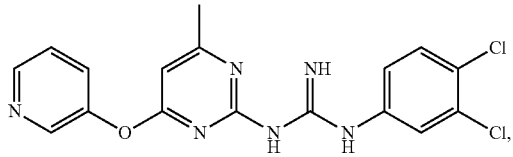

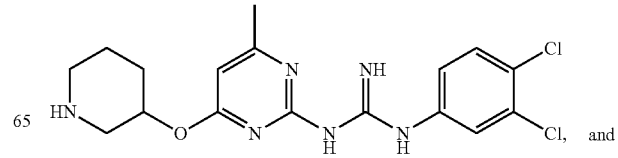, and

-continued

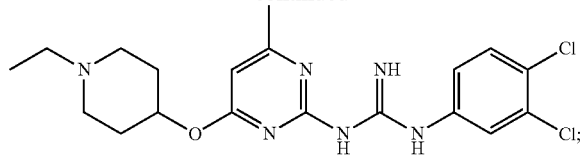

or a pharmaceutically acceptable salt, solvate, or prodrug thereof.

In another embodiment is a compound selected from:

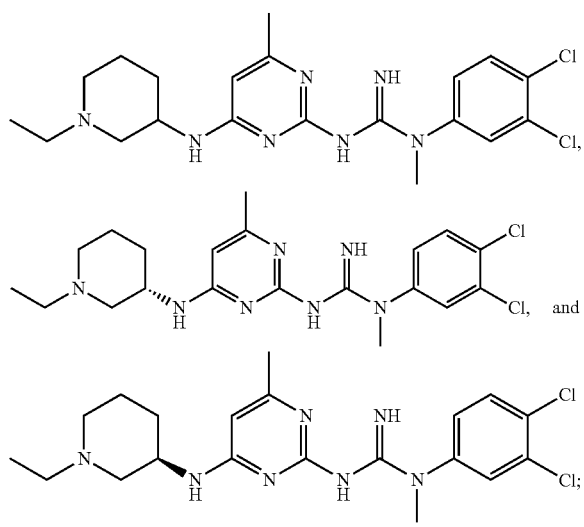

or a pharmaceutically acceptable salt, solvate, or prodrug thereof.

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. Generally, in chemical compounds with an H atom, the H atom actually represents a mixture of H and D, with about 0.015% being D. In some embodiments, deuterium-enriched compounds described herein are achieved by either exchanging protons with deuterium or via starting materials and/or intermediates enriched with deuterium.

Any combination of the groups described above for the various variables is contemplated herein.

Throughout the specification, groups and substituents thereof can be chosen to provide stable moieties and compounds.

Further Forms of Compounds

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some situations, compounds may exist as tautomers. All tautomers are included within the formulas described herein.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein may be prepared as prodrugs. A "prodrug" refers to an agent that is converted into the parent drug in vivo. Prodrugs are often useful because, in some situations, they may be easier to administer than the parent drug. They may, for instance, be bio available by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem. Vol.* 46, no. 24, 5097-5116, 2003; Aesop Cho, "Recent Advances in Oral Prodrug Discovery", *Annual Reports in Medicinal Chemistry*, Vol. 41, 395-407, 2006).

Prodrug forms of the herein described compounds, wherein the prodrug is metabolized in vivo to produce a compound of Formula (I), (IA), (IB), (II), (IIA), (IIB), (III), (IIIA), (IIIB), (IV), (IVA), (IVB), or (V) as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, Pro-drugs as Novel Delivery Systems, Vol. 14 of the A.C.S. Symposium Series; and Edward B. Roche, *Bioreversible Carriers in Drug Design,* American Pharmaceutical Association and Pergamon Press, 1987, all incorporated herein for such disclosure).

Sites on the aromatic ring portion of compounds described herein can be susceptible to various metabolic reactions, therefore incorporation of appropriate substituents on the aromatic ring structures, such as, by way of example only, halogens can reduce, minimize or eliminate this metabolic pathway.

The compounds described herein may be labeled isotopically (e.g. with a radioisotope) or by other means, including, but not limited to, the use of chromophores or fluorescent moieties, bioluminescent labels, photoactivatable or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}$H, $^{3}$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^{3}$H and $^{14}$C are incorporated, are useful in drug and/or substrate tissue distribution assays. Further, substitution with isotopes such as deuterium, i.e., $^{2}$H, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein, such as compounds of Formula (I), (IA), (IB), (II), (IIA), (IIB), (III), (IIIA), (IIIB), (IV), (IVA), (IVB), or (V), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential Scanning calorimetry (DSC), modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In some embodiments, compounds of Formula (I), (IA), (IB), (II), (IIA), (IIB), (III), (IIIA), (IIIB), (IV), (IVA), (IVB), or (V) are prepared according to the synthetic route shown in Scheme 1.

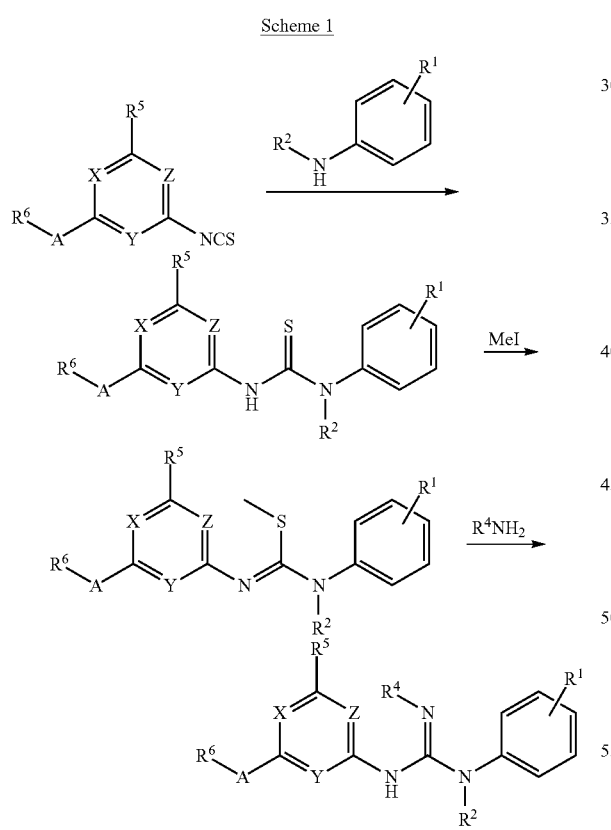

As depicted in Scheme 1, addition of the amine to the isothiocyanate gives the thiourea. The thiourea is then converted to the final product in two steps; alkylation followed by amine substitution.

Through a similar protocol, additional compounds of Formula (I), (IA), (IB), (II), (IIA), (IIB), (III), (IIIA), (IIIB), (IV), (IVA), (IVB), or (V) are prepared as shown in Scheme 2.

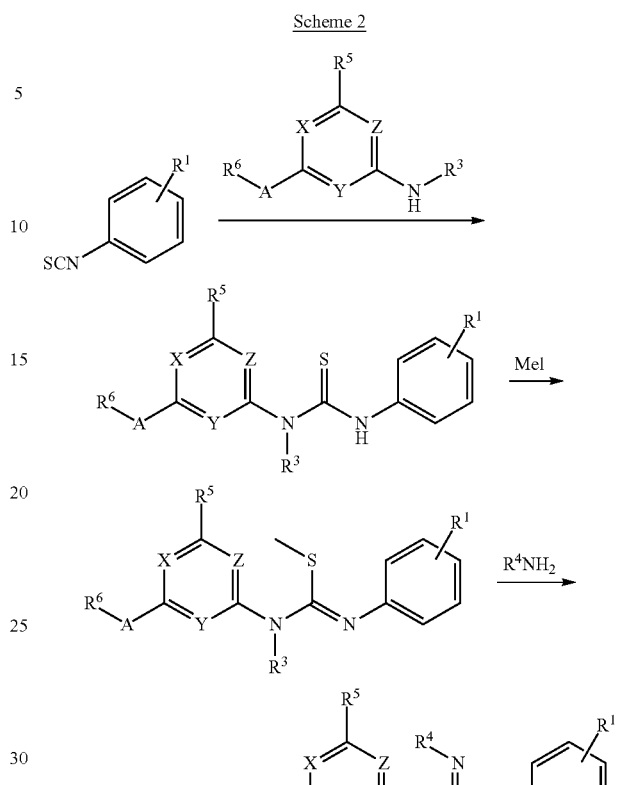

In some embodiments, the isothiocyanate and amine synthetic intermediates are prepared according to Schemes 3-5.

Scheme 3: Synthesis of pyridine/pyrimindine isothiocyanate (A=O, NR$_{10}$)

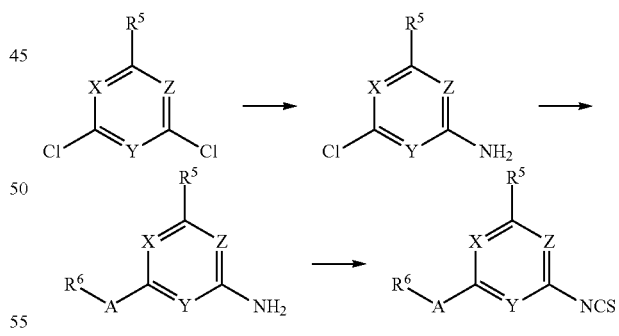

Scheme 4: Synthesis of pyridine/pyrimindine amine (A = O), NR$_{10}$)

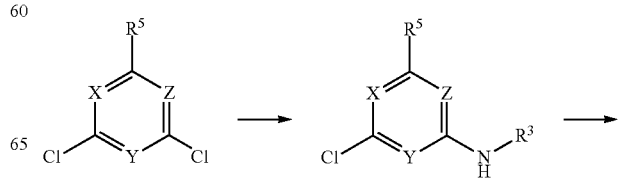

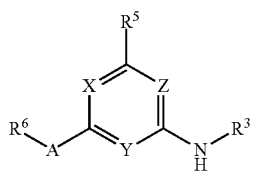

Scheme 5: Synthesis of pyridine/pyrimindine amine/isothiocyanate (A=CH$_2$)

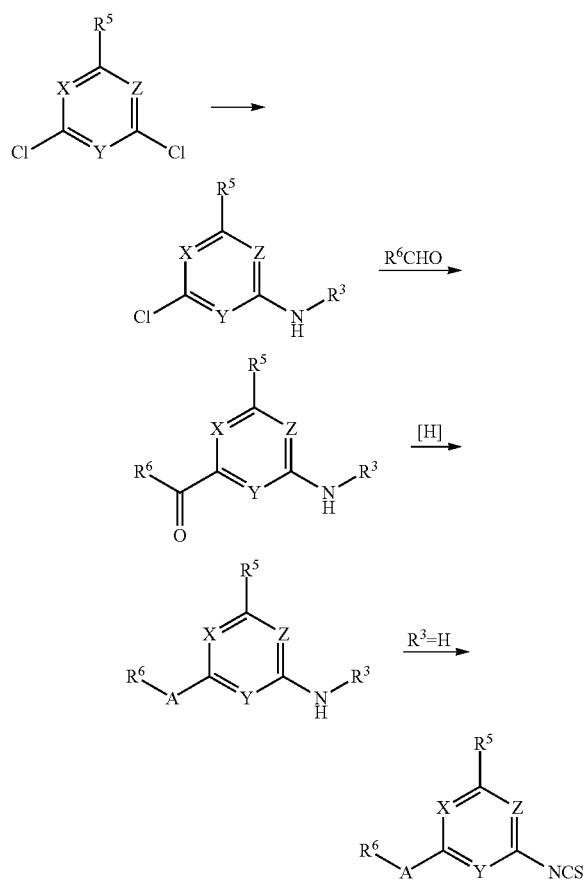

The synthesis of cyanoguanidines (R$_4$=—CN) of Formula (I), (IA), (IB), (II), (IIA), (IIB), (III), (IIIA), (IIIB), (IV), (IVA), (IVB), or (V) is depicted in Scheme 6. Alternatively, cyanamide may be used as the amine in the last step of Scheme 2 to afford the cyanoguanidine.

Scheme 6

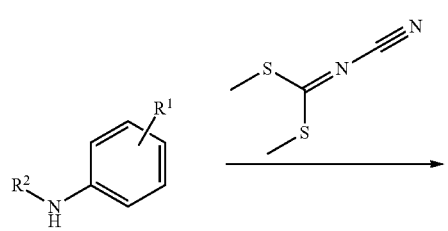

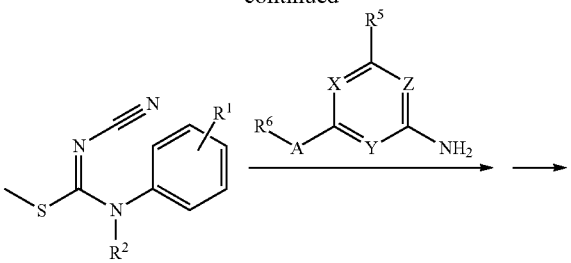

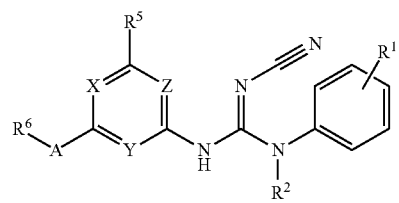

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), march, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Greene and Wuts, PROTECTIVE GROUPS IN ORGANIC SYNTHESIS 3$^{rd}$ Ed., (Wiley 1999) (all of which are incorporated by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$, includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 12 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which the first two atoms of the alkyl group form a double bond that is not part of an aromatic group. That is, an alkenyl group begins with the atoms —C(R)=CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the first two atoms of the alkyl group form a triple bond. That is, an alkynyl group begins with the atoms —C≡C—R, wherein R refers to the remaining portions of the alkynyl group. Non-limiting examples of an alkynyl group include —C≡CH, —C≡CCH$_3$, —C≡CCH$_2$CH$_3$ and —C≡CCH$_2$CH$_2$CH$_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

The term "carbocyclic ring" refers to a ring wherein each of the atoms forming the ring is a carbon atom. The carbocyclic ring may be aryl or cycloalkyl.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

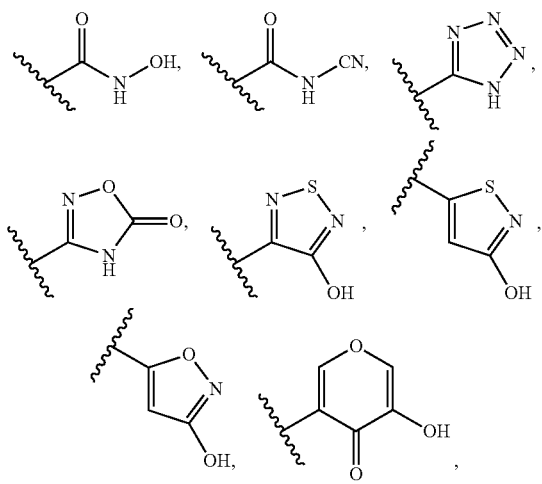

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

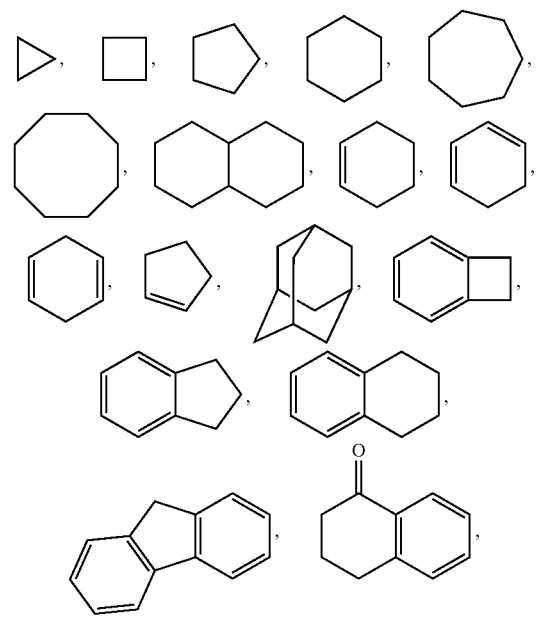

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

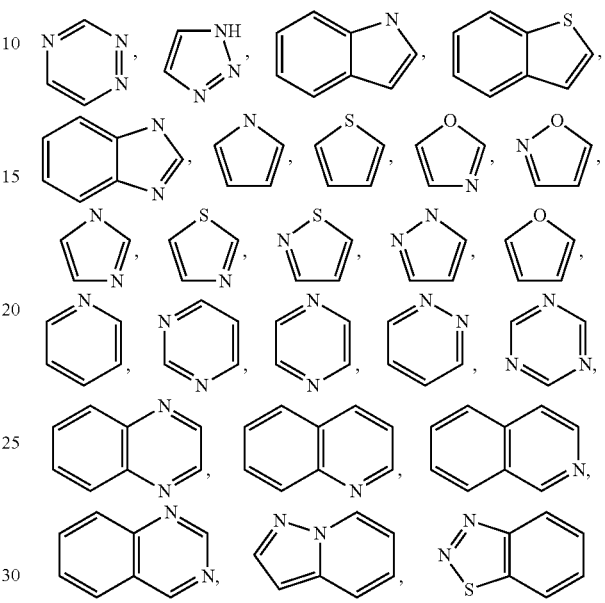

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

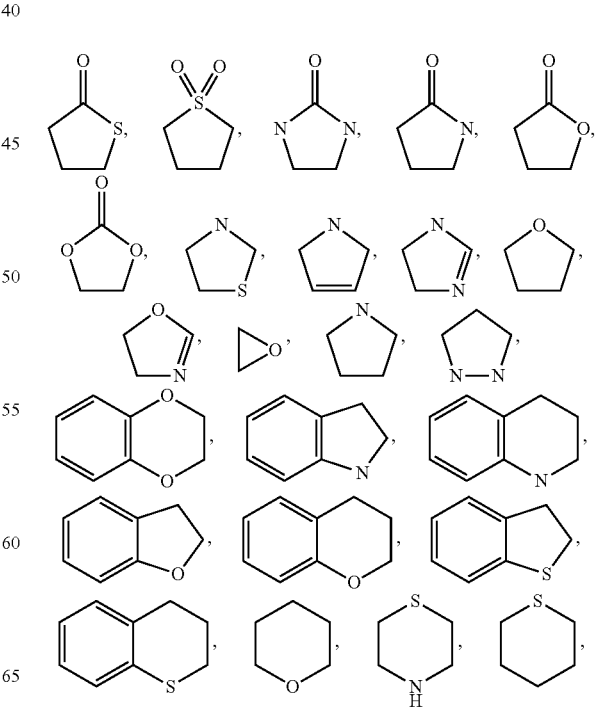

-continued

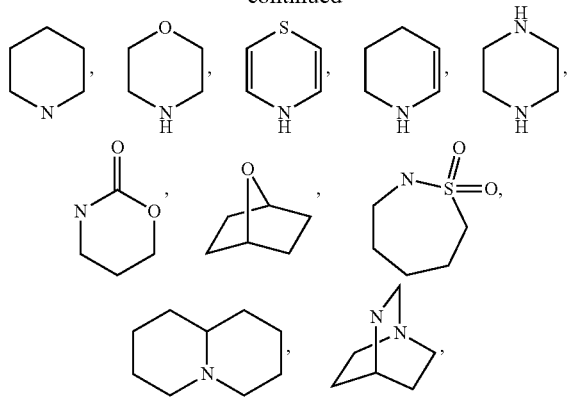

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "heterocyclic ring" refers to a ring wherein at least one skeletal ring atom is a heteroatom selected from nitrogen, oxygen and sulfur. The heterocyclic ring may be heteroaryl or heterocycloalkyl.

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, —$CF(CH_3)_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, —$CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each $L^s$ is independently selected from a bond, —O—, —C(=O)—, —S—, —S(=O)—, —S(=O)$_2$—, —NH—, —NHC(O)—, —C(O)NH—, —S(=O)$_2$NH—, —NHS(=O)$_2$—, —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

The methods and formulations described herein include the use of crystalline forms (also known as polymorphs), or pharmaceutically acceptable salts of compounds having the structure of Formula (I), (IA), (IB), (II), (IIA), (IIB), (III), (IIIA), (IIIB), (IV), (IVA), (IVB), or (V), as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "disease" or "condition" refer to a state of being or health status of a patient or subject capable of being treated with the compounds or methods provided herein. In embodiments, the disease is a disease related to (e.g. caused by) Olig2 or aberrant Olig2 activity (e.g. brain cancer, glioblastoma multiforme, medulloblastoma, astrocytomas, brain stem gliomas, meningiomas, oligodendrogliomas, melanomas, lung cancers, breast cancer, leukemias, or Down's Syndrome). Examples of diseases, disorders, or conditions include, but are not limited to brain cancer, glioblastoma multiforme, medulloblastoma, astrocytomas, brain stem gliomas, meningiomas, oligodendrogliomas, melanomas, lung cancers, breast cancer, leukemias, Down's Syndrome, colorectal cancer, papillary thyroid cancer, hepatocellular carcinoma, Alzheimer's disease, Parkinson's disease, Huntington's Disease, frontotemporal dementia, Creutzfeldt-Jakob disease, Gerstmann-Sträussler-Scheinker syndrome, prion disease, neurodegenerative diseases, cancer, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, migraine headaches, stroke, aneurysm, brain aneurysm, cerebral aneurysm, brain attack, cerebrovascular accident, ischemia, thrombosis, arterial embolism, hemorrhage, transient ischemic attack, anemia, embolism, systemic hypoperfusion, venous thrombosis, arthritis, reperfusion injury, skin diseases or conditions, acne, acne vulgaris, keratosis pilaris, acute, promyelocytic leukemia, baldness, acne rosacea, harlequin ichthyosis, xeroderma pigmentosum, keratoses, neuroblastoma, fibrodysplasia ossificans progressive, eczema, rosacea, sun damage, wrinkles, or cosmetic conditions. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals, including leukemia, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, baso squamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma exulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

A "cancer associated with aberrant Olig2 activity" (also referred to herein as "Olig2 related cancer") is a cancer caused by aberrant Olig2 activity (e.g. a mutated Olig2 gene). Olig2 related cancers may include brain cancer, glioblastoma multiforme, medulloblastoma, astrocytomas, brain stem gliomas, meningiomas, oligodendrogliomas, melanomas, lung cancers, breast cancer, leukemias, T cell leukemias.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. For example, in certain methods presented herein successfully treat cancer by decreasing the incidence of cancer and or causing remission of cancer. In some embodiments, certain methods presented herein successfully treat Down's Syndrome by decreasing the incidence of Down's Syndrome or reducing one or more symptoms of Down's Syndrome or reducing the severity of one or more symptoms of Down's Syndrome.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target. For example, a modulator can cause an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target. In some embodiments, an Olig2 modulator is a compound that reduces the activity of Olig2 in a cell. In some embodiments, an Olig2 disease modulator is a compound that reduces the severity of one or more symptoms of a disease associated with Olig2 (e.g. cancer or Down's Syndrome).

As used herein, the term "target activity" refers to a biological activity capable of being modulated by a modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "inhibits", "inhibiting", or "inhibitor" of Olig2 activity, as used herein, refer to inhibition of oligodendrocyte trasnsciption factor 2 activity. In reference to a protein-inhibitor interaction the terms mean negatively affecting (e.g. decreasing) the activity or function of the protein (e.g. decreasing gene transcription regulated by Olig2) relative to the activity or function of the protein (e.g. Olig2, transcription factor) in the absence of the inhibitor (e.g. Olig2 inhibitor or Olig2 inhibitor compound). In some embodiments inhibition refers to reduction of a disease or symptoms of disease. In some embodiments, inhibition refers to a reduction in the activity of a signal transduction pathway or signaling pathway (e.g. reduction of a pathway involving transcription regulation by Olig2 or transcription regulated by Olig2). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. Olig2). In some embodiments, inhibition refers to inhibition of Olig2.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutical combination" as used herein, means a product that results from the mixing or combining of more than one active ingredient and includes both fixed and non-fixed combinations of the active ingredients. The term "fixed combination" means that one active ingredient, e.g. a compound of Formula (I), (IA), (IB), (II), (IIA), (IIB), (III), (IIIA), (IIIB), (IV), (IVA), (IVB), or (V), and a co-agent, are both administered to a patient simultaneously in the form of a single entity or dosage. The term "non-fixed combination" means that one active ingredient, e.g. a compound of Formula (I), (IA), (IB), (II), (IIA), (IIB), (III), (IIIA), (IIIB), (IV), (IVA), (IVB), or (V), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of Formula (I), (IA), (IB), (II), (IIA), (IIB), (III), (IIIA), (IIIB), (IV), (IVA), (IVB), or (V) described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition that includes a compound of Formula (I), (IA), (IB), (II), (IIA), (IIB), (III), (IIIA), (IIIB), (IV), (IVA), (IVB), or (V) described herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. Olig2). In some embodiments, the protein may be Olig2. In some embodiments contacting includes allowing a compound described herein to interact with a protein or enzyme that is involved in transcription.

The terms "co-administration" or the like, as used herein, are meant to encompass administration of the selected therapeutic agents to a single patient, and are intended to include treatment regimens in which the agents are administered by the same or different route of administration or at the same or different time.

The term "excipient" or "carrier," as used herein, refers to relatively nontoxic chemical compounds or agents that facilitate the incorporation of a compound into cells or tissues.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds.

"Bioavailability" refers to the percentage of the weight of the compound disclosed herein (e.g. compound of Formula (I), (IA), (IB), (II), (IIA), (IIB), (III), (IIIA), (IIIB), (IV), (IVA), (IVB), or (V)), that is delivered into the general circulation of the animal or human being studied. The total exposure (AUC(0-∞)) of a drug when administered intravenously is usually defined as 100% bioavailable (F %). "Oral bioavailability" refers to the extent to which a compound disclosed herein, is absorbed into the general circulation when the pharmaceutical composition is taken orally as compared to intravenous injection.

"Blood plasma concentration" refers to the concentration of a compound of Formula (I), (IA), (IB), (II), (IIA), (IIB), (III), (IIIA), (IIIB), (IV), (IVA), (IVB), or (V) disclosed herein, in the plasma component of blood of a subject. It is understood that the plasma concentration of compounds described herein may vary significantly between subjects, due to variability with respect to metabolism and/or possible interactions with other therapeutic agents. In accordance with one embodiment disclosed herein, the blood plasma concentration of the compounds disclosed herein may vary from subject to subject. Likewise, values such as maximum plasma concentration (Cmax) or time to reach maximum plasma concentration (Tmax), or total area under the plasma concentration time curve (AUC(0-∞)) may vary from subject to subject. Due to this variability, the amount necessary to constitute "a therapeutically effective amount" of a compound may vary from subject to subject.

As used herein, "amelioration" refers to an improvement in a disease or condition or at least a partial relief of symptoms associated with a disease or condition.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

Treatment Methods

In another aspect is a pharmaceutical composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof, and at least one pharmaceutically acceptable excipient.

In another aspect is the use of a compound of Formula (I), (IA), (IB), (II), (IIA), (IIB), (III), (IIIA), (IIIB), (IV), (IVA), (IVB), or (V), or a pharmaceutically acceptable salt, pharmaceutically acceptable solvate, or a pharmaceutically acceptable prodrug thereof, for the formulation of a medicament for inhibiting the activity of Olig2 in a cell is provided. The method includes contacting the cell with a compound of Formula (I), (IA), (IB), (II), (IIA), (IIB), (III), (IIIA), (IIIB), (IV), (IVA), (IVB), or (V), including embodiments thereof.

In a further aspect is a method of treating a disease, disorder or condition in a subject that would benefit from inhibition of Olig2 activity comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof. In some embodiments is a method of treating a disease, disorder or condition in a subject that would benefit from inhibition of Olig2 activity comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof; wherein the disease is cancer or Down's Syndrome.

In another aspect is a method for treating a disease in a subject comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof; wherein the disease is cancer or Down's Syndrome. In some embodiments is a method for treating cancer in a subject comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof. In some embodiments is a method for treating Down's Syndrome in a subject comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof.

In another embodiment is a method for treating cancer in a subject comprising administering to the subject in need thereof a composition comprising a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof, wherein the cancer is brain cancer, glioblastoma multiforme, medulloblastoma, astrocytomas, brain stem gliomas, meningiomas, oligodendrogliomas, melanoma, lung cancer, breast cancer, or leukemia.

In another aspect is a method of inhibiting the activity of Olig2 in a cell comprising contacting the cell with a compound of Formula (I), (IA), (IB), (II), (IIA), (IIB), (III), (IIIA), (IIIB), (IV), (IVA), (IVB), or (V), or a pharmaceutically acceptable salt, solvate, or prodrug thereof.

In another aspect is the use of a compound of Formula (I), (IA), (IB), (II), (IIA), (IIB), (III), (IIIA), (IIIB), (IV), (IVA), (IVB), or (V) or a pharmaceutically acceptable salt, solvate, or prodrug thereof, in the manufacture of a medicament for the treatment of a disease, disorder, or condition that would benefit from inhibition of Olig2 activity.

In one aspect, provided herein is a pharmaceutical composition, which includes an effective amount of a compound provided herein, and a pharmaceutically acceptable excipient. In a further aspect, provided are compositions further including a second pharmaceutically active ingredient.

In certain embodiments, provided herein is a pharmaceutical composition containing: i) a physiologically acceptable carrier, diluent, and/or excipient; and ii) one or more compounds described herein.

In any of the aforementioned aspects are further embodiments that include single administrations of the effective amount of the compounds disclosed herein, including further embodiments in which: (i) the compound of Formula (I), (IA), (IB), (II), (IIA), (IIB), (III), (IIIA), (IIIB), (IV), (IVA), (IVB), or (V) is administered once; (ii) the compound of Formula (I), (IA), (IB), (II), (IIA), (IIB), (III), (IIIA), (IIIB), (IV), (IVA), (IVB), or (V) is administered to the mammal multiple times over the span of one day; (iii) continually; or (iv) continuously.

In any of the aforementioned aspects are further embodiments that include multiple administrations of the effective amount of the compound of Formula (I), (IA), (IB), (II), (IIA), (IIB), (III), (IIIA), (IIIB), (IV), (IVA), (IVB), or (V), including further embodiments in which (i) the compound of Formula (I), (IA), (IB), (II), (IIA), (IIB), (III), (IIIA), (IIIB), (IV), (IVA), (IVB), or (V) is administered in a single dose; (ii) the time between multiple administrations is every 6 hours; (iii) the compound of Formula (I), (IA), (IB), (II), (IIA), (IIB), (III), (IIIA), (IIIB), (IV), (IVA), (IVB), or (V) is administered to the mammal every 8 hours. In further or alternative embodiments, the method comprises a drug holiday, wherein the administration of the compound of Formula (I), (IA), (IB), (II), (IIA), (IIB), (III), (IIIA), (IIIB), (IV), (IVA), (IVB), or (V) is temporarily suspended or the dose of the compound of Formula (I), (IA), (IB), (II), (IIA), (IIB), (III), (IIIA), (IIIB), (IV), (IVA), (IVB), or (V) being administered is temporarily reduced; at the end of the drug holiday, dosing of the compound of Formula (I), (IA), (IB), (II), (IIA), (IIB), (III), (IIIA), (IIIB), (IV), (IVA), (IVB), or (V) is resumed. The length of the drug holiday can vary from 2 days to 1 year.

In one aspect, compounds described herein are administered to a human. In some embodiments, compounds described herein are orally administered.

Examples of Pharmaceutical Compositions and Methods of Administration

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (IA), (IB), (II), (IIA), (IIB), (III), (IIIA), (IIIB), (IV), (IVA), (IVB), or (V) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds of Formula (I), (IA), (IB), (II), (IIA), (IIB), (III), (IIIA), (IIIB), (IV), (IVA), (IVB), or (V) can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula (I), (IA), (IB), (II), (IIA), (IIB), (III), (IIIA), (IIIB), (IV), (IVA), (IVB), or (V) described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (IA), (IB), (II), (IIA), (IIB), (III), (IIIA), (IIIB), (IV), (IVA), (IVB), or (V) described herein, as an active ingredient in free-acid or free-base form, or in a pharmaceutically acceptable salt form. In addition, the methods and pharmaceutical compositions described herein include the use of crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipient with one or more of the compounds described herein (e.g. compounds of Formula (I), (IA), (IB), (II), (IIA), (IIB), (III), (IIIA), (IIIB), (IV), (IVA), (IVB), or (V)), optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula (I), (IA), (IB), (II), (IIA), (IIB), (III), (IIIA), (IIIB), (IV), (IVA), (IVB), or (V) described herein, with one or more pharmaceutical excipients to form a bulk blend composition. When referring to these bulk blend compositions as homogeneous, it is meant that the particles of the compound of Formula (I), (IA), (IB), (II), (IIA), (IIB), (III), (IIIA), (IIIB), (IV), (IVA), (IVB), or (V) described herein, are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound of Formula (I), (IA), (IB), (II), (IIA), (IIB), (III), (IIIA), (IIIB), (IV), (IVA), (IVB), or (V) described herein, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of Formula (I), (IA), (IB), (II), (IIA), (IIB), (III), (IIIA), (IIIB), (IV), (IVA), (IVB), or (V) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® C.L, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compounds of Formula (I), (IA), (IB), (II), (IIA), (IIB), (III), (IIIA), (IIIB), (IV), (IVA), (IVB), or (V) described herein from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of Formula (I), (IA), (IB), (II), (IIA), (IIB), (III), (IIIA), (IIIB), (IV), (IVA), (IVB), or (V) described herein and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients. Materials compatible with compounds described herein are those that delay the release of the compounds of Formula (I), (IA), (IB), (II), (IIA), (IIB), (III), (IIIA), (IIIB), (IV), (IVA), (IVB), or (V) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds described herein may be formulated by methods that include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound described herein, are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

The pharmaceutical solid oral dosage forms including formulations described herein, which include a compounds described herein, can be further formulated to provide a controlled release of the compound of Formula (I), (IA), (IB), (II), (IIA), (IIB), (III), (IIIA), (IIIB), (IV), (IVA), (IVB), or (V). Controlled release refers to the release of the compounds described herein from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. Coatings may be made from:

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (I), (IA), (IB), (II), (IIA), (IIB), (III), (IIIA), (IIIB), (IV), (IVA), (IVB), or (V) described herein, are delivered using a pulsatile dosage form. A pulsatile dosage form is capable of providing one or more immediate release pulses at predetermined time points after a controlled lag time or at specific sites. Pulsatile dosage forms may be administered using a variety of pulsatile formulations including, but are not limited to, those described in U.S. Pat. Nos. 5,011,692; 5,017,381; 5,229,135; 5,840,329; 4,871,549; 5,260,068; 5,260,069; 5,508,040; 5,567,441 and 5,837,284.

Many other types of controlled release systems are suitable for use with the formulations described herein. Examples of such delivery systems include, e.g., polymer-based systems, such as polylactic and polyglycolic acid, polyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

In some embodiments, pharmaceutical formulations are provided that include particles of the compounds described herein, e.g. compounds of Formula (I), (IA), (IB), (II), (IIA), (IIB), (III), (IIIA), (IIIB), (IV), (IVA), (IVB), or (V), and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound of; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound of Formula (I), (IA), (IB), (II), (IIA), (IIB), (III), (IIIA), (IIIB), (IV), (IVA), (IVB), or (V), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

Examples of Methods of Dosing and Treatment Regimens

The compounds described herein can be used in the preparation of medicaments for the treatment of cancer, or for the treatment of diseases or conditions that would benefit, at least in part, from Olig2 inhibition. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1 about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The compounds of Formula (I), (IA), (IB), (II), (IIA), (IIB), (III), (IIIA), (IIIB), (IV), (IVA), (IVB), or (V), and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving one of the compounds herein, such as a compound of Formula (I), (IA), (IB), (II), (IIA), (IIB), (III), (IIIA), (IIIB), (IV), (IVA), (IVB), or (V), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

For therapeutic applications, the compounds or drugs of the present invention can be administered alone or co-administered in combination with conventional chemotherapy, radiotherapy, hormonal therapy, and/or immunotherapy.

As a non-limiting example, the compounds of Formula (I), (IA), (IB), (II), (IIA), (IIB), (III), (IIIA), (IIIB), (IV), (IVA), (IVB), or (V) described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds of Formula (I), (IA), (IB), (II), (IIA), (IIB), (III), (IIIA), (IIIB), (IV), (IVA), (IVB), or (V) described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds of Formula (I), (IA), (IB), (II), (IIA), (IIB), (III), (IIIA), (IIIB), (IV), (IVA), (IVB), or (V) described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), (IA), (IB), (II), (IIA), (IIB), (III), (IIIA), (IIIB), (IV), (IVA), (IVB), or (V) described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Olig2 activity.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

HPLC methods: Platform: Agilent 1100 series HPLC, comprised of pumps, degasser and UV detector, equipped with an auto-sampler. MS detector (APCI) PE Sciex API 150 EX.

Method 1: Column—Zorbax C18, size 4.6 mm×7.5 cm; Solvent A: 0.05% TFA in water, Solvent B: 0.05% TFA in acetonitrile; Flow rate—0.7 mL/min; Gradient: 5% B to 100% B in 9 min, hold at 100% B for 4 min and 100% B to 5% B in 0.5 min; UV detector—channel 1=220 nm, channel 2=254 nm.

Method 2: Column—Zorbax C18, size 4.6 mm×7.5 cm; Solvent A: 0.05% TFA in water, Solvent B: 0.05% TFA in acetonitrile; Flow rate—0.7 mL/min; Gradient: 5% B to 100% B in 5 min, hold at 100% B for 2 min and 100% B to 5% B in 0.5 min; UV detector—channel 1=220 nm, channel 2=254 nm.

Method 3: Column—SunFire™ (Waters) C18, size 2.1 mm×50 mm; Solvent A: 0.05% TFA in water, Solvent B: 0.05% TFA in acetonitrile; Flow rate—0.8 mL/min; Gradient: 10% B to 90% B in 2.4 min, hold at 90% B for 1.25 min and 90% B to 10% B in 0.25 min, hold at 10% B for 1.5 min.; UV detector—channel 1=220 nm, channel 2=254 nm.

Platform: Agilent 1290 series HPLC, comprised of binary pumps, degasser and UV detector, equipped with an auto-sampler. MS detector AJS-ES. Method 4: Column—Zorbax Eclipse Plus C18, size 2.1×50 mm; Solvent A: 0.10% formic acid in water, Solvent B: 0.00% formic acid in acetonitrile; Flow rate—0.7 mL/min; Gradient: 5% B to 95% B in 5 min and hold at 95% B for 2 min; UV detector—channel 1=254 nm, channel 2=254 nm Example 1: Synthesis of (±)-2-[3-(3,4-dichlorophenyl)guanidino]-4-(1-ethyl-3-piperidylamino)-6-methylpyrimidine (7)

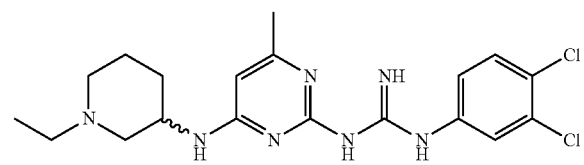

Step 1: 1-(3,4-Dichlorophenyl)guanidine hydrochloride (1)

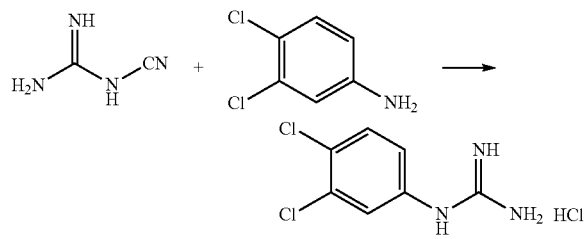

A mixture of dicyanamide (13.5 g, 160.5 mmol), 3,4-dichloroaniline (24.3 g, 150 mmol), concentrated HCl (15.5 mL) and isopropanol (100 mL) was heated at reflux for 18 hours. The reaction mixture was cooled to room temperature and then cooled to 4° C. for 4 hours. The white precipitate was filtered, rinsed with diethyl ether and air-dried. Yield=35.6 g (126 mmol, 84%). HPLC (254 nm): Method 3, Rt 2.09 min. MS (ESI) m/z 248 [M+H$^+$].

Step 2: 2-[3-(3,4-Dichlorophenyl)guanidino]-6-methyl-4-pyrimidinol (3)

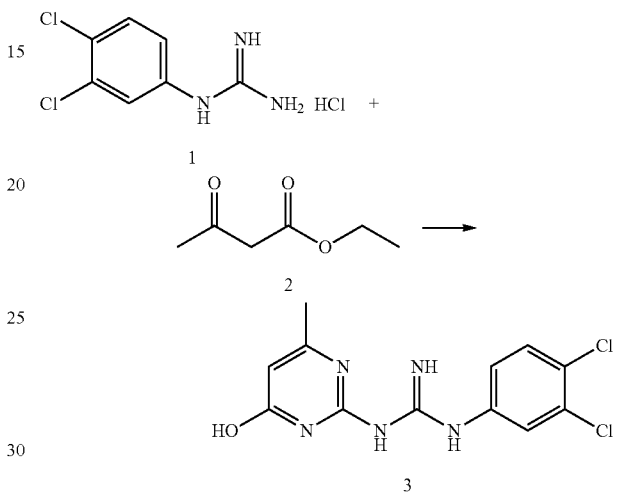

1-(3,4-Dichlorophenyl)guanidine hydrochloride (1) (46.2 g, 163.5 mmol) was added portionwise to a stirred mixture of 50% aqueous NaOH solution (10 mL) and ethanol/water 3:1 v/v (155 mL). The resulting mixture was stirred for 10 minutes at room temperature. The mixture was heated to 70° C. and treated with ethyl acetoacetate (42.6 mL, 327.0 mmol). After the addition, the resulting mixture was heated for another 30 minutes and then cooled to room temperature. The solids were filtered under vacuum, rinsed with ethanol and air-dried to yield the title compound as a white solid (84%). HPLC (254 nm): Method 3, Rt 2.92 min. MS (ESI) m/z 314.2 [M+H$^+$].

Step 3: 3-(4-Chloro-6-methyl-2-pyrimidinyl)-1-(3,4-dichlorophenyl)guanidine (4)

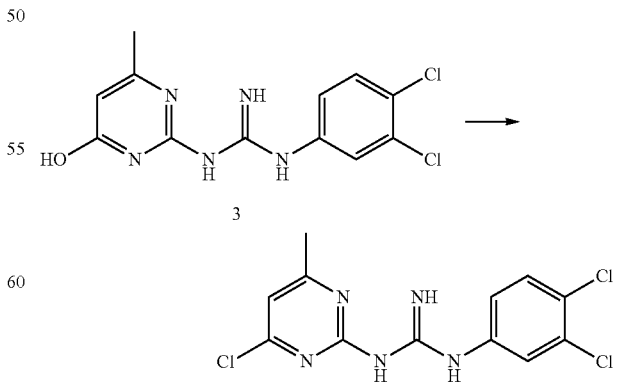

2-[3-(3,4-Dichlorophenyl)guanidino]-6-methyl-4-pyrimidinol (3) (12.5 g, 40.0 mmol) was placed in a round-bottom flask and cooled to 0° C. under a N₂ atmosphere. POCl₃ (37.5 mL) was added dropwise via a dropping funnel. The resulting mixture was slowly warmed to room temperature and kept at that temperature for 15 minutes. The reaction was heated to 90° C. for 4.5 hours, after which time the reaction was deemed complete by LCMS analysis. The mixture was cooled to room temperature, and the reaction contents were slowly poured over crushed ice under magnetic stirring. After the ice melted, the precipitate was filtered under vacuum, rinsed with water and ethyl acetate and air-dried. The title compound was obtained as a tan solid (9.81 g, 74%). HPLC (254 nm): Method 3, Rt 2.87 min. MS (ESI) m/z 332.3 [M+H⁺], Purity=>95%

Step 4: (±)-tert-Butyl 3-{2-[3-(3,4-dichlorophenyl)guanidino]-6-methyl-4-pyrimidinylamino}-1-piperidinecarboxylate (5)

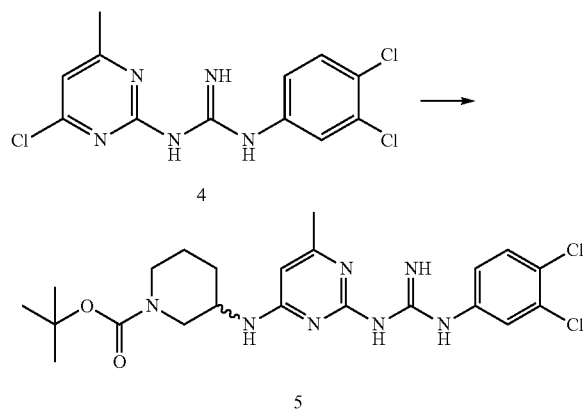

3-(4-Chloro-6-methyl-2-pyrimidinyl)-1-(3,4-dichlorophenyl)guanidine (4) (3.0 g, 10 mmol) was dissolved in dimethylacetamide (30 mL) and treated with diisopropylethylamine (2.1 mL, 12 mmol) and (R,S)—N-tert-butyl 3-amino-1-piperidinecarboxylate (2.4 g, 12 mmol) under N₂. The resulting mixture was heated to 90° C. with stirring for 18 hours. HPLC/MS monitoring indicated that the starting material was consumed and the product formed. The reaction was cooled to room temperature, poured onto water and extracted with ethyl acetate. The organic layer was separated, washed with brine, dried over anhydrous MgSO₄, filtered and evaporated to give the title compound as a light yellow fluffy solid (3.3 g) which was used in the next step without further purification. HPLC (254 nm): Method 3, Rt 3.5 min. MS (ESI) m/z 496.5 [M+H⁺].

Step 5: (±)-2-[3-(3,4-Dichlorophenyl)guanidino]-6-methyl-4-(3-piperidylamino)pyrimidine (6)

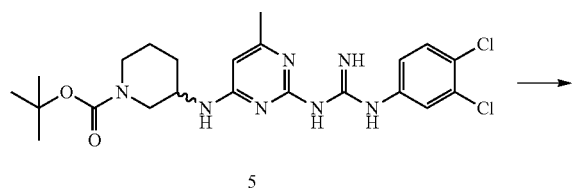

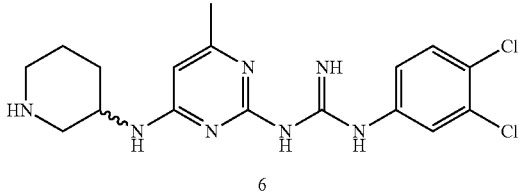

(±)-tert-Butyl 3-{2-[3-(3,4-dichlorophenyl)guanidino]-6-methyl-4-pyrimidinylamino}-1-piperidinecarboxylate (5) (3.28 g, 7.61 mmol) was dissolved in CH₂Cl₂ (40 mL) and treated with trifluoroacetic acid (6 mL). The resulting mixture was stirred at room temperature overnight. The volatiles were evaporated in vacuo and the residue was co-evaporated with acetonitrile (20 mL). The title compound was obtained as a solid in the form of trifluoroacetate salt and was used without further purification in the next step. Yield=3.4 g (7.6 mmol, quantitative). HPLC (254 nm): Method 3, Rt 1.06 min. MS (ESI) m/z 396.1 [M+H⁺].

Step 6: (±)-2-[3-(3,4-Dichlorophenyl)guanidino]-4-(1-ethyl-3-piperidylamino)-6-methylpyrimidine (7)

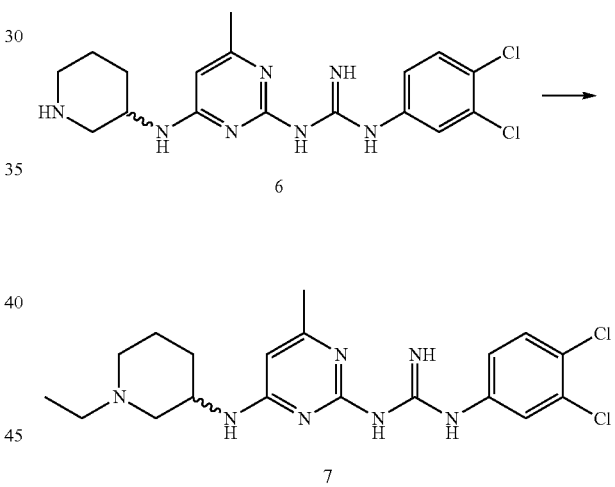

A solution of (±)-2-[3-(3,4-dichlorophenyl)guanidino]-6-methyl-4-(3-piperidylamino)pyrimidine (6) (1.41 g, 3.57 mmol) in CH₂Cl₂ (18 mL) was treated with acetaldehyde (402 μL, 7.14 mmol) followed by Na(OAc)₃BH (1.51 g, 7.14 mmol). The mixture was stirred at room temperature in a pressure vial for 30 minutes. Another portion of acetaldehyde (402 μL, 7.14 mmol) was added and the mixture stirred for another hour at room temperature. HPLC/MS analysis indicated reaction completed. The mixture was transferred to a separatory funnel, partitioned between CH₂Cl₂ and 0.5 N NaOH aqueous solution. The organic layer was separated, washed with water, dried over anhydrous MgSO₄, filtered and evaporated. The crude residue was purified by column chromatography on silica gel, eluting with a 400:50:2 v/v mixture of CH₂Cl₂, MeOH and NH₄OH, respectively. The title compound was obtained as a pale yellow foam. Yield=600 mg (40%). HPLC (254 nm): Method 3, Rt 2.81 min. MS (ESI) m/z 424.4 [M+H⁺].

Example 2: Synthesis of 1-(3,4-dichlorophenyl)-3-[6-methyl-4-(4-pyridyloxy)-2-pyrimidinyl]guanidine (8)

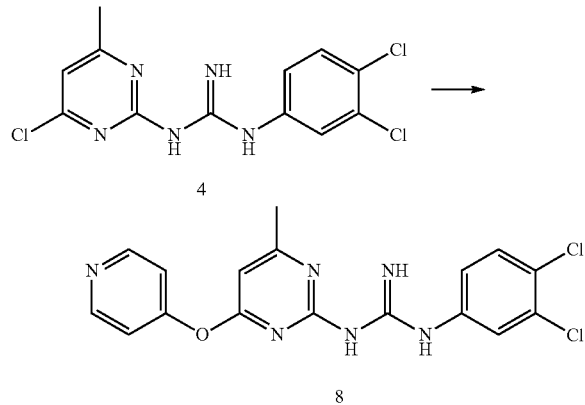

3-(4-Chloro-6-methyl-2-pyrimidinyl)-1-(3,4-dichlorophenyl)guanidine (4) (83 mg, 0.25 mmol) prepared in Example 1, Step 3 was dissolved in $CH_3CN$ (5 mL) and treated with $K_2CO_3$ (70 mg, 0.5 mmol) followed by 4-hydroxy-pyridine (26 mg, 0.25 mmol). The resulting suspension was heated to 100° C. for 14 hours and then cooled to room temperature. The crude reaction mixture was directly purified by preparative thin layer chromatography plate (1000 μm) eluting with a 400:50:2 v/v mixture of $CH_2Cl_2$, MeOH and $NH_4OH$, respectively. The title compound was isolated as a white solid (11 mg, 11%). HPLC (254 nm): Method 3, Rt 0.06 min. MS (ESI) m/z 389.3 [M+H$^+$].

Example 3: Synthesis of 2-[3-(3,4-dichlorophenyl)guanidino]-6-methyl-4-(4-piperidylamino)pyrimidine (9)

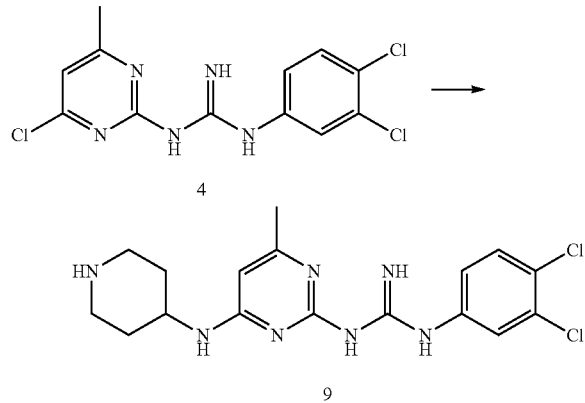

Step A: 3-(4-Chloro-6-methyl-2-pyrimidinyl)-1-(3,4-dichlorophenyl)guanidine (4) (330.5 mg, 1.0 mmol) was dissolved in dimethylacetamide (3.0 mL) and treated with diisopropylethylamine (210 μL, 1.2 mmol) and N-tert-butyl 4-amino-1-piperidinecarboxylate (248 mg, 1.2 mmol) under $N_2$. The resulting mixture was heated to 90° C. with stirring for 18 hours. HPLC/MS monitoring indicated that the starting material was consumed and the product formed. The reaction was cooled to room temperature, poured onto water and extracted with ethyl acetate. The organic layer was separated, washed with brine, dried over anhydrous $MgSO_4$, filtered and evaporated to give tert-butyl 3-{2-[3-(3,4-dichlorophenyl)guanidino]-6-methyl-4-pyrimidinylamino}-1-piperidinecarboxylate as a solid (467 mg) which was used in the next step without further purification. HPLC (254 nm): Method 3, Rt 2.9 min. MS (ESI) m/z 498.5 [M+H$^+$].

Step B: tert-Butyl 3-{2-[3-(3,4-dichlorophenyl)guanidino]-6-methyl-4-pyrimidinylamino}-1-piperidinecarboxylate (467 mg, 0.945 mmol) was dissolved in MeOH (8 mL) and treated with 4M HCl in dioxane (4 mL). The resulting mixture was stirred at room temperature overnight. The volatiles were evaporated in vacuo and the residue was co-evaporated with acetonitrile (20 mL). The crude product was purified by chromatography (silica plate, eluent: $NH_4OH$:MeOH:$CH_2Cl_2$: 0.6:15:84.5) to give the title compound (9). Yield=39 mg (10%). HPLC (254 nm): Method 3, Rt 2.43 min. MS (ESI) m/z 396.4 [M+H$^+$].

Example 4: Synthesis of (S)-1-(3,4-dichlorophenyl)-3-(4-methyl-6-(piperidin-3-ylamino)pyrimidin-2-yl)guanidine (10)

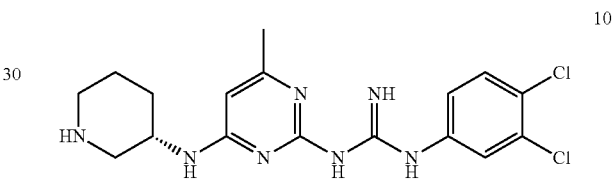

In a similar manner as described in Example 3, the title compound was prepared in two steps from 3-(4-chloro-6-methyl-2-pyrimidinyl)-1-(3,4-dichlorophenyl)guanidine (4) and (S)-tert-butyl 3-aminopiperidine-1-carboxylate.

Step A: 3-(4-Chloro-6-methyl-2-pyrimidinyl)-1-(3,4-dichlorophenyl)guanidine (4) (330.5 mg, 1.0 mmol) was dissolved in dimethylacetamide (3.0 mL) and treated with diisopropylethylamine (210 μL, 1.2 mmol) and (S)-tert-butyl 3-aminopiperidine-1-carboxylate (248 mg, 1.2 mmol) under $N_2$. The resulting mixture was heated to 90° C. with stirring for 18 hours. HPLC/MS monitoring indicated that the starting material was consumed and the product formed. The reaction was cooled to room temperature, poured onto water and extracted with ethyl acetate. The organic layer was separated, washed with brine, dried over anhydrous $MgSO_4$, filtered and evaporated to give (S)-tert-butyl 3-(2-(3-(3,4-dichlorophenyl)guanidino)-6-methylpyrimidin-4-ylamino)piperidine-1-carboxylate as a solid (814 mg) which was used in the next step without further purification. HPLC (254 nm): Method 3, Rt 0.08 min. MS (ESI) m/z 498.7 [M+H$^+$].

Step B: (S)-tert-Butyl 3-(2-(3-(3,4-dichlorophenyl)guanidino)-6-methylpyrimidin-4-ylamino)piperidine-1-carboxylate (814 mg) was dissolved in MeOH (8 mL) and treated with 4M HCl in dioxane (4 mL). The resulting mixture was stirred at room temperature overnight. The volatiles were evaporated in vacuo and the residue was co-evaporated with acetonitrile (20 mL). The crude product was obtained as a solid in the form of hydrochloride salt. The crude product was purified by chromatography (silica plate, eluent: $NH_4OH$:MeOH:$CH_2Cl_2$: 2:50:400) to give the title compound (10). Yield=19 mg (5%). HPLC (254 nm): Method 3, Rt 2.8 min. MS (ESI) m/z 396.4 [M+H$^+$].

Example 5: Synthesis of (R)-1-(3,4-dichlorophenyl)-3-(4-methyl-6-(piperidin-3-ylamino)pyrimidin-2-yl)guanidine (11)

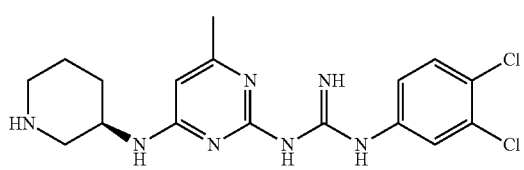

11

In a similar manner as described in Example 3, the title compound was prepared in two steps from 3-(4-chloro-6-methyl-2-pyrimidinyl)-1-(3,4-dichlorophenyl)guanidine (4) and (R)-tert-butyl 3-aminopiperidine-1-carboxylate.

Step A: A mixture of 3-(4-chloro-6-methyl-2-pyrimidinyl)-1-(3,4-dichlorophenyl)guanidine (4) (330.5 mg, 1.0 mmol), (R)-tert-butyl 3-aminopiperidine-1-carboxylate (248 mg, 1.2 mmol), diisopropylethylamine (210 µL, 1.2 mmol) in dimethylacetamide (3.0 mL) was heated to 90° C. for 18 hrs. The reaction mixture was cooled, poured into water and extracted with ethyl acetate (2×20 mL). Organic phase was washed with water, dried ($Na_2SO_4$), filtered and evaporated to yield (R)-tert-butyl 3-(2-(3-(3,4-dichlorophenyl)guanidino)-6-methylpyrimidin-4-ylamino)piperidine-1-carboxylate (416 mg) which was used for the next step.

Step B: A solution of (R)-tert-butyl 3-(2-(3-(3,4-dichlorophenyl)guanidino)-6-methylpyrimidin-4-ylamino)piperidine-1-carboxylate (416 mg) in MeOH (8 mL) was treated with 4M HCl in dioxane (4 mL) and stirred overnight at room temperature. Removal of volatiles under vacuum yielded crude title compound (526 mg). 100 mg of the crude compound was purified by chromatography (silica plate, eluent: $NH_4OH$:MeOH:$CH_2Cl_2$: 2:50:400 v/v) to yield the title compound (11) (43.0 mg, 54.5%). HPLC (254 nm): Method 3, Rt 2.77 min. MS (ESI) m/z 396.4 [M+H⁺].

Example 6: Synthesis of 4-[(3R)-1-ethyl-3-piperidylamino]-2-[3-(3,4-dichlorophenyl)guanidino]-6-methyl-pyrimidine (12)

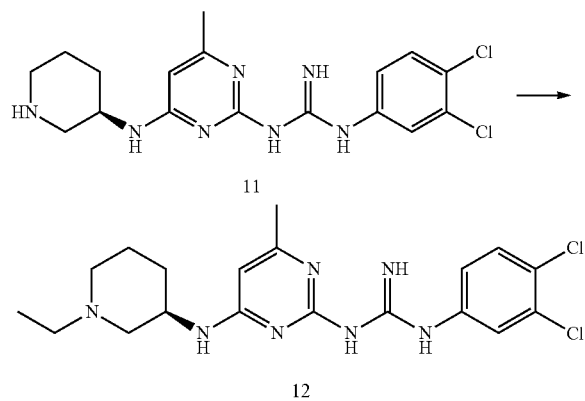

A mixture of 4-[(3R)-3-piperidylamino]-2-[3-(3,4-dichlorophenyl)guanidino]-6-methylpyrimidine (11) (400 mg, 1.02 mmol), acetaldehyde (115 mg, 2.6 mmol) and sodium cyanoborohydride (172 mg, 2.6 mmol) in $CH_2Cl_2$ (8.0 mL) was stirred overnight. The reaction mixture was quenched with MeOH and partitioned between ethyl acetate (30.0 mL) and water (60.0 mL). The ethyl acetate layer was washed with water, dried ($Na_2SO_4$), filtered and evaporated to yield crude product (290 mg). The crude product was purified by chromatography (silica plate, eluent: $NH_4OH$:MeOH:$CH_2Cl_2$: 2:50:400) to yield the title compound (12) (7 mg). HPLC (254 nm): Method 3, Rt 2.97 min. MS (ESI) m/z 424.2 [M+H⁺].

Example 7: Synthesis of 1-(3,4-dichlorophenyl)-3-[6-methyl-4-(3-pyridyloxy)-2-pyrimidinyl]guanidine (13)

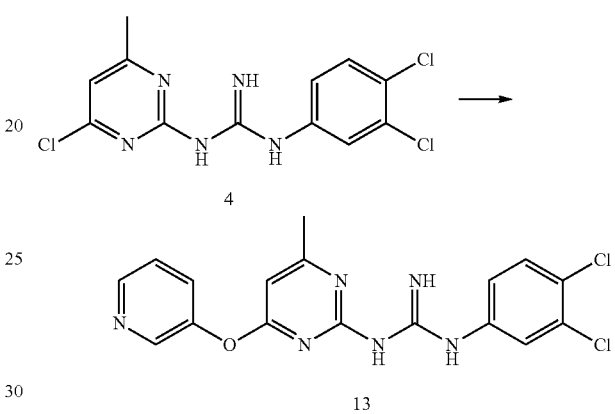

A mixture of 3-(4-chloro-6-methyl-2-pyrimidinyl)-1-(3,4-dichlorophenyl)guanidine (4) (215 mg, 0.71 mmol), $K_2CO_3$ (277 mg, 1.5 mmol) and 3-hydroxy-pyridine (71.4 mg, 0.75 mmol) in $CH_3CN$ (7.0 mL) was heated to 100° C. for 14 hours and then cooled to room temperature. The crude reaction mixture was directly purified by preparative thin layer chromatography plate (1000 µm) eluting with a 400:50:2 v/v mixture of $CH_2Cl_2$, MeOH and $NH_4OH$, respectively. The title compound (13) was isolated as a white solid (95 mg, 35%). HPLC (254 nm): Method 3, Rt 2.8 min. MS (ESI) m/z 391.3 [M+H⁺].

Example 8: Synthesis of 2-[3-(3,4-dichlorophenyl)guanidino]-6-methyl-4-(3-pyridylamino)pyrimidine (14)

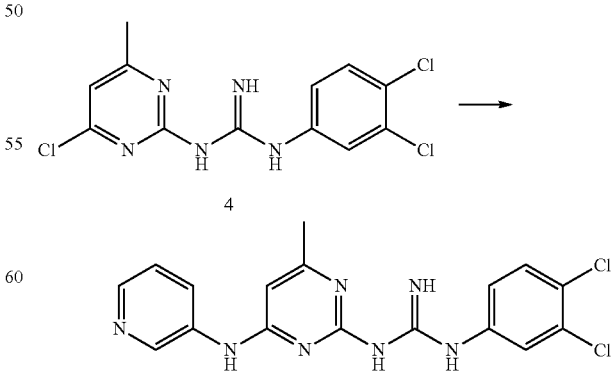

A mixture of 3-(4-chloro-6-methyl-2-pyrimidinyl)-1-(3,4-dichlorophenyl)guanidine (4) (238 mg, 0.72 mmol), 3-aminopyridine (57 mg, 0.6 mmol), and diisopropylethylamine (93 mg, 0.72 mmol) in dimethylacetamide (3.0 mL) was heated to 100° C. for 4 hours The reaction mixture was cooled to room temperature. Ethyl acetate (50.0 mL) was added and the mixture was stirred well. Insoluble materials were removed by filtration. The filtrate was washed with water, dried (Na$_2$SO$_4$), filtered and concentrated in vacuo to yield crude compound (75 mg). The crude compound was purified by chromatography (silica plate, 1000 μm) eluting with a 400:50:2 v/v mixture of CH$_2$Cl$_2$, MeOH and NH$_4$OH, respectively. Two purifications were carried out to obtain the title compound (14) (5 mg, 1.8%). HPLC (254 nm): Method 3, Rt 3.88 min. MS (ESI) m/z 390.4 [M+H$^+$].

Example 9: Synthesis of 4-(cyclohexylamino)-2-[3-(3,4-dichlorophenyl)guanidino]-6-methylpyrimidine (15)

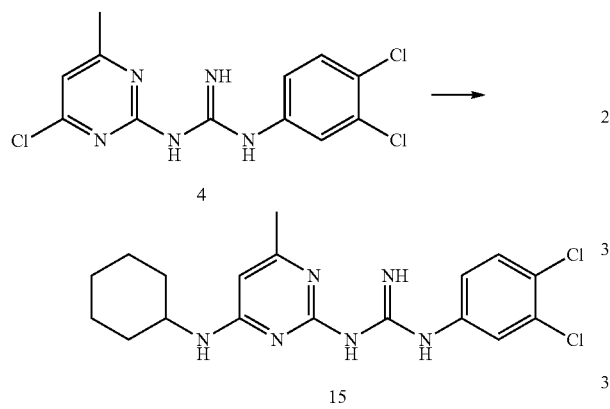

A mixture of 3-(4-chloro-6-methyl-2-pyrimidinyl)-1-(3,4-dichlorophenyl)guanidine (4) (238 mg, 0.72 mmol), cyclohexylamine (60 mg, 0.6 mmol), and diisopropylethylamine (93 mg, 0.72 mmol) in dimethylacetamide (3.0 mL) was heated to 100° C. for 4 hours The reaction mixture was cooled to room temperature. Ethyl acetate (50.0 mL) was added and the mixture was stirred well. Insoluble materials were removed by filtration. The filtrate was washed with water, dried (Na$_2$SO$_4$), filtered and concentrated in vacuo to yield crude compound (75 mg). The crude compound was purified by chromatography (silica plate, 1000 μm) eluting with a 400:50:2 v/v mixture of CH$_2$Cl$_2$, MeOH and NH$_4$OH, respectively. Two purifications were carried out to obtain the title compound (15) (28 mg, 9.8%). HPLC (254 nm): Method 3, Rt. 3.09 min. MS (ESI) m/z 395.3[M+H$^+$].

Example 10: Synthesis of 2-[3-(3,4-dichlorophenyl)guanidino]-6-methyl-4-(tetrahydro-2H-pyran-4-ylamino)-pyrimidine (16)

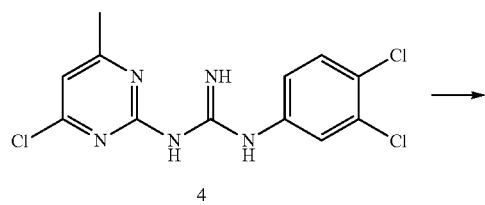

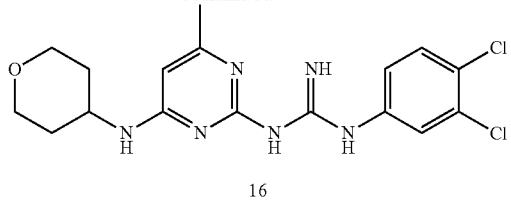

A mixture of 3-(4-chloro-6-methyl-2-pyrimidinyl)-1-(3,4-dichlorophenyl)guanidine (4) (238 mg, 0.72 mmol), 4-amino tetrahydropyran (61 mg, 0.6 mmol), and diisopropylethylamine (93 mg, 0.72 mmol) in dimethylacetamide (3.0 mL) was heated to 100° C. for 4 hrs. The reaction mixture was cooled to room temperature. Ethyl acetate (50 mL) was added and the mixture was stirred well. The mixture was washed with water, dried (Na$_2$SO$_4$), filtered and concentrated in vacuo to yield crude compound (80 mg). The crude compound was purified by chromatography (silica plate, 1000 μm) eluting with a 400:50:2 v/v mixture of CH$_2$Cl$_2$, MeOH and NH$_4$OH, respectively. Two purifications were carried out to obtain the title compound (16) (25 mg, 8.8%). HPLC (254 nm): Method 3, Rt 3.16 min. MS (ESI) m/z 397.3 [M+H$^+$].

Example 11: Synthesis of 1-(3,4-dichlorophenyl)-3-[6-methyl-4-(3-piperidyloxy)-2-pyrimidinyl]guanidine (17)

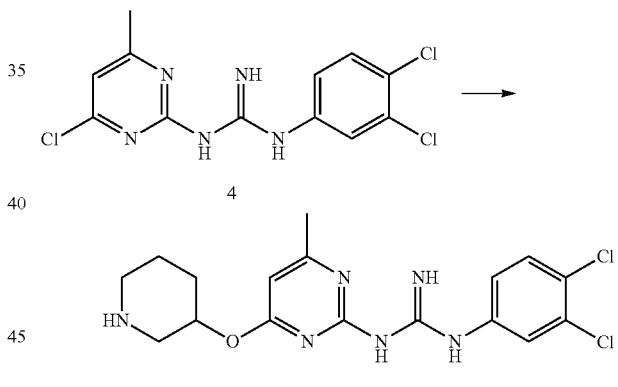

Step A: 1-BOC-3-hydroxy piperidine (403 mg, 2.0 mmol) was dissolved into dry THF (5.0 mL) under inert condition and NaH (60%, 85 mg, 2.1 mmol) was added at RT. The mixture was stirred for 40 minutes and then 3-(4-chloro-6-methyl-2-pyrimidinyl)-1-(3,4-dichlorophenyl)guanidine (4) (166 mg, 0.5 mmol) was added. The mixture was stirred at RT for 24 hrs. LC/MS after 24 hrs showed considerable amount of starting materials remained. An additional portion of piperidine sodium alkoxide (403 mg, 2 mmol) was made in a separate flask and then added to the reaction mixture. This mixture was stirred an additional 24 hours at RT. At this point the reaction mixture was poured into ice-water mixture (100 mL) and extracted with ethyl acetate (3×20 mL). The ethyl acetate layer was washed with water, dried (Na$_2$SO$_4$), filtered and concentrated in vacuo to yield tert-butyl 3-(2-(3-(3,4-dichlorophenyl)guanidino)-6-methylpyrimidin-4-yloxy)piperidine-1-carboxylate (1.0 g) which was carried forward to the next step.

Step B: tert-Butyl 3-(2-(3-(3,4-dichlorophenyl)guanidino)-6-methylpyrimidin-4-yloxy)piperidine-1-carboxylate (230 mg, 0.466 mmol) made above was dissolved into CH$_2$Cl$_2$ (2.5 mL) and then treated with 4M HCl in dioxane (2.5 mL). The mixture was stirred for 5 hours at RT before the volatiles were removed in vacuo. The residual crude product was purified by chromatography (silica column, eluent, mixture of CH$_2$Cl$_2$:MeOH:NH$_4$OH in the ratio 400:50:2 respectively). The eluent when concentrated gave a colorless foam. The foam was treated with 4M HCl in dioxane and precipitated out with diethyl ether which upon filtration gave the title compound (17) (18 mg, 10%). HPLC (254 nm): Method 3, Rt 3.2 min. MS (ESI) m/z 395 [M+H$^+$].

Example 12: Synthesis of 2-[3-(3,4-dichlorophenyl)-3-methylguanidino]-4-[1-ethyl-3-piperidylamino]-6-methylpyrimidine (21)

21

Step A: N-Methyl 3,4-dichloroaniline hydrochloride salt (18)

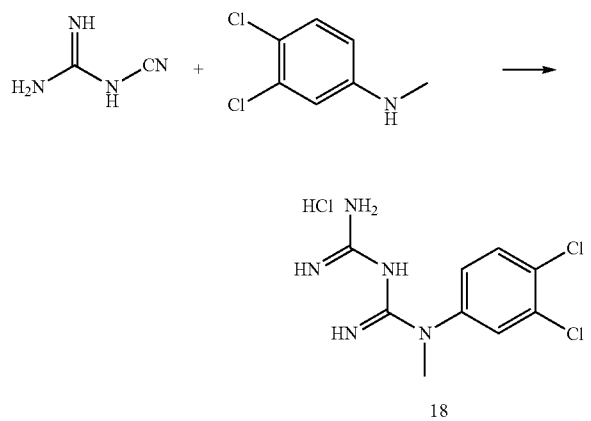

18

N-Methyl 3,4-dichloroaniline hydrochloride salt (6.38 g, 30 mmol) was suspended in isopropanol (100 mL) and treated with dicyandiamide (2.52 g, 30 mmol). The resulting mixture was heated to reflux for 6 hours. The reaction was cooled to room temperature, concentrated to dryness under vacuum and triturated with acetone. The resulting white precipitate was filtered, rinsed with acetone and air-dried to yield 3-[(azamethyl)azamethylidenemethyl]-1-(3,4-dichlorophenyl)-1-methylguanidine hydrochloride (18) (8.9 g, ~100%) as a highly hygroscopic solid, which was used immediately in the next step. HPLC (254 nm): Method 3, Rt 0.21 min. MS (ESI) m/z 260.2, 262.1 [M+H+].

Step B: 3-[(Azamethyl)azamethylidenemethyl]-1-(3,4-dichlorophenyl)-1-methylguanidine hydrochloride (19)

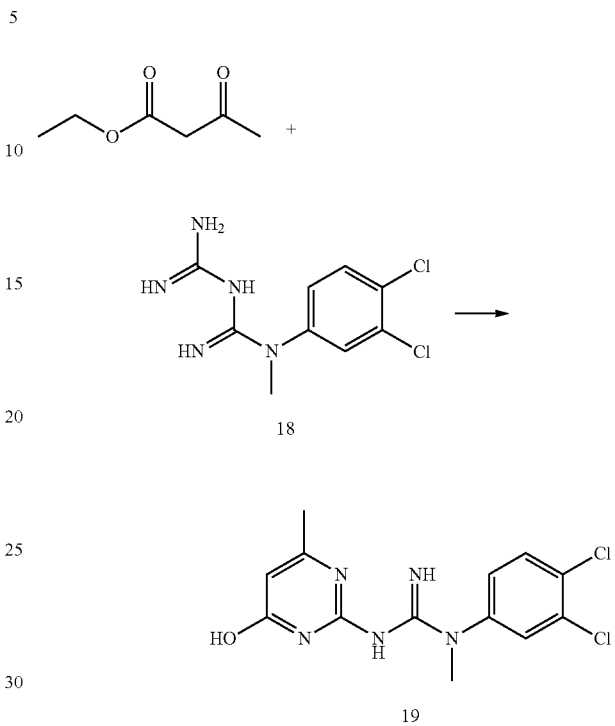

3-[(Azamethyl)azamethylidenemethyl]-1-(3,4-dichlorophenyl)-1-methylguanidine hydrochloride (8.9 g, 30 mmol) was added portionwise to a stirred mixture of 50% aqueous NaOH solution (3.72 mL, 46.5 mmol) and ethanol/water 3:1 v/v (30 mL). The resulting mixture was stirred for 10 minutes at room temperature. The mixture was heated to 70° C. and treated with ethyl acetoacetate (7.8 mL, 60 mmol). After the addition, the resulting mixture was heated for another 30 minutes and then cooled to room temperature. The volatiles were removed in vacuo and the aqueous residue was extracted with CH$_2$Cl$_2$. The organics were dried over anhydrous MgSO$_4$, filtered and concentrated in vacuo. The resulting sticky beige solid was triturated with diethyl ether to yield a white solid that was filtered and air dried to give 2-[3-(3,4-dichlorophenyl)-3-methylguanidino]-6-methyl-4-pyrimidinol (19) (3.05 g, 31%). HPLC (254 nm): Method 3, Rt 2.1 min. MS (ESI) m/z 326.1 [M+H$^+$].

Step C: 2-[3-(3,4-Dichlorophenyl)-3-methylguanidino]-6-methyl-4-pyrimidinol (20)

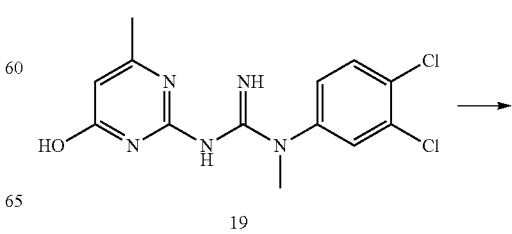

19

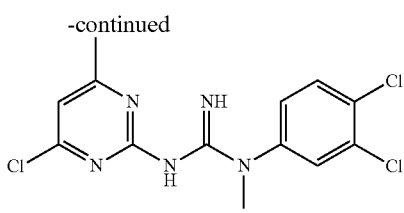

2-[3-(3,4-Dichlorophenyl)-3-methylguanidino]-6-methyl-4-pyrimidinol (978 mg, 3.0 mmol) was placed in a round-bottom flask and cooled to 0° C. under a N₂ atmosphere. POCl₃ (3 mL) was added dropwise. The resulting mixture was slowly heated to 80° C. for 2 hours, after which time the reaction was deemed complete by LCMS analysis. The mixture was cooled to room temperature, and the reaction contents were slowly poured over crushed ice under magnetic stirring. After the ice melted, the precipitate was filtered under vacuum, rinsed with water. The gummy solids were dissolved in ethyl acetate, washed with water and brine, dried over anhydrous MgSO₄, filtered and evaporated to give 3-(4-chloro-6-methyl-2-pyrimidinyl)-1-(3,4-dichlorophenyl)-1-methylguanidine (20) (831 mg, 80%) as a tan foam. HPLC (254 nm): Method 3, Rt 0.18 min. MS (ESI) m/z 346.0 [M+H⁺].

Step D: 3-(4-chloro-6-methyl-2-pyrimidinyl)-1-(3,4-dichlorophenyl)-1-methylguanidine (21)

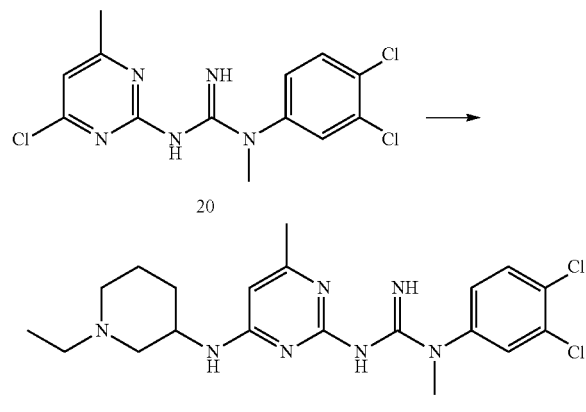

A solution of 3-(4-chloro-6-methyl-2-pyrimidinyl)-1-(3,4-dichlorophenyl)-1-methylguanidine (20) (378 mg, 1.1 mmol) in dimethylacetamide (3.0 mL) was treated with diisopropylethylamine (766 µL, 4.4 mmol) and 1-ethyl piperidine-3-amine HCl (221 mg, 1.1 mmol) under N₂. The resulting mixture was heated to 90° C. with stirring for 18 hours. HPLC/MS monitoring indicated that the starting material was consumed and the product formed. The reaction was cooled to room temperature, poured onto water and extracted with ethyl acetate. The required compound is in aqueous layer which was at pH 5, so the aqueous solution was treated with 1M NaOH to bring pH 9 and then extracted with ethyl acetate. The ethyl acetate layer was dried (Na₂SO₄), filtered and concentrated in vacuo to yield crude compound. The crude compound was purified by column chromatography (silica, eluent, mixture of CH₂Cl₂:MeOH: NH₄OH in the ratio 400:50:2 respectively) to give the title compound (21) (20 mg, 4%) as a white solid. HPLC (254 nm): Method 3, Rt 0.06 min. MS (ESI) m/z 436.5 [M+H⁺].

Example 13: Synthesis of (S)-1-(3,4-dichlorophenyl)-3-(4-(1-ethylpiperidin-3-ylamino)-6-methylpyrimidin-2-yl)guanidine (24)

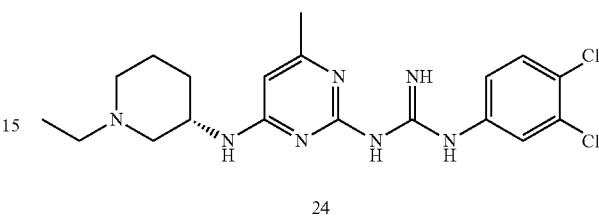

Step 1: (S)—N-(1-ethylpiperidin-3-yl)acetamide (20)

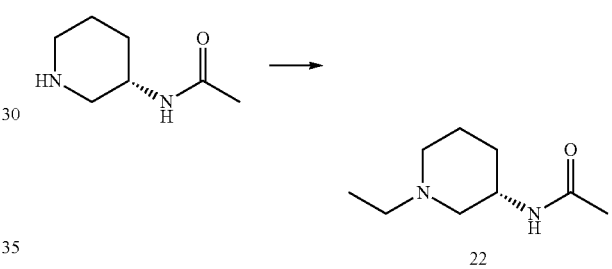

To a solution of (S)—N-(piperidin-3-yl)acetamide (916 mg, 5.1 mmol) in CH₂Cl₂ (15 mL) was added NaCNBH₄ (420 mg, 6.7 mmol) and acetaldehyde (900 mg, 20.4 mmol). The reaction mixture was stirred at RT for 16 hours. This mixture was diluted with CH₂Cl₂ (60 mL) and washed with 1M NaOH (15.0 mL) and water (2×15 mL). The organic phase was dried (Na₂SO₄), filtered and concentrated in vacuo to yield (S)—N-(1-ethylpiperidin-3-yl)acetamide (22) (689 mg, 80%). HPLC (254 nm): Method 3, Rt 0.45 min. MS (ESI) m/z 171.4 [M+H⁺] which was carried forward to the next step.

Step 2: (S)-1-ethylpiperidin-3-amine hydrochloride (23)

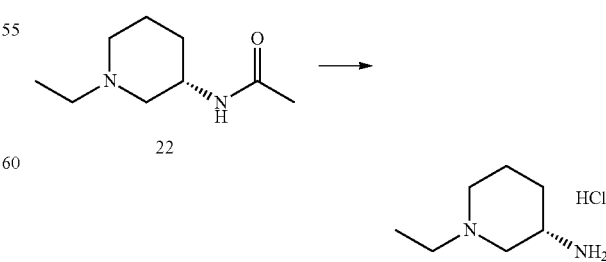

(S)—N-(1-Ethylpiperidin-3-yl)acetamide (20) (689 mg, 4.05 mmol) was taken into conc. HCl (15.0 mL) in a pressure tube and heated to 105° C. for 24 hours. The volatiles were then removed under vacuum. The residue was coevaporated with acetonitrile to obtain (S)-1-ethylpiperidin-3-amine hydrochloride (23) (522 mg, 64%) which was carried forward to the next step.

Step 3: (S)-1-(3,4-Dichlorophenyl)-3-(4-(1-ethylpiperidin-3-ylamino)-6-methylpyrimidin-2-yl)guanidine (24)

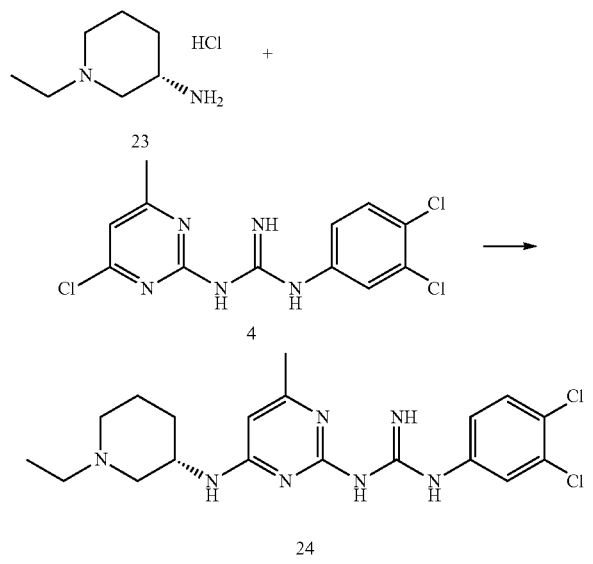

A solution of 3-(4-chloro-6-methyl-2-pyrimidinyl)-1-(3,4-dichlorophenyl)guanidine (4) (400 mg, 1.2 mmol) in dimethylacetamide (4.0 mL) was treated with diisopropylethylamine (1.05 mL, 6.0 mmol) and (S)-1-ethylpiperidin-3-amine hydrochloride (23) (326 mg, 1.6 mmol) under $N_2$. The resulting mixture was heated to 90° C. with stirring for 18 hours. HPLC/MS monitoring indicated that the starting material was consumed and the product formed. The reaction mixture was cooled to room temperature, poured onto water and extracted with $CH_2Cl_2$. The $CH_2Cl_2$ layer was dried ($Na_2SO_4$), filtered and concentrated in vacuo to yield crude compound (479 mg, 93.8%). The crude was purified by column chromatography (silica, eluent, mixture of $CH_2Cl_2$:MeOH:$NH_4OH$ in the ratio 400:50:2 respectively) to give the title compound (24) as a white solid (13 mg, 2.5%). HPLC (254 nm): Method 3, Rt 2.86 min. MS (ESI) m/z 424.4[M+H$^+$].

Example 14: Synthesis of 1-(3,4-dichlorophenyl)-3-[4-(1-ethyl-4-piperidyloxy)-6-methyl-2-pyrimidinyl]-guanidine (25)

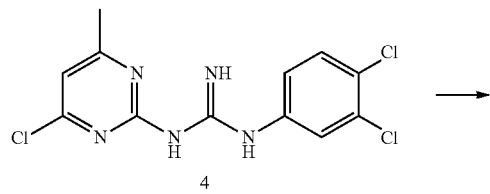

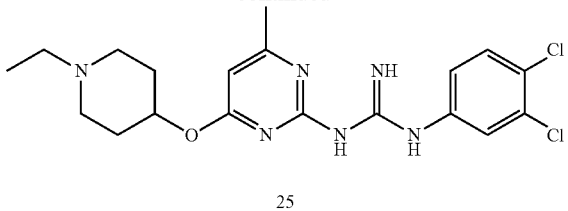 [SMILES: CCN1CCC[C@H](Nc2cc(C)nc(NC(=N)Nc3ccc(Cl)c(Cl)c3)n2)C1]

To a solution of 4-hydroxy-N-ethylpiperidine (267 mg, 2.0 mmol) in THF (5.0 mL) at RT was added NaH (60% w/w, 91 mg, 2.3 mmol) with stirring. The reaction mixture was stirred at RT under nitrogen for 45 minutes. To the reaction mixture was then added 3-(4-chloro-6-methyl-2-pyrimidinyl)-1-(3,4-dichlorophenyl)guanidine (4) (166 mg, 0.5 mmol). The reaction mixture was stirred at RT for 5 hours and then heated to 90° C. for 18 hrs. The reaction mixture was cooled, poured into ice-water mixture and extracted with $CH_2Cl_2$ (2×25 mL). The $CH_2Cl_2$ layer was washed with water and dried ($Na_2SO_4$), filtered and concentrated in vacuo to yield crude compound (200 mg, 94.8%). The crude compound was purified by column chromatography several times (silica, eluent, mixture of $CH_2Cl_2$:MeOH:$NH_4OH$ in the ratio 400:50:2 respectively) to obtain the title compound (25) (20 mg, 9%) as a solid. HPLC (254 nm): Method 3, Rt 2.89 min. MS (ESI) m/z 425.3 [M+H$^+$].

Example 15: Synthesis of 2-[3-(3,4-dichlorophenyl)guanidino]-4-(1-ethyl-4-piperidylamino)-6-methylpyrimidine (26)

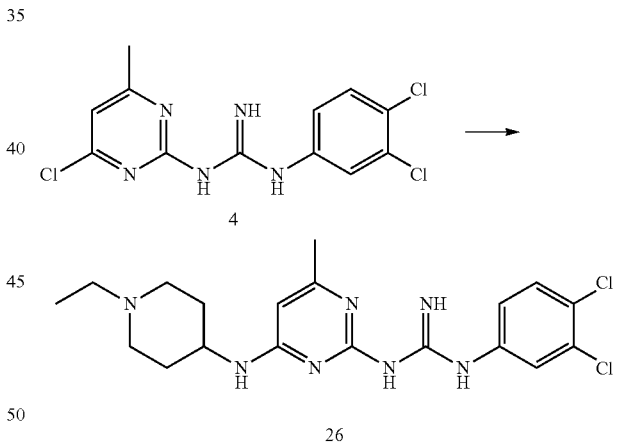

A solution of 3-(4-chloro-6-methyl-2-pyrimidinyl)-1-(3,4-dichlorophenyl)guanidine (4) (540 mg, 1.66 mmol), 1-ethyl-4-aminopiperidine HCl (450 mg, 2.23 mmol), and diisopropylethylamine (1.07 g, 8.3 mmol) in dimethylacetamide (9.0 mL) was heated at 90° C. for 18 hours. The reaction mixture was cooled to room temperature, poured onto water and extracted with $CH_2Cl_2$. The $CH_2Cl_2$ layer was dried ($Na_2SO_4$), filtered and concentrated in vacuo to yield crude compound (600 mg, 85.6%). The crude product was purified by column chromatography (silica, eluent, mixture of $CH_2Cl_2$:MeOH:$NH_4OH$ in the ratio 400:50:2 respectively) to afford the title compound (26) as a white solid (30 mg, 4.3%). HPLC (254 nm): Method 3 Rt 0.21 min. MS (ESI) m/z 424.2 [M+H$^+$].

Example 16: Synthesis of 1-(3,4-dichlorophenyl)-3-[6-methyl-4-(4-methyl-1-piperazinyl)-2-pyrimidinyl]-guanidine (27)

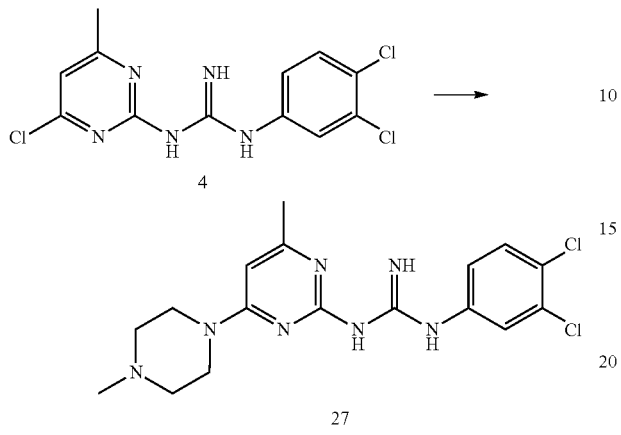

A solution of 3-(4-chloro-6-methyl-2-pyrimidinyl)-1-(3,4-dichlorophenyl)-guanidine (4) (318 mg, 0.96 mmol), 1-methyl piperazine (81 mg, 0.80 mmol), and diisopropylethylamine (119 mg, 0.96 mmol) in dimethylacetamide (3.0 mL) was heated at 90° C. for 18 hours. The reaction mixture was cooled to room temperature, poured onto water and extracted with $CH_2Cl_2$. The $CH_2Cl_2$ layer was dried ($Na_2SO_4$), filtered and concentrated in vacuo to yield crude compound (600 mg, 86%). The crude product was purified several times by column chromatography (silica, eluent, mixture of $CH_2Cl_2$:MeOH:$NH_4OH$ in the ratio 400:50:2 respectively) to afford the title compound (27) as a white solid (170 mg, 45%). HPLC (254 nm): Method 3, Rt 2.85 min. MS (ESI) m/z 396.3 [M+H$^+$].

Example 17: Synthesis of (N-methyl{2-[3-(3,4-dichlorophenyl)guanidino]-6-methyl-4-pyrimidinyl}amino)-methane (28)

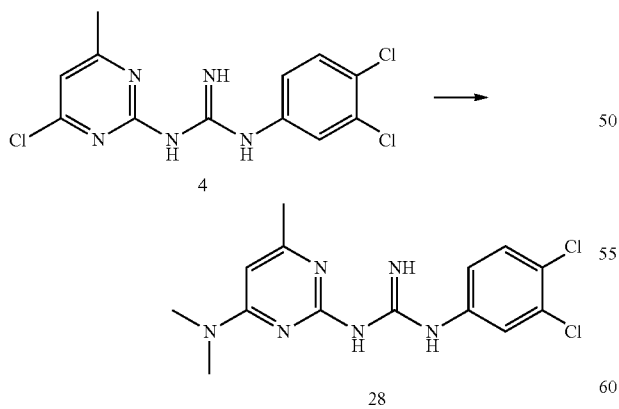

A solution of 3-(4-chloro-6-methyl-2-pyrimidinyl)-1-(3,4-dichlorophenyl)-guanidine (4) (318 mg, 0.96 mmol), dimethyl amine 2M solution in THF (400 μL, 0.80 mmol), and diisopropylethylamine (119 mg, 0.96 mmol) in dimethylacetamide (3.0 mL) was heated at 90° C. for 18 hours. The reaction mixture was cooled to room temperature, poured onto water and extracted with $CH_2Cl_2$. The $CH_2Cl_2$ layer was dried ($Na_2SO_4$), filtered and concentrated in vacuo to yield crude compound. The crude compound was purified by column chromatography (silica, eluent, mixture of $CH_2Cl_2$:MeOH:$NH_4OH$ in the ratio 400:50:2 respectively) to obtain the title compound (28) as a white solid (60 mg, 18.5%). HPLC (254 nm): Method 3, Rt 3.06 min. MS (ESI) m/z 341.1 [M+H$^+$].

Example 18: Synthesis of 1-(3,4-dichlorophenyl)-3-(4-methyl-6-morpholino-2-pyrimidinyl)guanidine (29)

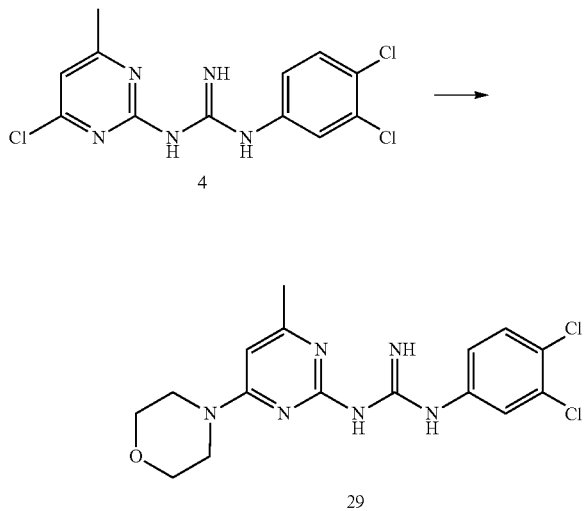

A solution of 3-(4-chloro-6-methyl-2-pyrimidinyl)-1-(3,4-dichlorophenyl)-guanidine (4) (318 mg, 0.96 mmol) and morpholine (243 mg, 2.78 mmol) in dimethylacetamide (10 mL) was heated at 90° C. for 18 hours. The reaction mixture was cooled to room temperature, poured onto water and extracted with $CH_2Cl_2$. The $CH_2Cl_2$ layer was dried ($Na_2SO_4$), filtered and concentrated in vacuo to yield crude oily compound (240 mg, 66%). The crude compound was purified by column chromatography (silica, eluent, mixture of $CH_2Cl_2$:MeOH:$NH_4OH$ in the ratio 400:50:2 respectively) to obtain the title compound (29) as a white solid (72 mg, 20%). HPLC (254 nm): Method 3, Rt 0.24 min. MS (ESI) m/z 383.4 [M+H$^+$].

Example 19: Synthesis of 1-{2-[3-(3,4-dichlorophenyl)guanidino]-6-methyl-4-pyrimidinylamino}-3-(dimethylamino)propane (30)

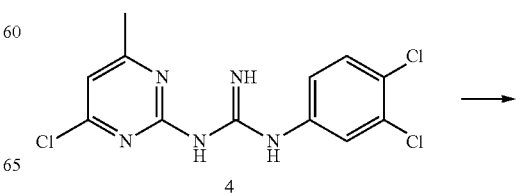

-continued

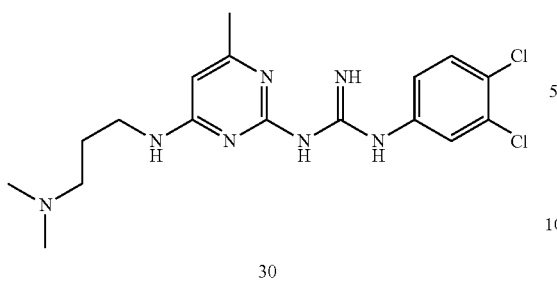

30

A solution of 3-(4-chloro-6-methyl-2-pyrimidinyl)-1-(3,4-dichlorophenyl)-guanidine (4) (50 mg, 0.15 mmol) and 3-(dimethylamino)-1-propylamine (57 µL, 0.45 mmol) in dimethylacetamide (1 mL) was heated at 90° C. for 3 hours. The reaction mixture was diluted with ethyl acetate (15.0 mL) and washed with water, sat. NaHCO₃ and water. The organic solution was dried (Na₂SO₄), filtered and concentrated in vacuo to yield the crude compound. The crude compound was purified by chromatography (silica gel plate, eluent, mixture of CH₂Cl₂:MeOH:NH₄OH in the ratio 400:50:2 respectively). Extraction of silica plate band gave the title compound (30) (5.7 mg, 10%). HPLC (254 nm): Method 3, Rt 0.11 min. MS (ESI) m/z 396.5 [M+H⁺].

Example 20: Synthesis of 3-{2-[3-(3,4-dichlorophenyl)guanidino]-6-methyl-4-pyrimidinylamino}propanol (31)

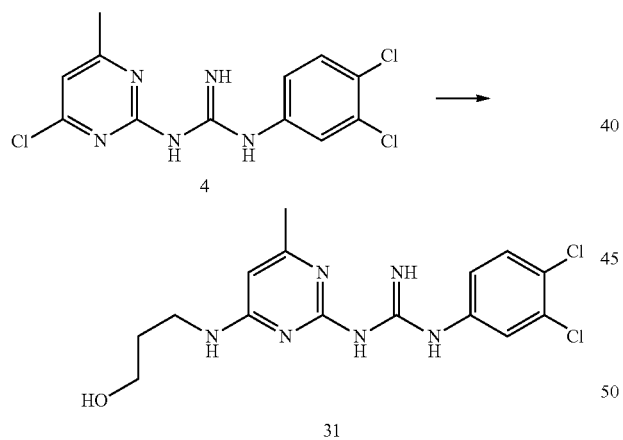

A solution of 3-(4-chloro-6-methyl-2-pyrimidinyl)-1-(3,4-dichlorophenyl)-guanidine (4) (50 mg, 0.15 mmol) and 3-amino-1-propanol (71 µL., 0.76 mmol) in dimethylacetamide (1 mL) was heated at 90° C. for 3 hours. The reaction mixture was diluted with ethyl acetate (15 mL) and washed with water, sat. NaHCO₃ and water. The organic layer was dried (Na₂SO₄), filtered and concentrated in vacuo to yield the crude compound. The crude compound was purified by chromatography (silica gel plate, eluent, mixture of CH₂Cl₂:MeOH:NH₄OH in the ratio 400:50:2 v/v respectively). Extraction of silica plate band gave the title compound (31) (5 mg, 9%). HPLC (254 nm): Method 3, Rt 0.20 min. MS (ESI) m/z 369.1 [M+H⁺].

Example 21: Synthesis of 1-(3,4-Dichlorophenyl)-3-{4-[3-(dimethylamino)propylamino]-6-methyl-2-pyrimidinyl}-2-guanidinecarbonitrile (32)

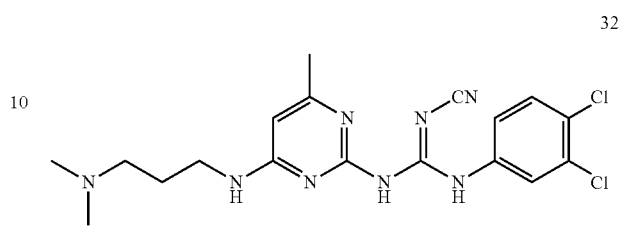

32

Step 1: 1-(2-Amino-6-methyl-4-pyrimidinylamino)-3-(dimethylamino)propane

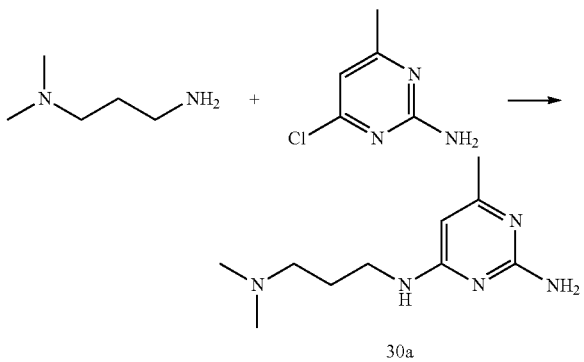

30a

A mixture of 2-amino-4-chloro-6methylpyrimidine (5 g, 34.5 mmole), 3-(Dimethylamino)-1-propylamine (4.6 g, 44.8 mmole) and sodium acetate (7.0 g, 70.0 mmole) in EtOH was heated at 120° C. in a pressure sealed tube overnight. The mixture was cooled to ambient temperature, filtered and concentrated in vacuo. The solvent was removed under reduced pressure and the resulting residue purified by flash chromatography (gradient elution, 0-20% 3M NH₃/MeOH in CH₂Cl₂) to obtain a pale yellow oil, which crystallized upon cooling to 0° C. to afford the titled compound as a white solid. Yield=2.5 g (12.0 mmole, 33%). HPLC (254 nm): Method 4, Rt 0.23 min. MS (ESI) m/z 210.2 [M+].

Step 2: 1-{2-[3-(3,4-Dichlorophenyl)thioureido]-6-methyl-4-pyrimidinylamino}-3-(dimethylamino)propane

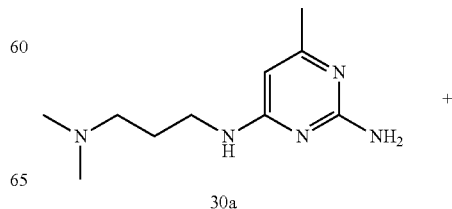

30a

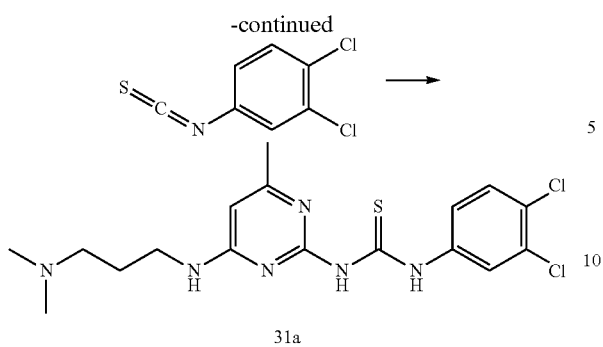

31a

A suspension of 1-(2-Amino-6-methyl-4-pyrimidinylamino)-3-(dimethylamino)propane (30a: 1.0 g, 4.5 mmole), 3,4-Dichlorophenyl isothiocyanate (0.96 g, 4.5 mmole) in 1,4-dioxane (15 mL) was heated at 120° C. in a pressure sealed tube overnight. TLC indicated that starting material remained and an additional 3,4-Dichlorophenyl isothiocyanate (0.96 g, 4.5 mmole) was added with continued heating for 6 h. An additional 3,4-Dichlorophenyl isothiocyanate (0.96 g, 4.5 mmole) was added and heating continued overnight. Upon cooling to ambient temperature, a yellow precipitate formed which was collected by filtration and washed with EtOH/Et$_2$O (1:1).

Yield=1.4 g (3.4 mmole, 71%). HPLC (254 nm): Method 4, Rt 2.31 min. MS (ESI) m/z 413.1-415.2 [M+H+].

Step 3: 1-(3,4-Dichlorophenyl)-3-{4-[3-(dimethylamino)propylamino]-6-methyl-2-pyrimidinyl}-2-guanidinecarbonitrile (32)

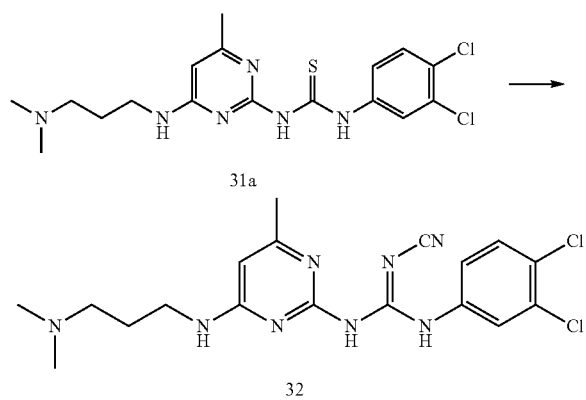

To a mixture of 1-{2-[3-(3,4-Dichlorophenyl)thioureido]-6-methyl-4-pyrimidinylamino}-3-(dimethylamino)propane (31a: 50 mg, 0.11 mmole) and 2-Chloro-1-methylpyridinium Iodide 4.5 mg, 0.17 mmole) in anhydrous DMF (1 mL) at room temperature was added triethylamine (56 mg, 0.57 mmole), and the resulting mixture was stirred for 1 h. The initial yellow suspension became homogeneous after addition of triethylamine and gradually obtained a wine red coloration. At this time, cyanamide (24 mg, 0.57 mmole) was added to the mixture, which was heated at 100° C. for 2 h. The mixture was allowed to cool and the solvent was removed in vacuo to give a residue that was purified by preparative TLC (20% 3M NH$_3$/MeOH in CH$_2$Cl$_2$ elution). From this a major band was isolated that was re-purified by major fraction by preparative TLC (isocratic elution, 1st run: 5% 3M NH$_3$/MeOH in CH$_2$Cl$_2$; 2nd run: 10% 3M NH$_3$/MeOH in CH$_2$Cl$_2$) to afford the title product (32) as a yellow solid. Yield=5 mg (0.01 mmole, 9%). HPLC (254 nm): Method 4, Rt 2.289 min. MS (ESI) m/z 421.2-423.2 [M+H+].

Example 22: Synthesis of 1-{2-[3-(3,4-Dichlorophenyl)-2-methylguanidino]-6-methyl-4-pyrimidinylamino}-3-(dimethylamino)propane (33)

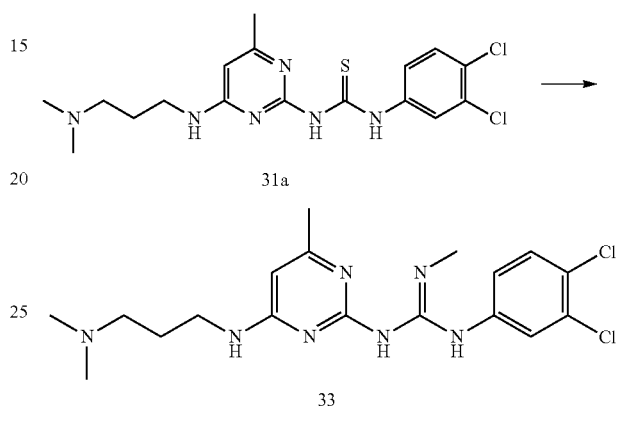

To a mixture of 1-{2-[3-(3,4-Dichlorophenyl)thioureido]-6-methyl-4-pyrimidinylamino}-3-(dimethylamino)propane (31a: 50 mg, 0.11 mmole) and 2-chloro-1-methylpyridinium iodide 4.5 mg, 0.17 mmole) in anhydrous DMF (1 mL) at room temperature was added triethylamine (56 mg, 0.57 mmole), and the resulting mixture was stirred for 1 h. The initial yellow suspension became homogeneous after addition of triethylamine and gradually obtained a wine red coloration. At this time, methylamine (2M in THF, 0.29 mL, 0.57 mmole) was added to the mixture, which was heated at 100° C. for 2 h. The mixture was allowed to cool and the solvent was removed in vacuo to give a residue that was purified by preparative TLC (20% 3M NH$_3$/MeOH in CH$_2$Cl$_2$ elution). From this a major band was isolated that was re-purified by major fraction by preparative TLC (isocratic elution, 1st run: 1% 3M NH$_3$/MeOH in CH$_2$Cl$_2$; 2nd run: 5% 3M NH$_3$/MeOH in CH$_2$Cl$_2$) to afford the title product (33) as a clear residue. Yield=3 mg (0.007 mmole, 5%). HPLC (254 nm): Method 4, Rt 3.25 min. MS (ESI) m/z 410.2-412.2 [M+H+].

Example 23: Synthesis of 1-{2-[3-(3,4-Dichlorophenyl)-1,1-dimethylguanidino]-6-methyl-4-pyrimidinylamino}-3-(dimethylamino)propane (34)

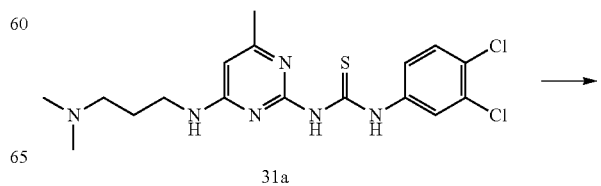

31a

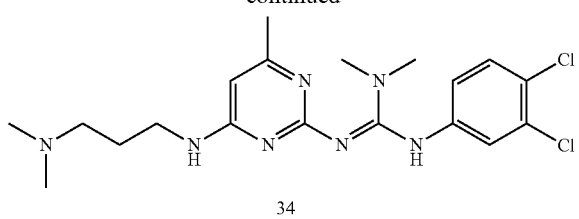

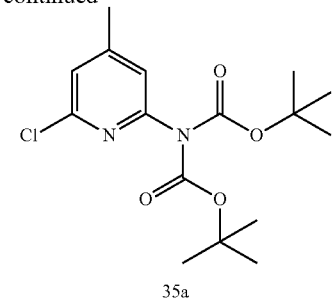

To a mixture of 1-{2-[3-(3,4-Dichlorophenyl)thioureido]-6-methyl-4-pyrimidinylamino}-3-(dimethylamino)propane (31a: 50 mg, 0.11 mmole) and 2-chloro-1-methylpyridinium iodide 4.5 mg, 0.17 mmole) in anhydrous DMF (1 mL) at room temperature was added triethylamine (56 mg, 0.57 mmole), and the resulting mixture was stirred for 1 h. The initial yellow suspension became homogeneous after addition of triethylamine and gradually obtained a wine red coloration. At this time, dimethylamine (2M in THF, 0.29 mL, 0.57 mmole) was added to the mixture, which was heated at 100° C. for 2 h. The mixture was allowed to cool and the solvent was removed in vacuo to give a residue that was purified by preparative TLC (20% 3M $NH_3$/MeOH in $CH_2Cl_2$ elution). From this a major band was isolated that was re-purified by major fraction by preparative TLC (isocratic elution, 1st run: 1% 3M $NH_3$/MeOH in $CH_2Cl_2$; 2nd run: 5% 3M $NH_3$/MeOH in $CH_2Cl_2$; 3rd run: 10% 3M $NH_3$/MeOH in $CH_2Cl_2$) to afford the title product (34) as a clear residue. Yield=6 mg (0.01 mmole, 10%). HPLC (254 nm): Method 4, Rt 1.128 min. MS (ESI) m/z 424.2-426.2 [M+H+].

Example 24: Synthesis of 1-{6-[3-(3,4-Dichlorophenyl)-2-methylguanidino]-4-methyl-2-pyridylamino}-3-(dimethylamino)propane (35)

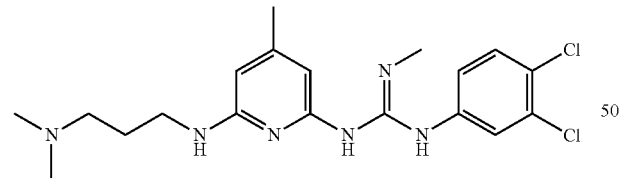

Step 1: N-tert-Butoxycarbonyl(6-chloro-4-methyl-2-pyridyl)amino 2,2-dimethylpropionate (35a)

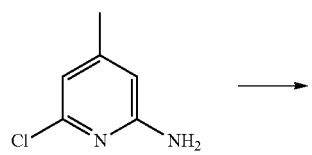

To a solution of 2-Amino-6-chloro-4-methylpyridine (0.1 g, 0.69 mmole) in anhydrous $CH_2Cl_2$ (2.5 mL) was added triethylamine (0.48 mL, 3.4 mmole), 4-dimethylaminopyridine (0.04 g, 0.34 mmole) followed by the addition of Di-tert-butyl dicarbonate (0.15 g, 0.69 mmole) in one portion. The mixture was stirred at room temperature for 3 h when TLC indicated the reaction was incomplete. An additional portion of Di-tert-butyl dicarbonate (0.30 g, 1.38 mmole) was added and the mixture stirred at 55° C. overnight. The reaction was diluted with $Et_2O$ and poured into a separatory funnel containing biphasic layer of $Et_2O$ and saturated ammonium chloride solution. The organic phase was separated and washed with saturated $NaHCO_3$ and brine, then dried over $Na_2SO_4$, and filtered. The solvent was removed in vacuo, and the resulting residue purified by flash chromatography (gradient elution, 0-7% EtOAc in hexanes) to obtain the title product. This material was used directly in the next step. Yield=0.15 g (0.45 mmole, 62%).

Step 2: N-tert-Butoxycarbonyl-(6-{[3-(dimethylamino)propyl]-N-tert-butoxycarbonylamino}-4-methyl-2-pyridyl)amino 2,2-dimethylpropionate (36)

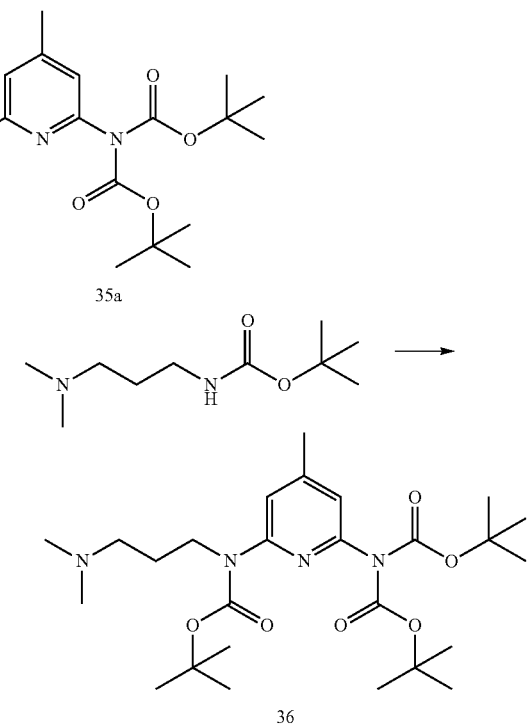

A mixture of palladium acetate (1.5 mg, 0.006 mmole), BINAP (6.5 mg, 0.01 mmole) and cesium carbonate (0.14 g, 0.41 mmole) in a sealed-cap vessel was degassed with nitrogen gas three times. Anhydrous 1,4-dioxane (1 mL) and N-tert-Butoxycarbonyl(6-chloro-4-methyl-2-pyridyl)amino 2,2-dimethylpropionate (35a: 50 mg, 0.14 mmole) were added to the mixture and the mixture was purged with nitrogen for 5 minutes. To this was added N-tert-Butoxycarbonyl-(6-{[3-(dimethylamino)propyl]-N-tert-butoxycarbonylamino}-4-methyl-2-pyridyl)amino 2,2-dimethylpropionate (88 mg, 0.41 mmoles). The mixture was heated to 95° C. and stirred overnight. After cooling, the mixture was diluted with EtOAc and filtered through a celite pad. The solvent was removed in vacuo and the resulting residue was purified by flash chromatography (gradient elution, 0-15% MeOH in $CH_2Cl_2$) to obtain the title compound as a yellow oil. This material was used directly in the next step. Yield=69 mg (0.14 mmole, 93%).

Step 3: 1-(6-Amino-4-methyl-2-pyridylamino)-3-(dimethylamino)propane (37)

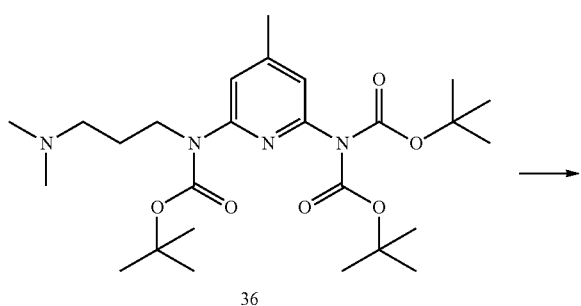

To a solution N-tert-Butoxycarbonyl-(6-{[3-(dimethylamino)propyl]-N-tert-butoxycarbonylamino}-4-methyl-2-pyridyl)amino 2,2-dimethylpropionate (36: 0.79 g, 1.48 mmole) in $CH_2Cl_2$ (15 mL) was added TFA/$CH_2Cl_2$ (1:1, 15 ml), and the resulting mixture was stirred at room temperature overnight. This mixture was concentrated in vacuo and neutralized with triethylamine (0.5 mL), before concentration in vacuo. The resulting residue was purified by flash chromatography (gradient elution, 0-35% 3M $NH_3$/MeOH in $CH_2Cl_2$) to afford the title compound (37) as a yellow gel. This material was used directly in the next step. Yield=0.30 g (1.48 mmole, 92%).

Step 4: 1-{6-[3-(3,4-Dichlorophenyl)thioureido]-4-methyl-2-pyridylamino}-3-(dimethylamino)propane (38)

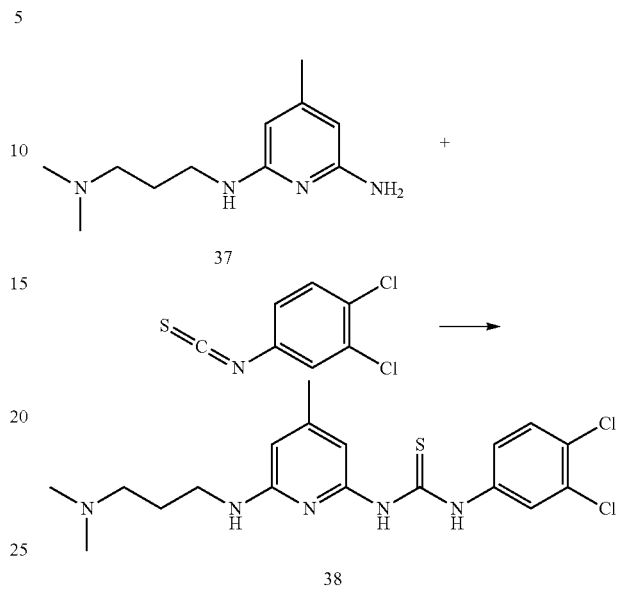

A mixture of 1-(6-Amino-4-methyl-2-pyridylamino)-3-(dimethylamino)propane (37: 0.23 g, 1.05 mmole) and 3,4-dichlorophenyl isothiocyanate (0.45 g, 2.10 mmole) was dissolved in anhydrous 1,4-dioxane (5 mL). The resulting mixture was heated to 90° C. for 5 h. After cooling to ambient temperature the mixture was diluted with $Et_2O$. The precipitate which formed was collected through filtration and washed repeatedly with $Et_2O$. Yield=0.15 g (0.36 mmole, 33%). HPLC (254 nm): Method 4, Rt 2.13 min. MS (ESI) m/z 412.2-414.1 [M+H+].

Step 5: 1-{6-[3-(3,4-Dichlorophenyl)-2-methylguanidino]-4-methyl-2-pyridylamino}-3-(dimethylamino)propane (35)

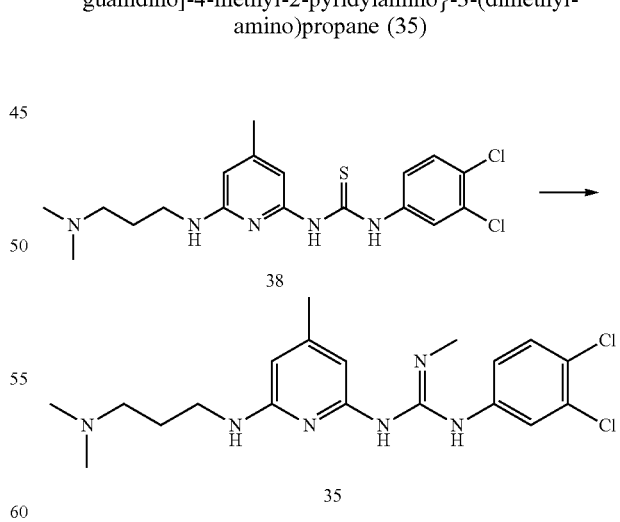

A mixture of 1-{6-[3-(3,4-Dichlorophenyl)thioureido]-4-methyl-2-pyridylamino}-3-(dimethylamino)propane (38: 30 mg, 0.07 mmole) and 2-chloro-1-methylpyridinium iodide (2.7 mg, 0.1 mmole) in anhydrous DMF (0.1 mL) was cooled to 0° C. and trimethylamine (48 μL, 0.35 mmole) added. The resulting mixture was warmed to room temperature and stirred for 30 min. Methylamine (2M in THF, 0.17 mL, 0.35 mmole) was added to the reaction mixture, and the mixture was stirred at 80° C. overnight. Upon cooling the solvent was removed in vacuo, and the resulting residue was purified by preparative TLC (isocratic elution, 1st run: 5% 3M $NH_3$/MeOH in $CH_2Cl_2$; 2nd run: 10% 3M $NH_3$/MeOH in $CH_2Cl_2$ elution) to obtain the title compound. Yield=13 mg (0.03 mmole, 39%). HPLC (254 nm): Method 4, Rt 1.442 min. MS (ESI) m/z 409.2-411.2 [M+H+].

Example 25: Synthesis of 1-{6-[3-(3,4-Dichlorophenyl)-1,1-dimethylguanidino]-4-methyl-2-pyridylamino}-3-(dimethylamino)propane (39)

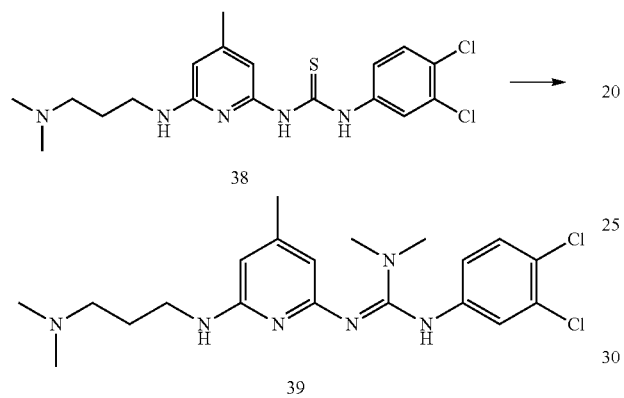

A mixture of 1-{6-[3-(3,4-Dichlorophenyl)thioureido]-4-methyl-2-pyridylamino}-3-(dimethylamino)propane (38: 30 mg, 0.07 mmole) and 2-chloro-1-methylpyridinium iodide (2.7 mg, 0.1 mmole) in anhydrous DMF (0.1 mL) was cooled to 0° C. and trimethylamine (48 μL, 0.35 mmole) added. The resulting mixture was warmed to room temperature and stirred for 30 min. Dimethylamine (2M in THF, 0.17 mL, 0.35 mmole) was added to the reaction mixture, and the mixture was stirred at 80° C. overnight. Upon cooling the solvent was removed in vacuo, and the resulting residue was purified by preparative TLC (isocratic elution, 1st run: 5% 3M $NH_3$/MeOH in $CH_2Cl_2$; 2nd run: 10% 3M $NH_3$/MeOH in $CH_2Cl_2$ elution) to obtain the title compound. Yield=13 mg (0.03 mmole, 39%). HPLC (254 nm): Method 4, Rt 1.297 min. MS (ESI) m/z 423.2-425.2 [M+H+].

Example 26: GBM4 and GBM8 Viability Assay

Cell culture medium was prepared from a NSA proliferation kit (Neurocult) and NeuroCult supplements (Stemcell Tech Cat. #05751) and treated with 20 μL of 10 μg/mL rh EGF, 10 μL of 10 μg/mL rh bFGF and 10 μL of 0.2% Heparin. In this medium, human glioblastoma cells were cultured in ultra-low attachment tissue culture flasks until 1×106 cells ml was achieved (GBM4 and GBM8 are distinct neuro sphere cell cultures derived from these human patient tissues). GBM4 and GBM8 cells were dissociated and 10 mL of media containing 4000 human glioblastoma cells per 90 uL were transferred to an ultra-low binding 96-well plate and incubated at 37° C. overnight. On the following day, 10 μL of a 1% DMSO solution of test compound in assay medium was added to wells containing the cell suspension and the mixture incubated at 37° C. for 3 days. At this time, the plate was removed from the incubator and allowed to reach room temperature. After about 30 minutes, 50 μL of Cell Titer Glo solution was added to each well and the plate shaken for 1 minute at low speed. After 10 minutes luminescence was recorded using a Tecan Safire2 reader.

Reduction in luminescence compared to DMSO only control wells was used to determine the percentage inhibition of cell growth. IC50s were calculated using the % inhibition of luminescence for serial dilutions of compounds fitted to a 4-parameter fit within the Prism (San Diego) curve fitting program. Table 1 below shows the GBM4 IC50 and GBM8 IC50 for compounds described herein.

TABLE 1

| Cmpd # | GBM4 (IC50) | FBM8 (IC50) |
|---|---|---|
| 7 | A | A |
| 8 | C | C |
| 9 | C | C |
| 10 | A | A |
| 11 | A | A |
| 12 | A | A |
| 13 | B | C |
| 14 | A | A |
| 15 | A | A |
| 16 | B | A |
| 17 | B | A |
| 21 | B | C |
| 24 | A | A |
| 25 | B | B |
| 26 | A | A |
| 27 | B | A |
| 28 | A | A |
| 29 | A | A |
| 31a |  | A |
| 32 |  | A |
| 33 |  | C |
| 34 |  | C |
| 35 |  | B |
| 39 |  | C |

IC50: A < 10 μM; 10 μM ≤ B ≤ 30 μM; C > 30 μM

Example 27: Phase II Clinical Trial of Compounds of Formula (I), (Ia), (Ib), (II), (IIa), (IIb), (III), (IIIA), (IIIB), (IV), (IVA), (IVB), or (V) in Patients with Recurrent Rb Positive Glioblastoma The purpose of this phase II trial is to determine the efficacy of a compound of Formula (I), (IA), (IB), (II), (IIA), (IIB), (III), (IIIA), (IIIB), (IV), (IVA), (IVB), or (V) (as measured by progression free survival at 6 months) in patients with recurrent glioblastoma multiforme or gliosarcoma who are Rb positive. A total of 30 patients will be treated; 15 will undergo a planned surgical resection and receive drug for 7 days prior to surgery, followed by drug after recovery from surgery, and the other 15 patients will receive drug without a planned surgical procedure.

Patients: Eligible subjects will be men and women 18 years and older

Criteria:

Inclusion Criteria:

Patients with radiographically proven recurrent, intracranial Glioblastoma multiforme or Gliosarcoma will be eligible for this protocol. Patients must have documentation of Rb positive disease.

All patients must sign an informed consent indicating that they are aware of the investigational nature of this study. Patients must have signed an authorization for the release of their protected health information. Patients must be registered prior to treatment with study drug. Treatment must take place within 7 days of registration; if treatment is delayed more than 7 days, the laboratory tests for eligibility and history and physical exam must be repeated.

Patients must have had prior external beam radiation and temozolomide chemotherapy; there is no limit to the number of prior chemotherapies used; patients may be treated in their first, second or third relapse Patients must be >18 years old, and with a life expectancy >8 weeks.

Patients must have a Karnofsky Performance Status of >60.

At the time of registration: Patients must have recovered from the toxic effects of prior therapy: >28 days from any investigational agent [NOTE: off-label use of FDA approved agents are not considered investigational for the purposes of this protocol], >28 days from prior cytotoxic therapy, >42 days from nitrosoureas, >28 days from bevacizumab, and >7 days for non-cytotoxic agents, e.g., interferon, tamoxifen, thalidomide, cis-retinoic acid, and erlotinib, for example. Any questions related to the definition of non-cytotoxic agents should be directed to the Study Chair.

Patients must have adequate bone marrow function (WBC>3,000/μl, ANC>1,500/mm3, platelet count of >100,000/mm3, and hemoglobin >10 gm/dl), adequate liver function (SGOT and bilirubin <2 times ULN), and adequate renal function (creatinine <1.5 mg/dL) before starting therapy. A pre-study EKG is required for all patients, and patients must have a normal QT interval. These tests must be performed within 14 days prior to registration. Eligibility level for hemoglobin may be reached by transfusion.

Patients must have shown unequivocal radiographic evidence for tumor progression by MRI scan. A scan should be performed within 14 days prior to registration and on a steroid dose that has been stable for at least 7 days. If the steroid dose is increased between the date of imaging and registration a new baseline MRI is required. The same type of scan, i.e., MRI must be used throughout the period of protocol treatment for tumor measurement. Patients unable to undergo MR imaging will not be eligible.

Patients having undergone recent resection of recurrent or progressive tumor will be eligible as long as all of the following conditions apply:

They have recovered from the effects of surgery.

Residual disease following resection of recurrent intracranial Glioblastoma Multiforme or Gliosarcoma is not mandated for eligibility into the study. To best assess the extent of residual disease post-operatively, an MRI should be done no later than 96 hours in the immediate post-operative period or at least 4 weeks post-operatively, within 14 days prior to registration. If the 96-hour scan is more than 14 days before registration, the scan needs to be repeated. If the steroid dose is increased between the date of imaging and registration, a new baseline MRI is required on a stable steroid dosage for at least 7 days.

Patients must have failed prior radiation therapy and temozolomide and must have an interval of greater than or equal to 42 days from the completion of radiation therapy to study entry.

Patients with prior therapy that included interstitial brachytherapy, stereotactic radiosurgery, or Gliadel wafers must have confirmation of true progressive disease rather than radiation necrosis based upon PET scanning, MR spectroscopy or surgical documentation of disease.

A subset of 15 patients will be enrolled prior to a planned, indicated surgical resection. Patients can be enrolled pre-operatively only if they are surgical candidates, do not have evidence of an acute intracranial hemorrhage and are able to start protocol treatment in a window of 7 days before surgery.

Male and female patients with reproductive potential must use an approved contraceptive method, if appropriate (for example, intrauterine device [IUD], birth control pills, or barrier device) during and for 3 months after discontinuation of study treatment. Women of child-bearing potential must have a negative beta-HCG pregnancy test documented within 14 days prior to registration.

Blocks or slides of tumor tissue from a previous surgery must be available to do IHC Rb staining. Patients with negative tumors (Rb negative) will be excluded from the study.

Exclusion Criteria:

Patients must not have any significant medical illnesses that in the investigator's opinion cannot be adequately controlled with appropriate therapy or would compromise the patient's ability to tolerate this therapy.

Patients with a history of any other cancer (except non-melanoma skin cancer or carcinoma in-situ of the cervix), unless in complete remission and off of all therapy for that disease for a minimum of 3 years are ineligible.

Patients must not have an active infection or serious intercurrent medical illness. Patients with a history of acute intracranial hemorrhage will also be excluded.

Patients must not be pregnant/breast feeding and must agree to practice adequate contraception.

Patients must not have any disease that will obscure toxicity or dangerously alter drug metabolism.

Because of the potential for drug interactions, patients on enzyme-inducing anti-epileptic drugs or other drugs that cause CYP3A enzyme induction or inhibition will not be eligible unless they are off therapy for at least 14 days Patients with congenital or other reasons for prolongation of the QT interval on EKG will be excluded.

Study Design:

A total of 30 patients with recurrent Glioblastoma or Gliosarcoma will be treated with a compound of Formula (I), (IA), (IB), (II), (IIA), (IIB), (III), (IIIA), (IIIB), (IV), (IVA), (IVB), or (V) at a dose of 125 mg daily for 21 consecutive days followed by a 7 day break off therapy (cycle length is 28 days). Of these 30 patients, 15 will receive drug for 7 days prior to an indicated, intended surgical resection for progression, and will then resume drug at the same dose after recovery from surgery. Treatment will be repeated every 28 days, and in the absence of disease progression patients may receive treatment for 12 cycles. At that time patients will be given the option to continue on study past 12 cycles, up to a maximum of 24 cycles.

Following registration, available blocks or slides from a previous surgery must be submitted for diagnosis review (confirmation of Glioblastoma multiforme or Gliosarcoma) and Rb status determination. Only patients with Rb positive tumors can be treated, and Rb tumor status must be known prior to any treatment. Additional tissue from previous surgeries will also be obtained to evaluate molecular abnormalities in the tumor. These studies will be done retrospectively and are not required to be performed prior to registration.

Monitoring will include a clinical and neurological exam before the beginning of each cycle (every 4 weeks). Complete blood counts with differential will be examined on days 1 and 15 of each cycle. Liver and renal function will be performed every 4 weeks. Toxicity and dose modifications will be based on the NCI CTCAE Version 4. Disease status will be assessed clinically each cycle (every 4 weeks) and radiographically after each second cycle (every 8 weeks).

Primary Outcome Measures:
Efficacy as determined by progression free survival [Time Frame: 1-2 years] [Designated as safety issue: No]
Determine the efficacy of a compound of Formula (I), (IA), (IB), (II), (IIA), (IIB), (III), (IIIA), (IIIB), (IV), (IVA), (IVB), or (V) in patients with recurrent glioblastoma multiforme or gliosarcoma who are Rb positive, as measured by progression free survival at 6 months. A total of 30 patients will be treated; 15 who will undergo a planned, intended surgical resection will receive drug for 7 days prior to surgery, followed by drug after recovery from surgery, and 15 patients who receive drug without a planned surgical procedure Secondary Outcome Measures:
Number of Participants with Adverse Events as a Measure of Safety and Tolerability [Time Frame: 1-2 years] [Designated as safety issue: Yes]

Example 28: Phase II Clinical Trial of the Safety and Efficacy of Compounds of Formula (I), (IA), (IB), (II), (IIA), (IIB), (III), (IIIA), (IIIB), (IV), (IVA), (IVB), or (V) in Adults With Recurrent or Refractory Medulloblastoma The purpose of this phase II trial is to how well a compound of Formula (I), (IA), (IB), (II), (IIA), (IIB), (III), (IIIA), (IIIB), (IV), (IVA), (IVB), or (V) works in treating adult patients with recurrent or refractory medulloblastoma.

Patients: Eligible subjects will be men and women 22 years and older.

Criteria:
Inclusion Criteria:
Patients with a histologically confirmed diagnosis of medulloblastoma (including posterior fossa PNET) that is recurrent, progressive, or refractory to standard therapy and for which there is no known curative therapy are eligible; there must be evidence of residual measurable disease or lesion in pre-study MRI as described in section; patients with spinal disease that is measurable will be eligible
The diagnosis should be confirmed at the treating institution and tissue (either from the diagnosis or relapse or preferably from both time points) must be available for biological studies
Patients with neurological deficits should have deficits that are stable for a minimum of 1 week prior to registration; this is to be documented in the database
Eastern Cooperative Oncology Group (ECOG) performance status 0-2
No other myelosuppressive chemotherapy or immunotherapy within 4 weeks prior to study entry (6 weeks if prior nitrosourea)
Decadron dose should also be stable or decreasing for at least 1 week (7 days) prior to starting therapy
Radiation therapy (XRT)>=3 months prior to study entry for craniospinal irradiation (>=23 Gy); >=8 weeks for local irradiation to primary tumor; >=2 weeks prior to study entry for focal irradiation for symptomatic metastatic sites
Off all colony stimulating factors >=1 week prior to study entry (GCSF, GM CSF, erythropoietin)
Absolute neutrophil count (ANC)>=1000/μL
Platelet count >=50,000/uL (transfusion independent)
Hemoglobin >=8.0 gm/dL (may receive RBC transfusions)
Creatinine clearance or radio-isotope GFR>=70 ml/min/1.73 m2 or
A serum creatinine=<2.0 mg/dL
Total bilirubin=<1.5×upper limit of normal (ULN) for age
Serum glutamic pyruvic transaminase (SGPT) (alanine aminotransferase [ALT])=<2.5× institutional ULN
Serum glutamic-oxalacetic transaminase (SGOT) (aspartate aminotransferase [AST])=<2.5 times institutional ULN
Serum albumin >=2.5 g/dL
Patient must have recovered from the significant acute toxicities of all prior therapy before entering this study and meet all other eligibility criteria
Pregnancy should be avoided for 12 months after the last dose for females of child-bearing potential; female patients of childbearing potential must not be pregnant or breast-feeding; female patients of childbearing potential must have a negative serum or urine pregnancy test within 24 hours prior to beginning treatment
Women of childbearing potential are required to use 2 forms of acceptable contraception, including one barrier method during participation in the study and for the 12 months following the last dose; for medical or personal reasons, 100% commitment to abstinence is considered an acceptable form of birth control. All patients should receive contraceptive counseling either by the investigator, or by an OB/gynecologist or other physician who is qualified in this area of expertise
Signed informed consent according to institutional guidelines must be obtained Exclusion Criteria:
Patients with any clinically significant unrelated systemic illness (serious infections or significant cardiac, pulmonary, hepatic or other organ dysfunction), that would compromise the patient's ability to tolerate protocol therapy or would likely interfere with the study procedures or results
Patients receiving any other anticancer or investigational drug therapy
Patients with inability to return for follow-up visits or obtain follow-up studies required to assess toxicity to therapy
Life expectancy <12 weeks as determined by treating physician
Inability to swallow capsules
Malabsorption syndrome or other condition that would interfere with enteral absorption
History of congestive heart failure
History of ventricular arrhythmia requiring medication
Uncontrolled hypocalcemia, hypomagnesemia, hyponatremia or hypokalemia defined as less than the lower limit of normal for the institution despite adequate electrolyte supplementation
Congenital long QT syndrome
Study Design: Patients receive a compound of Formula (I), (IA), (IB), (II), (IIA), (IIB), (III), (IIIA), (IIIB), (IV), (IVA), (IVB), or (V) PO once daily on days 1-28. Treatment repeats every 28 days for up to 26 courses in the absence of disease progression or unacceptable toxicity.

Primary Outcomes:
Objective response rates (PR and CR) graded using RECIST criteria [Time Frame: Up to 12 months] [Designated as safety issue: No]
Ninety-five percent confidence interval estimates of the true, unknown objective response rate will be constructed for each of the three strata. The proportions of patients with confirmed complete responses, partial responses and stable disease will be reported descriptively for each of the three strata. Cumulative incidence functions of time to objective response will also be provided.
Secondary Outcomes:
Duration of sustained objective response [Time Frame: From the initial scan documenting complete or partial response that was subsequently confirmed until the earlier of documented progression or death on study, assessed up to 12 months] [Designated as safety issue: No]
Progression-free survival [Time Frame: From the date of initial treatment with a compound of Formula (I), (IA), (IB), (II), (IIA), (IIB), (III), (IIIA), (IIIB), (IV), (IVA), (IVB), or (V) until the earliest of progression or death on study, assessed up to 12 months] [Designated as safety issue: No]
Medical costs during the first 6 months after transplantation
Patient and graft survival Example 29: Phase I/II Clinical Trial of the Safety, Tolerability, and Anti-tumor Efficacy of Compounds of Formula (I), (IA), (IB), (II), (IIA), (IIB), (III), (IIIA), (IIIB), (IV), (IVA), (IVB), or (V) in the Treatment of Recurrent Malignant Astrocytomas This is a single-center, open-label, non-randomized, Phase I/IIa study to investigate the safety, tolerability, and antitumor efficacy of a compound of Formula (I), (IA), (IB), (II), (IIA), (IIB), (III), (IIIA), (IIIB), (IV), (IVA), (IVB), or (V) in patients with recurrent malignant astrocytomas (glioblastoma, gliosarcoma, anaplastic astrocytoma, anaplastic oligodendroglioma, anaplastic oligoastrocytoma, and anaplastic ependymoma). Patients will be treated for up to 5 cycles. A treatment cycle is defined as 28 days+7 days rest (28+7 days during cycle 1 to 4, and 28 days during cycle 5). The following cycle will not be started until the treatment continuation criteria are fulfilled. Concomitant supportive therapies will be allowed.

Patients: Eligible subjects will be men and women ages 18 and older
Criteria:
Inclusion Criteria:
Be informed of the nature of the study and have provided written informed consent
At least 18 years of age
ECOG performance of 0, 1, or 2, or KPS (Karnofsky performance status) ≥60.
Pathological verification of a WHO grade 4 astrocytoma (glioblastoma or gliosarcoma), or WHO Grade 3 anaplastic astrocytoma, anaplastic oligodendroglioma, anaplastic oligoastrocytoma, or anaplastic ependymoma.
Documented recurrent glioblastoma, gliosarcoma, anaplastic astrocytoma, anaplastic oligodendroglioma, anaplastic oligoastrocytoma, or anaplastic ependymoma after at least one failed treatment of chemotherapy and radiation
Expected survival of at least 3 months
At least 2-weeks from cytoreductive surgery, if performed, 4-weeks from bevacizumab or other chemotherapy (6-weeks if prior chemotherapy was nitrosourea) and 12-weeks from completion of radiotherapy.
Ability to undergo MRI scanning without and with imaging dye on a periodic basis as defined in the protocol
At least seven (7) days off of medications with induce CYP2C9 and CYP3A4 before administration of the first dose of a compound of Formula (I), (IA), (IB), (II), (IIA), (IIB), (III), (IIIA), (IIIB), (IV), (IVA), (IVB), or (V)
Preserved major organ functions, i.e: Blood leukocyte count ≥3.0×109/L Blood absolute neutrophil count ≥1.5×109/L Blood platelet count ≥100×109/L Blood hemoglobin ≥100 g/L (transfusions are allowed) Plasma total bilirubin level ≤1.5 times the upper institutional limit (ULN) of the ||normal|| (i.e. reference) range Plasma AST (aspartate aminotransferase) or ALT≤2.5 times upper institutional limit (ULN) of the ||normal|| range Plasma creatinine ≤1.5 times upper institutional limit (ULN) of the ||normal|| range 12-lead ECG with normal tracings; or changes that are not clinically significant and do not require medical intervention, and QTc<500 ms At least seven (7) days off of medications which inhibit or induce CYP2C9 or CYP3A4 before first study treatment day.
Exclusion Criteria:
Ongoing infection or other major recent or ongoing disease that, according to the Investigator, poses an unacceptable risk to the patient
Grade 3 or higher constipation within the past 28 days or grade 2 constipation within the past 14 days before randomization. (Patients with grade 2 constipation within the past 14 days could be re-screened if constipation decreases to ≤grade 1 with optimal management of constipation.)
Coexisting uncontrolled medical condition, including, but not limited to, active cardiac disease and significant dementia
Hepatitis B or Hepatitis C, or HIV infection requiring anti-retroviral therapy
Active malignancy other than basal cell skin cancer
Other active malignancy during the previous 3 years
Major surgical procedure within 4 weeks
Prior stereotactic or gamma knife radiosurgery or proton radiation, unless unequivocal progression by functional neuro-imaging (PET, dynamic MRI, MRS, SPECT) or by re-operation with documented histologic confirmation of recurrence.
Prior anti-tumor therapy, as follows: at least 12-weeks from radiation therapy; at least 4-weeks from prior treatment with temozolomide or bevacizumab, 6-weeks from BCNU or CCNU.
Women of child bearing potential (WOCBP) who do not consent to using acceptable methods of birth control (oral contraceptives, IUD). For purposes of this study, WOCBP include any female who has experienced menarche, who has not undergone tubal ligation, and who is not postmenopausal. Post menopause is defined as: amenorrhea ≥12 consecutive months without another cause.

Medically uncontrolled Type 1 or Type 2 diabetes mellitus

Pregnancy or lactation

Current participation in any other investigational clinical trial within 4-weeks.

Eastern Cooperative Oncology Group (ECOG) performance status >2 after optimization of medications (See Appendix 4) or KPS<60

Anticipated Life expectancy less than 3 months

Contraindications to the investigational product or known or suspected hypersensitivity Patients who must take concomitant medications which induce or are potent inhibitors of CYP2C9 or sensitive substrates of CYP3A4 with narrow therapeutic range may not participate Lack of suitability for participation in the trial, for any reason, as judged by the Investigator Study Design:

The trial will be divided in two phases. In the first phase, 10-20 patients will be enrolled and treated with 300-520 mg BID of a compound of Formula (I), (IA), (IB), (II), (IIA), (IIB), (III), (IIIA), (IIIB), (IV), (IVA), (IVB), or (V) for 28 days. The primary endpoint of the first phase is to determine the recommended Phase 2 dose (RP2D) of the compound of Formula (I), (IA), (IB), (II), (IIA), (IIB), (III), (IIIA), (IIIB), (IV), (IVA), (IVB), or (V) in patients with recurrent or progressive glioblastoma and to assess the safety and toxicity of the compound of Formula (I), (IA), (IB), (II), (IIA), (IIB), (III), (IIIA), (IIIB), (IV), (IVA), (IVB), or (V) in this patient population. The study has a 3+3 design and the first cohort will be treated with 400 mg a compound of Formula (I), (IA), (IB), (II), (IIA), (IIB), (III), (IIIA), (IIIB), (IV), (IVA), (IVB), or (V) BID for 28 days repeated in up to 5 cycles. If dose-limiting toxicity (DLT) such as neutropenia occurs, dosing will be interrupted and the individual patient will, following normalization, be restarted on the same or a lower dose level according to standardized procedure. If two or three of the first 3 patients on a specific dose level experience a DLT during the first 28 days of treatment with the compound of Formula (I), (IA), (IB), (II), (IIA), (IIB), (III), (IIIA), (IIIB), (IV), (IVA), (IVB), or (V), the following patients will be treated with a lower dose level. If one DLT occurs during the first 28 days of dosing in the first 3 three patients another 3 patients will be treated with the same dose level. If 2 of the 6 patients display DLT, the next patients will be treated with a lower dose level. The highest dose level without DLT or with maximally one DLT out of 6 patients will be the RPTD. All assessments with respect to dose adjustments for subsequent cohorts will be done during the first 28 days of treatment. Non-progressing patients may be treated for a total of five 28-day cycles (24 weeks).

In the second phase, 12 patients will be enrolled and treated with the identified RP2D of the compound of Formula (I), (IA), (IB), (II), (IIA), (IIB), (III), (IIIA), (IIIB), (IV), (IVA), (IVB), or (V) for 28 days repeated in five cycles. The primary endpoints of phase II is to assess the proportion of patients who are progression-free at 24 weeks and to assess safety, tolerability, and adverse event profile of the compound of Formula (I), (IA), (IB), (II), (IIA), (IIB), (III), (IIIA), (IIIB), (IV), (IVA), (IVB), or (V).

Primary Outcomes:

Phase I—Determine recommended Phase II dose. [Time Frame: 8 months] [Designated as safety issue: Yes]

Phase II—Determine Antitumor effect [Time Frame: 4 months] [Designated as safety issue: Yes]

Phase I—Number of Participants with Adverse Events as a Measure of Safety and Tolerability [Time Frame: 6 months] [Designated as safety issue: Yes]

physical/neurological examinations (pathological findings and quality and quantity)

adverse events (quality and quantity per dose level)

vital signs, ECG, laboratory parameters (pathological findings as quality and quantity, for laboratory parameters, descriptive statistics)

Secondary Outcomes:

Renal Phase I—Maximum Tolerated Dose (MTD) [Time Frame: 8 months] [Designated as safety issue: Yes]

To identify the MTD of a compound of Formula (I), (IA), (IB), (II), (IIA), (IIB), (III), (IIIA), (IIIB), (IV), (IVA), (IVB), or (V).

Phase I—Molecular markers of optimum response [Time Frame: 8 months] [Designated as safety issue: Yes]

To assess potential molecular markers that might predict optimum response sub-population groups Phase I—Molecular Markers of IGF (insulin like growth factor)-1R pathway [Time Frame: 8 months] [Designated as safety issue: Yes]

To evaluate surrogate molecular markers of IGF-1R pathway activation/inhibition after treatment with the compound of Formula (I), (IA), (IB), (II), (IIA), (IIB), (III), (IIIA), (IIIB), (IV), (IVA), (IVB), or (V) in patients with malignant astrocytomas Phase II—Time-To-Progression (TTP) and Overall Survival (OS) [Time Frame: 4 months] [Designated as safety issue: Yes]

To determine time-to-progression (TTP) and overall survival (OS) of patients treated with the compound of Formula (I), (IA), (IB), (II), (IIA), (IIB), (III), (IIIA), (IIIB), (IV), (IVA), (IVB), or (V)

Phase II—Overall Response Rate [Time Frame: 4 months] [Designated as safety issue: Yes]

To assess overall response rate (ORR) in recurrent malignant astrocytomas after treatment with the compound of Formula (I), (IA), (IB), (II), (IIA), (IIB), (III), (IIIA), (IIIB), (IV), (IVA), (IVB), or (V)

Phase II—Imaging Evidence of Response. [Time Frame: 4 months] [Designated as safety issue: Yes]

To identify surrogate imaging evidence of response on MRI (magnetic resonance imaging) sequences by RANO criteria (with additional special attention to T2-FLAIR, DWI (diffusion-weighted imaging), perfusion MRI and multi-voxel MRS (magnetic resonance spectroscopy) sequences).

Example 30: Pharmaceutical Compositions

Example 30A

Parenteral Composition

To prepare a parenteral pharmaceutical composition suitable for administration by injection, 100 mg of a compound of Formula (I), (IA), (IB), (II), (IIA), (IIB), (III), (IIIA), (IIIB), (IV), (IVA), (IVB), or (V) is dissolved in DMSO and then mixed with 10 mL of 0.9% sterile saline. The mixture is incorporated into a dosage unit form suitable for administration by injection.

In another embodiment, the following ingredients are mixed to form an injectable formulation:

| Ingredient | Amount |
| --- | --- |
| Compound of Formula (I), (IA), (IB), (II), (IIA), (IIB), (III), (IIIA), (IIIB), (IV), (IVA), (IVB), or (V) | 1.2 g |
| sodium acetate buffer solution (0.4M) | 2.0 mL |
| HCl (1 N) or NaOH (1M) | q.s. to suitable pH |
| water (distilled, sterile) | q.s. to 20 mL |

All of the above ingredients, except water, are combined and stirred and if necessary, with slight heating if necessary. A sufficient quantity of water is then added.

Example 30B

Oral Composition

To prepare a pharmaceutical composition for oral delivery, 100 mg of a compound of Formula (I), (IA), (IB), (II), (IIA), (IIB), (III), (IIIA), (IIIB), (IV), (IVA), (IVB), or (V) is mixed with 750 mg of starch. The mixture is incorporated into an oral dosage unit, such as a hard gelatin capsule, which is suitable for oral administration.

In another embodiment, the following ingredients are mixed intimately and pressed into single scored tablets.

| Ingredient | Quantity per tablet, mg |
| --- | --- |
| compound of Formula (I), (IA), (IB), (II), (IIA), (IIB), (III), (IIIA), (IIIB), (IV), (IVA), (IVB), or (V) | 200 |
| Cornstarch | 50 |
| croscarmellose sodium | 25 |
| Lactose | 120 |
| magnesium stearate | 5 |

In yet another embodiment, the following ingredients are mixed intimately and loaded into a hard-shell gelatin capsule.

| Ingredient | Quantity per tablet, mg |
| --- | --- |
| compound of Formula (I), (IA), (IB), (II), (IIA), (IIB), (III), (IIIA), (IIIB), (IV), (IVA), (IVB), or (V) | 200 |
| lactose, spray-dried | 148 |
| magnesium stearate | 2 |

In yet another embodiment, the following ingredients are mixed to form a solution/suspension for oral administration:

| Ingredient | Amount |
| --- | --- |
| Compound of Formula (I), (IA), (IB), (II), (IIA), (IIB), (III), (IIIA), (IIIB), (IV), (IVA), (IVB), or (V) | 1 g |
| Anhydrous Sodium Carbonate | 0.1 g |
| Ethanol (200 proof), USP | 10 mL |
| Purified Water, USP | 90 mL |
| Aspartame | 0.003 g |

Example 30C

Sublingual (Hard Lozenge) Composition

To prepare a pharmaceutical composition for buccal delivery, such as a hard lozenge, mix 100 mg of a compound of Formula (I), (IA), (IB), (II), (IIA), (IIB), (III), (IIIA), (IIIB), (IV), (IVA), (IVB), or (V) with 420 mg of powdered sugar mixed with 1.6 mL of light corn syrup, 2.4 mL distilled water, and 0.42 mL mint extract. The mixture is gently blended and poured into a mold to form a lozenge suitable for buccal administration.

Example 30D

Inhalation Composition

To prepare a pharmaceutical composition for inhalation delivery, 20 mg of a compound of Formula (I), (IA), (IB), (II), (IIA), (IIB), (III), (IIIA), (IIIB), (IV), (IVA), (IVB), or (V) is mixed with 50 mg of anhydrous citric acid and 100 mL of 0.9% sodium chloride solution. The mixture is incorporated into an inhalation delivery unit, such as a nebulizer, which is suitable for inhalation administration.

Example 30E

Rectal Gel Composition

To prepare a pharmaceutical composition for rectal delivery, 100 mg of a compound of Formula (I), (IA), (IB), (II), (IIA), (IIB), (III), (IIIA), (IIIB), (IV), (IVA), (IVB), or (V) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 30F

Suppository Formulation

A suppository of total weight 2.5 g is prepared by mixing a compound of Formula (I), (IA), (IB), (II), (IIA), (IIB), (III), (IIIA), (IIIB), (IV), (IVA), (IVB), or (V) with Witepsol™ H-15 (triglycerides of saturated vegetable fatty acid; Riches-Nelson, Inc., New York), and has the following composition:

| Ingredient | Quantity per suppository, mg |
| --- | --- |
| compound of Formula (I), (IA), (IB), (II), (IIA), (IIB), (III), (IIIA), (IIIB), (IV), (IVA), (IVB), or (V) | 500 |
| Witepsol ® H-15 | balance |

Example 30G

Topical Gel Composition

To prepare a pharmaceutical topical gel composition, 100 mg of a compound of Formula (I), (IA), (IB), (II), (IIA), (IIB), (III), (IIIA), (IIIB), (IV), (IVA), (IVB), or (V) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 30H

Ophthalmic Solution Composition

To prepare a pharmaceutical opthalmic solution composition, 100 mg of a compound of Formula (I), (IA), (IB), (II), (IIA), (IIB), (III), (IIIA), (IIIB), (IV), (IVA), (IVB), or (V) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

The examples and embodiments described herein are for illustrative purposes only and in some embodiments, various modifications or changes are to be included within the purview of disclosure and scope of the appended claims.

What is claimed is:

1. A compound having the structure of Formula (I):

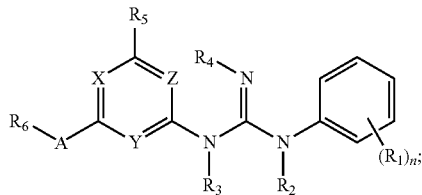

Formula (I)

A is O or $CH_2$;
X, Y, and Z are each independently N, or $C(R_7)$;
each $R_1$ is independently halogen, —CN, —$NO_2$, —OH, —$OCF_3$, —$OCH_2F$, —$OCF_2H$, —$CF_3$, —$SR_8$, —$N(R_8)S(=O)_2R_9$, —$S(=O)_2N(R_8)_2$, —$S(=O)R_9$, —$S(=O)_2R_9$, —$C(=O)R_9$, —$CO_2R_8$, —$N(R_8)_2$, —$C(=O)N(R_8)_2$, —$N(R_8)C(=O)R_9$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl; or two $R_1$ are taken together to form a substituted or unsubstituted heterocyclic ring or a substituted or unsubstituted carbocyclic ring;
$R_2$, $R_3$, and $R_4$ are each independently H, —CN, $C_1$-$C_4$alkyl, $C_3$-$C_6$cycloalkyl, or $C_2$-$C_7$heterocycloalkyl; or two of $R_2$, $R_3$, and $R_4$ are taken together to form a 5- or 6-membered heterocyclic ring;
$R_5$ is halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
$R_6$ is

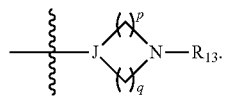

$R_{11}$ and $R_{12}$ are each independently H, or substituted or unsubstituted $C_1$-$C_6$alkyl; or $R_{11}$ and $R_{12}$ are taken together to form a 5-, 6-, 7-, or 8-membered heterocyclic ring;
J is C(H), or N;
$R_{13}$ is H, substituted or unsubstituted $C_1$-$C_6$alkyl, substituted or unsubstituted $C_2$-$C_7$heterocycloalkyl, substituted or unsubstituted $C_3$-$C_8$cycloalkyl, substituted or unsubstituted —$C_1$-$C_4$alkyl$C_6$-$C_{10}$aryl, or substituted or unsubstituted —$C_1$-$C_4$alkyl$C_2$-$C_7$heteroaryl;
each $R_7$ is independently H, halogen, —CN, —OH, —$CF_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{14}$ and $R_{15}$ are each independently H, or substituted or unsubstituted $C_1$-$C_6$alkyl; or $R_{14}$ and $R_{15}$ are taken together to form a 4-, 5-, 6-membered cycloalkyl ring;
$R_{21}$ is halogen, —CN, —$NO_2$, —OH, —$OCF_3$, —$OCH_2F$, —$OCF_2H$, —$CF_3$, —$SR_{22}$, —$N(R_{22})S(=O)_2R_{23}$, —$S(=O)_2N(R_{22})_2$, —$S(=O)R_{23}$, —$S(=O)_2R_{23}$, —$C(=O)R_{23}$, —$CO_2R_{22}$, —$C(=O)N(R_{22})_2$, —$N(R_{22})C(=O)R_{23}$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl;
each $R_{22}$ is independently H, or substituted or unsubstituted $C_1$-$C_6$alkyl;
$R_{23}$ is substituted or unsubstituted $C_1$-$C_6$alkyl;
each $R_8$ is independently H, or substituted or unsubstituted $C_1$-$C_6$alkyl;
$R_9$ is substituted or unsubstituted $C_1$-$C_6$alkyl;
$R_{10}$ is H, or $C_1$-$C_4$alkyl;
m is 2-6;
n is 0-5;
p is 1-3;
q is 1-3; or
a pharmaceutically acceptable salt or solvate thereof.

2. The compound of claim 1, wherein $R_2$, $R_3$, and $R_4$ are each independently H, —CN, $C_1$-$C_4$alkyl, $C_3$-$C_6$cycloalkyl, or $C_2$-$C_7$heterocycloalkyl.

3. The compound of claim 1, wherein $R_2$ is $C_1$-$C_4$alkyl, $C_3$-$C_6$cycloalkyl, or $C_2$-$C_7$heterocycloalkyl; $R_3$ is H; and $R_4$ is H.

4. The compound of claim 3, wherein $R_2$ is $CH_3$ or $C_3$-$C_6$cycloalkyl.

5. The compound of claim 1, wherein $R_2$ is H; $R_3$ is $C_1$-$C_4$alkyl, $C_3$-$C_6$cycloalkyl, or $C_2$-$C_7$heterocycloalkyl; and $R_4$ is H.

6. The compound of claim 5, wherein $R_3$ is $CH_3$.

7. The compound of claim 1, wherein $R_{13}$ is —$CH_3$ or —$CH_2CH_3$.

8. The compound of claim 1, wherein J is N.

9. The compound of claim 1, wherein $R_5$ is substituted or unsubstituted $C_1$-$C_6$alkyl.

10. The compound of claim 9, wherein $R_5$ is $CH_3$ or $CH_2CH_3$.

11. The compound of claim 1, wherein each $R_1$ is independently halogen, —CN, —NO$_2$, —OH, —CF$_3$, substituted or unsubstituted $C_1$-$C_6$alkyl, substituted or unsubstituted $C_1$-$C_6$alkoxy, substituted or unsubstituted $C_1$-$C_6$heteroalkyl, substituted or unsubstituted $C_2$-$C_7$heterocycloalkyl, substituted or unsubstituted $C_3$-$C_8$cycloalkyl, substituted or unsubstituted $C_6$-$C_{10}$aryl, or substituted or unsubstituted $C_2$-$C_7$heteroaryl.

12. The compound of claim 1, wherein X is C(R$_7$); Y is N; Z is N; and R$_7$ is H.

13. A compound having a structure selected from:

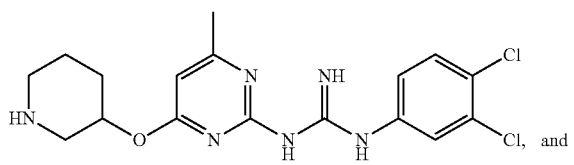

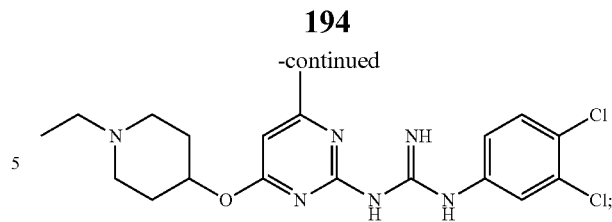

or a pharmaceutically acceptable salt or solvate thereof.

14. A pharmaceutical composition comprising a compound of claim 1, or a pharmaceutically acceptable salt or solvate thereof, and at least one pharmaceutically acceptable excipient.

15. A method for treating a disease in a subject comprising administering to the subject in need thereof a composition comprising a compound of claim 1, or a pharmaceutically acceptable salt or solvate thereof; wherein the disease is Down's Syndrome or cancer selected from brain cancer, glioblastoma multiforme, medulloblastoma, astrocytomas, brain stem gliomas, meningiomas, oligodendrogliomas, melanoma, lung cancer, breast cancer, or leukemia.

* * * * *